(12) United States Patent
Wittrup et al.

(10) Patent No.: US 7,413,737 B2
(45) Date of Patent: Aug. 19, 2008

(54) ANTI-HYDROXYLASE ANTIBODIES AND USES THEREOF

(75) Inventors: K. Dane Wittrup, Chestnut Hill, MA (US); Yik Andy Yeung, Cambridge, MA (US); Jack R. Wands, Providence, RI (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/989,462

(22) Filed: Nov. 15, 2004

(65) Prior Publication Data

US 2005/0220795 A1 Oct. 6, 2005

Related U.S. Application Data

(60) Provisional application No. 60/563,514, filed on Apr. 19, 2004, provisional application No. 60/520,114, filed on Nov. 14, 2003.

(51) Int. Cl.
*A61K 39/00* (2006.01)
*A61K 39/395* (2006.01)
*C12P 21/08* (2006.01)
*C07K 16/00* (2006.01)

(52) U.S. Cl. .............. 424/142.1; 424/152.1; 424/155.1; 530/387.3; 530/387.7; 530/388.15; 530/388.8

(58) Field of Classification Search ................ None
See application file for complete search history.

(56) References Cited

U.S. PATENT DOCUMENTS

| | | | |
|---|---|---|---|
| 4,946,778 A | * | 8/1990 | Ladner et al. .............. 435/69.6 |
| 5,565,332 A | | 10/1996 | Hoogenboom et al. |
| 6,166,176 A | | 12/2000 | Radosevich |
| 6,727,080 B1 | | 4/2004 | Radosevich |
| 6,783,758 B2 | | 8/2004 | Wands et al. |
| 6,797,696 B2 | | 9/2004 | Wands et al. |
| 6,812,206 B2 | | 11/2004 | Wands et al. |
| 6,815,415 B2 | | 11/2004 | Wands et al. |
| 6,835,370 B2 | | 12/2004 | Wands et al. |
| 7,094,556 B2 | | 8/2006 | Wands et al. |

FOREIGN PATENT DOCUMENTS

| | | | |
|---|---|---|---|
| WO | WO 82/01461 | * | 5/1982 |
| WO | WO 01/35102 | | 5/2001 |
| WO | WO 02/092782 A2 | | 11/2002 |
| WO | WO 03/100087 | | 12/2003 |
| WO | WO 2005/003302 | | 1/2005 |
| WO | WO 2005/016381 | | 2/2005 |

OTHER PUBLICATIONS

Gura (1997, Science 278:1041-1042).*
White et al. (2001, Ann. Rev. Med. 52:125-145).*
Bowie et al, Science, 247:1306-1310, 1990, p. 1306, col.2.*
Gussow et al. (1991, Methods in Enzymology 203:99-121).*
Rudikoff et al. (PNAS, USA, 1982, 79: 1979).*
Lavaissiere et al. (1996, J. Clin. Invest. 98(6):1313-1323).*
Daugherty et al. (2000, Proc. Natl. Acad. Sci. USA 97(5):2029-2034).*
D'Amico et al., "Use of anti-HAAH antibodies in cancer therapy:specific delivery of cytotoxic agents", AACR Annual Meeting, Apr. 14-18, 2007, Los Angeles, CA.
De la Monte, et al., "Aspartyl (Asparaginyl) β-Hydroxylase regulates hepatocellular carcinoma invasiveness", J. of Hepatology, 44:971-983 (2006).
Finney et al., "Anti-Proliferative and Anti-Metastatic Activities of Monoclonal Antibodies to Human Aspartyl (Asparaginyl) β-Hydroxylase", Abstract and Poster presented at the AACR Meeting of Nov. 17-21, 2003, Boston, MA.
Finney, et al, "Surface Expressed HAAH in Cancer Cells is an Internalizing Antigen", Abstract and Poster presented at the 97th Annual Meeting of AACR, Apr. 1-5, 2006, Washington, DC.
Gores, Gregory J., "Cholangiocarcinoma:preventing invasion as anti-cancer strategy", J. of Hepatology, 38:671-673 (2003).
Lebowitz et al., "Inhibition of cancer cell proliferation, motility and invasiveness by monoclonal antibodies specific for human aspartyl (asparaginyl) β-hydroxylase (HAAH)" Abstract published for the AACR-NCI-EORTC International Conference (Oct. 29-Nov. 2, 2001 (Miami Beach, Florida).
Palumbo et al., "Human Aspartyl (Asparaginyl) β-Hydroxlase Monoclonal Antibodies: Potential Biomarkers for Pancreatic Carcinoma", Pancreas, 25(1):39-44 (2002).
Xian et al., "Expression of aspartyl beta-hydroxylase and its clinicopathological significance in hepatocellular carcinoma", Modern Pathology.19:280-286 (2006).
Yeung et al, "Isolation and Engineering of Biologically Active Human Single-Chain Antibody Fragments (scFv) against Human Aspartyl (Asparaginyl) β-Hydroxylase", Abstract published for the AACR Meeting of Nov. 17-21, 2003, Boston, MA.
Boder et al., "Optimal Screening of Surface-Displayed Polypeptide Libraries," *Biotechnol. Prog.*, 14(1):55-62 (1998).
Boder et al., "Yeast surface display for screening combinatorial polypeptide libraries," *Nat. Biotechnol.*, 15(6):553-557 (1997).
Copeland et al., "Transfection by Exogenous and Endogenous Murine Retrovirus DNAs," *Cell*, 16(2):347-356 (1979).
Feldhaus et al., "Flow-cytometric isolation of human antibodies from a nonimmune *Saccharomyces cerevisiae* surface display library," *Nature Biotech.*, 21:163-170 (2003).
Gronke et al., "Aspartyl β-hydroxylase: In vitro hydroxylation of a synthetic peptide based on the structure of the first growth factor-like domain of human factor IX," *Proc. Natl. Acad. Sci. USA*, 86(10):3609-3613 (1989).
Gronke et al., "Partial Purification and Characterization of Bovine Liver Aspartyl β-Hydroxylase," *J. Biol. Chem.*, 265(15):8558-8565 (1990).
Jia et al., "A fully active catalytic domain of bovine aspartyl (asparaginyl) β-hydroxylase expressed in *Escherichia coli*: Characterization and evidence for the identification of an active-site region in vertebrate α-ketoglutarate-dependent dioxygenases," *Proc. Natl. Acad. Sci. USA*, 91(15):7227-7231 (1994).

(Continued)

*Primary Examiner*—Karen A. Canella
(74) *Attorney, Agent, or Firm*—Fish & Richardson P.C.

(57) ABSTRACT

Antibodies, or antigen-binding portions thereof, to aspartyl (asparaginyl) β-hydroxylase are provided. The anti-aspartyl (asparaginyl) β-hydroxylase antibodies, or antigen-binding portions thereof, can modulate activity of aspartyl (asparaginyl) β-hydroxylase.

16 Claims, 52 Drawing Sheets

OTHER PUBLICATIONS

Jia et al., "cDNA Cloning and Expression of Bovine Aspartyl (Asparaginyl) β-Hydroxylase," *J. Biol. Chem.*, 267(20):14322-14327 (1992).

Lavaissiere et al., "Overexpression of Human Aspartyl(Asparaginyl)β-Hydroxylase in Hepatocellular Carcinoma and Cholangiocarcinoma," *J. Clin. Invest.*, 98(6):1313-1323 (1996).

Sepe et al., "Role of the Aspartyl-Asparaginyl-β-Hydroxylase Gene in Neuroblastoma Cell Motility," *Lab. Investig.*, 82(7):881-891 (2002).

Swers et al., "Shuffled antibody libraries created by in vivo homologous recombination and yeast surface diaplay," *Nucl. Acids Res.*, 32(3):e36 (2004).

Vaickus et al., "Immune markers in hematologic malignancies," *Crit. Rev. in Oncol./Hematol.*, 11:267-297 (1991).

Wang et al., "Bovine Liver Aspartyl β-Hydroxylase," *J. Biol. Chem.*, 266(21):14004-14010 (1991).

Zaccolo et al., "An Approach to Random Mutagenesis of DNA Using Mixtures of Triphosphate Derivatives of Nucleoside Analogues," *J. Mol. Biol.*, 255:589-603 (1996).

Zaccolo et al., "The Effect of High-frequency Random Mutagenesis on in Vitro Protein Evolution: A Study of TEM-1 β-Lactamase," *J. Mol. Biol.*, 285:775-783 (1999).

Zhang et al., "Development of a Carbon Dioxide-Capture Assay in Microtiter Plate for Aspartyl-β-hydroxylase," *Anal. Biochem.*, 271:137-142 (1999).

Dinchuk et al., "Aspartyl beta-hydroxylase (Asph) and an evolutionary conserved isoform of Asph missing the catalytic domain share exons with junction," J. Biol. Chem., 275:39543-54 (2000).

Korioth et al., "Cloning and characterization of the human gene encoding aspartyyl beta-hydroxylase," Gene, 150:395-399 (1994).

Maeda et al., "Antisense oligodeoxynucleptides directed against aspartyl (asparaginyl) beta-hydroxylase suppress migration of cholangiocarcinoma cells," J. Hepatol., 38:615-622 (2003).

Yeung et al., "Quantitative screening of yeast surface-displayed polypeptide libraries by magnetic bead capture," Biotechnol. Prog., 18:212-220 (2002).

Yeung, "Antibody Engineering for Cancer Therapy," [Online thesis, retrieved from http://dspace.mit.edu/bitstream/1721.1/32325/1/61368509.pdf on Jul. 19, 2007] pp. 1-144 (2005).

* cited by examiner

FIG 2 Human scFv binds to HAAH

FIG 4 Affinities of Two Representative anti-HAAH Human scFvs

FIG 6

Soluble scFv binding to the catalytic domain of HAAH

Binding of an affinity-matured clone 11 to the catalytic domain of HAAH

FIG 11

Amino acid sequence of an affinity-matured clone 11

QPVLTQSPSASGTPGQRVTIPCSGSSSNIGSNYVYVWYQQLPGTAPKLLIYKNNQ
RPSGVPDRFSGSKSGTAASLAISGLQSEDEADYYCAAWDDSLRGYVFGTGTKLT
VLSGILGSGGGGSGGGGSGGGGSRPVLTQSPSASGTPGQRVTIPCSGSSSNIG
SNYVYVWYQQLPGTAPKLLIYKNNQRPSGVPDRFSGSKSGTAASLAISGLQSEDE
ADYYCAAWDDSLRGYVFGTGTKLTVLSGILGSGGGGSGGGGSGGGGSRPVLT
QSPSASGTPGQRVTIPCSGSSSNIGSNYVYVWYQQLPGTAPKLLIYKNNQRPSGV
PDRFSGSKSGTAASLAISGLQSEDEADYYCAAWDDSLRGYVFGTGTRLTVLSGS

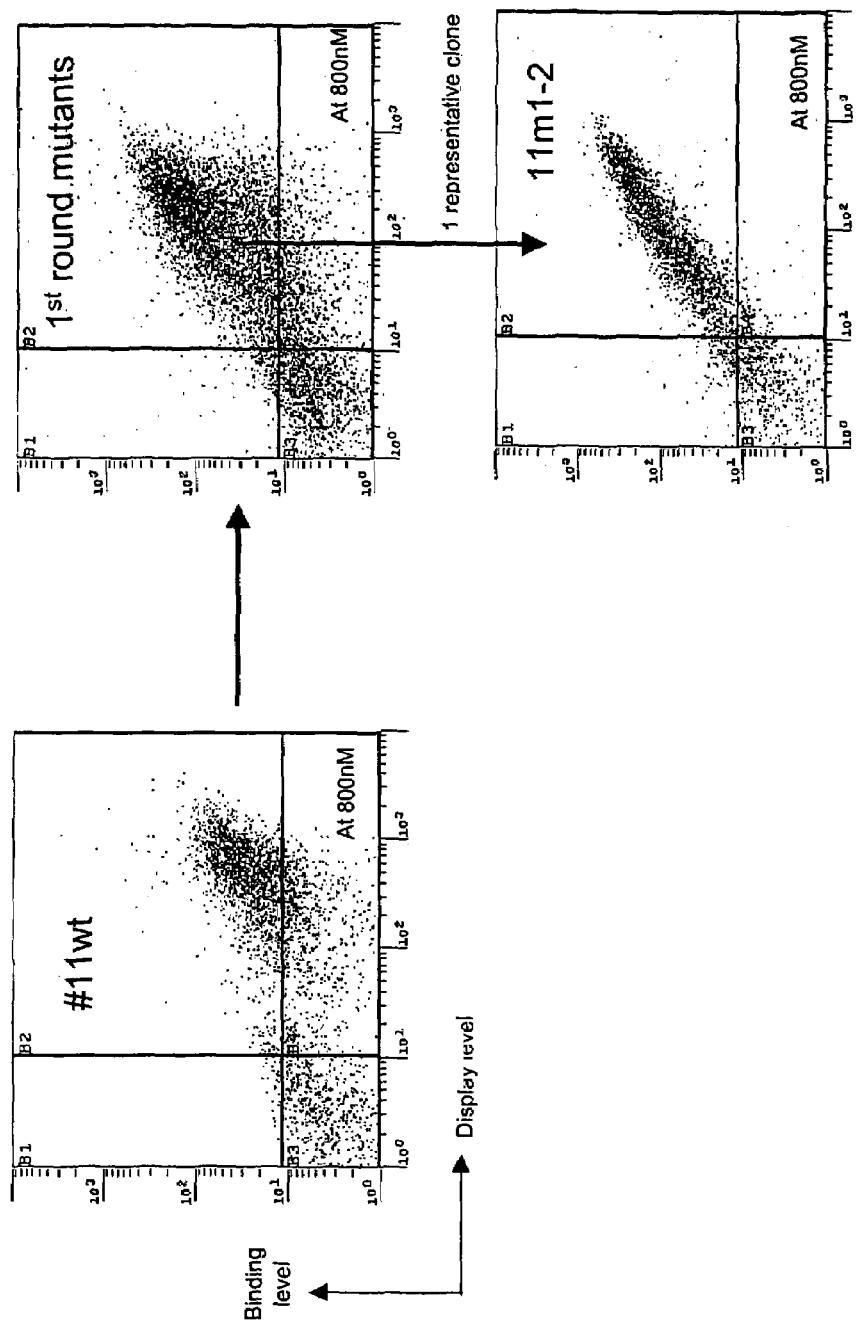
FIG 12 Anti-HAAH binding of affinity-matured clone 11 mutants

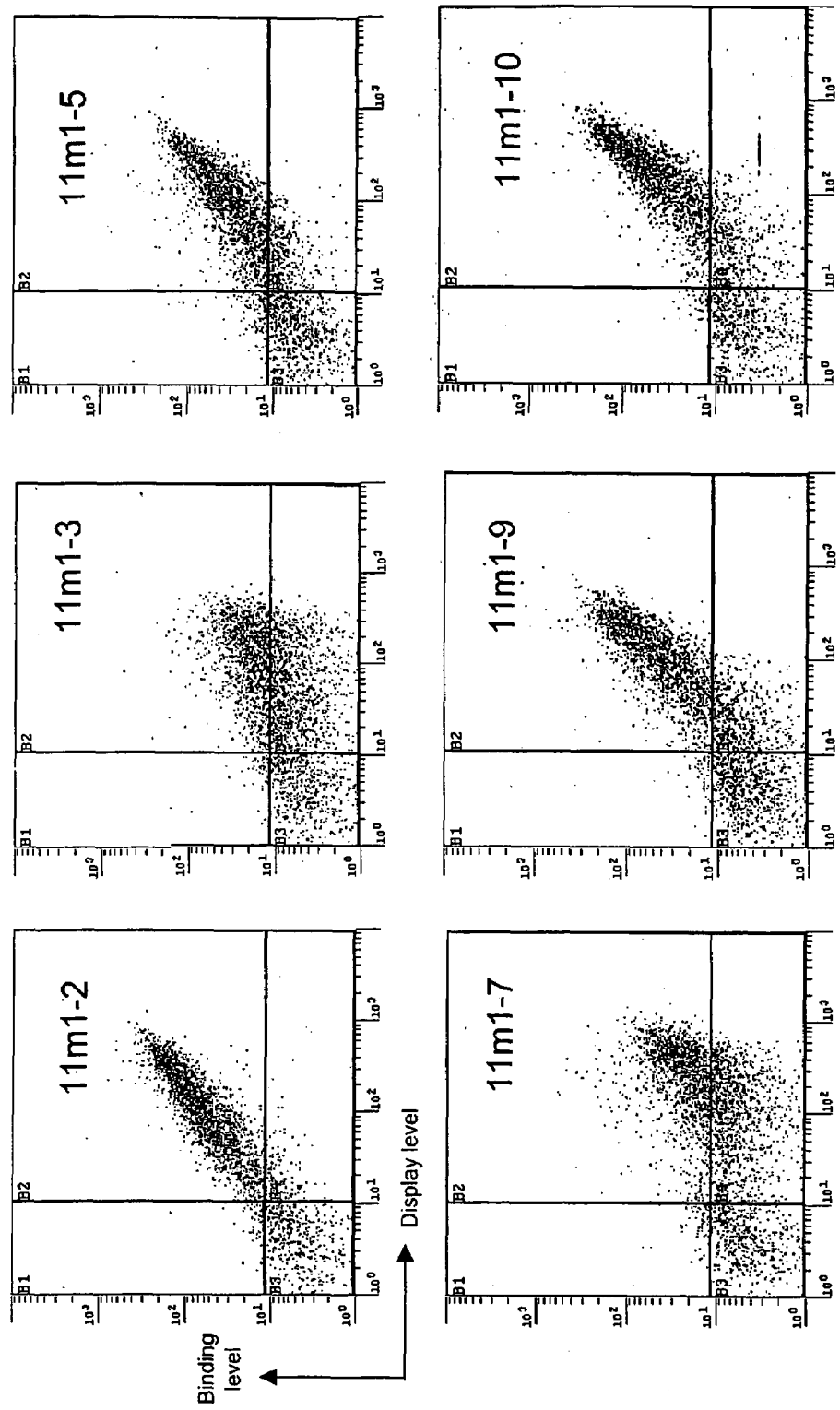
FIG 13 Anti-HAAH binding of clone 11 mutants

Binding of affinity matured clone 13 mutant, 13m1, to HAAH

FIG 15

Amino acid sequence of clone 13m1

QVQLVESEGGVVQPGRPLRLRLSCAASGFTFSSHAMHWVRQAPGKGLE
WVAVVSHDGSRDRYAGSVKGRFTISRDNSKNTLYLQMNSLRPEDTG
VYYCARVGRSSNWFSRYYYYGMDVWGQGTTVTVSSGILGSGGGGSG
GGDSGGGGSGIVLTQSPATLSLPPRERATLSCGTSQNVSHYLAWYQQ
KPGRAPRVLTYDVANRAAGTPARFSGSGSGTDFTPAISSLEPEDFAVY
YCQQRSNWPQAFGPGTKVDIKSG

Anti-HAAH binding of affinity-matured clone 13 mutants

Chain shuffling: Swapping heavy chain using NheI-BamHI restriction digest and subsequent ligation Initial library sampling

| ID | VH | VL |
|----|------|------|
| WT | VH6-1 | VI-17 |
| #1 | VH6-1* | VI-17 |
| #2 | VH3-30 | VI-17 |
| #3 | VH6-1* | VI-17 |
| #4 | VH6-1* | VI-17 |
| #5 | VH5-53 | VI-17 |

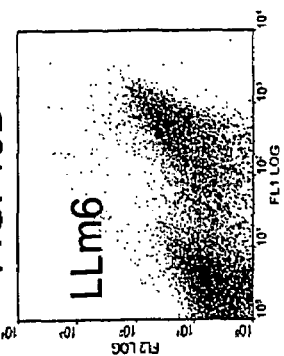 FIG. 19A LLm1
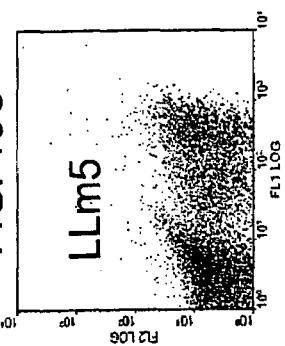 FIG. 19B LLm3
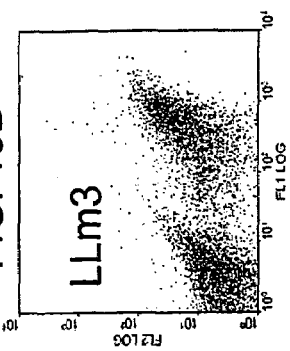 FIG. 19C LLm5
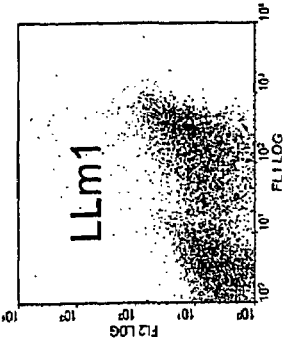 FIG. 19D LLm6
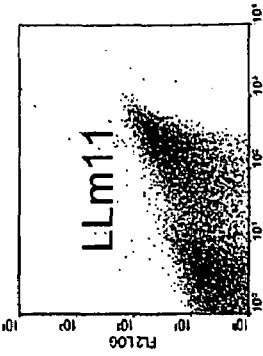 FIG. 19E LLm7
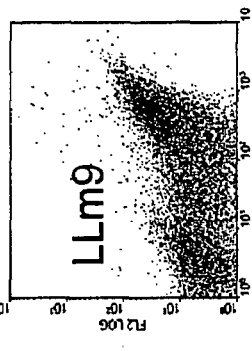 FIG. 19F LLm8
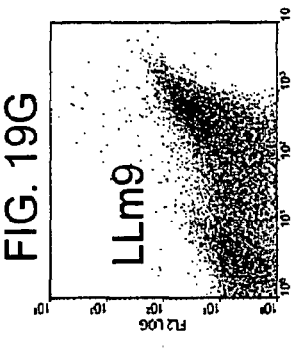 FIG. 19G LLm9
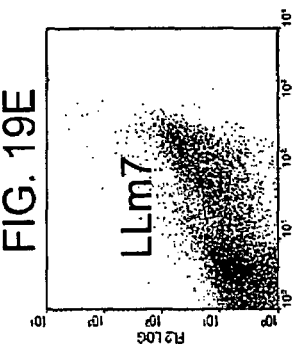 FIG. 19H LLm11
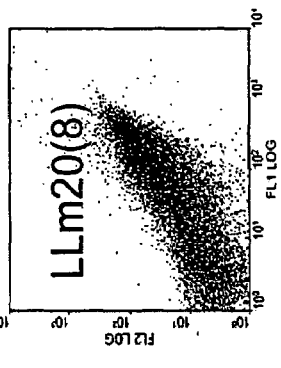 FIG. 19I LLm14(2)
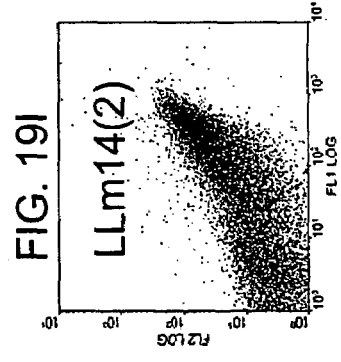 FIG. 19J LLm15(3), FIG. 19K LLm20(8)

FIG. 20

| | CDR1 | CDR2 | CDR3 |
|---|---|---|---|
| 6-22_wt1 | SSNSAAWN | RTYYRSKWYNDYAVSVKSR | TGYSS-S---WVVNFDY |
| 11LLm1 | SSITAAWN | RTYHRSKWYYDYAVSVKSR | GLAAR-GGGPSAHAFEI |
| 11LLm3 | SNNSAVWN | RTYYRSKWYNDYAVSVKSR | RTGAG------VDY |
| 11LLm5 | SGNNVIWN | RTYYRSKWYYDLLPSVKSR | TR----AVAGNQYFDL |
| 11LLm6 | SSYSAAWN | RTYYRSKWYNDYAVSVKSR | LAAAA-G---TVDY |
| 11LLm8 | SSNSAAWN | RTYYRSKWYNDYAVSVKSR | DRLLY-NYG--SNAMDV |
| 11LLm9 | SSNSAAWN | RTYYRSKWYNDYALSVKSR | DTPRYCSGGSCYKYFDL |
| 11LLm11 | SSKGAAWN | RAYYWSKWYYDYAVSVKSR | GATST---YYLPGGLDV |
| 11LLm13 | SADRVAWN | RIFYRSKWMVDYAVSVKSR | AT------TRGYFDL |
| 11LLm14 | SSNSAAWN | RTYYRSKWYNDYAVSMKGR | RS----GRTG-GYFDL |
| 11LLm15 | GSSNAAWN | RIFYGSKWYNDYAVSLKSR | RTGTG------IDY |
| 11LLm20 | GSSNAAWN | RIFYRSKWYNDYAVSVKTR | GQQK------RLDS |

CDR shuffling: Shuffling heavy chain CDR1, CDR1&2, CDR1&2&3

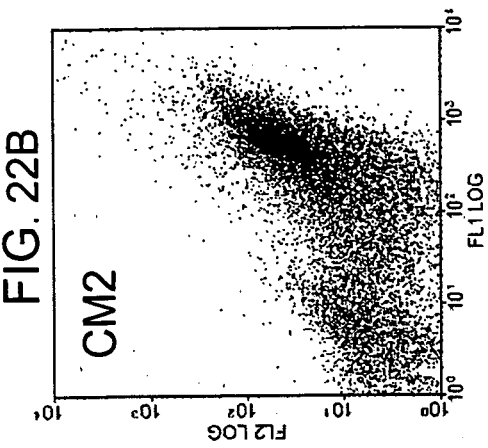
FIG. 22A CM1
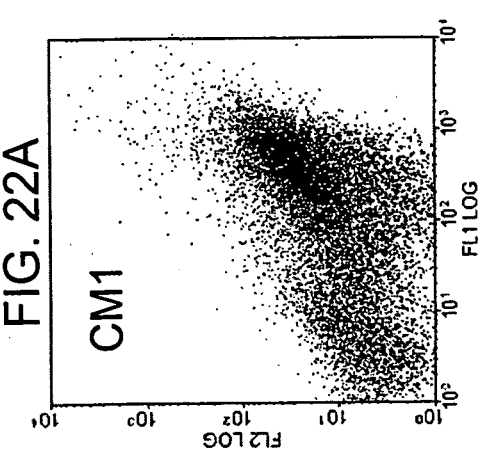
FIG. 22B CM2
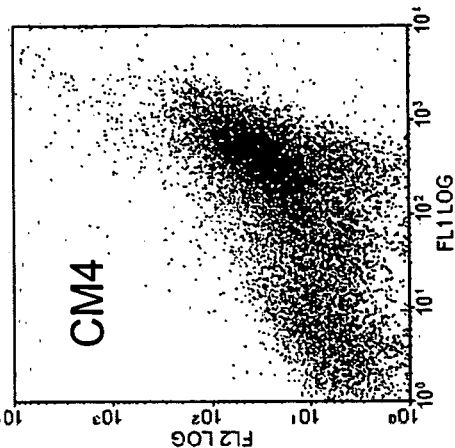
FIG. 22C CM3
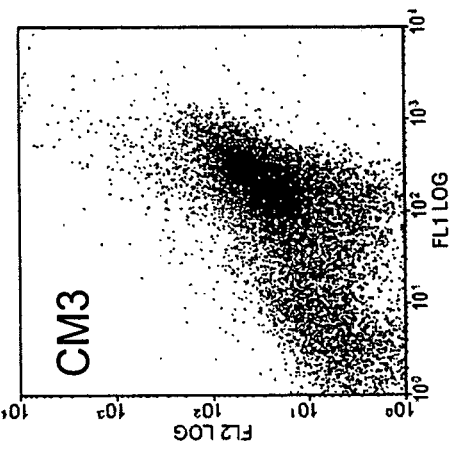
FIG. 22D CM4

FIG. 23

- wt  SSNSAAWN  RTYYRS-KWYNDYAVSVKSR  TGYSSSWVVNFDY
- C1  SSNSAAWN  RTYYRS-KWYNDYAVSVKSR  ASDYGDYFYFDY
- C2  SSNSAAWN  RIYYRS-KWYYDYAVSVKSR  GAGRS----FDL
- C3  SGNSGVWN  RTYYYTYKWYIDYAVSVKSR  VDYTGS----PV
- C4  SSNSAAWN  RTYYRS-KWYNDYAVSVRGR  TGYSSSWVVNFDY

This is the most correct and recent $K_D$ (dissociation constant). Yeasts displaying different scFv were titrated using unmodified HAAH and detected using FB50 and goat-anti mouse phycoerythrin conjugates. So it turns out that the KD of the first round mutant (CM4, LLm13) is about 20nM, while the 2nd round mutant C4-18 is about 0.6nM Fig. 26 ELISA binding of WT IgG Fig. 27 Tumor Cell binding of WT IgG Fig. 30 CDRm4 IgG Titration

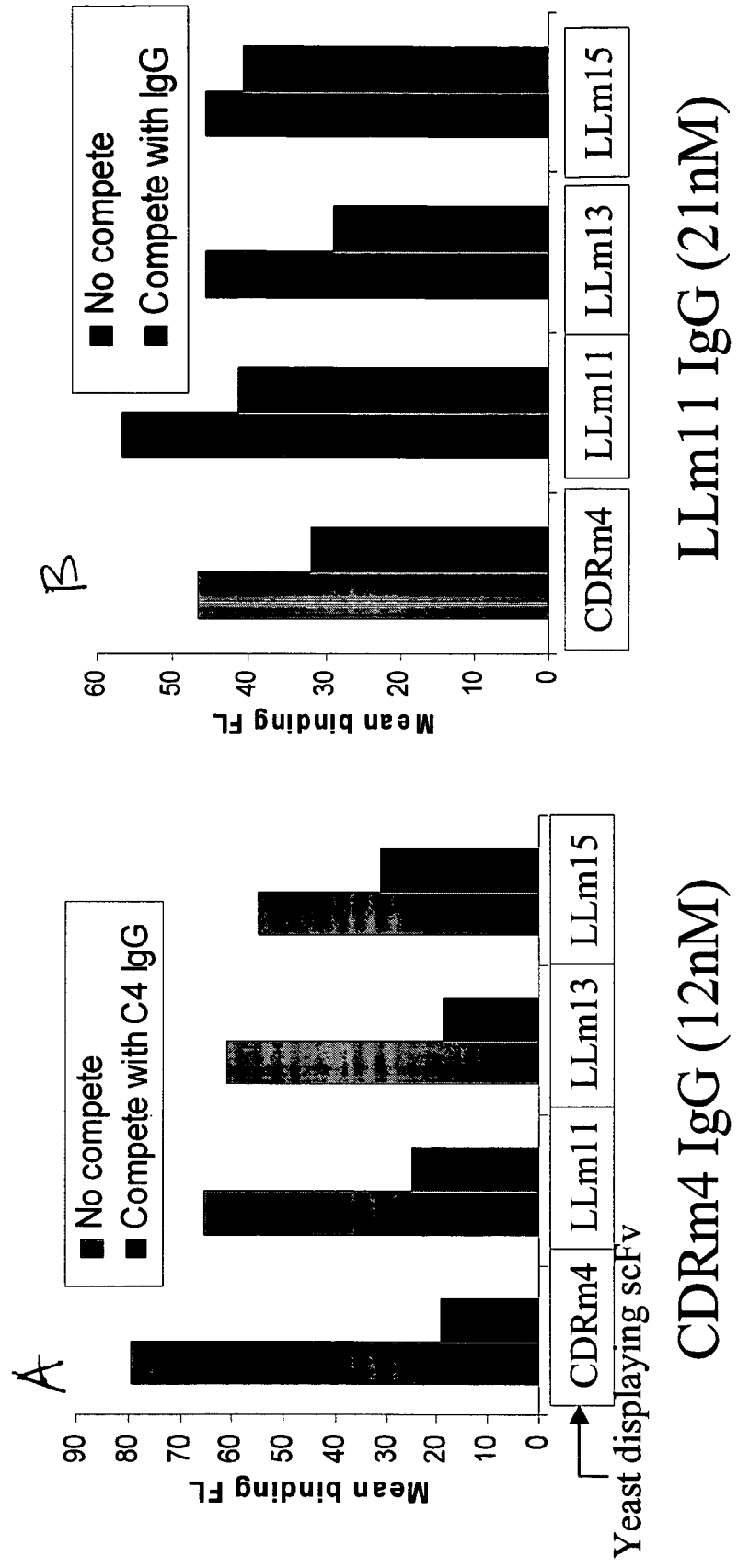
Fig. 32 Self competition experiment

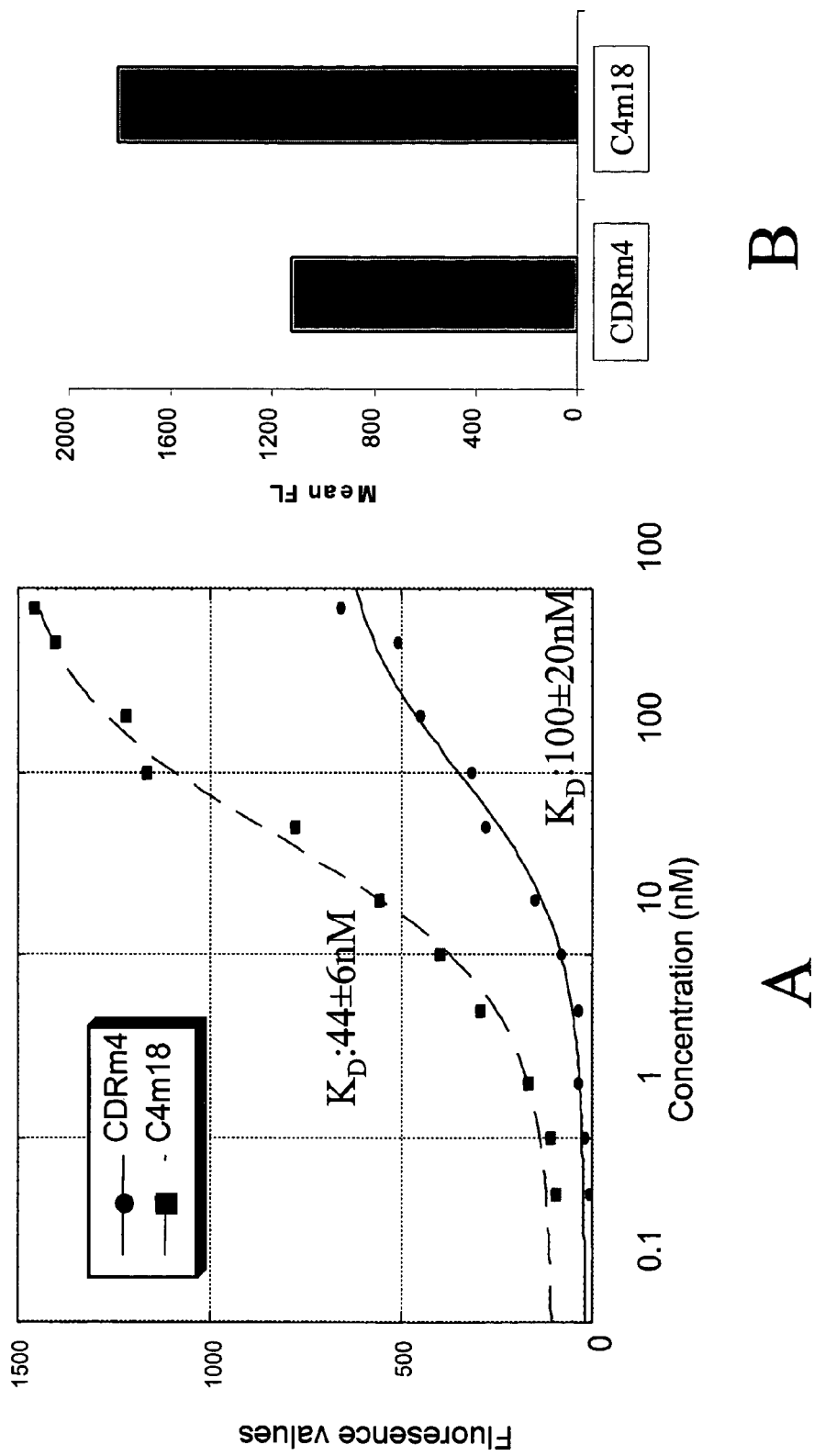
Fig. 33 Second generation mutant

Table of FIG. 34:. Amino Acid Sequences of Anti-HAAH Antibody Variable Regions

| Clone | Chain | Amino Acid Sequence | SEQ ID NO: |
|---|---|---|---|
| 11 | VH | QVQLQQSGPGLVKPSQTLSLTCAISGDSVSSNSAAWNWIRQSPSRGLEWLGRTYYRSKWYNDYAVSVKSRITINPDTSKNQFSLQLNSVTPEDTAVYYCARTGYSSSWVVNFDYWGQGTLVTVSS | 1 |
| 11 | VL | QPVLTQSPSASGTPGQRVTISCSGSSSNIGSNYVYWYQQLPGTAPKLLIYKNNQRPSGVPDRFSGSKSGTAASLAISGLQSEDEADYYCAAWDDSLRGYVFGTGTKLTVLSG | 2 |
| 13 | VH | QVQLVESEGGVVQPGRSLRLSCAASGFTFSSYAMHWVRQAPGKGLEWVAVVSYDGSQDYYADSVKGRFTISRDNSKNTLYLQMNSLRPEDTGVYYCAKVGRSSNWFSRYYYYGMDVWGQGTTVTVSS | 3 |
| 13 | VL | EIVLTQSPATLSLSPGERATLSCRASQSVSHYLAWYQQKPGQAPRVLIYDVANRAAGTPARFSGSGSGTDFTLTISSLEPEDFAVYYCQQRSNWPQTFGPGTKVDIKSG | 4 |
| 6-23 | VH | QVQLQQSGPGLVKPSQTLSLTCAISGDSVSSDSAAWNWIRQSPSRGLEWLGRTYYRSKWYNDYAVSVKSRISINPDTSKNQFSLQLNSVTPEDTAVYYCARAQNNIAVAGFDYWGLGTLVTVSS | 5 |
| 6-23 | VL | QPVLTQSPSASGTPGQRVTISCSGSSSNIGSNYVYWYQQLPGTAPTLLIYRNNQRPSGVPDRFSGSKSGTSASLAISGLRSEDEAEYYCAAWDDSLSGLYVFGTGTKVTVLS | 6 |
| 6-27 | VH | QVQLVESEGGVVQPGRSLRLSCAASGFTFGTYAMHWVRQAPGKGLEWVAVISNDGGHKYYADSVKGRFTISRDNSKDSMYLQMNSLRAEDTAVYHCAKGRPWYDPGAEYFQHWGQGTLVTVSS | 7 |
| 6-27 | VL | QSALIQPASVSGSPGQWITISCTGTSSDVGGYNYVSWYQQHPGKAPKLLIYDVSDRPSGVSNRFSGSKSGNTASLTISGLQAEDEADYYCSSYTSSNTVLFGGGTKLTVLS | 8 |
| 3 | VH | QVQLVQSEGGVVRPGGSLRLSCAASGFTFGDYAMGWVRQAPGKGLEWVSSINWNGGSTGYADSVKGRFTISRDNAKNSLYLQMNSLRAEDTALYYCARVSSGWPYYSLDVWGQGTTVTVSSGSASAPT | 9 |
| 3 | VL | QSALIQPRSVSGSPGQSVTISCTGTSSDVGGYNYVSWYQHHPGKAPQLMIYDVTKRPSGVPDRFSGSKSGNTASLTISGLQAEDEADYYCCSYAGDYTYAVFGTGTQLTVLS | 10 |
| 5-7 | VH | EVQLVESGGGVVQPGRSLRLSCAASGFTFSGYAMHWVRQAPGKGLEWVAAISFDGNYKYYADSVKGRFTVSRDNSRNTLYLQMNSLKVDDTAVYFCARDLYSSGHFGMDVWGQGTTVTVSSASTKGPS | 11 |
| 5-7 | VL | EIVMTQSPGTLSLSPGERATLSCRASQSVSSSYLAWYQQKPGQAPRLLIYGASSRATGIPDRFSGSGSGTDFTLTISRLEPEDFAVYYCQQYGSPITFGQGTRLEIK | 12 |
| 6-8 | VH | QVQLQQSGPGLVKPSQTLSLTCAISGDSVSSNSAAWNWIRQSPSRGLEWLGRTYYRTKWYNEYAASVKGRATINPDTSKNQFSLQLNSVTPEDTAVYYCATDPKGVTTQYWGQGTLVTVSS | 254 |
| 6-8 | VL | QPVLTQSPSASGTPGQRVTISCSGSTSNIGRNYVYWYQRLPGTAPKLLIYRNNQRPSGAPARFSGSKSGTSTSLAISGLRSEDEAEYFCAAWDDSLSGWVFGGGTQLTVL | 255 |

FIG. 34 (Page 1 of 2)

| 6-12 | VH | QVQLQQSGPGLVKPSQTLSLTCGISGDSVSSNSAAWNWIRQSPSRGLEWLGRTYYRSRWYNDYAASVKSRITVNADTSKNQFSLQLNSVTPEDTAVYYCARSVRYSSGWGFDYWGQGTLVTVSS | 256 |
|---|---|---|---|
| 6-12 | VL | QPVLTQSPSASGTPGQRITISCSGSSSNIGNNYVYWYQQFPGTAPKLLVYRNNQRPSGVPDRFSGSKSGTSASLAISGLRSEDEADYYCAAWDDSLSGRWVFGGGTKLTVL | 257 |
| 6-13 | VH | QVQLQQSGPGLVKPSQTLSLTCAISGDSVSRNSAAWNLIRQSPSRGLEWLGRTYYRSKWYTDYAVSVKSRITINPDTSKNQFSLRLNSVTPEDTAVYYCARSGGGHAAGKFDSWGRGTLVTVSS | 258 |
| 6-13 | VL | QPVLTQSPSASGTPGQRVTIPCSGSSSNIGSKYVYWYQHLPGTAPKLLIYRNNQRPSGVPDRFSGSKSGTSASLAISGLRSEDADYYCAAWDDSLSAWVFGGGTKLTVL | 259 |
| 6-14 | VH | QVQLQQSGPGLVKPSQTLSLTCAISGDSVSSNSATWNWIRQSPSRGLEWLGRTYYRSKWYNDYAVSVKSRMTINPDTSKNQFSLQLNSVTPDDRAVYYCARGGRLGGGMDVWGQGTTVTVSS | 260 |
| 6-14 | VL | QPVLTQSPSASGTPGQRVTISCSGSSSNIASNYVYWYQHLPGTAPKLLIYTNNRRPSGVPDRFSGSKSGTSASLAISGLRSEDADYFCAAWDDSLSGWVFGGGTKVTVL | 261 |
| 6-23rea | VH | QVQLVQSEGGVVQPGRSLRLSCGVSGFTFSSYAMHWVRQAPGKGLEWVAVISYDGSKKYYADSVKGRFTISRDNSKNTLYLQMNSLRAEDTAVYYCARRVTTGITRYFDLWGRGTLVTVSS | 262 |
| 6-23rea | VL | QSVLTQPASVSGSPGQSITISCTGTNSDIGGYNYVSWYQQHPGKAPKLMIFEVTNRPSGVPDRFSASKSGNTASLTISGLQADDEADYYCSSYAGSNTPSVFGTGTKLTVL | 263 |
| 6-26 | VH | QVQLQQSGPGLVKPSQTLSLTCAISGDSVSSNSAAWNWIRQSPSRGLEWLGRTYYRSKWYNDYAVSVKGRITINPDTSKNQFSLQLNSVTPEDTAMYYCVRSGGGRVDPWGQGTLVTVSS | 264 |
| 6-26 | VL | QPVLTQSPSASGTPGQRVTISCSGSRSNIGSNYVYWYQQLPGTAPKLLIYRNHQRPSGVPDRFSASKSGTSASLAISGLRSEDADYYCAAWDDSLSGYVFGTGTKLTVL | 265 |
| 6-28 | VH | QVQLVQSEGGVVQPGRSLRLSCAASGFTFNDYAMHWVRQAPGKGLEWVAVISYDGSNKYYTDSVKGRFTISRDNSKNTLYLQMDSLRPEDTALYYCAREASSGWYIDSWGQGTLVTVSS | 266 |
| 6-28 | VL | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSQVTFGQGTRLEVKS | 267 |

FIG. 34 (Page 2 of 2)

Table of FIG. 35: Amino Acid Sequences of Anti-HAAH Affinity-matured, Mutagenized Antibody Regions

| Clone | Chain | Amino Acid Sequence | SEQ ID NO: |
|---|---|---|---|
| 13m1 | VH | QVQLVESEGGVVQPGRPLRLSCAASGFTFSSHAMHWVRQAPGKGLEWVAVVSHDGSRDRYAGSVKGRFTISRDNSKNTLYLQMNSLRPEDTGVYYCARVGRSSNWFSRYYYYGMDVWGQGTTVTVSS | 13 |
| 13m1 | VL | GIVLTQSPATLSLPPRERATLSCGTSQNVSHYLAWYQQKPGRAPRVLTYDVANRAAGTPARFSGSGSGTDFTPAISSLEPEDFAVYYCQQRSNWPQAFGPGTKVDIK | 14 |
| 13m2-3 | VH | QVQLVESEGGVVQPGRPLRLSCAASGFAFSSHAMHWVRQAPGKGLEWVAVISHDGSRDRYAGSVKGRFTISRDNSKNTLYLQMNSLRPEDTGVYYCARVGRSSNWFSRYYYYDMDVWGQGTTVTVSS | 15 |
| 13m2-3 | VL | GIVLTQSPATLSLPPRERVTLSCGTSQNVSHHLAWYQQKPGRAPRVLTYDVANKAAGTPARFSGSGSETDFTPAISSLEPEDFAVYYCQQRSNWPQAFSPGTKVDIKSGSEQK | 16 |
| 13m2-6 | VH | QVQLVESEGGVVQPGRPLRLSCAASGFTFSSHAMHWVRQAPGKGLEWVAVVSHDGSRDRYAGSVKGRFTISRDNSKNTLYLQMNSLRPEDTGVYYCARVGRSSNWFSRYHYYGMDVWGQGTTVTVSS | 17 |
| 13m2-6 | VL | GIVLTQSPATLSLPPRERATLSCGTSQNVSHYLAWYQQKPGRAPRVLTYDVANRAAGTPARFSGSGSGTDFTPAISSLELEDFAVYYCQQRSNWPQAFGPGTKVDIK | 18 |
| 11m1-2 | VH | QVQLQQSGPGPVKPSQTLSLTRAIPGDSVSSNSAAWNWIRQFLSRGLEWLGRTYYRSKRYNDYAVSVKSRITINPDTSKNQFSLQLNSVTPEDTAVYYCARTGYSSSWVVNFDYWGQGTLVTVSS | 19 |
| 11m1-2 | VL | QSVLTQSPSASGTPGQRVTISCSGSSSNIGSNYVYWYQQLPGTAPKLLIYKDNQRPSGVPDRFSGSKSGTAASLAISGLQSEDEADYYCAAWDDSLRGYVFGTGTKLTVLS | 20 |
| 11m1-3 | VH | QVQLQQPGPGLVEPSQTLPLTRAISGDSVSGNGAAWSWIRQPPPRGLGWPGRTYYRPKRRNGYAVPAKSRMTISPDTSKNQFSLQLNSVTPEDTAVYYCARTGHSSSWVVSFDHWGQGALATISS | 21 |
| 11m1-3 | VL | SQPVPTQSPSASGTPGQRVTVSCSGSSSNIESNYVYWYQQLPGAAPRLFIHKNNQRPSGVPDRSSSSKSGTAASLAISGLQSKDEADYYCAAWDDSLRSYVFGTGTKLTVLS | 22 |
| 11m1-5 | VH | QVQLQRSGPGLVKPPQAPSLTCAVSGDSVSSNSAAWNWIRQSLSRGLEWLGRIHYGSRWYNDYAASAKSRVTINPDTPKGQLPPQLSPVTPKDAAAYYCARTECSSSWVVNFGYWGQGAPVTASP | 23 |
| 11m1-5 | VL | QPALIQSPPVSGTPGQRVTIPCSGSSFNIGSNHVYWHQQPPGTAPKLLVHKSNQRPSGVPDRSPGPRPGTAASLAISGLQSEDEADYYCAAWDDSLRGYVLGAGTKLTARS | 24 |
| 11m1-7 | VH | QVQLQQSGPGLVKPSQTLSLTCAIPGDSVSSNSAAWNWIRQSPSRGLEWLGRTYHRFKWYNDHAVSVKSRITINPDTSKNQFSLQLNSVTPEDTAVYYCARTGYSSSWVVNFDYWGQGTPVTVSS | 25 |

FIG. 35 (Page 1 of 4)

| 11m1-7 | VL | QPVLTQPPSASGTPGQRVTISCSGSSSNIGSNYVYRYQQL PGAAPKLLIYKNNQRSSGVPARFSGPKSGAAAPLTTSGLQ SGDEAGYYCAAWDDSLRGYVFGTGTKLTVLS | 26 |
|---|---|---|---|
| 11m1-9 | VH | QVQLQWSGPGLVKPSQTLSLTRAISGNSVSSNSAAWSWI RQSLSRGLEWLGRTYYGSKRYNDYAVSVKSRITINPDTP KNQFSLQLNSVTPEDAAVYYCARTGYSGSRVVNFGYWG QGTLVTVSS | 27 |
| 11m1-9 | VL | QPVLTQSPPASGTPGQRVTISCSGSSSNIGSNYVHRYQQPP GAAPELLIHKNNQRPSGVPDRFSGSKSGTAASPAISGPQS EDEANYYCVAWDDSPCGYVFGAGTKLTVLS | 28 |
| 11m1-10 | VH | QVQLQQSGPGLVKPSQTFSLTYAVSGGSASSNSAAWNWI RQSLSRGLEWLGRTYYRSKWYNDYAVSVKSRTTINPDTS KNQFSLQLNSVTPGDAAVCYCAGAGYSSSRAVNFDCWG QGTLVTVSS | 29 |
| 11m1-10 | VL | QPVLTQSPSASGTPGQRVTISCSGSSSNIGSNYVYWYQQL PGTAPKLLIYKNNQRPSGVPDRFSGSKSGTAASLAISGLQ PEGEADYYCAAWDDSLRGYVLGTGTKLTVLS | 30 |
| LLm1 | VH | QVQLQQSGPGLVKPSQTLSLTCAISGDSVSSITAAWNWL RQSPSRGLEWLGRTYHRSKWYYDYAVSVKSRITVNPDT SKNQFSLHLNSVTPEDTAVYYCARGLAARGGGPSAHAFE IWGQGTMVTVSSASTKGPS | 119 |
| LLm1 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 120 |
| LLm3 | VH | QVQLQQSGPGLVKPSQTLSLTCVISGDSVSNNSAVWNWI RQSLSRGLEWLGRTYYRSKWYNDYAVSVKSRIIINPDTS KNQFSLQLNSVTPEDTAVYYCARRTGAGVDYWGQGTL VTVSS | 121 |
| LLm3 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 122 |
| LLm5 | VH | QVQLQQSGPGLVKPSQTLSLTCAISGDGVSGNNVIWNWI RQSPSRGLEWLGRTYYRSKWYYDLLPSVKSRIAINPDTS KSQFSLQLSSVTPEDTAVYYCARTRAVAGNQYFDLWGR GTLVTVSS | 123 |
| LLm5 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 124 |
| LLm6 | VH | QVQLQQSGPGLVKPSQTLSLTCAISGDSVSSYSAAWNWI RQSLSRGLEWLGRTYYRSKWYNDYAVSVKSRITINPDTS KNQFSLQLNSVTPEDTAVYYCASLAAAAGTVDYWGQGT LVTVSSGSASAPT | 125 |
| LLm6 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 126 |
| LLm8 | VH | QVQLQQSGPGLVKPSQTLSLTCAISGDSVSSNSAAWNWI RQSLSRGLEWLGRTYYRSKWYNDYALSVKSRININADTS KSQFSLQLDSVTPEDTAVYFCAKDRLLYNYGSNAMDVW GQGTTVTVSS | 127 |

FIG. 35 (Page 2 of 4)

| | | | |
|---|---|---|---|
| LLm8 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 128 |
| LLm9 | VH | QVQLQQSGPGLVKPSETLSLTCAISGDSVSSNSAAWNWI RQSLSRGLEWLGRTYYRSKWYNDYAVSVKSRITINPDTS KNQFSLQLNSVTPEDTAVYYCARDTPRYCSGGSCYKYFD YWGQGTLVTVSSASTKSPS | 129 |
| LLm9 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 130 |
| LLm11 | VH | QVQLQQSGPGLVKSSQTLSLTCAISGDSVSSKGAAWNWI RQSPSRGLEWLGRAYYWSKWYYDYAVSVKSRITINPDT SKNQFSLQLNSLTPEDTAVFYCARGATSTYYLPGGLDVW GQGTTVTVSS | 131 |
| LLm11 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 132 |
| LLm13 | VH | QVQLQQSGAGLVKPSQTLSLTCTISGDSVSADRVAWNWI RQSPLRGLEWLGRIFYRSKWMVDYAVSVKSRISINPDTS KNQFSLQLNSVTPEDTAMYYCARATTRGYFDLWGRGTL VTVSS | 133 |
| LLm13 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 134 |
| LLm14 | VH | QVQLQQSGPGLVKPSQTLSLTCVVSGDGVSSNSAAWNW IRQSLSRGLEWLGRTYYRSKWYNDYAVSMKGRITINPDT SKNQFSLQLDSVTPEDTAVYYCARRSGRTGGYFDLWGR GTLVAVSS | 135 |
| LLm14 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 136 |
| LLm15 | VH | QVQLQQSGPGLVKPSQTLSLTCAIPGHSVGSSNAAWNWI RQSPSRGLEWLGRIFYGSKWYNDYAVSLKSRLTINPDTS KNQFSLQLNSVTPEDTAVYYCARRTGTGIDYWGQGTLV TVSS | 137 |
| LLm15 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 138 |
| LLm20 | VH | QVQLQQSGPGLVKPSQTLSLTCAISGHSVGSSNAAWNWI RQSPSRGLEWLGRIFYRSKWYNDYAVSVKTRISINPDTA KNQFSLHLNSVTAEDTGVYYCARGQQKRLDSWGQGTL VTVSS | 139 |
| LLm20 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 140 |
| CDRm1 | VH | PVQLQQSGPGLVKPSQTLSLPCAISGDSVSSNSAAWNWIR QSLSRGLEWLGRTYYRSKWYNDYAVSVKSRITINPDTSK NQFSLQLNSVTPDDTAIYYCARASDYGDYFYYFDYWGQ GTLVTVSSGSASAPT | 141 |

FIG. 35 (Page 3 of 4)

| | | | |
|---|---|---|---|
| CDRm1 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 142 |
| CDRm2 | VH | QVQLQQSGPGLVKPSQTLSLTCAISGDSVSSNSAAWNWI RQSPSRGLEWLGRIYYRSKWYYDYAVSVKSRIAIKPDTS KNQFSLQLNSVTPEDTAVYYCARGAGRSFDLWGRGTLV TVSSGSASAPT | 143 |
| CDRm2 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 144 |
| CDRm3 | VH | QVQLQQSSPGLVKPSQTLSLTCAVSGDSVSGNSGVWNWI RQSPSRGLEWLGRTYYYTYKWYIDYAVSVKSRITVNPDT SRNQFSLQLNSVTPEDTAVYYCARVDYTGSPVWGQGTL VTVSSGSASAPT | 145 |
| CDRm3 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 146 |
| CDRm4 | VH | QVQLQQSGPGLVKPSQTLSLTCAISGDSVSSNSAAWNWI RQSLSRGLEWLGRTYYRSKWYNDYAVSVRGRITINADTS KNQFSLQLNSVTPEDTAVYYCARTGYSSSWVVNFDYWG QGTLVTVSSGSASAPT | 147 |
| CDRm4 | VL | QPVLTQSPSASGTPGQRVTISCSGSSSNIGSNYVYWYQQL PGTAPKLLIYKNNQRPSGVPDRFSGSKSGTAASLAISGLQ SEDEADYYCAAWDDSLRGYVFGTGTKLTVLS | 148 |
| C4m8 | VH | RVQLQQLGPGLVKPSQTLSLTCAIFGDSVSSNGAAWSWI RQSLSRGLEWLGRAYYRSKWYNDYAVSVRGRITINADT SKNQFSLQLNSVTPEDTAVYYCARTGYSSSRVVSSGYWG QGTLVAVSS | 268 |
| C4m8 | VL | QPVLTQSPSASGTPGQRVTISCSGSSSNIGSNYVYWYQQL PGTAPKLLIYKSNRRPSGVPGRFSGSKSGTAASLAISGLQS EDEADYYCAAWDDSLRGYVFGTGTKLTVL | 269 |
| C4m18 | VH | QVQLQQSGPGLVKPSPTLSLTCAISGDSVSSNSAAWNWV RQSLSRGLEWLGRTYYRSKWYNGYAVSVRGRITTNADT SRNQFSLQLNSVTPEDTAVYYCARTGYSSSWVVNSNYW GQGTLVTVSS | 270 |
| C4m18 | VL | QPALTQSPSASGTPGQRVTISCSGSSSNIGSNYVYWYQQL PGTAPKLLIYKNNQRPSGVPGRFSGSKSGTAASLAISGLR SKDEADYYCAAWDDSLRGYVFGTGTKLTVL | 271 |

FIG. 35 (Page 4 of 4)

Table of FIG. 36. Amino Acid Sequences of Anti-HAAH Single-chain Fv Antibody Fragments

| ScFv Clone | Amino Acid Sequence | SEQ ID NO: |
|---|---|---|
| 11 | QVQLQQSGPGLVKPSQTLSLTCAISGDSVSSNSAAWNWIRQSPSRG LEWLGRTYYRSKWYNDYAVSVKSRITINPDTSKNQFSLQLNSVTP EDTAVYYCARTGYSSSWVVNFDYWGQGTLVTVSSGSASAPTGIL GSGGGGSGGGGSGGGGSQPVLTQSPSASGTPGQRVTISCSGSSSNI GSNYVYWYQQLPGTAPKLLIYKNNQRPSGVPDRFSGSKSGTAASL AISGLQSEDEADYYCAAWDDSLRGYVFGTGTKLTVLSG | 31 |
| 13 | QVQLVESEGGVVQPGRSLRLSCAASGFTFSSYAMHWVRQAPGKG LEWVAVVSYDGSQDYYADSVKGRFTISRDNSKNTLYLQMNSLRP EDTGVYYCAKVGRSSNWFSRYYYYGMDVWGQGTTVTVSSGILG SGGGGSGGGGSGGGGSEIVLTQSPATLSLSPGERATLSCRASQSVS HYLAWYQQKPGQAPRVLIYDVANRAAGTPARFSGSGSGTDFTLTI SSLEPEDFAVYYCQQRSNWPQTFGPGTKVDIKSG | 32 |
| 6-23 | QVQLQQSGPGLVKPSQTLSLTCAISGDSVSSDSAAWNWIRQSPSRG LEWLGRTYYRSKWYNDYAVSVKSRISINPDTSKNQFSLQLNSVTP EDTAVYYCARAQNNIAVAGFDYWGLGTLVTVSSGILGSGGGGSG GGGSGGGGSQPVLTQSPSASGTPGQRVTISCSGSSSNIGSNYVYWY QQLPGTAPTLLIYRNNQRPSGVPDRFSGSKSGTSASLAISGLRSEDE AEYYCAAWDDSLSGLYVFGTGTKVTVLSGIL | 33 |
| 6-27 | QVQLVESEGGVVQPGRSLRLSCAASGFTFGTYAMHWVRQAPGKG LEWVAVISNDGGHKYYADSVKGRFTISRDNSKDSMYLQMNSLRA EDTAVYHCAKGRPWYDPGAEYFQHWGQGTLVTVSSGILGSGGGG SGGGGSGGGGSQSALIQPASVSGSPGQWITISCTGTSSDVGGYNYV SWYQQHPGKAPKLLIYDVSDRPSGVSNRFSGSKSGNTASLTISGLQ AEDEADYYCSSYTSSNTVLFGGGTKLTVLSGIL | 34 |
| 3 | QVQLVQSEGGVVRPGGSLRLSCAASGFTFGDYAMGWVRQAPGK GLEWVSSINWNGGSTGYADSVKGRFTISRDNAKNSLYLQMNSLR AEDTALYYCARVSSGWPYYSLDVWGQGTTVTVSSGSASAPTGILG SGGGGSGGGGSGGGGSQSALIQPRSVSGSPGQSVTISCTGTSSDVG GYNYVSWYQHHPGKAPQLMIYDVTKRPSGVPDRFSGSKSGNTAS LTISGLQAEDEADYYCCSYAGDYTYAVFGTGTQLTVLSGIL | 35 |
| 5-7 | EVQLVESGGGVVQPGRSLRLSCAASGFTFSGYAMHWVRQAPGKG LEWVAAISFDGNYKYYADSVKGRFTVSRDNSRNTLYLQMNSLKV DDTAVYFCARDLYSSGHFGMDVWGQGTTVTVSSASTKGPSGILGS GGGGSGGGGSGGGGSEIVMTQSPGTLSLSPGERATLSCRASQSVSS SYLAWYQQKPGQAPRLLIYGASSRATGIPDRFSGSGSGTDFTLTISR LEPEDFAVYYCQQYGSPITFGQGTRLEIKSGIL | 36 |
| 13m1 | QVQLVESEGGVVQPGRPLRLSCAASGFTFSSHAMHWVRQAPGKG LEWVAVVSHDGSRDRYAGSVKGRFTISRDNSKNTLYLQMNSLRP EDTGVYYCARVGRSSNWFSRYYYYGMDVWGQGTTVTVSSGILGS GGGSGGGDSGGGGSGIVLTQSPATLSLPPRERATLSCGTSQNVSH YLAWYQQKPGRAPRVLTYDVANRAAGTPARFSGSGSGTDFTPAIS SLEPEDFAVYYCQQRSNWPQAFGPGTKVDIKSG | 37 |

FIG. 36 (Page 1 of 5)

| | | |
|---|---|---|
| 13m2-3 | QVQLVESEGGVVQPGRPLRLSCAASGFAFSSHAMHWVRQAPGKG LEWVAVISHDGSRDRYAGSVKGRFTISRDNSKNTLYLQMNSLRPE DTGVYYCARVGRSSNWFSRYYYYDMDVWGQGTTVTVSSGILGS GGGGSGGGDSGGGGSGIVLTQSPATLSLPPRERVTLSCGTSQNVSH HLAWYQQKPGRAPRVLTYDVANKAAGTPARFSGSGSETDFTPAIS SLEPEDFAVYYCQQRSNWPQAFSPGTKVDIKSGSEQKLISE | 38 |
| 13m2-6 | QVQLVESEGGVVQPGRPLRLSCAASGFTFSSHAMHWVRQAPGKG LEWVAVVSHDGSRDRYAGSVKGRFTISRDNSKNTLYLQMNSLRP EDTGVYYCARVGRSSNWFSRYHYYGMDVWGQGTTVTVSSGILGS GGGGSGGGDSGGGGSGIVLTQSPATLSLPPRERATLSCGTSQNVSH YLAWYQQKPGRAPRVLTYDVANRAAGTPARFSGSGSGTDFTPAIS SLELEDFAVYYCQQRSNWPQAFGPGTKVDIKSGSEQKLISEEAL | 39 |
| 11m1-2 | QVQLQQSGPGPVKPSQTLSLTRAIPGDSVSSNSAAWNWIRQFLSRG LEWLGRTYYRSKRYNDYAVSVKSRITINPDTSKNQFSLQLNSVTPE DTAVYYCARTGYSSSWVVNFDYWGQGTLVTVSSGSASAPTGILG FGGGGSGGGGSGGGGSQSVLTQSPSASGTPGQRVTISCSGSSSNIGS NYVYWYQQLPGTAPKLLIYKDNQRPSGVPDRFSGSKSGTAASLAI SGLQSEDEADYYCAAWDDSLRGYVFGTGTKLTVLSGIL | 40 |
| 11m1-3 | QVQLQQPGPGLVEPSQTLPLTRAISGDSVSGNGAAWSWIRQPPPRG LGWPGRTYYRPKRRNGYAVPAKSRMTISPDTSKNQFSLQLNSVTP EDTAVYYCARTGHSSSWVVSFDHWGQGALATISSGNASAPTGVL GSGGGGSGGGGSGGGSSQPVPTQSPSASGTPGQRVTVSCSGSSSNI ESNYVYWYQQLPGAAPRLFIHKNNQRPSGVPDRSSSSKSGTAASL AISGLQSKDEADYYCAAWDDSLRSYVFGTGTKLTVLSGIL | 41 |
| 11m1-5 | QVQLQRSGPGLVKPPQAPSLTCAVSGDSVSSNSAAWNWIRQSLSR GLEWLGRIHYGSRWYNDYAASAKSRVTINPDTPKGQLPPQLSPVT PKDAAAYYCARTECSSSWVVNFGYWGQGAPVTASPGSAPAPTGI LGPGGGGSGGGGSGGGGPQPALIQSPPVSGTPGQRVTIPCSGSSFNI GSNHVYWHQQPPGTAPKLLVHKSNQRPSGVPDRSPGPRPGTAASL AISGLQSEDEADYYCAAWDDSLRGYVLGAGTKLTARSGIL | 42 |
| 11m1-7 | QVQLQQSGPGLVKPSQTLSLTCAIPGDSVSSNSAAWNWIRQSPSRG LEWLGRTYHRFKWYNDHAVSVKSRITINPDTSKNQFSLQLNSVTP EDTAVYYCARTGYSSSWVVNFDYWGQGTPVTVSSGSASAPTGVL GPGGGGSGGGGSGGGGSQPVLTQPPSASGTPGQRVTISCSGSSSNI GSNYVYRYQQLPGAAPKLLIYKNNQRSSGVPARFSGPKSGAAAPL TTSGLQSGDEAGYYCAAWDDSLRGYVFGTGTKLTVLSGIL | 43 |
| 11m1-9 | QVQLQWSGPGLVKPSQTLSLTRAISGNSVSSNSAAWSWIRQSLSR GLEWLGRTYYGSKRYNDYAVSVKSRITINPDTPKNQFSLQLNSVT PEDAAVYYCARTGYSGSRVVNFGYWGQGTLVTVSSGRAPAPTGI LGSGGGGSGGGGSGGGGPQPVLTQSPPASGTPGQRVTISCSGSSSN IGSNYVHRYQQPPGAAPELLIHKNNQRPSGVPDRFSGSKSGTAASP AISGPQSEDEANYYCVAWDDSPCGYVFGAGTKLTVLSGIL | 44 |
| 11m1-10 | QVQLQQSGPGLVKPSQTFSLTYAVSGGSASSNSAAWNWIRQSLSR GLEWLGRTYYRSKWYNDYAVSVKSRTTINPDTSKNQFSLQLNSVT PGDAAVCYCAGAGYSSSRAVNFDCWGQGTLVTVSSGSASTPTGIL GSGGGSGGGGPGGGSQPVLTQSPSASGTPGQRVTISCSGSSSNIGS NYVYWYQQLPGTAPKLLIYKNNQRPSGVPDRFSGSKSGTAASLAI SGLQPEGEADYYCAAWDDSLRGYVLGTGTKLTVLSGIL | 45 |

FIG. 36 (Page 2 of 5)

| | | |
|---|---|---|
| LLm1 | QVQLQQSGPGLVKPSQTLSLTCAISGDSVSSITAAWNWLRQSPSRG LEWLGRTYHRSKWYYDYAVSVKSRITVNPDTSKNQFSLHLNSVTP EDTAVYYCARGLAARGGGPSAHAFEIWGQGTMVTVSSASTKGPS GILGSGGGGSGGGGSGGGGSQPVLTQSPSASGTPGQRVTISCSGSS SNIGSNYVYWYQQLPGTAPKLLIYKNNQRPSGVPDRFSGSKSGTA ASLAISGLQSEDEADYYCAAWDDSLRGYVFGTGTKLTVLSGIL | 149 |
| LLm3 | QVQLQQSGPGLVKPSQTLSLTCVISGDSVSNNSAVWNWIRQSLSR GLEWLGRTYYRSKWYNDYAVSVKSRIIINPDTSKNQFSLQLNSVTP EDTAVYYCARRTGAGVDYWGQGTLVTVSSGILGSGGGGSGGGGS GGGGSQPVLTQSPSASGTPGQRVTISCSGSSSNIGSNYVYWYQQLP GTAPKLLIYKNNQRPSGVPDRFSGSKSGTAASLAISGLQSEDEADY YCAAWDDSLRGYVFGTGTKLTVLSGIL | 150 |
| LLm5 | QVQLQQSGPGLVKPSQTLSLTCAISGDGVSGNNVIWNWIRQSPSR GLEWLGRTYYRSKWYYDLLPSVKSRIAINPDTSKSQFSLQLSSVTP EDTAVYYCARTRAVAGNQYFDLWGRGTLVTVSSGILGSGGGGSG GGGSGGGGSQPVLTQSPSASGTPGQRVTISCSGSSSNIGSNYVYWY QQLPGTAPKLLIYKNNQRPSGVPDRFSGSKSGTAASLAISGLQSED EADYYCAAWDDSLRGYVFGTGTKLTVLSGIL | 151 |
| LLm6 | QVQLQQSGPGLVKPSQTLSLTCAISGDSVSSYSAAWNWIRQSLSRG LEWLGRTYYRSKWYNDYAVSVKSRITINPDTSKNQFSLQLNSVTP EDTAVYYCASLAAAAGTVDYWGQGTLVTVSSGSASAPTGILGSG GGGSGGGGSGGGGSQPVLTQSPSASGTPGQRVTISCSGSSSNIGSN YVYWYQQLPGTAPKLLIYKNNQRPSGVPDRFSGSKSGTAASLAIS GLQSEDEADYYCAAWDDSLRGYVFGTGTKLTVLSGIL | 152 |
| LLm8 | QVQLQQSGPGLVKPSQTLSLTCAISGDSVSSNSAAWNWIRQSLSRG LEWLGRTYYRSKWYNDYALSVKSRININADTSKSQFSLQLDSVTP EDTAVYFCAKDRLLYNYGSNAMDVWGQGTTVTVSSGILGSGGGG SGGGGSGGGGSQPVLTQSPSASGTPGQRVTISCSGSSSNIGSNYVY WYQQLPGTAPKLLIYKNNQRPSGVPDRFSGSKSGTAASLAISGLQS EDEADYYCAAWDDSLRGYVFGTGTKLTVLSGIL | 153 |
| LLm9 | QVQLQQSGPGLVKPSETLSLTCAISGDSVSSNSAAWNWIRQSLSRG LEWLGRTYYRSKWYNDYAVSVKSRITINPDTSKNQFSLQLNSVTP EDTAVYYCARDTPRYCSGGSCYKYFDYWGQGTLVTVSSASTKSP SGILGSGGGGSGGGGSGGGGSQPVLTQSPSASGTPGQRVTISCSGS SSNIGSNYVYWYQQLPGTAPKLLIYKNNQRPSGVPDRFSGSKSGT AASLAISGLQSEDEADYYCAAWDDSLRGYVFGTGTKLTVLSGIL | 154 |
| LLm11 | QVQLQQSGPGLVKSSQTLSLTCAISGDSVSSKGAAWNWIRQSPSR GLEWLGRAYYWSKWYYDYAVSVKSRITINPDTSKNQFSLQLNSLT PEDTAVFYCARGATSTYYLPGGLDVWGQGTTVTVSSGILGSGGGG SGGGGSGGGGSQPVLTQSPSASGTPGQRVTISCSGSSSNIGSNYVY WYQQLPGTAPKLLIYKNNQRPSGVPDRFSGSKSGTAASLAISGLQS EDEADYYCAAWDDSLRGYVFGTGTKLTVLSGIL | 155 |
| LLm13 | QVQLQQSGAGLVKPSQTLSLTCTISGDSVSADRVAWNWIRQSPLR GLEWLGRIFYRSKWMVDYAVSVKSRISINPDTSKNQFSLQLNSVTP EDTAMYYCARATTRGYFDLWGRGTLVTVSSGILGSGGGGSGGGG SGGGGSQPVLTQSPSASGTPGQRVTISCSGSSSNIGSNYVYWYQQL PGTAPKLLIYKNNQRPSGVPDRFSGSKSGTAASLAISGLQSEDEAD YYCAAWDDSLRGYVFGTGTKLTVLSGIL | 156 |

FIG. 36 (Page 3 of 5)

| | | |
|---|---|---|
| LLm14 | QVQLQQSGPGLVKPSQTLSLTCVVSDGVSSNSAAWNWIRQSLSR GLEWLGRTYYRSKWYNDYAVSMKGRITINPDTSKNQFSLQLDSV TPEDTAVYYCARRSGRTGGYFDLWGRGTLVAVSSGILGSGGGGS GGGGSGGGGSQPVLTQSPSASGTPGQRVTISCSGSSSNIGSNYVYW YQQLPGTAPKLLIYKNNQRPSGVPDRFSGSKSGTAASLAISGLQSE DEADYYCAAWDDSLRGYVFGTGTKLTVLSGIL | 157 |
| LLm15 | QVQLQQSGPGLVKPSQTLSLTCAIPGHSVGSSNAAWNWIRQSPSR GLEWLGRIFYGSKWYNDYAVSLKSRLTINPDTSKNQFSLQLNSVT PEDTAVYYCARRTGTGIDYWGQGTLVTVSSGILGSGGGGSGGGGS GGGGSQPVLTQSPSASGTPGQRVTISCSGSSSNIGSNYVYWYQQLP GTAPKLLIYKNNQRPSGVPDRFSGSKSGTAASLAISGLQSEDEADY YCAAWDDSLRGYVFGTGTKLTVLSGIL | 158 |
| LLm20 | QVQLQQSGPGLVKPSQTLSLTCAISGHSVGSSNAAWNWIRQSPSR GLEWLGRIFYRSKWYNDYAVSVKTRISINPDTAKNQFSLHLNSVT AEDTGVYYCARGQQKRLDSWGQGTLVTVSSGILGSGGGGSGGGG SGGGGSQPVLTQSPSASGTPGQRVTISCSGSSSNIGSNYVYWYQQL PGTAPKLLIYKNNQRPSGVPDRFSGSKSGTAASLAISGLQSEDEAD YYCAAWDDSLRGYVFGTGTKLTVLSGIL | 159 |
| CDRm1 | PVQLQQSGPGLVKPSQTLSLPCAISGDSVSSNSAAWNWIRQSLSRG LEWLGRTYYRSKWYNDYAVSVKSRITINPDTSKNQFSLQLNSVTP DDTAIYYCARASDYGDYFYYFDYWGQGTLVTVSSGSASAPTGILG SGGGGSGGGGSGGGGSQPVLTQSPSASGTPGQRVTISCSGSSSNIGS NYVYWYQQLPGTAPKLLIYKNNQRPSGVPDRFSGSKSGTAASLAI SGLQSEDEADYYCAAWDDSLRGYVFGTGTKLTVLSGIL | 160 |
| CDRm2 | QVQLQQSGPGLVKPSQTLSLTCAISGDSVSSNSAAWNWIRQSPSRG LEWLGRIYYRSKWYYDYAVSVKSRIAIKPDTSKNQFSLQLNSVTPE DTAVYYCARGAGRSFDLWGRGTLVTVSSGSASAPTGILGSGGGGS GGGGSGGGGSQPVLTQSPSASGTPGQRVTISCSGSSSNIGSNYVYW YQQLPGTAPKLLIYKNNQRPSGVPDRFSGSKSGTAASLAISGLQSE DEADYYCAAWDDSLRGYVFGTGTKLTVLSGIL | 161 |
| CDRm3 | QVQLQQSSPGLVKPSQTLSLTCAVSGDSVSGNSGVWNWIRQSPSR GLEWLGRTYYYTYKWYIDYAVSVKSRITVNPDTSRNQFSLQLNSV TPEDTAVYYCARVDYTGSPVWGQGTLVTVSSGSASAPTGILGSGG GGSGGGGSGGGGSQPVLTQSPSASGTPGQRVTISCSGSSSNIGSNY VYWYQQLPGTAPKLLIYKNNQRPSGVPDRFSGSKSGTAASLAISGL QSEDEADYYCAAWDDSLRGYVFGTGTKLTVLSGIL | 162 |
| CDRm4 | QVQLQQSGPGLVKPSQTLSLTCAISGDSVSSNSAAWNWIRQSLSRG LEWLGRTYYRSKWYNDYAVSVRGRITINADTSKNQFSLQLNSVTP EDTAVYYCARTGYSSSWVVNFDYWGQGTLVTVSSGSASAPTGIL GSGGGGSGGGGSGGGGSQPVLTQSPSASGTPGQRVTISCSGSSSNI GSNYVYWYQQLPGTAPKLLIYKNNQRPSGVPDRFSGSKSGTAASL AISGLQSEDEADYYCAAWDDSLRGYVFGTGTKLTVLSGIL | 163 |
| 6-8 | QVQLQQSGPGLVKPSQTLSLTCAISGDSVSSNSAAWNWIRQSPSRG LEWLGRTYYRTKWYNEYAASVKGRATINPDTSKNQFSLQLNSVT PEDTAVYYCATDPKGVTTQYWGQGTLVTVSSGSASASTGILGSGG GGSGGGGSGGGGSQPVLTQSPSASGTPGQRVTISCSGSTSNIGRNY VYWYQRLPGTAPKLLIYRNNQRPSGAPARFSGSKSGTSTSLAISGL RSEDEAEYFCAAWDDSLSGWVFGGGTQLTVL | 272 |

FIG. 36 (Page 4 of 5)

| | | |
|---|---|---|
| 6-12 | QVQLQQSGPGLVKPSQTLSLTCGISGDSVSSNSAAWNWIRQSPSRGLEWLGRTYYRSRWYNDYAASVKSRITVNADTSKNQFSLQLNSVTPEDTAVYYCARSVRYSSGWGFDYWGQGTLVTVSSGILGSGGGSGGGGSGGGGSQPVLTQSPSASGTPGQRITISCSGSSSNIGNNYVYWYQQFPGTAPKLLVYRNNQRPSGVPDRFSGSKSGTSASLAISGLRSEDEADYYCAAWDDSLSGRWVFGGGTKLTVL | 273 |
| 6-13 | QVQLQQSGPGLVKPSQTLSLTCAISGDSVSRNSAAWNLIRQSPSRGLEWLGRTYYRSKWYTDYAVSVKSRITINPDTSKNQFSLRLNSVTPEDTAVYYCARSGGGHAAGKFDSWGRGTLVTVSSGILGSGGGGSGGGGSGGGGSQPVLTQSPSASGTPGQRVTIPCSGSSSNIGSKYVYWYQHLPGTAPKLLIYRNNQRPSGVPDRFSGSKSGTSASLAISGLRSEDEADYYCAAWDDSLSAWVFGGGTKLTVL | 274 |
| 6-14 | QVQLQQSGPGLVKPSQTLSLTCAISGDSVSSNSATWNWIRQSPSRGLEWLGRTYYRSKWYNDYAVSVKSRMTINPDTSKNQFSLQLNSVTPDDRAVYYCARGGRLGGGMDVWGQGTTVTVSSGILGSGGGGSGGGGSGGGGSQPVLTQSPSASGTPGQRVTISCSGSSSNIASNYVYWYQHLPGTAPKLLIYTNNRRPSGVPDRFSGSKSGTSASLAISGLRSEDEADYFCAAWDDSLSGWVFGGGTKVTVL | 275 |
| 6-23rea | QVQLVQSEGGVVQPGRSLRLSCGVSGFTFSSYAMHWVRQAPGKGLEWVAVISYDGSKKYYADSVKGRFTISRDNSKNTLYLQMNSLRAEDTAVYYCARRVTTGITRYFDLWGRGTLVTVSSGILGSGGGGSGGGGSGGGGSQSVLTQPASVSGSPGQSITISCTGTNSDIGGYNYVSWYQQHPGKAPKLMIFEVTNRPSGVPDRFSASKSGNTASLTISGLQADDEADYYCSSYAGSNTPSVFGTGTKLTVL | 276 |
| 6-26 | QVQLQQSGPGLVKPSQTLSLTCAISGDSVSSNSAAWNWIRQSPSRGLEWLGRTYYRSKWYNDYAVSVKGRITINPDTSKNQFSLQLNSVTPEDTAMYYCVRSGGGRVDPWGQGTLVTVSSGILGSGGGGSGGGGSGGGGSQPVLTQSPSASGTPGQRVTISCSGSRSNIGSNYVYWYQQLPGTAPKLLIYRNHQRPSGVPDRFSASKSGTSASLAISGLRSEDEADYYCAAWDDSLSGYVFGTGTKLTVL | 277 |
| 6-28 | QVQLVQSEGGVVQPGRSLRLSCAASGFTFNDYAMHWVRQAPGKGLEWVAVISYDGSNKYYTDSVKGRFTISRDNSKNTLYLQMDSLRPEDTALYYCAREASSGWYIDSWGQGTLVTVSSASTKGPSGILGSGGGGSGGGGSGGGGSEIVLTQSPGTLSLSPGERATLSCRASQSVSSSYLAWYQQKPGQAPRLLIYGASSRATGIPDRFSGSGSGTDFTLTISRLEPEDFAVYYCQQYGSSQVTFGQGTRLEVKS | 278 |
| C4m8 | RVQLQQLGPGLVKPSQTLSLTCAIFGDSVSSNGAAWSWIRQSLSRGLEWLGRAYYRSKWYNDYAVSVRGRITINADTSKNQFSLQLNSVTPEDTAVYYCARTGYSSSRVVSSGYWGQGTLVAVSSGSASAPIGILGSGGGGSGGGGSGGGGSQPVLTQSPSASGTPGQRVTISCSGSSSNIGSNYVYWYQQLPGTAPKLLIYKSNRRPSGVPGRFSGSKSGTAASLAISGLQSEDEADYYCAAWDDSLRGYVFGTGTKLTVL | 279 |
| C4m18 | QVQLQQSGPGLVKPSPTLSLTCAISGDSVSSNSAAWNWVRQSLSRGLEWLGRTYYRSKWYNGYAVSVRGRITTNADTSRNQFSLQLNSVTPEDTAVYYCARTGYSSSWVVNSNYWGQGTLVTVSSGSASAPTGILGSGGGGSGGGGSGGGGSQPALTQSPSASGTPGQRVTISCSGSSSNIGSNYVYWYQQLPGTAPKLLIYKNNQRPSGVPGRFSGSKSGTAASLAISGLRSKDEADYYCAAWDDSLRGYVFGTGTKLTVL | 280 |

FIG. 36 (Page 5 of 5)

Table of FIG. 37. Amino Acid Sequences of Anti-HAAH Antibody CDRs

| Clone | Chain | CDR | Amino Acid Sequence | SEQ ID NO: |
|---|---|---|---|---|
| 11 | VH | 1 | SNSAAWN | 46 |
|  |  | 2 | RTYYRSKWYNDYAVSVKS | 47 |
|  |  | 3 | TGYSSSWVVNFDY | 48 |
| 11 | VL | 1 | SGSSSNIGSNYVY | 49 |
|  |  | 2 | KLLIYKNNQRPS | 50 |
|  |  | 3 | AAWDDSLRGYV | 51 |
| 13 | VH | 1 | SYAMH | 52 |
|  |  | 2 | VVSYDGSQDYYADSVKG | 53 |
|  |  | 3 | VGRSSNWFSRYYYYGMDV | 54 |
| 13 | VL | 1 | RASQSVSHYLA | 55 |
|  |  | 2 | DVANRAA | 56 |
|  |  | 3 | QQRSNWPQT | 57 |
| 6-23 | VH | 1 | SDSAAWN | 58 |
|  |  | 2 | RTYYRSKWYNDYAVSVKS | 47 |
|  |  | 3 | AQNNIAVAGFDY | 60 |
| 6-23 | VL | 1 | SGSSSNIGSNYVY | 49 |
|  |  | 2 | TLLIYRNNQRPS | 62 |
|  |  | 3 | AAWDDSLSGLYV | 63 |
| 6-27 | VH | 1 | TYAMH | 64 |
|  |  | 2 | VISNDGGHKYYADSVKG | 65 |
|  |  | 3 | GRPWYDPGAEYFQH | 66 |
| 6-27 | VL | 1 | TGTSSDVGGYNYVS | 67 |
|  |  | 2 | DVSDRPS | 68 |
|  |  | 3 | SSYTSSNTVL | 69 |
| 3 | VH | 1 | DYAMG | 70 |
|  |  | 2 | SINWNGGSTGYADSVKG | 71 |
|  |  | 3 | VSSGWPYYSLDV | 72 |
| 3 | VL | 1 | TGTSSDVGGYNYVS | 73 |
|  |  | 2 | DVTKRPS | 74 |
|  |  | 3 | CSYAGDYTYAV | 75 |
| 5-7 | VH | 1 | GYAMH | 76 |
|  |  | 2 | AISFDGNYKYYADSVKG | 77 |
|  |  | 3 | DLYSSGHFGMDV | 78 |
| 5-7 | VL | 1 | RASQSVSSSYLA | 79 |
|  |  | 2 | GASSRAT | 80 |
|  |  | 3 | QQYGSPIT | 81 |

FIG. 37 (Page 1 of 3)

| 6-8 | VH | 1 | SNSAAWN | 46 |
|---|---|---|---|---|
| | | 2 | RTYYRTKWYNEYAASVKG | 281 |
| | | 3 | DPKGVTTQY | 282 |
| 6-8 | VL | 1 | SGSTSNIGRNYVY | 283 |
| | | 2 | KLLIYRNNQRPS | 284 |
| | | 3 | AAWDDSLSGWV | 285 |
| 6-12 | VH | 1 | SNSAAWN | 46 |
| | | 2 | RTYYRSRWYNDYAASVKS | 286 |
| | | 3 | SVRYSSGWGFDY | 287 |
| 6-12 | VL | 1 | SGSSSNIGNNYVY | 288 |
| | | 2 | KLLVYRNNQRPS | 289 |
| | | 3 | AAWDDSLSGRWV | 290 |
| 6-13 | VH | 1 | RNSAAWN | 291 |
| | | 2 | RTYYRSKWYTDYAVSVKS | 292 |
| | | 3 | SGGGHAAGKFDS | 293 |
| 6-13 | VL | 1 | SGSSSNIGSKYVY | 294 |
| | | 2 | KLLIYRNNQRPS | 284 |
| | | 3 | AAWDDSLSAWV | 295 |
| 6-14 | VH | 1 | SNSATWN | 296 |
| | | 2 | RTYYRSKWYNDYAVSVKS | 47 |
| | | 3 | GGRLGGGMDV | 297 |
| 6-14 | VL | 1 | SGSSSNIASNYVY | 298 |
| | | 2 | KLLIYTNNRRPS | 299 |
| | | 3 | AAWDDSLSGWV | 285 |
| 6-23rea | VH | 1 | SYAMH | 52 |
| | | 2 | VISYDGSKKYYADSVKG | 300 |
| | | 3 | RVTTGITRYFDL | 301 |
| 6-23rea | VL | 1 | TGTNSDIGGYNYVS | 302 |
| | | 2 | KLMIFEVTNRPS | 303 |
| | | 3 | SSYAGSNTPSV | 304 |
| 6-26 | VH | 1 | SNSAAWN | 46 |
| | | 2 | RTYYRSKWYNDYAVSVKG | 305 |
| | | 3 | SGGGRVDP | 306 |
| 6-26 | VL | 1 | SGSRSNIGSNYVY | 307 |
| | | 2 | KLLIYRNHQRPS | 308 |
| | | 3 | AAWDDSLSGYV | 309 |
| 6-28 | VH | 1 | DYAMH | 310 |
| | | 2 | VISYDGSNKYYTDSVKG | 311 |
| | | 3 | EASSGWYIDS | 312 |

FIG. 37 (Page 2 of 3)

| 6-28 | VL | 1 | RASQSVSSSYLA | 79 |
| --- | --- | --- | --- | --- |
| | | 2 | GASSRAT | 80 |
| | | 3 | QQYGSSQVT | 313 |

FIG. 37 (Page 3 of 3)

Table of FIG. 38. Amino Acid Sequences of Affinity-matured, Mutagenized Anti-HAAH Antibody CDRs

| Clone | Chain | CDR | Amino Acid Sequence | SEQ ID NO: |
|---|---|---|---|---|
| 13m1 | VH | 1 | SHAMH | 82 |
| | | 2 | VVSHDGSRDRYAGSVKG | 83 |
| | | 3 | VGRSSNWFSRYYYYGMDV | 54 |
| 13m1 | VL | 1 | CGTSQNVSHYLA | 84 |
| | | 2 | DVANRAA | 56 |
| | | 3 | QQRSNWPQA | 85 |
| 13m2-3 | VH | 1 | SHAMH | 82 |
| | | 2 | VISHDGSRDRYAGSVKG | 86 |
| | | 3 | VGRSSNWFSRYYYYDMDV | 87 |
| 13m2-3 | VL | 1 | GTSQNVSHHLA | 88 |
| | | 2 | DVANKAA | 89 |
| | | 3 | QQRSNWPQA | 90 |
| 13m2-6 | VH | 1 | SHAMH | 82 |
| | | 2 | VVSHDGSRDRYAGSVKG | 83 |
| | | 3 | VGRSSNWFSRYHYYGMDV | 91 |
| 13m2-6 | VL | 1 | GTSQNVSHYLA | 92 |
| | | 2 | DVANRAA | 56 |
| | | 3 | QQRSNWPQA | 93 |
| 11m1-2 | VH | 1 | SNSAAWN | 46 |
| | | 2 | RTYYRSKRYNDYAVSVKS | 95 |
| | | 3 | TGYSSSWVVNFDY | 96 |
| 11m1-2 | VL | 1 | SGSSSNIGSNYVY | 49 |
| | | 2 | KLLIYKDNQRPS | 98 |
| | | 3 | AAWDDSLRGYV | 51 |
| 11m1-3 | VH | 1 | GNGAAWS | 99 |
| | | 2 | RTYYRPKRRNGYAVPAKS | 100 |
| | | 3 | TGHSSSWVVSFDH | 101 |
| 11m1-3 | VL | 1 | SGSSSNIESNYVY | 102 |
| | | 2 | RLFIHKNNQRPS | 103 |
| | | 3 | AAWDDSLRSYV | 104 |

FIG. 38 (Page 1 of 5)

| | | | | | |
|---|---|---|---|---|---|
| 11m1-5 | VH | 1 | SNSAAWN | 46 |
| | | 2 | RIHYGSRWYNDYAASAKS | 105 |
| | | 3 | TECSSSWVVNFGY | 106 |
| 11m1-5 | VL | 1 | SGSSFNIGSNHVY | 107 |
| | | 2 | KLLVHKSNQRPS | 108 |
| | | 3 | AAWDDSLRGYV | 51 |
| 11m1-7 | VH | 1 | SNSAAWN | 46 |
| | | 2 | RTYHRFKWYNDHAVSVKS | 109 |
| | | 3 | TGYSSSWVVNFDY | 48 |
| 11m1-7 | VL | 1 | SGSSSNIGSNYVY | 49 |
| | | 2 | KLLIYKNNQRSS | 110 |
| | | 3 | AAWDDSLRGYV | 51 |
| 11m1-9 | VH | 1 | SNSAAWS | 111 |
| | | 2 | RTYYGSKRYNDYAVSVKS | 112 |
| | | 3 | TGYSGSRVVNFGY | 113 |
| 11m1-9 | VL | 1 | SGSSSNIGSNYVH | 114 |
| | | 2 | ELLIHKNNQRPS | 115 |
| | | 3 | VAWDDSPCGYV | 116 |
| 11m1-10 | VH | 1 | SNSAAWN | 46 |
| | | 2 | RTYYRSKWYNDYAVSVKS | 47 |
| | | 3 | AGYSSSRAVNFDC | 117 |
| 11m1-10 | VL | 1 | SGSSSNIGSNYVY | 49 |
| | | 2 | KLLIYKNNQRPS | 50 |
| | | 3 | AAWDDSLRGYV | 51 |
| LLm1 | VH | 1 | SITAAWN | 164 |
| | | 2 | RTYHRSKWYYDYAVSVKS | 165 |
| | | 3 | GLAARGGGPSAHAFEI | 166 |
| LLm1 | VL | 1 | SGSSSNIGSNYVY | 49 |
| | | 2 | KLLIYKNNQRPS | 50 |
| | | 3 | AAWDDSLRGYV | 51 |
| LLm3 | VH | 1 | NNSAVWN | 170 |
| | | 2 | RTYYRSKWYNDYAVSVKS | 47 |
| | | 3 | RTGAGVDY | 172 |
| LLm3 | VL | 1 | SGSSSNIGSNYVY | 49 |
| | | 2 | KLLIYKNNQRPS | 50 |
| | | 3 | AAWDDSLRGYV | 51 |

FIG. 38 (Page 2 of 5)

| | | | | |
|---|---|---|---|---|
| LLm5 | VH | 1 | GNNVIWN | 176 |
| | | 2 | RTYYRSKWYYDLLPSVKS | 177 |
| | | 3 | TRAVAGNQYFDL | 178 |
| LLm5 | VL | 1 | SGSSSNIGSNYVY | 49 |
| | | 2 | KLLIYKNNQRPS | 50 |
| | | 3 | AAWDDSLRGYV | 51 |
| LLm6 | VH | 1 | SYSAAWN | 182 |
| | | 2 | RTYYRSKWYNDYAVSVKS | 47 |
| | | 3 | LAAAAGTVDY | 184 |
| LLm6 | VL | 1 | SGSSSNIGSNYVY | 49 |
| | | 2 | KLLIYKNNQRPS | 50 |
| | | 3 | AAWDDSLRGYV | 51 |
| LLm8 | VH | 1 | SNSAAWN | 46 |
| | | 2 | RTYYRSKWYNDYALSVKS | 189 |
| | | 3 | DRLLYNYGSNAMDV | 190 |
| LLm8 | VL | 1 | SGSSSNIGSNYVY | 49 |
| | | 2 | KLLIYKNNQRPS | 50 |
| | | 3 | AAWDDSLRGYV | 51 |
| LLm9 | VH | 1 | SNSAAWN | 46 |
| | | 2 | RTYYRSKWYNDYAVSVKS | 47 |
| | | 3 | DTPRYCSGGSCYKYFDY | 196 |
| LLm9 | VL | 1 | SGSSSNIGSNYVY | 49 |
| | | 2 | KLLIYKNNQRPS | 50 |
| | | 3 | AAWDDSLRGYV | 51 |
| LLm11 | VH | 1 | SKGAAWN | 200 |
| | | 2 | RAYYWSKWYYDYAVSVKS | 201 |
| | | 3 | GATSTYYLPGGLDV | 202 |
| LLm11 | VL | 1 | SGSSSNIGSNYVY | 49 |
| | | 2 | KLLIYKNNQRPS | 50 |
| | | 3 | AAWDDSLRGYV | 51 |
| LLm13 | VH | 1 | ADRVAWN | 206 |
| | | 2 | RIFYRSKWMVDYAVSVKS | 207 |
| | | 3 | ATTRGYFDL | 208 |
| LLm13 | VL | 1 | SGSSSNIGSNYVY | 49 |
| | | 2 | KLLIYKNNQRPS | 50 |
| | | 3 | AAWDDSLRGYV | 51 |
| LLm14 | VH | 1 | SNSAAWN | 46 |
| | | 2 | RTYYRSKWYNDYAVSMKG | 213 |
| | | 3 | RSGRTGGYFDL | 214 |

FIG. 38 (Page 3 of 5)

| | | | | |
|---|---|---|---|---|
| LLm14 | VL | 1 | SGSSSNIGSNYVY | 49 |
| | | 2 | KLLIYKNNQRPS | 50 |
| | | 3 | AAWDDSLRGYV | 51 |
| LLm15 | VH | 1 | SSNAAWN | 218 |
| | | 2 | RIFYGSKWYNDYAVSLKS | 219 |
| | | 3 | RTGTGIDY | 220 |
| LLm15 | VL | 1 | SGSSSNIGSNYVY | 49 |
| | | 2 | KLLIYKNNQRPS | 50 |
| | | 3 | AAWDDSLRGYV | 51 |
| LLm20 | VH | 1 | SSNAAWN | 224 |
| | | 2 | RIFYRSKWYNDYAVSVKT | 225 |
| | | 3 | GQQKRLDS | 226 |
| LLm20 | VL | 1 | SGSSSNIGSNYVY | 49 |
| | | 2 | KLLIYKNNQRPS | 50 |
| | | 3 | AAWDDSLRGYV | 51 |
| CDRm1 | VH | 1 | SNSAAWN | 46 |
| | | 2 | RTYYRSKWYNDYAVSVKS | 47 |
| | | 3 | ASDYGDYFYYFDY | 232 |
| CDRm1 | VL | 1 | SGSSSNIGSNYVY | 49 |
| | | 2 | KLLIYKNNQRPS | 50 |
| | | 3 | AAWDDSLRGYV | 51 |
| CDRm2 | VH | 1 | SNSAAWN | 46 |
| | | 2 | RIYYRSKWYYDYAVSVKS | 237 |
| | | 3 | GAGRSFDL | 238 |
| CDRm2 | VL | 1 | SGSSSNIGSNYVY | 49 |
| | | 2 | KLLIYKNNQRPS | 50 |
| | | 3 | AAWDDSLRGYV | 51 |
| CDRm3 | VH | 1 | GNSGVWNW | 242 |
| | | 2 | TYYYTYKWYIDYAVSVKS | 243 |
| | | 3 | VDYTGSPV | 244 |
| CDRm3 | VL | 1 | SGSSSNIGSNYVY | 49 |
| | | 2 | KLLIYKNNQRPS | 50 |
| | | 3 | AAWDDSLRGYV | 51 |
| CDRm4 | VH | 1 | SNSAAWN | 46 |
| | | 2 | RTYYRSKWYNDYAVSVRG | 249 |
| | | 3 | TGYSSSWVVNFDY | 250 |
| CDRm4 | VL | 1 | SGSSSNIGSNYVY | 49 |
| | | 2 | KLLIYKNNQRPS | 50 |
| | | 3 | AAWDDSLRGYV | 51 |

FIG. 38 (Page 4 of 5)

| C4m8 | VH | 1 | SNGAAWS | 314 |
|---|---|---|---|---|
| | | 2 | RAYYRSKWYNDYAVSVRG | 315 |
| | | 3 | TGYSSSRVVSSGY | 316 |
| C4m8 | VL | 1 | SGSSSNIGSNYVY | 49 |
| | | 2 | KLLIYKSNRRPS | 317 |
| | | 3 | AAWDDSLRGYV | 51 |
| C4m18 | VH | 1 | SNSAAWN | 46 |
| | | 2 | RTYYRSKWYNGYAVSVRG | 318 |
| | | 3 | TGYSSSWVVNSNY | 319 |
| C4m18 | VL | 1 | SGSSSNIGSNYVY | 49 |
| | | 2 | KLLIYKNNQRPS | 50 |
| | | 3 | AAWDDSLRGYV | 51 |

FIG. 38 (Page 5 of 5)

SEQUENCE LISTING

<160> NUMBER OF SEQ ID NOS: 319

<210> SEQ ID NO 1
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 1

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

-continued

```
Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                85                  90                  95

Tyr Tyr Cys Ala Arg Thr Gly Tyr Ser Ser Ser Trp Val Val Asn Phe
            100                 105                 110

Asp Tyr Trp Gly Gln Gly Thr Leu Val Thr Val Ser Ser
            115                 120                 125

<210> SEQ ID NO 2
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 2

Gln Pro Val Leu Thr Gln Ser Pro Ser Ala Ser Gly Thr Pro Gly Gln
  1               5                  10                  15

Arg Val Thr Ile Ser Cys Ser Gly Ser Ser Asn Ile Gly Ser Asn
                 20                  25                  30

Tyr Val Tyr Trp Tyr Gln Gln Leu Pro Gly Thr Ala Pro Lys Leu Leu
                35                  40                  45

Ile Tyr Lys Asn Asn Gln Arg Pro Ser Gly Val Pro Asp Arg Phe Ser
        50                  55                  60

Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                85                  90                  95

Arg Gly Tyr Val Phe Gly Thr Gly Thr Lys Leu Thr Val Leu Ser Gly
            100                 105                 110

<210> SEQ ID NO 3
<211> LENGTH: 127
<212> TYPE: PRT
<213> ORGANISM: Artificial Sequence
<220> FEATURE:
<223> OTHER INFORMATION: Synthetically generated peptide

<400> SEQUENCE: 3

Gln Val Gln Leu Val Glu Ser Glu Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
                35                  40                  45

Ala Val Val Ser Tyr Asp Gly Ser Gln Asp Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Gly Val Tyr Tyr Cys
                85                  90                  95

Ala Lys Val Gly Arg Ser Ser Asn Trp Phe Ser Arg Tyr Tyr Tyr Tyr
            100                 105                 110

Gly Met Asp Val Trp Gly Gln Gly Thr Thr Val Thr Val Ser Ser
            115                 120                 125
```

<210> SEQ ID NO 4
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 4

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser His Tyr
            20                  25                  30

Leu Ala Trp Tyr Gln Gln Lys Pro Gly Gln Ala Pro Arg Val Leu Ile
        35                  40                  45

Tyr Asp Val Ala Asn Arg Ala Ala Gly Thr Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Gln
                85                  90                  95

Thr Phe Gly Pro Gly Thr Lys Val Asp Ile Lys Ser Gly
            100                 105
```

<210> SEQ ID NO 5
<211> LENGTH: 124
<212> TYPE: PRT
<213> ORGANISM: Artificial Sequence
<220> FEATURE:
<223> OTHER INFORMATION: Synthetically generated peptide

<400> SEQUENCE: 5

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ala Gln Asn Asn Ile Ala Val Ala Gly Phe Asp
            100                 105                 110

Tyr Trp Gly Leu Gly Thr Leu Val Thr Val Ser Ser
        115                 120
```

<210> SEQ ID NO 6
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 6

```
Gln Pro Val Leu Thr Gln Ser Pro Ser Ala Ser Gly Thr Pro Gly Gln
1               5                   10                  15
```

```
Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Thr Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Glu Tyr Tyr Cys Ala Ala Trp Asp Asp Ser Leu
                85                  90                  95

Ser Gly Val Phe Gly Thr Gly Thr Lys Val Thr Val Leu Ser
            100                 105                 110
```

<210> SEQ ID NO 7
<211> LENGTH: 123
<212> TYPE: PRT
<213> ORGANISM: Artificial Sequence
<220> FEATURE:
<223> OTHER INFORMATION: Synthetically generated peptide

<400> SEQUENCE: 7

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Gly Thr Tyr
            20                  25                  30

Ala Met His Trp Val Arg Gln Ala Pro Gly Lys Gly Leu Glu Trp Val
        35                  40                  45

Ala Val Ile Ser Asn Asp Gly Gly His Lys Tyr Tyr Ala Asp Ser Val
    50                  55                  60

Lys Gly Arg Phe Thr Ile Ser Arg Asp Asn Ser Lys Asp Ser Met Tyr
65                  70                  75                  80

Leu Gln Met Asn Ser Leu Arg Ala Glu Asp Thr Ala Val Tyr His Cys
                85                  90                  95

Ala Lys Gly Arg Pro Trp Tyr Asp Pro Gly Ala Glu Tyr Phe Gln His
            100                 105                 110

Trp Gly Gln Gly Thr Leu Val Thr Val Ser Ser
        115                 120
```

<210> SEQ ID NO 8
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 8

```
Gln Ser Ala Leu Ile Gln Pro Ala Ser Val Ser Gly Ser Pro Gly Gln
1               5                   10                  15

Trp Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95
```

Asn Thr Val Leu Phe Gly Gly Gly Thr Lys Leu Thr Val Leu Ser
            100                 105                 110

<210> SEQ ID NO 9
<211> LENGTH: 128
<212> TYPE: PRT
<213> ORGANISM: Artificial Sequence
<220> FEATURE:
<223> OTHER INFORMATION: Synthetically generated peptide

<400> SEQUENCE: 9

Gln Val Gln Leu Val Gln Ser Glu Gly Val Val Arg Pro Gly Gly
 1               5                  10                  15

Ser Leu Arg Leu Ser Cys Ala Ala Ser Gly Phe Thr Phe Gly Asp Tyr
            20                  25                  30

Ala Met Gly Trp Val Arg Gln Ala Pro Gly Lys Gly Leu Glu Trp Val
        35                  40                  45

Ser Ser Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Val Ser Ser Gly Trp Pro Tyr Tyr Ser Leu Asp Val Trp Gly
            100                 105                 110

Gln Gly Thr Thr Val Thr Val Ser Ser Gly Ser Ala Ser Ala Pro Thr
        115                 120                 125

<210> SEQ ID NO 10
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 10

Gln Ser Ala Leu Ile Gln Pro Arg Ser Val Ser Gly Ser Pro Gly Gln
 1               5                  10                  15

Ser Val Thr Ile Ser Cys Thr Gly Thr Ser Ser Asp Val Gly Gly Tyr
            20                  25                  30

Asn Tyr Val Ser Trp Tyr Gln His His Pro Gly Lys Ala Pro Gln Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Tyr Ala Val Phe Gly Thr Gly Thr Gln Leu Thr Val Leu Ser
            100                 105                 110

<210> SEQ ID NO 11
<211> LENGTH: 126
<212> TYPE: PRT
<213> ORGANISM: Artificial Sequence
<220> FEATURE:
<223> OTHER INFORMATION: Synthetically generated peptide

<400> SEQUENCE: 11

-continued

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Ala Met His Trp Val Arg Gln Ala Pro Gly Lys Gly Leu Glu Trp Val
        35                  40                  45

Ala Ala Ile Ser Phe Asp Gly Asn Tyr Lys Tyr Tyr Ala Asp Ser Val
    50                  55                  60

Lys Gly Arg Phe Thr Val Ser Arg Asp Asn Ser Arg Asn Thr Leu Tyr
65                  70                  75                  80

Leu Gln Met Asn Ser Leu Lys Val Asp Asp Thr Ala Val Tyr Phe Cys
                85                  90                  95

Ala Arg Asp Lys Ser Gly His Phe Gly Met Asp Val Trp Gly Gln Gly
                100                 105                 110

Thr Thr Val Thr Val Ser Ser Ala Ser Thr Lys Gly Pro Ser
            115                 120                 125

<210> SEQ ID NO 12
<211> LENGTH: 107
<212> TYPE: PRT
<213> ORGANISM: Artificial Sequence
<220> FEATURE:
<223> OTHER INFORMATION: Synthetically generated peptide

<400> SEQUENCE: 12

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro Ile
                85                  90                  95

Thr Phe Gly Gln Gly Thr Arg Leu Glu Ile Lys
                100                 105

<210> SEQ ID NO 13
<211> LENGTH: 127
<212> TYPE: PRT
<213> ORGANISM: Artificial Sequence
<220> FEATURE:
<223> OTHER INFORMATION: Synthetically generated peptide

<400> SEQUENCE: 13

Gln Val Gln Leu Val Glu Ser Glu Gly Gly Val Val Gln Pro Gly Arg
1               5                   10                  15

Pro Leu Arg Leu Ser Cys Ala Ala Ser Gly Phe Thr Phe Ser Ser His
            20                  25                  30

Ala Met His Trp Val Arg Gln Ala Pro Gly Lys Gly Leu Glu Trp Val
        35                  40                  45

Ala Val Val Ser His Asp Gly Ser Arg Asp Arg Tyr Ala Gly Ser Val
    50                  55                  60

Lys Gly Arg Phe Thr Ile Ser Arg Asp Asn Ser Lys Asn Thr Leu Tyr
65                  70                  75                  80

-continued

Leu Gln Met Asn Ser Leu Arg Pro Glu Asp Thr Gly Val Tyr Tyr Cys
                85                  90                  95

Ala Arg Val Gly Arg Ser Ser Asn Trp Phe Ser Arg Tyr Tyr Tyr Tyr
            100                 105                 110

Gly Met Asp Val Trp Gly Gln Gly Thr Thr Val Thr Val Ser Ser
        115                 120                 125

<210> SEQ ID NO 14
<211> LENGTH: 107
<212> TYPE: PRT
<213> ORGANISM: Artificial Sequence
<220> FEATURE:
<223> OTHER INFORMATION: Synthetically generated peptide

<400> SEQUENCE: 14

Gly Ile Val Leu Thr Gln Ser Pro Ala Thr Leu Ser Leu Pro Pro Arg
1               5                   10                  15

Glu Arg Ala Thr Leu Ser Cys Gly Thr Ser Gln Asn Val Ser His Tyr
            20                  25                  30

Leu Ala Trp Tyr Gln Gln Lys Pro Gly Arg Ala Pro Arg Val Leu Thr
        35                  40                  45

Tyr Asp Val Ala Asn Arg Ala Ala Gly Thr Pro Ala Arg Phe Ser Gly
    50                  55                  60

Ser Gly Ser Gly Thr Asp Phe Thr Pro Ala Ile Ser Ser Leu Glu Pro
65                  70                  75                  80

Glu Asp Phe Ala Val Tyr Tyr Cys Gln Gln Arg Ser Asn Trp Pro Gln
                85                  90                  95

Ala Phe Gly Pro Gly Thr Lys Val Asp Ile Lys
            100                 105

<210> SEQ ID NO 15
<211> LENGTH: 127
<212> TYPE: PRT
<213> ORGANISM: Artificial Sequence
<220> FEATURE:
<223> OTHER INFORMATION: Synthetically generated peptide

<400> SEQUENCE: 15

Gln Val Gln Leu Val Glu Ser Glu Gly Val Val Gln Pro Gly Arg
1               5                   10                  15

Pro Leu Arg Leu Ser Cys Ala Ala Ser Gly Phe Ala Phe Ser Ser His
            20                  25                  30

Ala Met His Trp Val Arg Gln Ala Pro Gly Lys Gly Leu Glu Trp Val
        35                  40                  45

Ala Val Ile Ser His Asp Gly Ser Arg Asp Arg Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Gly Val Tyr Tyr Cys
                85                  90                  95

Ala Arg Val Gly Arg Ser Ser Asn Trp Phe Ser Arg Tyr Tyr Tyr Tyr
            100                 105                 110

Asp Met Asp Val Trp Gly Gln Gly Thr Thr Val Thr Val Ser Ser
        115                 120                 125

<210> SEQ ID NO 16
<211> LENGTH: 113
<212> TYPE: PRT

<213> ORGANISM: Artificial Sequence
<220> FEATURE:
<223> OTHER INFORMATION: Synthetically generated peptide

<400> SEQUENCE: 16

Gly Ile Val Leu Thr Gln Ser Pro Ala Thr Leu Ser Leu Pro Pro Arg
1               5                   10                  15
Glu Arg Val Thr Leu Ser Cys Gly Thr Ser Gln Asn Val Ser His His
            20                  25                  30
Leu Ala Trp Tyr Gln Gln Lys Pro Gly Arg Ala Pro Arg Val Leu Thr
        35                  40                  45
Tyr Asp Val Ala Asn Lys Ala Ala Gly Thr Pro Ala Arg Phe Ser Gly
50                  55                  60
Ser Gly Ser Glu Thr Asp Phe Thr Pro Ala Ile Ser Ser Leu Glu Pro
65                  70                  75                  80
Glu Asp Phe Ala Val Tyr Tyr Cys Gln Gln Arg Ser Asn Trp Pro Gln
                85                  90                  95
Ala Phe Ser Pro Gly Thr Lys Val Asp Ile Lys Ser Gly Ser Glu Gln
            100                 105                 110
Lys

<210> SEQ ID NO 17
<211> LENGTH: 127
<212> TYPE: PRT
<213> ORGANISM: Artificial Sequence
<220> FEATURE:
<223> OTHER INFORMATION: Synthetically generated peptide

<400> SEQUENCE: 17

Gln Val Gln Leu Val Glu Ser Glu Gly Gly Val Val Gln Pro Gly Arg
1               5                   10                  15
Pro Leu Arg Leu Ser Cys Ala Ala Ser Gly Phe Thr Phe Ser Ser His
            20                  25                  30
Ala Met His Trp Val Arg Gln Ala Pro Gly Lys Gly Leu Glu Trp Val
        35                  40                  45
Ala Val Val Ser His Asp Gly Ser Arg Asp Arg Tyr Ala Gly Ser Val
50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Pro Glu Asp Thr Gly Val Tyr Tyr Cys
                85                  90                  95
Ala Arg Val Gly Arg Ser Ser Asn Trp Phe Ser Arg Tyr His Tyr Tyr
            100                 105                 110
Gly Met Asp Val Trp Gly Gln Gly Thr Thr Val Thr Val Ser Ser
        115                 120                 125

<210> SEQ ID NO 18
<211> LENGTH: 107
<212> TYPE: PRT
<213> ORGANISM: Artificial Sequence
<220> FEATURE:
<223> OTHER INFORMATION: Synthetically generated peptide

<400> SEQUENCE: 18

Gly Ile Val Leu Thr Gln Ser Pro Ala Thr Leu Ser Leu Pro Pro Arg
1               5                   10                  15
Glu Arg Ala Thr Leu Ser Cys Gly Thr Ser Gln Asn Val Ser His Tyr
            20                  25                  30

-continued

```
Leu Ala Trp Tyr Gln Gln Lys Pro Gly Arg Ala Pro Arg Val Leu Thr
        35                  40                  45

Tyr Asp Val Ala Asn Arg Ala Ala Gly Thr Pro Ala Arg Phe Ser Gly
 50                  55                  60

Ser Gly Ser Gly Thr Asp Phe Thr Pro Ala Ile Ser Ser Leu Glu Leu
 65                  70                  75                  80

Glu Asp Phe Ala Val Tyr Tyr Cys Gln Gln Arg Ser Asn Trp Pro Gln
                 85                  90                  95

Ala Phe Gly Pro Gly Thr Lys Val Asp Ile Lys
                100                 105
```

<210> SEQ ID NO 19
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 19

```
Gln Val Gln Leu Gln Gln Ser Gly Pro Gly Val Lys Pro Ser Gln
 1               5                  10                  15

Thr Leu Ser Leu Thr Arg Ala Ile Pro Gly Asp Ser Val Ser Ser Asn
                 20                  25                  30

Ser Ala Ala Trp Asn Trp Ile Arg Gln Phe Leu Ser Arg Gly Leu Glu
             35                  40                  45

Trp Leu Gly Arg Thr Tyr Tyr Arg Ser Lys Arg Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Thr Gly Tyr Ser Ser Ser Trp Val Asn Phe
            100                 105                 110

Asp Tyr Trp Gly Gln Gly Thr Leu Val Thr Val Ser Ser
        115                 120                 125
```

<210> SEQ ID NO 20
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 20

```
Gln Ser Val Leu Thr Gln Ser Pro Ser Ala Ser Gly Thr Pro Gly Gln
 1               5                  10                  15

Arg Val Thr Ile Ser Cys Ser Gly Ser Ser Ser Asn Ile Gly Ser Asn
                 20                  25                  30

Tyr Val Tyr Trp Tyr Gln Gln Leu Pro Gly Thr Ala Pro Lys Leu Leu
             35                  40                  45

Ile Tyr Lys Asp Asn Gln Arg Pro Ser Gly Val Pro Asp Arg Phe Ser
 50                  55                  60

Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser
            100                 105                 110
```

<210> SEQ ID NO 21
<211> LENGTH: 123
<212> TYPE: PRT
<213> ORGANISM: Artificial Sequence
<220> FEATURE:
<223> OTHER INFORMATION: Synthetically generated peptide

<400> SEQUENCE: 21

```
Gln Val Gln Leu Gln Gln Pro Gly Pro Gly Leu Val Glu Pro Ser Gln
1               5                   10                  15

Thr Leu Pro Leu Thr Arg Ala Ile Ser Gly Asp Ser Val Ser Gly Asn
            20                  25                  30

Gly Ala Ala Trp Ser Trp Ile Arg Gln Pro Pro Arg Gly Leu Gly
        35                  40                  45

Trp Pro Gly Arg Thr Tyr Tyr Arg Pro Lys Arg Arg Asn Gly Tyr Ala
    50                  55                  60

Val Pro Ala Lys Ser Arg Met Thr Ile Ser Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Thr Gly His Ser Ser Ser Trp Val Val Ser Phe
            100                 105                 110

Asp His Trp Gly Gln Gly Ala Thr Ile Ser Ser
            115                 120
```

<210> SEQ ID NO 22
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 22

```
Ser Gln Pro Val Pro Thr Gln Ser Pro Ser Ala Ser Gly Thr Pro Gly
1               5                   10                  15

Gln Arg Val Thr Val Ser Cys Ser Gly Ser Ser Ser Asn Ile Glu Ser
            20                  25                  30

Asn Tyr Val Tyr Trp Tyr Gln Gln Leu Pro Gly Ala Ala Pro Arg Leu
        35                  40                  45

Phe Ile His Lys Asn Asn Gln Arg Pro Ser Gly Val Pro Asp Arg Ser
    50                  55                  60

Ser Ser Ser Lys Ser Gly Thr Ala Ala Ser Leu Ala Ile Ser Gly Leu
65                  70                  75                  80

Gln Ser Lys Asp Glu Ala Asp Tyr Tyr Cys Ala Ala Trp Asp Asp Ser
                85                  90                  95

Leu Arg Ser Tyr Val Phe Gly Thr Gly Thr Lys Leu Thr Val Leu Ser
            100                 105                 110
```

<210> SEQ ID NO 23
<211> LENGTH: 123
<212> TYPE: PRT
<213> ORGANISM: Artificial Sequence
<220> FEATURE:
<223> OTHER INFORMATION: Synthetically generated peptide

<400> SEQUENCE: 23

```
Gln Val Gln Leu Gln Arg Ser Gly Pro Gly Leu Val Lys Pro Pro Gln
1               5                   10                  15
```

```
Ala Pro Ser Leu Thr Cys Ala Val Ser Gly Asp Ser Val Ser Ser Asn
            20                  25                  30

Ser Ala Ala Trp Asn Trp Ile Arg Gln Ser Leu Ser Arg Gly Leu Glu
        35                  40                  45

Trp Leu Gly Arg Ile His Tyr Gly Ser Arg Trp Tyr Asn Asp Tyr Ala
    50                  55                  60

Ala Ser Ala Lys Ser Arg Val Thr Ile Asn Pro Asp Thr Pro Lys Gly
65                  70                  75                  80

Gln Leu Pro Pro Gln Leu Ser Pro Val Thr Pro Lys Asp Ala Ala Ala
                85                  90                  95

Tyr Tyr Cys Ala Arg Thr Glu Cys Ser Ser Trp Val Val Asn Phe
            100                 105                 110

Gly Tyr Trp Gly Gln Gly Ala Pro Val Thr Asp
        115                 120
```

<210> SEQ ID NO 24
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 24

```
Gln Pro Ala Leu Ile Gln Ser Pro Val Ser Gly Thr Pro Gly Gln
1               5                   10                  15

Arg Val Thr Ile Pro Cys Ser Gly Ser Ser Phe Asn Ile Gly Ser Asn
            20                  25                  30

His Val Tyr Trp His Gln Gln Pro Gly Thr Ala Pro Lys Leu Leu
        35                  40                  45

Val His Lys Ser Asn Gln Arg Pro Ser Gly Val Pro Asp Arg Ser Pro
    50                  55                  60

Gly Pro Arg Pro Gly Thr Ala Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Arg Gly Tyr Val Leu Gly Ala Gly Thr Lys Leu Thr Ala Arg Ser
            100                 105                 110
```

<210> SEQ ID NO 25
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 25

```
Gln Val Gln Leu Gln Gln Ser Gly Pro Gly Leu Val Lys Pro Ser Gln
1               5                   10                  15

Thr Leu Ser Leu Thr Cys Ala Ile Pro Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr His Arg Phe Lys Trp Tyr Asn Asp His Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95
```

Tyr Tyr Cys Ala Arg Thr Gly Tyr Ser Ser Trp Val Val Asn Phe
            100                 105                 110

Asp Tyr Trp Gly Gln Gly Thr Pro Val Thr Val Ser Ser
        115                 120                 125

<210> SEQ ID NO 26
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 26

Gln Pro Val Leu Thr Gln Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Arg Tyr Gln Gln Leu Pro Gly Ala Ala Pro Lys Leu Leu
                35                  40                  45

Ile Tyr Lys Asn Asn Gln Arg Ser Ser Gly Val Pro Ala Arg Phe Ser
    50                  55                  60

Gly Pro Lys Ser Gly Ala Ala Ala Pro Leu Thr Thr Ser Gly Leu Gln
65                  70                  75                  80

Ser Gly Asp Glu Ala Gly Tyr Tyr Cys Ala Ala Trp Asp Asp Ser Leu
                85                  90                  95

Arg Gly Tyr Val Phe Gly Thr Gly Thr Lys Leu Thr Val Leu Ser
                100                 105                 110

<210> SEQ ID NO 27
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 27

Gln Val Gln Leu Gln Trp Ser Gly Pro Gly Leu Val Lys Pro Ser Gln
1               5                   10                  15

Thr Leu Ser Leu Thr Arg Ala Ile Ser Gly Asn Ser Val Ser Ser Asn
                20                  25                  30

Ser Ala Ala Trp Ser Trp Ile Arg Gln Ser Leu Ser Arg Gly Leu Glu
            35                  40                  45

Trp Leu Gly Arg Thr Tyr Tyr Gly Ser Lys Arg Tyr Asn Asp Tyr Ala
    50                  55                  60

Val Ser Val Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Ala Ala Val
                85                  90                  95

Tyr Tyr Cys Ala Arg Thr Gly Tyr Ser Gly Ser Arg Val Val Asn Phe
            100                 105                 110

Gly Tyr Trp Gly Gln Gly Thr Leu Val Thr Val Ser Ser
        115                 120                 125

<210> SEQ ID NO 28
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 28

Gln Pro Val Leu Thr Gln Ser Pro Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val His Arg Tyr Gln Gln Pro Pro Gly Ala Ala Pro Glu Leu Leu
        35                  40                  45

Ile His Lys Asn Asn Gln Arg Pro Ser Gly Val Pro Asp Arg Phe Ser
    50                  55                  60

Gly Ser Lys Ser Gly Thr Ala Asp Ala Ile Ser Gly Pro Gln Ser Glu
65                  70                  75                  80

Asp Glu Ala Asn Tyr Tyr Cys Val Ala Trp Asp Asp Ser Pro Cys Gly
                85                  90                  95

Tyr Val Phe Gly Ala Gly Thr Lys Leu Thr Val Leu Ser
            100                 105

<210> SEQ ID NO 29
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 29

Gln Val Gln Leu Gln Gln Ser Gly Pro Gly Leu Val Lys Pro Ser Gln
1               5                   10                  15

Thr Phe Ser Leu Thr Tyr Ala Val Ser Gly Gly Ser Ala Ser Ser Asn
            20                  25                  30

Ser Ala Ala Trp Asn Trp Ile Arg Gln Ser Leu Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Thr Thr Ile Asn Pro Asp Thr Ser Lys Asn
65                  70                  75                  80

Gln Phe Ser Leu Gln Leu Asn Ser Val Thr Pro Gly Asp Ala Ala Val
                85                  90                  95

Cys Tyr Cys Ala Gly Ala Gly Tyr Ser Ser Ser Arg Ala Val Asn Phe
            100                 105                 110

Asp Cys Trp Gly Gln Gly Thr Leu Val Thr Val Ser Ser
        115                 120                 125

<210> SEQ ID NO 30
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 30

Gln Pro Val Leu Thr Gln Ser Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

```
Gly Ser Lys Ser Gly Thr Ala Ala Ser Leu Ala Ile Ser Gly Leu Gln
 65                  70                  75                  80

Pro Glu Gly Glu Ala Asp Tyr Tyr Cys Ala Ala Trp Asp Asp Ser Leu
             85                  90                  95

Arg Gly Tyr Val Leu Gly Thr Gly Thr Lys Leu Thr Val Leu Ser
            100                 105                 110
```

<210> SEQ ID NO 31
<211> LENGTH: 264
<212> TYPE: PRT
<213> ORGANISM: Artificial Sequence
<220> FEATURE:
<223> OTHER INFORMATION: Synthetically generated peptide

<400> SEQUENCE: 31

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
             85                  90                  95

Tyr Tyr Cys Ala Arg Thr Gly Tyr Ser Ser Ser Trp Val Val Asn Phe
            100                 105                 110

Asp Tyr Trp Gly Gln Gly Thr Leu Val Thr Val Ser Ser Gly Ser Ala
        115                 120                 125

Ser Ala Pro Thr Gly Ile Leu Gly Ser Gly Gly Gly Ser Gly Gly Gly
    130                 135                 140

Gly Gly Ser Gly Gly Gly Ser Gln Pro Val Leu Thr Gln Ser Pro
145                 150                 155                 160

Ser Ala Ser Gly Thr Pro Gly Gln Arg Val Thr Ile Ser Cys Ser Gly
                165                 170                 175

Ser Ser Ser Asn Ile Gly Ser Asn Tyr Val Tyr Trp Tyr Gln Gln Leu
            180                 185                 190

Pro Gly Thr Ala Pro Lys Leu Leu Ile Tyr Lys Asn Asn Gln Arg Pro
        195                 200                 205

Ser Gly Val Pro Asp Arg Phe Ser Gly Ser Lys Ser Gly Thr Ala Ala
    210                 215                 220

Ser Leu Ala Ile Ser Gly Leu Gln Ser Glu Asp Glu Ala Asp Tyr Tyr
225                 230                 235                 240

Cys Ala Ala Trp Asp Asp Ser Leu Arg Gly Tyr Val Phe Gly Thr Gly
                245                 250                 255

Thr Lys Leu Thr Val Leu Ser Gly
            260
```

<210> SEQ ID NO 32
<211> LENGTH: 256
<212> TYPE: PRT
<213> ORGANISM: Artificial Sequence
<220> FEATURE:
<223> OTHER INFORMATION: Synthetically generated peptide

<400> SEQUENCE: 32

```
Gln Val Gln Leu Val Glu Ser Glu Gly Gly Val Val Gln Pro Gly Arg
  1               5                  10                  15
Ser Leu Arg Leu Ser Cys Ala Ala Ser Gly Phe Thr Phe Ser Ser Tyr
             20                  25                  30
Ala Met His Trp Val Arg Gln Ala Pro Gly Lys Gly Leu Glu Trp Val
         35                  40                  45
Ala Val Val Ser Tyr Asp Gly Ser Gln Asp Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Pro Glu Asp Thr Gly Val Tyr Tyr Cys
                 85                  90                  95
Ala Lys Val Gly Arg Ser Ser Asn Trp Phe Ser Arg Tyr Tyr Tyr Tyr
            100                 105                 110
Gly Met Asp Val Trp Gly Gln Gly Thr Val Thr Val Ser Ser Gly
            115                 120                 125
Ile Leu Gly Ser Gly Gly Gly Ser Gly Gly Gly Ser Gly Gly
        130                 135                 140
Gly Gly Ser Glu Ile Val Leu Thr Gln Ser Pro Ala Thr Leu Ser Leu
145                 150                 155                 160
Ser Pro Gly Glu Arg Ala Thr Leu Ser Cys Arg Ala Ser Gln Ser Val
                165                 170                 175
Ser His Tyr Leu Ala Trp Tyr Gln Gln Lys Pro Gly Gln Ala Pro Arg
            180                 185                 190
Val Leu Ile Tyr Asp Val Ala Asn Arg Ala Ala Gly Thr Pro Ala Arg
        195                 200                 205
Phe Ser Gly Ser Gly Ser Gly Thr Asp Phe Thr Leu Thr Ile Ser Ser
    210                 215                 220
Leu Glu Pro Glu Asp Phe Ala Val Tyr Tyr Cys Gln Gln Arg Ser Asn
225                 230                 235                 240
Trp Pro Gln Thr Phe Gly Pro Gly Thr Lys Val Asp Ile Lys Ser Gly
                245                 250                 255
```

<210> SEQ ID NO 33
<211> LENGTH: 257
<212> TYPE: PRT
<213> ORGANISM: Artificial Sequence
<220> FEATURE:
<223> OTHER INFORMATION: Synthetically generated peptide

<400> SEQUENCE: 33

```
Gln Val Gln Leu Gln Gln Ser Gly Pro Gly Leu Val Lys Pro Ser Gln
  1               5                  10                  15
Thr Leu Ser Leu Thr Cys Ala Ile Ser Gly Asp Ser Val Ser Ser Asp
             20                  25                  30
Ser Ala Ala Trp Asn Trp Ile Arg Gln Ser Pro Ser Arg Gly Leu Glu
         35                  40                  45
Trp Leu Gly Arg Thr Tyr Tyr Arg Ser Lys Trp Tyr Asn Asp Tyr Ala
     50                  55                  60
Val Ser Val Lys Ser Arg Ile Ser Ile Asn Pro Asp Thr Ser Lys Asn
 65                  70                  75                  80
Gln Phe Ser Leu Gln Leu Asn Ser Val Thr Pro Glu Asp Thr Ala Val
                 85                  90                  95
Tyr Tyr Cys Ala Arg Ala Gln Asn Asn Ile Ala Val Ala Gly Phe Asp
```

```
            100                 105                 110
Tyr Trp Gly Leu Gly Thr Leu Val Thr Val Ser Ser Gly Ile Leu Gly
        115                 120                 125

Ser Gly Gly Gly Gly Ser Gly Gly Gly Ser Gly Gly Gly Gly Ser
130                 135                 140

Gln Pro Val Leu Thr Gln Ser Pro Ser Ala Ser Gly Thr Pro Gly Gln
145                 150                 155                 160

Arg Val Thr Ile Ser Cys Ser Gly Ser Ser Asn Ile Gly Ser Asn
                165                 170                 175

Tyr Val Tyr Trp Tyr Gln Gln Leu Pro Gly Thr Ala Pro Thr Leu Leu
        180                 185                 190

Ile Tyr Arg Asn Asn Gln Arg Pro Ser Gly Val Pro Asp Arg Phe Ser
        195                 200                 205

Gly Ser Lys Ser Gly Thr Ser Ala Ser Leu Ala Ile Ser Gly Leu Arg
        210                 215                 220

Ser Glu Asp Glu Ala Glu Tyr Tyr Cys Ala Ala Trp Asp Asp Ser Leu
225                 230                 235                 240

Ser Gly Val Phe Gly Thr Gly Thr Lys Val Thr Val Leu Ser Gly Ile
                245                 250                 255

Leu
```

<210> SEQ ID NO 34
<211> LENGTH: 257
<212> TYPE: PRT
<213> ORGANISM: Artificial Sequence
<220> FEATURE:
<223> OTHER INFORMATION: Synthetically generated peptide

<400> SEQUENCE: 34

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Gly Thr Tyr
            20                  25                  30

Ala Met His Trp Val Arg Gln Ala Pro Gly Lys Gly Leu Glu Trp Val
        35                  40                  45

Ala Val Ile Ser Asn Asp Gly Gly His Lys Tyr Tyr Ala Asp Ser Val
    50                  55                  60

Lys Gly Arg Phe Thr Ile Ser Arg Asp Asn Ser Lys Asp Ser Met Tyr
65                  70                  75                  80

Leu Gln Met Asn Ser Leu Arg Ala Glu Asp Thr Ala Val Tyr His Cys
            85                  90                  95

Ala Lys Gly Arg Pro Trp Tyr Asp Pro Gly Ala Glu Tyr Phe Gln His
        100                 105                 110

Trp Gly Gln Gly Thr Leu Val Thr Val Ser Ser Gly Ile Leu Gly Ser
        115                 120                 125

Gly Gly Gly Gly Ser Gly Gly Gly Ser Gly Gly Gly Gly Ser Gln
        130                 135                 140

Ser Ala Leu Ile Gln Pro Ala Ser Val Ser Gly Ser Pro Gly Gln Trp
145                 150                 155                 160

Ile Thr Ile Ser Cys Thr Gly Thr Ser Ser Asp Val Gly Gly Tyr Asn
                165                 170                 175

Tyr Val Ser Trp Tyr Gln Gln His Pro Gly Lys Ala Pro Lys Leu Leu
            180                 185                 190

Ile Tyr Asp Val Ser Asp Arg Pro Ser Gly Val Ser Asn Arg Phe Ser
        195                 200                 205
```

```
Gly Ser Lys Ser Gly Asn Thr Ala Ser Leu Thr Ile Ser Gly Leu Gln
    210                 215                 220

Ala Glu Asp Glu Ala Asp Tyr Tyr Cys Ser Ser Tyr Thr Ser Ser Asn
225                 230                 235                 240

Thr Val Leu Phe Gly Gly Thr Lys Leu Thr Val Leu Ser Gly Ile
                245                 250                 255

Leu

<210> SEQ ID NO 35
<211> LENGTH: 263
<212> TYPE: PRT
<213> ORGANISM: Artificial Sequence
<220> FEATURE:
<223> OTHER INFORMATION: Synthetically generated peptide

<400> SEQUENCE: 35

Gln Val Gln Leu Val Gln Ser Glu Gly Gly Val Val Arg Pro Gly Gly
  1               5                  10                  15

Ser Leu Arg Leu Ser Cys Ala Ala Ser Gly Phe Thr Phe Gly Asp Tyr
             20                  25                  30

Ala Met Gly Trp Val Arg Gln Ala Pro Gly Lys Gly Leu Glu Trp Val
         35                  40                  45

Ser Ser Ile Asn Trp Asn Gly Gly Ser Thr Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Val Ser Ser Gly Trp Pro Tyr Tyr Ser Leu Asp Val Trp Gly
            100                 105                 110

Gln Gly Thr Thr Val Thr Val Ser Ser Gly Ser Ala Ser Ala Pro Thr
        115                 120                 125

Gly Ile Leu Gly Ser Gly Gly Gly Gly Ser Gly Gly Gly Gly Ser Gly
    130                 135                 140

Gly Gly Gly Ser Gln Ser Ala Leu Ile Gln Pro Arg Ser Val Ser Gly
145                 150                 155                 160

Ser Pro Gly Gln Ser Val Thr Ile Ser Cys Thr Gly Thr Ser Ser Asp
                165                 170                 175

Val Gly Gly Tyr Asn Tyr Val Ser Trp Tyr Gln His His Pro Gly Lys
            180                 185                 190

Ala Pro Gln Leu Met Ile Tyr Asp Val Thr Lys Arg Pro Ser Gly Val
        195                 200                 205

Pro Asp Arg Phe Ser Gly Ser Lys Ser Gly Asn Thr Ala Ser Leu Thr
    210                 215                 220

Ile Ser Gly Leu Gln Ala Glu Asp Glu Ala Asp Tyr Tyr Cys Cys Ser
225                 230                 235                 240

Tyr Ala Gly Asp Tyr Thr Tyr Ala Val Phe Gly Thr Gly Thr Gln Leu
                245                 250                 255

Thr Val Leu Ser Gly Ile Leu
            260

<210> SEQ ID NO 36
<211> LENGTH: 257
<212> TYPE: PRT
<213> ORGANISM: Artificial Sequence
<220> FEATURE:
```

<223> OTHER INFORMATION: Synthetically generated peptide

<400> SEQUENCE: 36

```
Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Gly Tyr
            20                  25                  30

Ala Met His Trp Val Arg Gln Ala Pro Gly Lys Gly Leu Glu Trp Val
        35                  40                  45

Ala Ala Ile Ser Phe Asp Gly Asn Tyr Lys Tyr Tyr Ala Asp Ser Val
    50                  55                  60

Lys Gly Arg Phe Thr Val Ser Arg Asp Asn Ser Arg Asn Thr Leu Tyr
65                  70                  75                  80

Leu Gln Met Asn Ser Leu Lys Val Asp Asp Thr Ala Val Tyr Phe Cys
                85                  90                  95

Ala Arg Asp Lys Ser Gly His Phe Gly Met Asp Val Trp Gly Gln Gly
            100                 105                 110

Thr Thr Val Thr Val Ser Ser Ala Ser Thr Lys Gly Pro Ser Gly Ile
        115                 120                 125

Leu Gly Ser Gly Gly Gly Gly Ser Gly Gly Gly Ser Gly Gly Gly
    130                 135                 140

Gly Ser Glu Ile Val Met Thr Gln Ser Pro Gly Thr Leu Ser Leu Ser
145                 150                 155                 160

Pro Gly Glu Arg Ala Thr Leu Ser Cys Arg Ala Ser Gln Ser Val Ser
                165                 170                 175

Ser Ser Tyr Leu Ala Trp Tyr Gln Gln Lys Pro Gly Gln Ala Pro Arg
            180                 185                 190

Leu Leu Ile Tyr Gly Ala Ser Ser Arg Ala Thr Gly Ile Pro Asp Arg
        195                 200                 205

Phe Ser Gly Ser Gly Ser Gly Thr Asp Phe Thr Leu Thr Ile Ser Arg
    210                 215                 220

Leu Glu Pro Glu Asp Phe Ala Val Tyr Tyr Cys Gln Gln Tyr Gly Ser
225                 230                 235                 240

Pro Ile Thr Phe Gly Gln Gly Thr Arg Leu Glu Ile Lys Ser Gly Ile
                245                 250                 255

Leu
```

<210> SEQ ID NO 37
<211> LENGTH: 256
<212> TYPE: PRT
<213> ORGANISM: Artificial Sequence
<220> FEATURE:
<223> OTHER INFORMATION: Synthetically generated peptide

<400> SEQUENCE: 37

```
Gln Val Gln Leu Val Glu Ser Glu Gly Gly Val Val Gln Pro Gly Arg
 1               5                  10                  15

Pro Leu Arg Leu Ser Cys Ala Ala Ser Gly Phe Thr Phe Ser Ser His
            20                  25                  30

Ala Met His Trp Val Arg Gln Ala Pro Gly Lys Gly Leu Glu Trp Val
        35                  40                  45

Ala Val Val Ser His Asp Gly Ser Arg Asp Arg Tyr Ala Gly Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Pro Glu Asp Thr Gly Val Tyr Tyr Cys
                 85                  90                  95

Ala Arg Val Gly Arg Ser Ser Asn Trp Phe Ser Arg Tyr Tyr Tyr Tyr
            100                 105                 110

Gly Met Asp Val Trp Gly Gln Gly Thr Thr Val Thr Val Ser Ser Gly
        115                 120                 125

Ile Leu Gly Ser Gly Gly Gly Ser Gly Gly Asp Ser Gly Gly
    130             135             140

Gly Gly Ser Gly Ile Val Leu Thr Gln Ser Pro Ala Thr Leu Ser Leu
145             150                 155                 160

Pro Pro Arg Glu Arg Ala Thr Leu Ser Cys Gly Thr Ser Gln Asn Val
            165                 170                 175

Ser His Tyr Leu Ala Trp Tyr Gln Gln Lys Pro Gly Arg Ala Pro Arg
        180                 185                 190

Val Leu Thr Tyr Asp Val Ala Asn Arg Ala Ala Gly Thr Pro Ala Arg
    195                 200                 205

Phe Ser Gly Ser Gly Ser Gly Thr Asp Phe Thr Pro Ala Ile Ser Ser
    210             215                 220

Leu Glu Pro Glu Asp Phe Ala Val Tyr Tyr Cys Gln Gln Arg Ser Asn
225             230                 235                 240

Trp Pro Gln Ala Phe Gly Pro Gly Thr Lys Val Asp Ile Lys Ser Gly
                245                 250                 255
```

<210> SEQ ID NO 38
<211> LENGTH: 264
<212> TYPE: PRT
<213> ORGANISM: Artificial Sequence
<220> FEATURE:
<223> OTHER INFORMATION: Synthetically generated peptide

<400> SEQUENCE: 38

```
Gln Val Gln Leu Val Glu Ser Gly Gly Val Val Gln Pro Gly Arg
  1               5                  10                  15

Pro Leu Arg Leu Ser Cys Ala Ala Ser Gly Phe Ala Phe Ser Ser His
             20                  25                  30

Ala Met His Trp Val Arg Gln Ala Pro Gly Lys Gly Leu Glu Trp Val
         35                  40                  45

Ala Val Ile Ser His Asp Gly Ser Arg Asp Arg Tyr Ala Gly Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Gly Val Tyr Tyr Cys
                 85                  90                  95

Ala Arg Val Gly Arg Ser Ser Asn Trp Phe Ser Arg Tyr Tyr Tyr Tyr
            100                 105                 110

Asp Met Asp Val Trp Gly Gln Gly Thr Thr Val Thr Val Ser Ser Gly
        115                 120                 125

Ile Leu Gly Ser Gly Gly Gly Ser Gly Gly Asp Ser Gly Gly
    130             135             140

Gly Gly Ser Gly Ile Val Leu Thr Gln Ser Pro Ala Thr Leu Ser Leu
145             150                 155                 160

Pro Pro Arg Glu Arg Val Thr Leu Ser Cys Gly Thr Ser Gln Asn Val
            165                 170                 175

Ser His His Leu Ala Trp Tyr Gln Gln Lys Pro Gly Arg Ala Pro Arg
        180                 185                 190
```

```
Val Leu Thr Tyr Asp Val Ala Asn Lys Ala Ala Gly Thr Pro Ala Arg
            195                 200                 205

Phe Ser Gly Ser Gly Ser Glu Thr Asp Phe Thr Pro Ala Ile Ser Ser
        210                 215                 220

Leu Glu Pro Glu Asp Phe Ala Val Tyr Tyr Cys Gln Gln Arg Ser Asn
225                 230                 235                 240

Trp Pro Gln Ala Phe Ser Pro Gly Thr Lys Val Asp Ile Lys Ser Gly
                245                 250                 255

Ser Glu Gln Lys Leu Ile Ser Glu
            260

<210> SEQ ID NO 39
<211> LENGTH: 267
<212> TYPE: PRT
<213> ORGANISM: Artificial Sequence
<220> FEATURE:
<223> OTHER INFORMATION: Synthetically generated peptide

<400> SEQUENCE: 39

Gln Val Gln Leu Val Glu Ser Glu Gly Gly Val Val Gln Pro Gly Arg
  1               5                  10                  15

Pro Leu Arg Leu Ser Cys Ala Ala Ser Gly Phe Thr Phe Ser Ser His
            20                  25                  30

Ala Met His Trp Val Arg Gln Ala Pro Gly Lys Gly Leu Glu Trp Val
        35                  40                  45

Ala Val Val Ser His Asp Gly Ser Arg Asp Arg Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Gly Val Tyr Tyr Cys
                85                  90                  95

Ala Arg Val Gly Arg Ser Ser Asn Trp Phe Ser Arg Tyr His Tyr Tyr
            100                 105                 110

Gly Met Asp Val Trp Gly Gln Gly Thr Thr Val Thr Val Ser Ser Gly
        115                 120                 125

Ile Leu Gly Ser Gly Gly Gly Ser Gly Gly Asp Ser Gly Gly
    130                 135                 140

Gly Gly Ser Gly Ile Val Leu Thr Gln Ser Pro Ala Thr Leu Ser Leu
145                 150                 155                 160

Pro Pro Arg Glu Arg Ala Thr Leu Ser Cys Gly Thr Ser Gln Asn Val
                165                 170                 175

Ser His Tyr Leu Ala Trp Tyr Gln Gln Lys Pro Gly Arg Ala Pro Arg
            180                 185                 190

Val Leu Thr Tyr Asp Val Ala Asn Arg Ala Ala Gly Thr Pro Ala Arg
        195                 200                 205

Phe Ser Gly Ser Gly Ser Gly Thr Asp Phe Thr Pro Ala Ile Ser Ser
    210                 215                 220

Leu Glu Leu Glu Asp Phe Ala Val Tyr Tyr Cys Gln Gln Arg Ser Asn
225                 230                 235                 240

Trp Pro Gln Ala Phe Gly Pro Gly Thr Lys Val Asp Ile Lys Ser Gly
                245                 250                 255

Ser Glu Gln Lys Leu Ile Ser Glu Glu Ala Leu
            260                 265

<210> SEQ ID NO 40
<211> LENGTH: 266
```

<212> TYPE: PRT
<213> ORGANISM: Artificial Sequence
<220> FEATURE:
<223> OTHER INFORMATION: Synthetically generated peptide

<400> SEQUENCE: 40

```
Gln Val Gln Leu Gln Gln Ser Gly Pro Gly Pro Val Lys Pro Ser Gln
1               5                   10                  15

Thr Leu Ser Leu Thr Arg Ala Ile Pro Gly Asp Ser Val Ser Ser Asn
            20                  25                  30

Ser Ala Ala Trp Asn Trp Ile Arg Gln Phe Leu Ser Arg Gly Leu Glu
        35                  40                  45

Trp Leu Gly Arg Thr Tyr Tyr Arg Ser Lys Arg Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Thr Gly Tyr Ser Ser Trp Val Val Asn Phe
            100                 105                 110

Asp Tyr Trp Gly Gln Gly Thr Leu Val Thr Val Ser Ser Gly Ser Ala
        115                 120                 125

Ser Ala Pro Thr Gly Ile Leu Gly Phe Gly Gly Gly Ser Gly Gly
130                 135                 140

Gly Gly Ser Gly Gly Gly Ser Gln Ser Val Leu Thr Gln Ser Pro
145                 150                 155                 160

Ser Ala Ser Gly Thr Pro Gly Gln Arg Val Thr Ile Ser Cys Ser Gly
                165                 170                 175

Ser Ser Ser Asn Ile Gly Ser Asn Tyr Val Tyr Trp Tyr Gln Gln Leu
            180                 185                 190

Pro Gly Thr Ala Pro Lys Leu Leu Ile Tyr Lys Asp Asn Gln Arg Pro
        195                 200                 205

Ser Gly Val Pro Asp Arg Phe Ser Gly Ser Lys Ser Gly Thr Ala Ala
    210                 215                 220

Ser Leu Ala Ile Ser Gly Leu Gln Ser Glu Asp Glu Ala Asp Tyr Tyr
225                 230                 235                 240

Cys Ala Ala Trp Asp Asp Ser Leu Arg Gly Tyr Val Phe Gly Thr Gly
                245                 250                 255

Thr Lys Leu Thr Val Leu Ser Gly Ile Leu
            260                 265
```

<210> SEQ ID NO 41
<211> LENGTH: 264
<212> TYPE: PRT
<213> ORGANISM: Artificial Sequence
<220> FEATURE:
<223> OTHER INFORMATION: Synthetically generated peptide

<400> SEQUENCE: 41

```
Gln Val Gln Leu Gln Gln Pro Gly Pro Gly Leu Val Glu Pro Ser Gln
1               5                   10                  15

Thr Leu Pro Leu Thr Arg Ala Ile Ser Gly Asp Ser Val Ser Gly Asn
            20                  25                  30

Gly Ala Ala Trp Ser Trp Ile Arg Gln Pro Pro Arg Gly Leu Gly
        35                  40                  45

Trp Pro Gly Arg Thr Tyr Tyr Arg Pro Lys Arg Asn Gly Tyr Ala
    50                  55                  60
```

```
Val Pro Ala Lys Ser Arg Met Thr Ile Ser Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Thr Gly His Ser Ser Trp Val Val Ser Phe
            100                 105                 110

Asp His Trp Gly Gln Gly Ala Thr Ile Ser Ser Gly Asn Ala Ser Ala
            115                 120                 125

Pro Thr Gly Val Leu Gly Ser Gly Gly Gly Ser Gly Gly Gly Gly
    130                 135                 140

Ser Gly Gly Gly Ser Ser Gln Pro Val Pro Thr Gln Ser Pro Ser Ala
145                 150                 155                 160

Ser Gly Thr Pro Gly Gln Arg Val Thr Val Ser Cys Ser Gly Ser Ser
                165                 170                 175

Ser Asn Ile Glu Ser Asn Tyr Val Tyr Trp Tyr Gln Gln Leu Pro Gly
                180                 185                 190

Ala Ala Pro Arg Leu Phe Ile His Lys Asn Asn Gln Arg Pro Ser Gly
                195                 200                 205

Val Pro Asp Arg Ser Ser Ser Lys Ser Gly Thr Ala Ala Ser Leu
    210                 215                 220

Ala Ile Ser Gly Leu Gln Ser Lys Asp Glu Ala Asp Tyr Tyr Cys Ala
225                 230                 235                 240

Ala Trp Asp Asp Ser Leu Arg Ser Tyr Val Phe Gly Thr Gly Thr Lys
                245                 250                 255

Leu Thr Val Leu Ser Gly Ile Leu
                260

<210> SEQ ID NO 42
<211> LENGTH: 264
<212> TYPE: PRT
<213> ORGANISM: Artificial Sequence
<220> FEATURE:
<223> OTHER INFORMATION: Synthetically generated peptide

<400> SEQUENCE: 42

Gln Val Gln Leu Gln Arg Ser Gly Pro Gly Leu Val Lys Pro Pro Gln
 1               5                  10                  15

Ala Pro Ser Leu Thr Cys Ala Val Ser Gly Asp Ser Val Ser Ser Asn
                20                  25                  30

Ser Ala Ala Trp Asn Trp Ile Arg Gln Ser Leu Ser Arg Gly Leu Glu
            35                  40                  45

Trp Leu Gly Arg Ile His Tyr Gly Ser Arg Trp Tyr Asn Asp Tyr Ala
    50                  55                  60

Ala Ser Ala Lys Ser Arg Val Thr Ile Asn Pro Asp Thr Pro Lys Gly
 65                  70                  75                  80

Gln Leu Pro Pro Gln Leu Ser Pro Val Thr Pro Lys Asp Ala Ala Ala
                 85                  90                  95

Tyr Tyr Cys Ala Arg Thr Glu Cys Ser Ser Trp Val Val Asn Phe
            100                 105                 110

Gly Tyr Trp Gly Gln Gly Ala Pro Val Thr Asp Gly Ser Ala Pro Ala
            115                 120                 125

Pro Thr Gly Ile Leu Gly Pro Gly Gly Gly Ser Gly Gly Gly Gly
    130                 135                 140

Ser Gly Gly Gly Gly Pro Gln Pro Ala Leu Ile Gln Ser Pro Pro Val
145                 150                 155                 160
```

Ser Gly Thr Pro Gly Gln Arg Val Thr Ile Pro Cys Ser Gly Ser Ser
                165                 170                 175

Phe Asn Ile Gly Ser Asn His Val Tyr Trp His Gln Pro Pro Gly
            180                 185                 190

Thr Ala Pro Lys Leu Leu Val His Lys Ser Asn Gln Arg Pro Ser Gly
            195                 200                 205

Val Pro Asp Arg Ser Pro Gly Pro Arg Pro Gly Thr Ala Ala Ser Leu
    210                 215                 220

Ala Ile Ser Gly Leu Gln Ser Glu Asp Glu Ala Asp Tyr Tyr Cys Ala
225                 230                 235                 240

Ala Trp Asp Asp Ser Leu Arg Gly Tyr Val Leu Gly Ala Gly Thr Lys
                245                 250                 255

Leu Thr Ala Arg Ser Gly Ile Leu
            260

<210> SEQ ID NO 43
<211> LENGTH: 266
<212> TYPE: PRT
<213> ORGANISM: Artificial Sequence
<220> FEATURE:
<223> OTHER INFORMATION: Synthetically generated peptide

<400> SEQUENCE: 43

Gln Val Gln Leu Gln Gln Ser Gly Pro Gly Leu Val Lys Pro Ser Gln
1               5                   10                  15

Thr Leu Ser Leu Thr Cys Ala Ile Pro Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr His Arg Phe Lys Trp Tyr Asn Asp His Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Thr Gly Tyr Ser Ser Ser Trp Val Val Asn Phe
            100                 105                 110

Asp Tyr Trp Gly Gln Gly Thr Pro Val Thr Val Ser Ser Gly Ser Ala
        115                 120                 125

Ser Ala Pro Thr Gly Val Leu Gly Pro Gly Gly Gly Ser Gly Gly
    130                 135                 140

Gly Gly Ser Gly Gly Gly Ser Gln Pro Val Leu Thr Gln Pro Pro
145                 150                 155                 160

Ser Ala Ser Gly Thr Pro Gly Gln Arg Val Thr Ile Ser Cys Ser Gly
                165                 170                 175

Ser Ser Ser Asn Ile Gly Ser Asn Tyr Val Tyr Arg Tyr Gln Gln Leu
            180                 185                 190

Pro Gly Ala Ala Pro Lys Leu Leu Ile Tyr Lys Asn Asn Gln Arg Ser
        195                 200                 205

Ser Gly Val Pro Ala Arg Phe Ser Gly Pro Lys Ser Gly Ala Ala Ala
    210                 215                 220

Pro Leu Thr Thr Ser Gly Leu Gln Ser Gly Asp Glu Ala Gly Tyr Tyr
225                 230                 235                 240

Cys Ala Ala Trp Asp Asp Ser Leu Arg Gly Tyr Val Phe Gly Thr Gly
                245                 250                 255

```
Thr Lys Leu Thr Val Leu Ser Gly Ile Leu
            260                 265
```

<210> SEQ ID NO 44
<211> LENGTH: 264
<212> TYPE: PRT
<213> ORGANISM: Artificial Sequence
<220> FEATURE:
<223> OTHER INFORMATION: Synthetically generated peptide

<400> SEQUENCE: 44

```
Gln Val Gln Leu Gln Trp Ser Gly Pro Gly Leu Val Lys Pro Ser Gln
 1               5                  10                  15

Thr Leu Ser Leu Thr Arg Ala Ile Ser Gly Asn Ser Val Ser Ser Asn
            20                  25                  30

Ser Ala Ala Trp Ser Trp Ile Arg Gln Ser Leu Ser Arg Gly Leu Glu
        35                  40                  45

Trp Leu Gly Arg Thr Tyr Tyr Gly Ser Lys Arg Tyr Asn Asp Tyr Ala
    50                  55                  60

Val Ser Val Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Ala Ala Val
                85                  90                  95

Tyr Tyr Cys Ala Arg Thr Gly Tyr Ser Gly Ser Arg Val Val Asn Phe
            100                 105                 110

Gly Tyr Trp Gly Gln Gly Thr Leu Val Thr Val Ser Ser Gly Arg Ala
        115                 120                 125

Pro Ala Pro Thr Gly Ile Leu Gly Ser Gly Gly Gly Gly Ser Gly Gly
    130                 135                 140

Gly Gly Ser Gly Gly Gly Pro Gln Pro Val Leu Thr Gln Ser Pro
145                 150                 155                 160

Pro Ala Ser Gly Thr Pro Gly Gln Arg Val Thr Ile Ser Cys Ser Gly
                165                 170                 175

Ser Ser Ser Asn Ile Gly Ser Asn Tyr Val His Arg Tyr Gln Gln Pro
            180                 185                 190

Pro Gly Ala Ala Pro Glu Leu Leu Ile His Lys Asn Asn Gln Arg Pro
        195                 200                 205

Ser Gly Val Pro Asp Arg Phe Ser Gly Ser Lys Ser Gly Thr Ala Asp
    210                 215                 220

Ala Ile Ser Gly Pro Gln Ser Glu Asp Glu Ala Asn Tyr Tyr Cys Val
225                 230                 235                 240

Ala Trp Asp Asp Ser Pro Cys Gly Tyr Val Phe Gly Ala Gly Thr Lys
                245                 250                 255

Leu Thr Val Leu Ser Gly Ile Leu
            260
```

<210> SEQ ID NO 45
<211> LENGTH: 265
<212> TYPE: PRT
<213> ORGANISM: Artificial Sequence
<220> FEATURE:
<223> OTHER INFORMATION: Synthetically generated peptide

<400> SEQUENCE: 45

```
Gln Val Gln Leu Gln Gln Ser Gly Pro Gly Leu Val Lys Pro Ser Gln
 1               5                  10                  15

Thr Phe Ser Leu Thr Tyr Ala Val Ser Gly Gly Ser Ala Ser Ser Asn
```

-continued

```
                20                  25                  30
Ser Ala Ala Trp Asn Trp Ile Arg Gln Ser Leu Ser Arg Gly Leu Glu
             35                  40                  45

Trp Leu Gly Arg Thr Tyr Tyr Arg Ser Lys Trp Tyr Asn Asp Tyr Ala
 50                  55                  60

Val Ser Val Lys Ser Arg Thr Thr Ile Asn Pro Asp Thr Ser Lys Asn
 65                  70                  75                  80

Gln Phe Ser Leu Gln Leu Asn Ser Val Thr Pro Gly Asp Ala Ala Val
             85                  90                  95

Cys Tyr Cys Ala Gly Ala Gly Tyr Ser Ser Arg Ala Val Asn Phe
            100                 105                 110

Asp Cys Trp Gly Gln Gly Thr Leu Val Thr Val Ser Ser Gly Ser Ala
            115                 120                 125

Ser Thr Pro Thr Gly Ile Leu Gly Ser Gly Gly Ser Gly Gly
            130                 135                 140

Gly Pro Gly Gly Gly Ser Gln Pro Val Leu Thr Gln Ser Pro Ser
145                 150                 155                 160

Ala Ser Gly Thr Pro Gly Gln Arg Val Thr Ile Ser Cys Ser Gly Ser
            165                 170                 175

Ser Ser Asn Ile Gly Ser Asn Tyr Val Tyr Trp Tyr Gln Gln Leu Pro
            180                 185                 190

Gly Thr Ala Pro Lys Leu Leu Ile Tyr Lys Asn Asn Gln Arg Pro Ser
            195                 200                 205

Gly Val Pro Asp Arg Phe Ser Gly Ser Lys Ser Gly Thr Ala Ala Ser
210                 215                 220

Leu Ala Ile Ser Gly Leu Gln Pro Glu Gly Glu Ala Asp Tyr Tyr Cys
225                 230                 235                 240

Ala Ala Trp Asp Asp Ser Leu Arg Gly Tyr Val Leu Gly Thr Gly Thr
            245                 250                 255

Lys Leu Thr Val Leu Ser Gly Ile Leu
            260                 265

<210> SEQ ID NO 46
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 46

Ser Asn Ser Ala Ala Trp Asn
 1               5

<210> SEQ ID NO 47
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 47

Arg Thr Tyr Tyr Arg Ser Lys Trp Tyr Asn Asp Tyr Ala Val Ser Val
 1               5                  10                  15

Lys Ser

<210> SEQ ID NO 48
<211> LENGTH: 13
<212> TYPE: PRT
```

-continued

```
<213> ORGANISM: Artificial Sequence
<220> FEATURE:
<223> OTHER INFORMATION: Synthetically generated peptide

<400> SEQUENCE: 48

Thr Gly Tyr Ser Ser Ser Trp Val Val Asn Phe Asp Tyr
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 49

Ser Gly Ser Ser Ser Asn Ile Gly Ser Asn Tyr Val Tyr
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 50

Lys Leu Leu Ile Tyr Lys Asn Asn Gln Arg Pro Ser
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 51

Ala Ala Trp Asp Asp Ser Leu Arg Gly Tyr Val
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 52

Ser Tyr Ala Met His
1               5

<210> SEQ ID NO 53
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 53

Val Val Ser Tyr Asp Gly Ser Gln Asp Tyr Tyr Ala Asp Ser Val Lys
1               5                   10                  15

Gly

<210> SEQ ID NO 54
<211> LENGTH: 18
```

```
<212> TYPE: PRT
<213> ORGANISM: Artificial Sequence
<220> FEATURE:
<223> OTHER INFORMATION: Synthetically generated peptide

<400> SEQUENCE: 54

Val Gly Arg Ser Ser Asn Trp Phe Ser Arg Tyr Tyr Tyr Gly Met
 1               5                  10                  15

Asp Val

<210> SEQ ID NO 55
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 55

Arg Ala Ser Gln Ser Val Ser His Tyr Leu Ala
 1               5                  10

<210> SEQ ID NO 56
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 56

Asp Val Ala Asn Arg Ala Ala
 1               5

<210> SEQ ID NO 57
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 57

Gln Gln Arg Ser Asn Trp Pro Gln Thr
 1               5

<210> SEQ ID NO 58
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 58

Ser Asp Ser Ala Ala Trp Asn
 1               5

<210> SEQ ID NO 59
<211> LENGTH: 375
<212> TYPE: PRT
<213> ORGANISM: Artificial Sequence
<220> FEATURE:
<223> OTHER INFORMATION: Synthetically generated peptide

<400> SEQUENCE: 59

Gln Pro Val Leu Thr Gln Ser Pro Ser Ala Ser Gly Thr Pro Gly Gln
 1               5                  10                  15

Arg Val Thr Ile Pro Cys Ser Gly Ser Ser Ser Asn Ile Gly Ser Asn
                20                  25                  30
```

```
Tyr Val Tyr Trp Tyr Gln Gln Leu Pro Gly Thr Ala Pro Lys Leu Leu
         35                  40                  45

Ile Tyr Lys Asn Asn Gln Arg Pro Ser Gly Val Pro Asp Arg Phe Ser
 50                  55                  60

Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser Gly
            100                 105                 110

Ile Leu Gly Ser Gly Gly Gly Ser Gly Gly Gly Ser Gly Gly
        115                 120                 125

Gly Gly Ser Arg Pro Val Leu Thr Gln Ser Pro Ser Ala Ser Gly Thr
130                 135                 140

Pro Gly Gln Arg Val Thr Ile Pro Cys Ser Gly Ser Ser Ser Asn Ile
145                 150                 155                 160

Gly Ser Asn Tyr Val Tyr Trp Tyr Gln Gln Leu Pro Gly Thr Ala Pro
                165                 170                 175

Lys Leu Leu Ile Tyr Lys Asn Asn Gln Arg Pro Ser Gly Val Pro Asp
                180                 185                 190

Arg Phe Ser Gly Ser Lys Ser Gly Thr Ala Ala Ser Leu Ala Ile Ser
            195                 200                 205

Gly Leu Gln Ser Glu Asp Glu Ala Asp Tyr Tyr Cys Ala Ala Trp Asp
        210                 215                 220

Asp Ser Leu Arg Gly Tyr Val Phe Gly Thr Gly Thr Lys Leu Thr Val
225                 230                 235                 240

Leu Ser Gly Ile Leu Gly Ser Gly Gly Gly Ser Gly Gly Gly Gly
                245                 250                 255

Ser Gly Gly Gly Ser Arg Pro Val Leu Thr Gln Ser Pro Ser Ala
            260                 265                 270

Ser Gly Thr Pro Gly Gln Arg Val Thr Ile Pro Cys Ser Gly Ser Ser
        275                 280                 285

Ser Asn Ile Gly Ser Asn Tyr Val Tyr Trp Tyr Gln Gln Leu Pro Gly
290                 295                 300

Thr Ala Pro Lys Leu Leu Ile Tyr Lys Asn Asn Gln Arg Pro Ser Gly
305                 310                 315                 320

Val Pro Asp Arg Phe Ser Gly Ser Lys Ser Gly Thr Ala Ala Ser Leu
                325                 330                 335

Ala Ile Ser Gly Leu Gln Ser Glu Asp Glu Ala Asp Tyr Tyr Cys Ala
            340                 345                 350

Ala Trp Asp Asp Ser Leu Arg Gly Tyr Val Phe Gly Thr Gly Thr Arg
        355                 360                 365

Leu Thr Val Leu Ser Gly Ser
370                 375

<210> SEQ ID NO 60
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 60

Ala Gln Asn Asn Ile Ala Val Ala Gly Phe Asp Tyr
 1               5                  10
```

<210> SEQ ID NO 61
<211> LENGTH: 256
<212> TYPE: PRT
<213> ORGANISM: Artificial Sequence
<220> FEATURE:
<223> OTHER INFORMATION: Synthetically generated peptide

<400> SEQUENCE: 61

Gln Val Gln Leu Val Glu Ser Glu Gly Gly Val Val Gln Pro Gly Arg
 1               5                  10                  15

Pro Leu Arg Leu Ser Cys Ala Ala Ser Gly Phe Thr Phe Ser Ser His
            20                  25                  30

Ala Met His Trp Val Arg Gln Ala Pro Gly Lys Gly Leu Glu Trp Val
        35                  40                  45

Ala Val Val Ser His Asp Gly Ser Arg Asp Arg Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Gly Val Tyr Tyr Cys
                85                  90                  95

Ala Arg Val Gly Arg Ser Ser Asn Trp Phe Ser Arg Tyr Tyr Tyr Tyr
            100                 105                 110

Gly Met Asp Val Trp Gly Gln Gly Thr Thr Val Thr Val Ser Ser Gly
        115                 120                 125

Ile Leu Gly Ser Gly Gly Gly Ser Gly Gly Asp Ser Gly Gly
    130                 135                 140

Gly Gly Ser Gly Ile Val Leu Thr Gln Ser Pro Ala Thr Leu Ser Leu
145                 150                 155                 160

Pro Pro Arg Glu Arg Ala Thr Leu Ser Cys Gly Thr Ser Gln Asn Val
                165                 170                 175

Ser His Tyr Leu Ala Trp Tyr Gln Gln Lys Pro Gly Arg Ala Pro Arg
            180                 185                 190

Val Leu Thr Tyr Asp Val Ala Asn Arg Ala Ala Gly Thr Pro Ala Arg
        195                 200                 205

Phe Ser Gly Ser Gly Ser Gly Thr Asp Phe Thr Pro Ala Ile Ser Ser
    210                 215                 220

Leu Glu Pro Glu Asp Phe Ala Val Tyr Tyr Cys Gln Gln Arg Ser Asn
225                 230                 235                 240

Trp Pro Gln Ala Phe Gly Pro Gly Thr Lys Val Asp Ile Lys Ser Gly
                245                 250                 255

<210> SEQ ID NO 62
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 62

Thr Leu Leu Ile Tyr Arg Asn Asn Gln Arg Pro Ser
 1               5                  10

<210> SEQ ID NO 63
<211> LENGTH: 10
<212> TYPE: PRT
<213> ORGANISM: Artificial Sequence
<220> FEATURE:
<223> OTHER INFORMATION: Synthetically generated peptide

```
<400> SEQUENCE: 63

Ala Ala Trp Asp Asp Ser Leu Ser Gly Val
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 64

Thr Tyr Ala Met His
1               5

<210> SEQ ID NO 65
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 65

Val Ile Ser Asn Asp Gly Gly His Lys Tyr Tyr Ala Asp Ser Val Lys
1               5                   10                  15

Gly

<210> SEQ ID NO 66
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 66

Gly Arg Pro Trp Tyr Asp Pro Gly Ala Glu Tyr Phe Gln His
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 67

Thr Gly Thr Ser Ser Asp Val Gly Gly Tyr Asn Tyr Val Ser
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 68

Asp Val Ser Asp Arg Pro Ser
1               5

<210> SEQ ID NO 69
<211> LENGTH: 10
<212> TYPE: PRT
<213> ORGANISM: Artificial Sequence
<220> FEATURE:
```

<223> OTHER INFORMATION: Synthetically generated peptide

<400> SEQUENCE: 69

Ser Ser Tyr Thr Ser Ser Asn Thr Val Leu
1               5                   10

<210> SEQ ID NO 70
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 70

Asp Tyr Ala Met Gly
1               5

<210> SEQ ID NO 71
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 71

Ser Ile Asn Trp Asn Gly Gly Ser Thr Gly Tyr Ala Asp Ser Val Lys
1               5                   10                  15

Gly

<210> SEQ ID NO 72
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 72

Val Ser Ser Gly Trp Pro Tyr Tyr Ser Leu Asp Val
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 73

Thr Gly Thr Ser Ser Asp Val Gly Gly Tyr Asn Tyr Val Ser
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 74

Asp Val Thr Lys Arg Pro Ser
1               5

<210> SEQ ID NO 75
<211> LENGTH: 11
<212> TYPE: PRT
<213> ORGANISM: Artificial Sequence

```
<220> FEATURE:
<223> OTHER INFORMATION: Synthetically generated peptide

<400> SEQUENCE: 75

Cys Ser Tyr Ala Gly Asp Tyr Thr Tyr Ala Val
1               5                   10

<210> SEQ ID NO 76
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 76

Gly Tyr Ala Met His
1               5

<210> SEQ ID NO 77
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 77

Ala Ile Ser Phe Asp Gly Asn Tyr Lys Tyr Tyr Ala Asp Ser Val Lys
1               5                   10                  15

Gly

<210> SEQ ID NO 78
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 78

Asp Lys Ser Gly His Phe Gly Met Asp Val
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 79

Arg Ala Ser Gln Ser Val Ser Ser Ser Tyr Leu Ala
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 80

Gly Ala Ser Ser Arg Ala Thr
1               5

<210> SEQ ID NO 81
<211> LENGTH: 8
<212> TYPE: PRT
```

<213> ORGANISM: Artificial Sequence
<220> FEATURE:
<223> OTHER INFORMATION: Synthetically generated peptide

<400> SEQUENCE: 81

Gln Gln Tyr Gly Ser Pro Ile Thr
 1               5

<210> SEQ ID NO 82
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 82

Ser His Ala Met His
 1               5

<210> SEQ ID NO 83
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 83

Val Val Ser His Asp Gly Ser Arg Asp Arg Tyr Ala Gly Ser Val Lys
 1               5                  10                  15

Gly

<210> SEQ ID NO 84
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 84

Cys Gly Thr Ser Gln Asn Val Ser His Tyr Leu Ala
 1               5                  10

<210> SEQ ID NO 85
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 85

Gln Gln Arg Ser Asn Trp Pro Gln Ala
 1               5

<210> SEQ ID NO 86
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 86

Val Ile Ser His Asp Gly Ser Arg Asp Arg Tyr Ala Gly Ser Val Lys
 1               5                  10                  15

Gly

```
<210> SEQ ID NO 87
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 87

Val Gly Arg Ser Ser Asn Trp Phe Ser Arg Tyr Tyr Tyr Asp Met
 1               5                  10                  15

Asp Val

<210> SEQ ID NO 88
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 88

Gly Thr Ser Gln Asn Val Ser His His Leu Ala
 1               5                  10

<210> SEQ ID NO 89
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 89

Asp Val Ala Asn Lys Ala Ala
 1               5

<210> SEQ ID NO 90
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 90

Gln Gln Arg Ser Asn Trp Pro Gln Ala
 1               5

<210> SEQ ID NO 91
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 91

Val Gly Arg Ser Ser Asn Trp Phe Ser Arg Tyr His Tyr Tyr Gly Met
 1               5                  10                  15

Asp Val

<210> SEQ ID NO 92
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 92

Gly Thr Ser Gln Asn Val Ser His Tyr Leu Ala
```

-continued

```
1               5                   10
```

<210> SEQ ID NO 93
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 93

```
Gln Gln Arg Ser Asn Trp Pro Gln Ala
1               5
```

<210> SEQ ID NO 94
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 94

```
Ser Ser Asn Ser Ala Ala Trp Asn
1               5
```

<210> SEQ ID NO 95
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 95

```
Arg Thr Tyr Tyr Arg Ser Lys Arg Tyr Asn Asp Tyr Ala Val Ser Val
1               5                   10                  15

Lys Ser
```

<210> SEQ ID NO 96
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 96

```
Thr Gly Tyr Ser Ser Ser Trp Val Val Asn Phe Asp Tyr
1               5                   10
```

<210> SEQ ID NO 97
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 97

```
Arg Thr Tyr Tyr Arg Ser Lys Trp Tyr Asn Asp Tyr Ala Val Ser Val
1               5                   10                  15

Lys Ser Arg
```

<210> SEQ ID NO 98
<211> LENGTH: 12
<212> TYPE: PRT
<213> ORGANISM: Artificial Sequence
<220> FEATURE:
<223> OTHER INFORMATION: Synthetically generated peptide

```
<400> SEQUENCE: 98

Lys Leu Leu Ile Tyr Lys Asp Asn Gln Arg Pro Ser
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 99

Gly Asn Gly Ala Ala Trp Ser
1               5

<210> SEQ ID NO 100
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 100

Arg Thr Tyr Tyr Arg Pro Lys Arg Arg Asn Gly Tyr Ala Val Pro Ala
1               5                   10                  15

Lys Ser

<210> SEQ ID NO 101
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 101

Thr Gly His Ser Ser Ser Trp Val Val Ser Phe Asp His
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 102

Ser Gly Ser Ser Ser Asn Ile Glu Ser Asn Tyr Val Tyr
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 103

Arg Leu Phe Ile His Lys Asn Asn Gln Arg Pro Ser
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetically generated peptide
```

```
<400> SEQUENCE: 104

Ala Ala Trp Asp Asp Ser Leu Arg Ser Tyr Val
1               5                   10

<210> SEQ ID NO 105
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 105

Arg Ile His Tyr Gly Ser Arg Trp Tyr Asn Asp Tyr Ala Ala Ser Ala
1               5                   10                  15

Lys Ser

<210> SEQ ID NO 106
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 106

Thr Glu Cys Ser Ser Ser Trp Val Val Asn Phe Gly Tyr
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 107

Ser Gly Ser Ser Phe Asn Ile Gly Ser Asn His Val Tyr
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 108

Lys Leu Leu Val His Lys Ser Asn Gln Arg Pro Ser
1               5                   10

<210> SEQ ID NO 109
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 109

Arg Thr Tyr His Arg Phe Lys Trp Tyr Asn Asp His Ala Val Ser Val
1               5                   10                  15

Lys Ser

<210> SEQ ID NO 110
<211> LENGTH: 12
<212> TYPE: PRT
```

```
<213> ORGANISM: Artificial Sequence
<220> FEATURE:
<223> OTHER INFORMATION: Synthetically generated peptide

<400> SEQUENCE: 110

Lys Leu Leu Ile Tyr Lys Asn Asn Gln Arg Ser Ser
 1               5                  10

<210> SEQ ID NO 111
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 111

Ser Asn Ser Ala Ala Trp Ser
 1               5

<210> SEQ ID NO 112
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 112

Arg Thr Tyr Tyr Gly Ser Lys Arg Tyr Asn Asp Tyr Ala Val Ser Val
 1               5                  10                  15

Lys Ser

<210> SEQ ID NO 113
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 113

Thr Gly Tyr Ser Gly Ser Arg Val Val Asn Phe Gly Tyr
 1               5                  10

<210> SEQ ID NO 114
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 114

Ser Gly Ser Ser Ser Asn Ile Gly Ser Asn Tyr Val His
 1               5                  10

<210> SEQ ID NO 115
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 115

Glu Leu Leu Ile His Lys Asn Asn Gln Arg Pro Ser
 1               5                  10

<210> SEQ ID NO 116
<211> LENGTH: 11
```

```
<212> TYPE: PRT
<213> ORGANISM: Artificial Sequence
<220> FEATURE:
<223> OTHER INFORMATION: Synthetically generated peptide

<400> SEQUENCE: 116

Val Ala Trp Asp Asp Ser Pro Cys Gly Tyr Val
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 117

Ala Gly Tyr Ser Ser Ser Arg Ala Val Asn Phe Asp Cys
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 118

Thr Gly Tyr Ser Ser Ser Trp Val Val Asn Phe Asp Tyr
1               5                   10

<210> SEQ ID NO 119
<211> LENGTH: 131
<212> TYPE: PRT
<213> ORGANISM: Artificial Sequence
<220> FEATURE:
<223> OTHER INFORMATION: Synthetically generated peptide

<400> SEQUENCE: 119

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ile
            20                  25                  30

Thr Ala Ala Trp Asn Trp Leu Arg Gln Ser Pro Ser Arg Gly Leu Glu
        35                  40                  45

Trp Leu Gly Arg Thr Tyr His Arg Ser Lys Trp Tyr Tyr Asp Tyr Ala
    50                  55                  60

Val Ser Val Lys Ser Arg Ile Thr Val Asn Pro Asp Thr Ser Lys Asn
65                  70                  75                  80

Gln Phe Ser Leu His Leu Asn Ser Val Thr Pro Glu Asp Thr Ala Val
                85                  90                  95

Tyr Tyr Cys Arg Leu Ala Arg Gly Gly Pro Ser Ala His Ala Phe Glu
            100                 105                 110

Ile Trp Gly Gln Gly Thr Met Val Thr Val Ser Ser Ala Ser Thr Lys
        115                 120                 125

Gly Pro Ser
    130

<210> SEQ ID NO 120
<211> LENGTH: 111
<212> TYPE: PRT
<213> ORGANISM: Artificial Sequence
<220> FEATURE:
```

-continued

<223> OTHER INFORMATION: Synthetically generated peptide

<400> SEQUENCE: 120

Gln Pro Val Leu Thr Gln Ser Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Thr Ala Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Arg Gly Tyr Val Phe Gly Thr Gly Thr Lys Leu Thr Val Leu Ser
            100                 105                 110

<210> SEQ ID NO 121
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 121

Gln Val Gln Leu Gln Gln Ser Gly Pro Gly Leu Val Lys Pro Ser Gln
1               5                   10                  15

Thr Leu Ser Leu Thr Cys Val Ile Ser Gly Asp Ser Val Ser Asn Asn
            20                  25                  30

Ser Ala Val Trp Asn Trp Ile Arg Gln Ser Leu Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Ile Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Arg Thr Gly Ala Gly Val Asp Tyr Trp Gly Gln
            100                 105                 110

Gly Thr Leu Val Thr Val Ser Ser
        115                 120

<210> SEQ ID NO 122
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 122

Gln Pro Val Leu Thr Gln Ser Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Lys Asn Asn Gln Arg Pro Ser Gly Val Pro Asp Arg Phe Ser

```
                    50                  55                  60
Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser
                100                 105                 110

<210> SEQ ID NO 123
<211> LENGTH: 124
<212> TYPE: PRT
<213> ORGANISM: Artificial Sequence
<220> FEATURE:
<223> OTHER INFORMATION: Synthetically generated peptide

<400> SEQUENCE: 123

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Gly Val Ser Gly Asn
                 20                  25                  30

Asn Val Ile Trp Asn Trp Ile Arg Gln Ser Pro Ser Arg Gly Leu Glu
                 35                  40                  45

Trp Leu Gly Arg Thr Tyr Tyr Arg Ser Lys Trp Tyr Tyr Asp Leu Leu
     50                  55                  60

Pro Ser Val Lys Ser Arg Ile Ala Ile Asn Pro Asp Thr Ser Lys Ser
 65                  70                  75                  80

Gln Phe Ser Leu Gln Leu Ser Ser Val Thr Pro Glu Asp Thr Ala Val
                 85                  90                  95

Tyr Tyr Cys Ala Arg Thr Arg Ala Val Ala Gly Asn Gln Tyr Phe Asp
                100                 105                 110

Leu Trp Gly Arg Gly Thr Leu Val Thr Val Ser Ser
            115                 120

<210> SEQ ID NO 124
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 124

Gln Pro Val Leu Thr Gln Ser Pro Ser Ala Ser Gly Thr Pro Gly Gln
  1               5                  10                  15

Arg Val Thr Ile Ser Cys Ser Gly Ser Ser Asn Ile Gly Ser Asn
                 20                  25                  30

Tyr Val Tyr Trp Tyr Gln Gln Leu Pro Gly Thr Ala Pro Lys Leu Leu
                 35                  40                  45

Ile Tyr Lys Asn Asn Gln Arg Pro Ser Gly Val Pro Asp Arg Phe Ser
     50                  55                  60

Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser
                100                 105                 110

<210> SEQ ID NO 125
<211> LENGTH: 129
```

```
<212> TYPE: PRT
<213> ORGANISM: Artificial Sequence
<220> FEATURE:
<223> OTHER INFORMATION: Synthetically generated peptide

<400> SEQUENCE: 125

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Tyr
             20                  25                  30

Ser Ala Ala Trp Asn Trp Ile Arg Gln Ser Leu Ser Arg Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Ser Leu Ala Ala Ala Gly Thr Val Asp Tyr Trp
            100                 105                 110

Gly Gln Gly Thr Leu Val Thr Val Ser Ser Gly Ser Ala Ser Ala Pro
                115                 120                 125

Thr

<210> SEQ ID NO 126
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 126

Gln Pro Val Leu Thr Gln Ser Pro Ser Ala Ser Gly Thr Pro Gly Gln
  1               5                  10                  15

Arg Val Thr Ile Ser Cys Ser Gly Ser Ser Ser Asn Ile Gly Ser Asn
             20                  25                  30

Tyr Val Tyr Trp Tyr Gln Gln Leu Pro Gly Thr Ala Pro Lys Leu Leu
         35                  40                  45

Ile Tyr Lys Asn Asn Gln Arg Pro Ser Gly Val Pro Asp Arg Phe Ser
     50                  55                  60

Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser
            100                 105                 110

<210> SEQ ID NO 127
<211> LENGTH: 126
<212> TYPE: PRT
<213> ORGANISM: Artificial Sequence
<220> FEATURE:
<223> OTHER INFORMATION: Synthetically generated peptide

<400> SEQUENCE: 127

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30
```

```
Ser Ala Ala Trp Asn Trp Ile Arg Gln Ser Leu Ser Arg Gly Leu Glu
            35                  40                  45

Trp Leu Gly Arg Thr Tyr Tyr Arg Ser Lys Trp Tyr Asn Asp Tyr Ala
    50                  55                  60

Leu Ser Val Lys Ser Arg Ile Asn Ile Asn Ala Asp Thr Ser Lys Ser
65                  70                  75                  80

Gln Phe Ser Leu Gln Leu Asp Ser Val Thr Pro Glu Asp Thr Ala Val
                85                  90                  95

Tyr Phe Cys Ala Lys Asp Arg Leu Leu Tyr Asn Tyr Gly Ser Asn Ala
                100                 105                 110

Met Asp Val Trp Gly Gln Gly Thr Thr Val Thr Val Ser Ser
                115                 120                 125

<210> SEQ ID NO 128
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 128

Gln Pro Val Leu Thr Gln Ser Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
            35                  40                  45

Ile Tyr Lys Asn Asn Gln Arg Pro Ser Gly Val Pro Asp Arg Phe Ser
        50                  55                  60

Gly Ser Lys Ser Gly Thr Ala Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Arg Gly Tyr Val Phe Gly Thr Gly Thr Lys Leu Thr Val Leu Ser
                100                 105                 110

<210> SEQ ID NO 129
<211> LENGTH: 136
<212> TYPE: PRT
<213> ORGANISM: Artificial Sequence
<220> FEATURE:
<223> OTHER INFORMATION: Synthetically generated peptide

<400> SEQUENCE: 129

Gln Val Gln Leu Gln Gln Ser Gly Pro Gly Leu Val Lys Pro Ser Glu
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Leu Ser Arg Gly Leu Glu
            35                  40                  45

Trp Leu Gly Arg Thr Tyr Tyr Arg Ser Lys Trp Tyr Asn Asp Tyr Ala
            50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Thr Pro Arg Tyr Cys Ser Gly Gly Ser Cys
```

```
                    100                 105                 110
Tyr Lys Tyr Phe Asp Tyr Trp Gly Gln Gly Thr Leu Val Thr Val Ser
            115                 120                 125

Ser Ala Ser Thr Lys Ser Pro Ser
        130                 135

<210> SEQ ID NO 130
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 130

Gln Pro Val Leu Thr Gln Ser Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Lys Asn Asn Gln Arg Pro Ser Gly Val Pro Asp Arg Phe Ser
50                  55                  60

Gly Ser Lys Ser Gly Thr Ala Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Arg Gly Tyr Val Phe Gly Thr Gly Thr Lys Leu Thr Val Leu Ser
            100                 105                 110

<210> SEQ ID NO 131
<211> LENGTH: 124
<212> TYPE: PRT
<213> ORGANISM: Artificial Sequence
<220> FEATURE:
<223> OTHER INFORMATION: Synthetically generated peptide

<400> SEQUENCE: 131

Gln Val Gln Leu Gln Gln Ser Gly Pro Gly Leu Val Lys Ser Ser Gln
1               5                   10                  15

Thr Leu Ser Leu Thr Cys Ala Ile Ser Gly Asp Ser Val Ser Ser Lys
            20                  25                  30

Gly Ala Ala Trp Asn Trp Ile Arg Gln Ser Pro Ser Arg Gly Leu Glu
        35                  40                  45

Trp Leu Gly Arg Ala Tyr Tyr Trp Ser Lys Trp Tyr Tyr Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Leu Thr Pro Glu Asp Thr Ala Val
                85                  90                  95

Phe Tyr Cys Arg Ala Thr Ser Thr Tyr Tyr Leu Pro Gly Gly Leu Asp
            100                 105                 110

Val Trp Gly Gln Gly Thr Thr Val Thr Val Ser Ser
        115                 120

<210> SEQ ID NO 132
<211> LENGTH: 111
<212> TYPE: PRT
<213> ORGANISM: Artificial Sequence
<220> FEATURE:
```

-continued

<223> OTHER INFORMATION: Synthetically generated peptide

<400> SEQUENCE: 132

Gln Pro Val Leu Thr Gln Ser Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Thr Ala Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Arg Gly Tyr Val Phe Gly Thr Gly Thr Lys Leu Thr Val Leu Ser
            100                 105                 110

<210> SEQ ID NO 133
<211> LENGTH: 121
<212> TYPE: PRT
<213> ORGANISM: Artificial Sequence
<220> FEATURE:
<223> OTHER INFORMATION: Synthetically generated peptide

<400> SEQUENCE: 133

Gln Val Gln Leu Gln Gln Ser Gly Ala Gly Leu Val Lys Pro Ser Gln
1               5                   10                  15

Thr Leu Ser Leu Thr Cys Thr Ile Ser Gly Asp Ser Val Ser Ala Asp
            20                  25                  30

Arg Val Ala Trp Asn Trp Ile Arg Gln Ser Pro Leu Arg Gly Leu Glu
        35                  40                  45

Trp Leu Gly Arg Ile Phe Tyr Arg Ser Lys Trp Met Val Asp Tyr Ala
    50                  55                  60

Val Ser Val Lys Ser Arg Ile Ser Ile Asn Pro Asp Thr Ser Lys Asn
65                  70                  75                  80

Gln Phe Ser Leu Gln Leu Asn Ser Val Thr Pro Glu Asp Thr Ala Met
                85                  90                  95

Tyr Tyr Cys Ala Arg Ala Thr Arg Gly Tyr Phe Asp Leu Trp Gly
            100                 105                 110

Arg Gly Thr Leu Val Thr Val Ser Ser
        115                 120

<210> SEQ ID NO 134
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 134

Gln Pro Val Leu Thr Gln Ser Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Lys Asn Asn Gln Arg Pro Ser Gly Val Pro Asp Arg Phe Ser

```
                50                  55                  60
Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser
                100                 105                 110

<210> SEQ ID NO 135
<211> LENGTH: 123
<212> TYPE: PRT
<213> ORGANISM: Artificial Sequence
<220> FEATURE:
<223> OTHER INFORMATION: Synthetically generated peptide

<400> SEQUENCE: 135

Gln Val Gln Leu Gln Gln Ser Gly Pro Gly Leu Val Lys Pro Ser Gln
  1               5                  10                  15

Thr Leu Ser Leu Thr Cys Val Val Ser Gly Asp Gly Val Ser Ser Asn
                 20                  25                  30

Ser Ala Ala Trp Asn Trp Ile Arg Gln Ser Leu Ser Arg Gly Leu Glu
                 35                  40                  45

Trp Leu Gly Arg Thr Tyr Tyr Arg Ser Lys Trp Tyr Asn Asp Tyr Ala
 50                  55                  60

Val Ser Met Lys Gly Arg Ile Thr Ile Asn Pro Asp Thr Ser Lys Asn
 65                  70                  75                  80

Gln Phe Ser Leu Gln Leu Asp Ser Val Thr Pro Glu Asp Thr Ala Val
                 85                  90                  95

Tyr Tyr Cys Ala Arg Arg Ser Gly Arg Thr Gly Gly Tyr Phe Asp Leu
                100                 105                 110

Trp Gly Arg Gly Thr Leu Val Ala Val Ser Ser
            115                 120

<210> SEQ ID NO 136
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 136

Gln Pro Val Leu Thr Gln Ser Pro Ser Ala Ser Gly Thr Pro Gly Gln
  1               5                  10                  15

Arg Val Thr Ile Ser Cys Ser Gly Ser Ser Asn Ile Gly Ser Asn
                 20                  25                  30

Tyr Val Tyr Trp Tyr Gln Gln Leu Pro Gly Thr Ala Pro Lys Leu Leu
                 35                  40                  45

Ile Tyr Lys Asn Asn Gln Arg Pro Ser Gly Val Pro Asp Arg Phe Ser
 50                  55                  60

Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser
                100                 105                 110

<210> SEQ ID NO 137
<211> LENGTH: 120
```

```
<212> TYPE: PRT
<213> ORGANISM: Artificial Sequence
<220> FEATURE:
<223> OTHER INFORMATION: Synthetically generated peptide

<400> SEQUENCE: 137

Gln Val Gln Leu Gln Gln Ser Gly Pro Gly Leu Val Lys Pro Ser Gln
1               5                   10                  15

Thr Leu Ser Leu Thr Cys Ala Ile Pro Gly His Ser Val Gly Ser Ser
            20                  25                  30

Asn Ala Ala Trp Asn Trp Ile Arg Gln Ser Pro Ser Arg Gly Leu Glu
        35                  40                  45

Trp Leu Gly Arg Ile Phe Tyr Gly Ser Lys Trp Tyr Asn Asp Tyr Ala
    50                  55                  60

Val Ser Leu Lys Ser Arg Leu Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Arg Thr Gly Thr Gly Ile Asp Tyr Trp Gly Gln
            100                 105                 110

Gly Thr Leu Val Thr Val Ser Ser
            115                 120

<210> SEQ ID NO 138
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 138

Gln Pro Val Leu Thr Gln Ser Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Thr Ala Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Arg Gly Tyr Val Phe Gly Thr Gly Thr Lys Leu Thr Val Leu Ser
            100                 105                 110

<210> SEQ ID NO 139
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 139

Gln Val Gln Leu Gln Gln Ser Gly Pro Gly Leu Val Lys Pro Ser Gln
1               5                   10                  15

Thr Leu Ser Leu Thr Cys Ala Ile Ser Gly His Ser Val Gly Ser Ser
            20                  25                  30

Asn Ala Ala Trp Asn Trp Ile Arg Gln Ser Pro Ser Arg Gly Leu Glu
```

```
                35                  40                  45
Trp Leu Gly Arg Ile Phe Tyr Arg Ser Lys Trp Tyr Asn Asp Tyr Ala
    50                  55                  60

Val Ser Val Lys Thr Arg Ile Ser Ile Asn Pro Asp Thr Ala Lys Asn
65                  70                  75                  80

Gln Phe Ser Leu His Leu Asn Ser Val Thr Ala Glu Asp Thr Gly Val
                85                  90                  95

Tyr Tyr Cys Arg Gln Gln Lys Arg Leu Asp Ser Trp Gly Gln Gly Thr
            100                 105                 110

Leu Val Thr Val Ser Ser
        115

<210> SEQ ID NO 140
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 140

Gln Pro Val Leu Thr Gln Ser Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Thr Ala Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Arg Gly Tyr Val Phe Gly Thr Gly Thr Lys Leu Thr Val Leu Ser
            100                 105                 110

<210> SEQ ID NO 141
<211> LENGTH: 132
<212> TYPE: PRT
<213> ORGANISM: Artificial Sequence
<220> FEATURE:
<223> OTHER INFORMATION: Synthetically generated peptide

<400> SEQUENCE: 141

Pro Val Gln Leu Gln Gln Ser Gly Pro Gly Leu Val Lys Pro Ser Gln
1               5                   10                  15

Thr Leu Ser Leu Pro Cys Ala Ile Ser Gly Asp Ser Val Ser Ser Asn
            20                  25                  30

Ser Ala Ala Trp Asn Trp Ile Arg Gln Ser Leu Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Asp Asp Thr Ala Ile
                85                  90                  95

Tyr Tyr Cys Ala Arg Ala Ser Asp Tyr Gly Asp Tyr Phe Tyr Tyr Phe
            100                 105                 110
```

Asp Tyr Trp Gly Gln Gly Thr Leu Val Thr Val Ser Ser Gly Ser Ala
            115                 120                 125

Ser Ala Pro Thr
        130

<210> SEQ ID NO 142
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 142

Gln Pro Val Leu Thr Gln Ser Pro Ser Ala Ser Gly Thr Pro Gly Gln
  1               5                  10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
                35                  40                  45

Ile Tyr Lys Asn Asn Gln Arg Pro Ser Gly Val Pro Asp Arg Phe Ser
         50                  55                  60

Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser
               100                 105                 110

<210> SEQ ID NO 143
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 143

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
                35                  40                  45

Trp Leu Gly Arg Ile Tyr Tyr Arg Ser Lys Trp Tyr Tyr Asp Tyr Ala
         50                  55                  60

Val Ser Val Lys Ser Arg Ile Ala Ile Lys Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Arg Ala Gly Arg Ser Phe Asp Leu Trp Gly Arg Gly Thr
               100                 105                 110

Leu Val Thr Val Ser Ser Gly Ser Ala Ser Ala Pro Thr
            115                 120                 125

<210> SEQ ID NO 144
<211> LENGTH: 111
<212> TYPE: PRT
<213> ORGANISM: Artificial Sequence
<220> FEATURE:
<223> OTHER INFORMATION: Synthetically generated peptide

```
<400> SEQUENCE: 144

Gln Pro Val Leu Thr Gln Ser Pro Ser Ala Ser Gly Thr Pro Gly Gln
  1               5                  10                  15

Arg Val Thr Ile Ser Cys Ser Gly Ser Ser Asn Ile Gly Ser Asn
             20                  25                  30

Tyr Val Tyr Trp Tyr Gln Gln Leu Pro Gly Thr Ala Pro Lys Leu Leu
             35                  40                  45

Ile Tyr Lys Asn Asn Gln Arg Pro Ser Gly Val Pro Asp Arg Phe Ser
 50                  55                  60

Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser
                100                 105                 110

<210> SEQ ID NO 145
<211> LENGTH: 128
<212> TYPE: PRT
<213> ORGANISM: Artificial Sequence
<220> FEATURE:
<223> OTHER INFORMATION: Synthetically generated peptide

<400> SEQUENCE: 145

Gln Val Gln Leu Gln Gln Ser Ser Pro Gly Leu Val Lys Pro Ser Gln
  1               5                  10                  15

Thr Leu Ser Leu Thr Cys Ala Val Ser Gly Asp Ser Val Ser Gly Asn
             20                  25                  30

Ser Gly Val Trp Asn Trp Ile Arg Gln Ser Pro Ser Arg Gly Leu Glu
             35                  40                  45

Trp Leu Gly Arg Thr Tyr Tyr Tyr Thr Tyr Lys Trp Tyr Ile Asp Tyr
 50                  55                  60

Ala Val Ser Val Lys Ser Arg Ile Thr Val Asn Pro Asp Thr Ser Arg
 65                  70                  75                  80

Asn Gln Phe Ser Leu Gln Leu Asn Ser Val Thr Pro Glu Asp Thr Ala
                 85                  90                  95

Val Tyr Tyr Cys Ala Arg Val Asp Tyr Thr Gly Ser Pro Val Trp Gly
                100                 105                 110

Gln Gly Thr Leu Val Thr Val Ser Ser Gly Ser Ala Ser Ala Pro Thr
            115                 120                 125

<210> SEQ ID NO 146
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 146

Gln Pro Val Leu Thr Gln Ser Pro Ser Ala Ser Gly Thr Pro Gly Gln
  1               5                  10                  15

Arg Val Thr Ile Ser Cys Ser Gly Ser Ser Asn Ile Gly Ser Asn
             20                  25                  30

Tyr Val Tyr Trp Tyr Gln Gln Leu Pro Gly Thr Ala Pro Lys Leu Leu
             35                  40                  45

Ile Tyr Lys Asn Asn Gln Arg Pro Ser Gly Val Pro Asp Arg Phe Ser
 50                  55                  60
```

```
Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser
            100                 105                 110

<210> SEQ ID NO 147
<211> LENGTH: 132
<212> TYPE: PRT
<213> ORGANISM: Artificial Sequence
<220> FEATURE:
<223> OTHER INFORMATION: Synthetically generated peptide

<400> SEQUENCE: 147

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Leu Ser Arg Gly Leu Glu
             35                  40                  45

Trp Leu Gly Arg Thr Tyr Tyr Arg Ser Lys Trp Tyr Asn Asp Tyr Ala
 50                  55                  60

Val Ser Val Arg Gly Arg Ile Thr Ile Asn Ala Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Thr Gly Tyr Ser Ser Ser Trp Val Val Asn Phe
            100                 105                 110

Asp Tyr Trp Gly Gln Gly Thr Leu Val Thr Val Ser Ser Gly Ser Ala
            115                 120                 125

Ser Ala Pro Thr
            130

<210> SEQ ID NO 148
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 148

Gln Pro Val Leu Thr Gln Ser Pro Ser Ala Ser Gly Thr Pro Gly Gln
  1               5                  10                  15

Arg Val Thr Ile Ser Cys Ser Gly Ser Ser Ser Asn Ile Gly Ser Asn
             20                  25                  30

Tyr Val Tyr Trp Tyr Gln Gln Leu Pro Gly Thr Ala Pro Lys Leu Leu
             35                  40                  45

Ile Tyr Lys Asn Asn Gln Arg Pro Ser Gly Val Pro Asp Arg Phe Ser
 50                  55                  60

Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu Ser
            100                 105                 110

<210> SEQ ID NO 149
```

<211> LENGTH: 265
<212> TYPE: PRT
<213> ORGANISM: Artificial Sequence
<220> FEATURE:
<223> OTHER INFORMATION: Synthetically generated peptide

<400> SEQUENCE: 149

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Ile
            20                  25                  30

Thr Ala Ala Trp Asn Trp Leu Arg Gln Ser Pro Ser Arg Gly Leu Glu
        35                  40                  45

Trp Leu Gly Arg Thr Tyr His Arg Ser Lys Trp Tyr Tyr Asp Tyr Ala
    50                  55                  60

Val Ser Val Lys Ser Arg Ile Thr Val Asn Pro Asp Thr Ser Lys Asn
 65                  70                  75                  80

Gln Phe Ser Leu His Leu Asn Ser Val Thr Pro Glu Asp Thr Ala Val
                85                  90                  95

Tyr Tyr Cys Arg Leu Ala Arg Gly Gly Pro Ser Ala His Ala Phe Glu
            100                 105                 110

Ile Trp Gly Gln Gly Thr Met Val Thr Val Ser Ser Ala Ser Thr Lys
        115                 120                 125

Gly Pro Ser Gly Ile Leu Gly Ser Gly Gly Gly Ser Gly Gly Gly
    130                 135                 140

Gly Ser Gly Gly Gly Ser Gln Pro Val Leu Thr Gln Ser Pro Ser
145                 150                 155                 160

Ala Ser Gly Thr Pro Gly Gln Arg Val Thr Ile Ser Cys Ser Gly Ser
                165                 170                 175

Ser Ser Asn Ile Gly Ser Asn Tyr Val Tyr Trp Tyr Gln Gln Leu Pro
            180                 185                 190

Gly Thr Ala Pro Lys Leu Leu Ile Tyr Lys Asn Asn Gln Arg Pro Ser
        195                 200                 205

Gly Val Pro Asp Arg Phe Ser Gly Ser Lys Ser Gly Thr Ala Ala Ser
    210                 215                 220

Leu Ala Ile Ser Gly Leu Gln Ser Glu Asp Glu Ala Asp Tyr Tyr Cys
225                 230                 235                 240

Ala Ala Trp Asp Asp Ser Leu Arg Gly Tyr Val Phe Gly Thr Gly Thr
                245                 250                 255

Lys Leu Thr Val Leu Ser Gly Ile Leu
            260                 265
```

<210> SEQ ID NO 150
<211> LENGTH: 254
<212> TYPE: PRT
<213> ORGANISM: Artificial Sequence
<220> FEATURE:
<223> OTHER INFORMATION: Synthetically generated peptide

<400> SEQUENCE: 150

```
Gln Val Gln Leu Gln Gln Ser Gly Pro Gly Leu Val Lys Pro Ser Gln
 1               5                  10                  15

Thr Leu Ser Leu Thr Cys Val Ile Ser Gly Asp Ser Val Ser Asn Asn
            20                  25                  30

Ser Ala Val Trp Asn Trp Ile Arg Gln Ser Leu Ser Arg Gly Leu Glu
        35                  40                  45

Trp Leu Gly Arg Thr Tyr Tyr Arg Ser Lys Trp Tyr Asn Asp Tyr Ala
```

```
                 50                  55                  60
Val Ser Val Lys Ser Arg Ile Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Arg Thr Gly Ala Gly Val Asp Tyr Trp Gly Gln
                100                 105                 110

Gly Thr Leu Val Thr Val Ser Ser Gly Ile Leu Gly Ser Gly Gly
                115                 120                 125

Gly Ser Gly Gly Gly Ser Gly Gly Gly Ser Gln Pro Val Leu
130                 135                 140

Thr Gln Ser Pro Ser Ala Ser Gly Thr Pro Gly Gln Arg Val Thr Ile
145                 150                 155                 160

Ser Cys Ser Gly Ser Ser Ser Asn Ile Gly Ser Asn Tyr Val Tyr Trp
                165                 170                 175

Tyr Gln Gln Leu Pro Gly Thr Ala Pro Lys Leu Leu Ile Tyr Lys Asn
                180                 185                 190

Asn Gln Arg Pro Ser Gly Val Pro Asp Arg Phe Ser Gly Ser Lys Ser
                195                 200                 205

Gly Thr Ala Ala Ser Leu Ala Ile Ser Gly Leu Gln Ser Glu Asp Glu
                210                 215                 220

Ala Asp Tyr Tyr Cys Ala Ala Trp Asp Asp Ser Leu Arg Gly Tyr Val
225                 230                 235                 240

Phe Gly Thr Gly Thr Lys Leu Thr Val Leu Ser Gly Ile Leu
                245                 250

<210> SEQ ID NO 151
<211> LENGTH: 258
<212> TYPE: PRT
<213> ORGANISM: Artificial Sequence
<220> FEATURE:
<223> OTHER INFORMATION: Synthetically generated peptide

<400> SEQUENCE: 151

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Gly Val Ser Gly Asn
                20                  25                  30

Asn Val Ile Trp Asn Trp Ile Arg Gln Ser Pro Ser Arg Gly Leu Glu
                35                  40                  45

Trp Leu Gly Arg Thr Tyr Tyr Arg Ser Lys Trp Tyr Tyr Asp Leu Leu
                50                  55                  60

Pro Ser Val Lys Ser Arg Ile Ala Ile Asn Pro Asp Thr Ser Lys Ser
 65                 70                  75                  80

Gln Phe Ser Leu Gln Leu Ser Ser Val Thr Pro Glu Asp Thr Ala Val
                85                  90                  95

Tyr Tyr Cys Ala Arg Thr Arg Ala Val Ala Gly Asn Gln Tyr Phe Asp
                100                 105                 110

Leu Trp Gly Arg Gly Thr Leu Val Thr Val Ser Ser Gly Ile Leu Gly
                115                 120                 125

Ser Gly Gly Gly Gly Ser Gly Gly Gly Ser Gly Gly Gly Ser
                130                 135                 140

Gln Pro Val Leu Thr Gln Ser Pro Ser Ala Ser Gly Thr Pro Gly Gln
145                 150                 155                 160

Arg Val Thr Ile Ser Cys Ser Gly Ser Ser Ser Asn Ile Gly Ser Asn
```

```
              165                 170                 175
Tyr Val Tyr Trp Tyr Gln Gln Leu Pro Gly Thr Ala Pro Lys Leu Leu
            180                 185                 190

Ile Tyr Lys Asn Asn Gln Arg Pro Ser Gly Val Pro Asp Arg Phe Ser
        195                 200                 205

Gly Ser Lys Ser Gly Thr Ala Ala Ser Leu Ala Ile Ser Gly Leu Gln
    210                 215                 220

Ser Glu Asp Glu Ala Asp Tyr Tyr Cys Ala Ala Trp Asp Ser Leu
225                 230                 235                 240

Arg Gly Tyr Val Phe Gly Thr Gly Thr Lys Leu Thr Val Leu Ser Gly
                245                 250                 255

Ile Leu

<210> SEQ ID NO 152
<211> LENGTH: 263
<212> TYPE: PRT
<213> ORGANISM: Artificial Sequence
<220> FEATURE:
<223> OTHER INFORMATION: Synthetically generated peptide

<400> SEQUENCE: 152

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Tyr
            20                  25                  30

Ser Ala Ala Trp Asn Trp Ile Arg Gln Ser Leu Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Ser Leu Ala Ala Ala Gly Thr Val Asp Tyr Trp
            100                 105                 110

Gly Gln Gly Thr Leu Val Thr Val Ser Ser Gly Ser Ala Ser Ala Pro
        115                 120                 125

Thr Gly Ile Leu Gly Ser Gly Gly Gly Ser Gly Gly Gly Ser
    130                 135                 140

Gly Gly Gly Gly Ser Gln Pro Val Leu Thr Gln Ser Pro Ser Ala Ser
145                 150                 155                 160

Gly Thr Pro Gly Gln Arg Val Thr Ile Ser Cys Ser Gly Ser Ser Ser
                165                 170                 175

Asn Ile Gly Ser Asn Tyr Val Tyr Trp Tyr Gln Gln Leu Pro Gly Thr
            180                 185                 190

Ala Pro Lys Leu Leu Ile Tyr Lys Asn Asn Gln Arg Pro Ser Gly Val
        195                 200                 205

Pro Asp Arg Phe Ser Gly Ser Lys Ser Gly Thr Ala Ala Ser Leu Ala
    210                 215                 220

Ile Ser Gly Leu Gln Ser Glu Asp Glu Ala Asp Tyr Tyr Cys Ala Ala
225                 230                 235                 240

Trp Asp Ser Leu Arg Gly Tyr Val Phe Gly Thr Gly Thr Lys Leu
                245                 250                 255

Thr Val Leu Ser Gly Ile Leu
            260
```

<210> SEQ ID NO 153
<211> LENGTH: 260
<212> TYPE: PRT
<213> ORGANISM: Artificial Sequence
<220> FEATURE:
<223> OTHER INFORMATION: Synthetically generated peptide

<400> SEQUENCE: 153

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Leu Ser Arg Gly Leu Glu
         35                  40                  45

Trp Leu Gly Arg Thr Tyr Tyr Arg Ser Lys Trp Tyr Asn Asp Tyr Ala
     50                  55                  60

Leu Ser Val Lys Ser Arg Ile Asn Ile Asn Ala Asp Thr Ser Lys Ser
 65                  70                  75                  80

Gln Phe Ser Leu Gln Leu Asp Ser Val Thr Pro Glu Asp Thr Ala Val
                 85                  90                  95

Tyr Phe Cys Ala Lys Asp Arg Leu Leu Tyr Asn Tyr Gly Ser Asn Ala
            100                 105                 110

Met Asp Val Trp Gly Gln Gly Thr Thr Val Thr Val Ser Ser Gly Ile
        115                 120                 125

Leu Gly Ser Gly Gly Gly Gly Ser Gly Gly Gly Gly Ser Gly Gly Gly
    130                 135                 140

Gly Ser Gln Pro Val Leu Thr Gln Ser Pro Ser Ala Ser Gly Thr Pro
145                 150                 155                 160

Gly Gln Arg Val Thr Ile Ser Cys Ser Gly Ser Ser Ser Asn Ile Gly
                165                 170                 175

Ser Asn Tyr Val Tyr Trp Tyr Gln Gln Leu Pro Gly Thr Ala Pro Lys
            180                 185                 190

Leu Leu Ile Tyr Lys Asn Asn Gln Arg Pro Ser Gly Val Pro Asp Arg
        195                 200                 205

Phe Ser Gly Ser Lys Ser Gly Thr Ala Ala Ser Leu Ala Ile Ser Gly
    210                 215                 220

Leu Gln Ser Glu Asp Glu Ala Asp Tyr Tyr Cys Ala Ala Trp Asp Asp
225                 230                 235                 240

Ser Leu Arg Gly Tyr Val Phe Gly Thr Gly Thr Lys Leu Thr Val Leu
                245                 250                 255

Ser Gly Ile Leu
            260
```

<210> SEQ ID NO 154
<211> LENGTH: 270
<212> TYPE: PRT
<213> ORGANISM: Artificial Sequence
<220> FEATURE:
<223> OTHER INFORMATION: Synthetically generated peptide

<400> SEQUENCE: 154

```
Gln Val Gln Leu Gln Gln Ser Gly Pro Gly Leu Val Lys Pro Ser Glu
  1               5                  10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Leu Ser Arg Gly Leu Glu
```

```
            35                  40                  45
Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Thr Pro Arg Tyr Cys Ser Gly Gly Ser Cys
            100                 105                 110

Tyr Lys Tyr Phe Asp Tyr Trp Gly Gln Gly Thr Leu Val Thr Val Ser
            115                 120                 125

Ser Ala Ser Thr Lys Ser Pro Ser Gly Ile Leu Gly Ser Gly Gly Gly
            130                 135                 140

Gly Ser Gly Gly Gly Ser Gly Gly Gly Ser Gln Pro Val Leu
145                 150                 155                 160

Thr Gln Ser Pro Ser Ala Ser Gly Thr Pro Gly Gln Arg Val Thr Ile
                165                 170                 175

Ser Cys Ser Gly Ser Ser Asn Ile Gly Ser Asn Tyr Val Tyr Trp
            180                 185                 190

Tyr Gln Gln Leu Pro Gly Thr Ala Pro Lys Leu Leu Ile Tyr Lys Asn
            195                 200                 205

Asn Gln Arg Pro Ser Gly Val Pro Asp Arg Phe Ser Gly Ser Lys Ser
    210                 215                 220

Gly Thr Ala Ala Ser Leu Ala Ile Ser Gly Leu Gln Ser Glu Asp Glu
225                 230                 235                 240

Ala Asp Tyr Tyr Cys Ala Ala Trp Asp Ser Leu Arg Gly Tyr Val
            245                 250                 255

Phe Gly Thr Gly Thr Lys Leu Thr Val Leu Ser Gly Ile Leu
            260                 265                 270

<210> SEQ ID NO 155
<211> LENGTH: 258
<212> TYPE: PRT
<213> ORGANISM: Artificial Sequence
<220> FEATURE:
<223> OTHER INFORMATION: Synthetically generated peptide

<400> SEQUENCE: 155

Gln Val Gln Leu Gln Gln Ser Gly Pro Gly Leu Val Lys Ser Ser Gln
1               5                   10                  15

Thr Leu Ser Leu Thr Cys Ala Ile Ser Gly Asp Ser Val Ser Ser Lys
                20                  25                  30

Gly Ala Ala Trp Asn Trp Ile Arg Gln Ser Pro Ser Arg Gly Leu Glu
            35                  40                  45

Trp Leu Gly Arg Ala Tyr Tyr Trp Ser Lys Trp Tyr Tyr Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Leu Thr Pro Glu Asp Thr Ala Val
                85                  90                  95

Phe Tyr Cys Arg Ala Thr Ser Thr Tyr Tyr Leu Pro Gly Gly Leu Asp
            100                 105                 110

Val Trp Gly Gln Gly Thr Thr Val Thr Val Ser Ser Gly Ile Leu Gly
            115                 120                 125

Ser Gly Gly Gly Gly Ser Gly Gly Gly Gly Ser Gly Gly Gly Gly Ser
```

```
              130                 135                 140
Gln Pro Val Leu Thr Gln Ser Pro Ser Ala Ser Gly Thr Pro Gly Gln
145                 150                 155                 160

Arg Val Thr Ile Ser Cys Ser Gly Ser Ser Asn Ile Gly Ser Asn
                165                 170                 175

Tyr Val Tyr Trp Tyr Gln Gln Leu Pro Gly Thr Ala Pro Lys Leu Leu
                180                 185                 190

Ile Tyr Lys Asn Asn Gln Arg Pro Ser Gly Val Pro Asp Arg Phe Ser
                195                 200                 205

Gly Ser Lys Ser Gly Thr Ala Ala Ser Leu Ala Ile Ser Gly Leu Gln
                210                 215                 220

Ser Glu Asp Glu Ala Asp Tyr Tyr Cys Ala Ala Trp Asp Asp Ser Leu
225                 230                 235                 240

Arg Gly Tyr Val Phe Gly Thr Gly Thr Lys Leu Thr Val Leu Ser Gly
                245                 250                 255

Ile Leu

<210> SEQ ID NO 156
<211> LENGTH: 255
<212> TYPE: PRT
<213> ORGANISM: Artificial Sequence
<220> FEATURE:
<223> OTHER INFORMATION: Synthetically generated peptide

<400> SEQUENCE: 156

Gln Val Gln Leu Gln Gln Ser Gly Ala Gly Leu Val Lys Pro Ser Gln
1               5                   10                  15

Thr Leu Ser Leu Thr Cys Thr Ile Ser Gly Asp Ser Val Ser Ala Asp
                20                  25                  30

Arg Val Ala Trp Asn Trp Ile Arg Gln Ser Pro Leu Arg Gly Leu Glu
            35                  40                  45

Trp Leu Gly Arg Ile Phe Tyr Arg Ser Lys Trp Met Val Asp Tyr Ala
        50                  55                  60

Val Ser Val Lys Ser Arg Ile Ser Ile Asn Pro Asp Thr Ser Lys Asn
65                  70                  75                  80

Gln Phe Ser Leu Gln Leu Asn Ser Val Thr Pro Glu Asp Thr Ala Met
                85                  90                  95

Tyr Tyr Cys Ala Arg Ala Thr Thr Arg Gly Tyr Phe Asp Leu Trp Gly
            100                 105                 110

Arg Gly Thr Leu Val Thr Val Ser Ser Gly Ile Leu Gly Ser Gly Gly
            115                 120                 125

Gly Gly Ser Gly Gly Gly Gly Ser Gly Gly Gly Gly Ser Gln Pro Val
        130                 135                 140

Leu Thr Gln Ser Pro Ser Ala Ser Gly Thr Pro Gly Gln Arg Val Thr
145                 150                 155                 160

Ile Ser Cys Ser Gly Ser Ser Asn Ile Gly Ser Asn Tyr Val Tyr
                165                 170                 175

Trp Tyr Gln Gln Leu Pro Gly Thr Ala Pro Lys Leu Leu Ile Tyr Lys
                180                 185                 190

Asn Asn Gln Arg Pro Ser Gly Val Pro Asp Arg Phe Ser Gly Ser Lys
                195                 200                 205

Ser Gly Thr Ala Ala Ser Leu Ala Ile Ser Gly Leu Gln Ser Glu Asp
            210                 215                 220

Glu Ala Asp Tyr Tyr Cys Ala Ala Trp Asp Asp Ser Leu Arg Gly Tyr
225                 230                 235                 240
```

Val Phe Gly Thr Gly Thr Lys Leu Thr Val Leu Ser Gly Ile Leu
                245                 250                 255

<210> SEQ ID NO 157
<211> LENGTH: 257
<212> TYPE: PRT
<213> ORGANISM: Artificial Sequence
<220> FEATURE:
<223> OTHER INFORMATION: Synthetically generated peptide

<400> SEQUENCE: 157

Gln Val Gln Leu Gln Gln Ser Gly Pro Gly Leu Val Lys Pro Ser Gln
1               5                   10                  15

Thr Leu Ser Leu Thr Cys Val Val Ser Gly Asp Gly Val Ser Ser Asn
            20                  25                  30

Ser Ala Ala Trp Asn Trp Ile Arg Gln Ser Leu Ser Arg Gly Leu Glu
        35                  40                  45

Trp Leu Gly Arg Thr Tyr Tyr Arg Ser Lys Trp Tyr Asn Asp Tyr Ala
50                  55                  60

Val Ser Met Lys Gly Arg Ile Thr Ile Asn Pro Asp Thr Ser Lys Asn
65                  70                  75                  80

Gln Phe Ser Leu Gln Leu Asp Ser Val Thr Pro Glu Asp Thr Ala Val
                85                  90                  95

Tyr Tyr Cys Ala Arg Arg Ser Gly Arg Thr Gly Tyr Phe Asp Leu
            100                 105                 110

Trp Gly Arg Gly Thr Leu Val Ala Val Ser Ser Gly Ile Leu Gly Ser
            115                 120                 125

Gly Gly Gly Gly Ser Gly Gly Gly Ser Gly Gly Gly Gly Ser Gln
130                 135                 140

Pro Val Leu Thr Gln Ser Pro Ser Ala Ser Gly Thr Pro Gly Gln Arg
145                 150                 155                 160

Val Thr Ile Ser Cys Ser Gly Ser Ser Asn Ile Gly Ser Asn Tyr
            165                 170                 175

Val Tyr Trp Tyr Gln Gln Leu Pro Gly Thr Ala Pro Lys Leu Leu Ile
            180                 185                 190

Tyr Lys Asn Asn Gln Arg Pro Ser Gly Val Pro Asp Arg Phe Ser Gly
            195                 200                 205

Ser Lys Ser Gly Thr Ala Ala Ser Leu Ala Ile Ser Gly Leu Gln Ser
210                 215                 220

Glu Asp Glu Ala Asp Tyr Tyr Cys Ala Ala Trp Asp Asp Ser Leu Arg
225                 230                 235                 240

Gly Tyr Val Phe Gly Thr Gly Thr Lys Leu Thr Val Leu Ser Gly Ile
                245                 250                 255

Leu

<210> SEQ ID NO 158
<211> LENGTH: 254
<212> TYPE: PRT
<213> ORGANISM: Artificial Sequence
<220> FEATURE:
<223> OTHER INFORMATION: Synthetically generated peptide

<400> SEQUENCE: 158

Gln Val Gln Leu Gln Gln Ser Gly Pro Gly Leu Val Lys Pro Ser Gln
1               5                   10                  15

Thr Leu Ser Leu Thr Cys Ala Ile Pro Gly His Ser Val Gly Ser Ser
            20                  25                  30

```
Asn Ala Ala Trp Asn Trp Ile Arg Gln Ser Pro Ser Arg Gly Leu Glu
            35                  40                  45

Trp Leu Gly Arg Ile Phe Tyr Gly Ser Lys Trp Tyr Asn Asp Tyr Ala
 50                  55                  60

Val Ser Leu Lys Ser Arg Leu Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Arg Thr Gly Thr Gly Ile Asp Tyr Trp Gly Gln
            100                 105                 110

Gly Thr Leu Val Thr Val Ser Ser Gly Ile Leu Gly Ser Gly Gly Gly
            115                 120                 125

Gly Ser Gly Gly Gly Ser Gly Gly Gly Ser Gln Pro Val Leu
            130                 135                 140

Thr Gln Ser Pro Ser Ala Ser Gly Thr Pro Gly Gln Arg Val Thr Ile
145                 150                 155                 160

Ser Cys Ser Gly Ser Ser Asn Ile Gly Ser Asn Tyr Val Tyr Trp
            165                 170                 175

Tyr Gln Gln Leu Pro Gly Thr Ala Pro Lys Leu Leu Ile Tyr Lys Asn
            180                 185                 190

Asn Gln Arg Pro Ser Gly Val Pro Asp Arg Phe Ser Gly Ser Lys Ser
            195                 200                 205

Gly Thr Ala Ala Ser Leu Ala Ile Ser Gly Leu Gln Ser Glu Asp Glu
 210                 215                 220

Ala Asp Tyr Tyr Cys Ala Ala Trp Asp Asp Ser Leu Arg Gly Tyr Val
225                 230                 235                 240

Phe Gly Thr Gly Thr Lys Leu Thr Val Leu Ser Gly Ile Leu
            245                 250

<210> SEQ ID NO 159
<211> LENGTH: 252
<212> TYPE: PRT
<213> ORGANISM: Artificial Sequence
<220> FEATURE:
<223> OTHER INFORMATION: Synthetically generated peptide

<400> SEQUENCE: 159

Gln Val Gln Leu Gln Gln Ser Gly Pro Gly Leu Val Lys Pro Ser Gln
 1               5                  10                  15

Thr Leu Ser Leu Thr Cys Ala Ile Ser Gly His Ser Val Gly Ser Ser
            20                  25                  30

Asn Ala Ala Trp Asn Trp Ile Arg Gln Ser Pro Ser Arg Gly Leu Glu
            35                  40                  45

Trp Leu Gly Arg Ile Phe Tyr Arg Ser Lys Trp Tyr Asn Asp Tyr Ala
 50                  55                  60

Val Ser Val Lys Thr Arg Ile Ser Ile Asn Pro Asp Thr Ala Lys Asn
 65                  70                  75                  80

Gln Phe Ser Leu His Leu Asn Ser Val Thr Ala Glu Asp Thr Gly Val
                 85                  90                  95

Tyr Tyr Cys Arg Gln Gln Lys Arg Leu Asp Ser Trp Gly Gln Gly Thr
            100                 105                 110

Leu Val Thr Val Ser Ser Gly Ile Leu Gly Ser Gly Gly Gly Gly Ser
            115                 120                 125

Gly Gly Gly Gly Ser Gly Gly Gly Ser Gln Pro Val Leu Thr Gln
            130                 135                 140
```

```
Ser Pro Ser Ala Ser Gly Thr Pro Gly Gln Arg Val Thr Ile Ser Cys
145                 150                 155                 160

Ser Gly Ser Ser Ser Asn Ile Gly Ser Asn Tyr Val Tyr Trp Tyr Gln
            165                 170                 175

Gln Leu Pro Gly Thr Ala Pro Lys Leu Leu Ile Tyr Lys Asn Asn Gln
        180                 185                 190

Arg Pro Ser Gly Val Pro Asp Arg Phe Ser Gly Ser Lys Ser Gly Thr
            195                 200                 205

Ala Ala Ser Leu Ala Ile Ser Gly Leu Gln Ser Glu Asp Glu Ala Asp
    210                 215                 220

Tyr Tyr Cys Ala Ala Trp Asp Asp Ser Leu Arg Gly Tyr Val Phe Gly
225                 230                 235                 240

Thr Gly Thr Lys Leu Thr Val Leu Ser Gly Ile Leu
            245                 250
```

<210> SEQ ID NO 160
<211> LENGTH: 266
<212> TYPE: PRT
<213> ORGANISM: Artificial Sequence
<220> FEATURE:
<223> OTHER INFORMATION: Synthetically generated peptide

<400> SEQUENCE: 160

```
Pro Val Gln Leu Gln Gln Ser Gly Pro Gly Leu Val Lys Pro Ser Gln
1               5                   10                  15

Thr Leu Ser Leu Pro Cys Ala Ile Ser Gly Asp Ser Val Ser Ser Asn
            20                  25                  30

Ser Ala Ala Trp Asn Trp Ile Arg Gln Ser Leu Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Asp Asp Thr Ala Ile
            85                  90                  95

Tyr Tyr Cys Ala Arg Ala Ser Asp Tyr Gly Asp Tyr Phe Tyr Tyr Phe
        100                 105                 110

Asp Tyr Trp Gly Gln Gly Thr Leu Val Thr Val Ser Ser Gly Ser Ala
    115                 120                 125

Ser Ala Pro Thr Gly Ile Leu Gly Ser Gly Gly Gly Gly Ser Gly Gly
130                 135                 140

Gly Gly Ser Gly Gly Gly Ser Gln Pro Val Leu Thr Gln Ser Pro
145                 150                 155                 160

Ser Ala Ser Gly Thr Pro Gly Gln Arg Val Thr Ile Ser Cys Ser Gly
            165                 170                 175

Ser Ser Ser Asn Ile Gly Ser Asn Tyr Val Tyr Trp Tyr Gln Gln Leu
        180                 185                 190

Pro Gly Thr Ala Pro Lys Leu Leu Ile Tyr Lys Asn Asn Gln Arg Pro
    195                 200                 205

Ser Gly Val Pro Asp Arg Phe Ser Gly Ser Lys Ser Gly Thr Ala Ala
    210                 215                 220

Ser Leu Ala Ile Ser Gly Leu Gln Ser Glu Asp Glu Ala Asp Tyr Tyr
225                 230                 235                 240

Cys Ala Ala Trp Asp Asp Ser Leu Arg Gly Tyr Val Phe Gly Thr Gly
            245                 250                 255
```

Thr Lys Leu Thr Val Leu Ser Gly Ile Leu
            260                 265

<210> SEQ ID NO 161
<211> LENGTH: 259
<212> TYPE: PRT
<213> ORGANISM: Artificial Sequence
<220> FEATURE:
<223> OTHER INFORMATION: Synthetically generated peptide

<400> SEQUENCE: 161

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Lys Trp Tyr Tyr Asp Tyr Ala
    50                  55                  60

Val Ser Val Lys Ser Arg Ile Ala Ile Lys Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Arg Ala Gly Arg Ser Phe Asp Leu Trp Gly Arg Gly Thr
            100                 105                 110

Leu Val Thr Val Ser Ser Gly Ser Ala Ser Ala Pro Thr Gly Ile Leu
        115                 120                 125

Gly Ser Gly Gly Gly Ser Gly Gly Gly Ser Gly Gly Gly Gly Gly Gly
    130                 135                 140

Ser Gln Pro Val Leu Thr Gln Ser Pro Ser Ala Ser Gly Thr Pro Gly
145                 150                 155                 160

Gln Arg Val Thr Ile Ser Cys Ser Gly Ser Ser Ser Asn Ile Gly Ser
                165                 170                 175

Asn Tyr Val Tyr Trp Tyr Gln Gln Leu Pro Gly Thr Ala Pro Lys Leu
            180                 185                 190

Leu Ile Tyr Lys Asn Asn Gln Arg Pro Ser Gly Val Pro Asp Arg Phe
        195                 200                 205

Ser Gly Ser Lys Ser Gly Thr Ala Ala Ser Leu Ala Ile Ser Gly Leu
    210                 215                 220

Gln Ser Glu Asp Glu Ala Asp Tyr Tyr Cys Ala Ala Trp Asp Asp Ser
225                 230                 235                 240

Leu Arg Gly Tyr Val Phe Gly Thr Gly Thr Lys Leu Thr Val Leu Ser
                245                 250                 255

Gly Ile Leu

<210> SEQ ID NO 162
<211> LENGTH: 262
<212> TYPE: PRT
<213> ORGANISM: Artificial Sequence
<220> FEATURE:
<223> OTHER INFORMATION: Synthetically generated peptide

<400> SEQUENCE: 162

Gln Val Gln Leu Gln Gln Ser Ser Pro Gly Leu Val Lys Pro Ser Gln
 1               5                  10                  15

Thr Leu Ser Leu Thr Cys Ala Val Ser Gly Asp Ser Val Ser Gly Asn
            20                  25                  30

```
Ser Gly Val Trp Asn Trp Ile Arg Gln Ser Pro Ser Arg Gly Leu Glu
            35                  40                  45

Trp Leu Gly Arg Thr Tyr Tyr Thr Tyr Lys Trp Tyr Ile Asp Tyr
        50                  55                  60

Ala Val Ser Val Lys Ser Arg Ile Thr Val Asn Pro Asp Thr Ser Arg
 65                  70                  75                  80

Asn Gln Phe Ser Leu Gln Leu Asn Ser Val Thr Pro Glu Asp Thr Ala
                85                  90                  95

Val Tyr Tyr Cys Ala Arg Val Asp Tyr Thr Gly Ser Pro Val Trp Gly
                100                 105                 110

Gln Gly Thr Leu Val Thr Val Ser Ser Gly Ser Ala Ser Ala Pro Thr
            115                 120                 125

Gly Ile Leu Gly Ser Gly Gly Gly Ser Gly Gly Gly Ser Gly
            130                 135                 140

Gly Gly Gly Ser Gln Pro Val Leu Thr Gln Ser Pro Ser Ala Ser Gly
145                 150                 155                 160

Thr Pro Gly Gln Arg Val Thr Ile Ser Cys Ser Gly Ser Ser Ser Asn
                165                 170                 175

Ile Gly Ser Asn Tyr Val Tyr Trp Tyr Gln Gln Leu Pro Gly Thr Ala
                180                 185                 190

Pro Lys Leu Leu Ile Tyr Lys Asn Asn Gln Arg Pro Ser Gly Val Pro
            195                 200                 205

Asp Arg Phe Ser Gly Ser Lys Ser Gly Thr Ala Ala Ser Leu Ala Ile
        210                 215                 220

Ser Gly Leu Gln Ser Glu Asp Glu Ala Asp Tyr Tyr Cys Ala Ala Trp
225                 230                 235                 240

Asp Asp Ser Leu Arg Gly Tyr Val Phe Gly Thr Gly Thr Lys Leu Thr
                245                 250                 255

Val Leu Ser Gly Ile Leu
            260

<210> SEQ ID NO 163
<211> LENGTH: 266
<212> TYPE: PRT
<213> ORGANISM: Artificial Sequence
<220> FEATURE:
<223> OTHER INFORMATION: Synthetically generated peptide

<400> SEQUENCE: 163

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Leu Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Arg Gly Arg Ile Thr Ile Asn Ala Asp Thr Ser Lys Asn
 65                  70                  75                  80

Gln Phe Ser Leu Gln Leu Asn Ser Val Thr Pro Glu Asp Thr Ala Val
                85                  90                  95

Tyr Tyr Cys Ala Arg Thr Gly Tyr Ser Ser Ser Trp Val Val Asn Phe
            100                 105                 110

Asp Tyr Trp Gly Gln Gly Thr Leu Val Thr Val Ser Ser Gly Ser Ala
        115                 120                 125
```

```
Ser Ala Pro Thr Gly Ile Leu Gly Ser Gly Gly Gly Ser Gly Gly
    130                 135                 140

Gly Gly Ser Gly Gly Gly Ser Gln Pro Val Leu Thr Gln Ser Pro
145                 150                 155                 160

Ser Ala Ser Gly Thr Pro Gly Gln Arg Val Thr Ile Ser Cys Ser Gly
                165                 170                 175

Ser Ser Ser Asn Ile Gly Ser Asn Tyr Val Tyr Trp Tyr Gln Gln Leu
            180                 185                 190

Pro Gly Thr Ala Pro Lys Leu Leu Ile Tyr Lys Asn Asn Gln Arg Pro
        195                 200                 205

Ser Gly Val Pro Asp Arg Phe Ser Gly Ser Lys Ser Gly Thr Ala Ala
    210                 215                 220

Ser Leu Ala Ile Ser Gly Leu Gln Ser Glu Asp Glu Ala Asp Tyr Tyr
225                 230                 235                 240

Cys Ala Ala Trp Asp Asp Ser Leu Arg Gly Tyr Val Phe Gly Thr Gly
                245                 250                 255

Thr Lys Leu Thr Val Leu Ser Gly Ile Leu
            260                 265

<210> SEQ ID NO 164
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 164

Ser Ile Thr Ala Ala Trp Asn
1               5

<210> SEQ ID NO 165
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 165

Arg Thr Tyr His Arg Ser Lys Trp Tyr Tyr Asp Tyr Ala Val Ser Val
1               5                   10                  15

Lys Ser

<210> SEQ ID NO 166
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 166

Gly Leu Ala Ala Arg Gly Gly Gly Pro Ser Ala His Ala Phe Glu Ile
1               5                   10                  15

<210> SEQ ID NO 167
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 167
```

```
Ser Ser Ile Thr Ala Ala Trp Asn
1               5
```

```
<210> SEQ ID NO 168
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 168

Arg Thr Tyr His Arg Ser Lys Trp Tyr Tyr Asp Tyr Ala Val Ser Val
1               5                   10                  15

Lys Ser Arg
```

```
<210> SEQ ID NO 169
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 169

Gly Leu Ala Ala Arg Gly Gly Gly Pro Ser Ala His Ala Phe Glu Ile
1               5                   10                  15
```

```
<210> SEQ ID NO 170
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 170

Asn Asn Ser Ala Val Trp Asn
1               5
```

```
<210> SEQ ID NO 171
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 171

Ser Asn Asn Ser Ala Val Trp Asn
1               5
```

```
<210> SEQ ID NO 172
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 172

Arg Thr Gly Ala Gly Val Asp Tyr
1               5
```

```
<210> SEQ ID NO 173
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 173
```

```
Ser Gly Asn Asn Val Ile Trp Asn
  1               5
```

<210> SEQ ID NO 174
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 174

```
Arg Thr Tyr Tyr Arg Ser Lys Trp Tyr Tyr Asp Leu Leu Pro Ser Val
  1               5                  10                  15

Lys Ser Arg
```

<210> SEQ ID NO 175
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 175

```
Thr Arg Ala Val Ala Gly Asn Gln Tyr Phe Asp Leu
  1               5                  10
```

<210> SEQ ID NO 176
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 176

```
Gly Asn Asn Val Ile Trp Asn
  1               5
```

<210> SEQ ID NO 177
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 177

```
Arg Thr Tyr Tyr Arg Ser Lys Trp Tyr Tyr Asp Leu Leu Pro Ser Val
  1               5                  10                  15

Lys Ser
```

<210> SEQ ID NO 178
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 178

```
Thr Arg Ala Val Ala Gly Asn Gln Tyr Phe Asp Leu
  1               5                  10
```

<210> SEQ ID NO 179
<211> LENGTH: 8
<212> TYPE: PRT
<213> ORGANISM: Artificial Sequence
<220> FEATURE:

<223> OTHER INFORMATION: Synthetically generated peptide

<400> SEQUENCE: 179

Ser Ser Tyr Ser Ala Ala Trp Asn
 1               5

<210> SEQ ID NO 180
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 180

Arg Thr Tyr Tyr Arg Ser Lys Trp Tyr Asn Asp Tyr Ala Val Ser Val
 1               5                  10                  15

Lys Ser Arg

<210> SEQ ID NO 181
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 181

Leu Ala Ala Ala Ala Gly Thr Val Asp Tyr
 1               5                  10

<210> SEQ ID NO 182
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 182

Ser Tyr Ser Ala Ala Trp Asn
 1               5

<210> SEQ ID NO 183
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 183

Ser Ser Asn Ser Ala Ala Trp Asn
 1               5

<210> SEQ ID NO 184
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 184

Leu Ala Ala Ala Ala Gly Thr Val Asp Tyr
 1               5                  10

<210> SEQ ID NO 185
<211> LENGTH: 19
<212> TYPE: PRT
<213> ORGANISM: Artificial Sequence

```
<220> FEATURE:
<223> OTHER INFORMATION: Synthetically generated peptide

<400> SEQUENCE: 185

Arg Thr Tyr Tyr Arg Ser Lys Trp Tyr Asn Asp Tyr Ala Leu Ser Val
 1               5                  10                  15

Lys Ser Arg

<210> SEQ ID NO 186
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 186

Asp Arg Leu Leu Tyr Asn Tyr Gly Ser Asn Ala Met Asp
 1               5                  10

<210> SEQ ID NO 187
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 187

Ser Ser Asn Ser Ala Ala Trp Asn
 1               5

<210> SEQ ID NO 188
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 188

Arg Thr Tyr Tyr Arg Ser Lys Trp Tyr Asn Asp Tyr Ala Val Ser Val
 1               5                  10                  15

Lys Ser Arg

<210> SEQ ID NO 189
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 189

Arg Thr Tyr Tyr Arg Ser Lys Trp Tyr Asn Asp Tyr Ala Leu Ser Val
 1               5                  10                  15

Lys Ser

<210> SEQ ID NO 190
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 190

Asp Arg Leu Leu Tyr Asn Tyr Gly Ser Asn Ala Met Asp Val
 1               5                  10
```

```
<210> SEQ ID NO 191
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 191

Asp Thr Pro Arg Tyr Cys Ser Gly Gly Ser Cys Tyr Lys Tyr Phe Asp
 1               5                  10                  15

<210> SEQ ID NO 192
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 192

Ser Ser Lys Gly Ala Ala Trp Asn
 1               5

<210> SEQ ID NO 193
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 193

Arg Ala Tyr Tyr Trp Ser Lys Trp Tyr Tyr Asp Tyr Ala Val Ser Val
 1               5                  10                  15

Lys Ser Arg

<210> SEQ ID NO 194
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 194

Gly Ala Thr Ser Thr Tyr Tyr Leu Pro Gly Gly Leu Asp Val
 1               5                  10

<210> SEQ ID NO 195
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 195

Ser Ala Asp Arg Val Ala Trp Asn
 1               5

<210> SEQ ID NO 196
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 196

Asp Thr Pro Arg Tyr Cys Ser Gly Gly Ser Cys Tyr Lys Tyr Phe Asp
 1               5                  10                  15
```

Tyr

<210> SEQ ID NO 197
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 197

Arg Ile Phe Tyr Arg Ser Lys Trp Met Val Asp Tyr Ala Val Ser Val
 1               5                  10                  15

Lys Ser Arg

<210> SEQ ID NO 198
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 198

Ala Thr Thr Arg Gly Tyr Phe Asp Leu
 1               5

<210> SEQ ID NO 199
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 199

Arg Thr Tyr Tyr Arg Ser Lys Trp Tyr Asn Asp Tyr Ala Val Ser Met
 1               5                  10                  15

Lys Gly Arg

<210> SEQ ID NO 200
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 200

Ser Lys Gly Ala Ala Trp Asn
 1               5

<210> SEQ ID NO 201
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 201

Arg Ala Tyr Tyr Trp Ser Lys Trp Tyr Tyr Asp Tyr Ala Val Ser Val
 1               5                  10                  15

Lys Ser

<210> SEQ ID NO 202
<211> LENGTH: 14
<212> TYPE: PRT
<213> ORGANISM: Artificial Sequence

```
<220> FEATURE:
<223> OTHER INFORMATION: Synthetically generated peptide

<400> SEQUENCE: 202

Gly Ala Thr Ser Thr Tyr Tyr Leu Pro Gly Gly Leu Asp Val
 1               5                  10

<210> SEQ ID NO 203
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 203

Arg Ser Gly Arg Thr Gly Gly Tyr Phe Asp Leu
 1               5                  10

<210> SEQ ID NO 204
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 204

Gly Ser Ser Asn Ala Ala Trp Asn
 1               5

<210> SEQ ID NO 205
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 205

Arg Ile Phe Tyr Gly Ser Lys Trp Tyr Asn Asp Tyr Ala Val Ser Leu
 1               5                  10                  15

Lys Ser Arg

<210> SEQ ID NO 206
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 206

Ala Asp Arg Val Ala Trp Asn
 1               5

<210> SEQ ID NO 207
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 207

Arg Ile Phe Tyr Arg Ser Lys Trp Met Val Asp Tyr Ala Val Ser Val
 1               5                  10                  15

Lys Ser

<210> SEQ ID NO 208
```

```
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 208

Ala Thr Thr Arg Gly Tyr Phe Asp Leu
1               5

<210> SEQ ID NO 209
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 209

Arg Thr Gly Thr Gly Ile Asp Tyr
1               5

<210> SEQ ID NO 210
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 210

Arg Ile Phe Tyr Arg Ser Lys Trp Tyr Asn Asp Tyr Ala Val Ser Val
1               5                   10                  15

Lys Thr Arg

<210> SEQ ID NO 211
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 211

Gly Gln Gln Lys Arg Leu Asp Ser
1               5

<210> SEQ ID NO 212
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 212

Thr Gly Tyr Ser Ser Ser Trp Val Val Asn Phe Asp Tyr
1               5                   10

<210> SEQ ID NO 213
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 213

Arg Thr Tyr Tyr Arg Ser Lys Trp Tyr Asn Asp Tyr Ala Val Ser Met
1               5                   10                  15

Lys Gly
```

```
<210> SEQ ID NO 214
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 214

Arg Ser Gly Arg Thr Gly Gly Tyr Phe Asp Leu
1               5                   10

<210> SEQ ID NO 215
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 215

Ala Ser Asp Tyr Gly Asp Tyr Phe Tyr Tyr Phe Asp Tyr
1               5                   10

<210> SEQ ID NO 216
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 216

Arg Ile Tyr Tyr Arg Ser Lys Trp Tyr Tyr Asp Tyr Ala Val Ser Val
1               5                   10                  15

Lys Ser Arg

<210> SEQ ID NO 217
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 217

Gly Ala Gly Arg Ser Phe Asp Leu
1               5

<210> SEQ ID NO 218
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 218

Ser Ser Asn Ala Ala Trp Asn
1               5

<210> SEQ ID NO 219
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 219

Arg Ile Phe Tyr Gly Ser Lys Trp Tyr Asn Asp Tyr Ala Val Ser Leu
```

```
              1               5                  10                  15

Lys Ser

<210> SEQ ID NO 220
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 220

Arg Thr Gly Thr Gly Ile Asp Tyr
 1               5

<210> SEQ ID NO 221
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 221

Ser Gly Asn Ser Gly Val Trp Asn
 1               5

<210> SEQ ID NO 222
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 222

Arg Thr Tyr Tyr Tyr Thr Tyr Lys Trp Tyr Ile Asp Tyr Ala Val Ser
 1               5                  10                  15

Val Lys Ser Arg
            20

<210> SEQ ID NO 223
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 223

Val Asp Tyr Thr Gly Ser Pro Val
 1               5

<210> SEQ ID NO 224
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 224

Ser Ser Asn Ala Ala Trp Asn
 1               5

<210> SEQ ID NO 225
<211> LENGTH: 18
<212> TYPE: PRT
<213> ORGANISM: Artificial Sequence
<220> FEATURE:
<223> OTHER INFORMATION: Synthetically generated peptide
```

```
<400> SEQUENCE: 225

Arg Ile Phe Tyr Arg Ser Lys Trp Tyr Asn Asp Tyr Ala Val Ser Val
1               5                   10                  15

Lys Thr

<210> SEQ ID NO 226
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 226

Gly Gln Gln Lys Arg Leu Asp Ser
1               5

<210> SEQ ID NO 227
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 227

Arg Thr Tyr Tyr Arg Ser Lys Trp Tyr Asn Asp Tyr Ala Val Ser Val
1               5                   10                  15

Arg Gly Arg

<210> SEQ ID NO 228
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 228

Thr Gly Tyr Ser Ser Ser Trp Val Val Asn Phe Asp Tyr
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Ser or Asn
<220> FEATURE:
<221> NAME/KEY: VARIANT
<222> LOCATION: 6
<223> OTHER INFORMATION: Xaa = Ser or His
<220> FEATURE:
<221> NAME/KEY: VARIANT
<222> LOCATION: 7
<223> OTHER INFORMATION: Xaa = any amino acid or absent
<220> FEATURE:
<221> NAME/KEY: VARIANT
<222> LOCATION: 8
<223> OTHER INFORMATION: Xaa = Tyr or His

<400> SEQUENCE: 229

Ser Gln Xaa Val Ser Xaa Xaa Xaa Leu Ala
1               5                   10
```

```
<210> SEQ ID NO 230
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 5
<223> OTHER INFORMATION: Xaa = any amino acid or absent

<400> SEQUENCE: 230

Asp Val Ala Asn Xaa Ala Ala
 1               5

<210> SEQ ID NO 231
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 231

Gln Gln Arg Ser Gln Trp Pro Gln
 1               5

<210> SEQ ID NO 232
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 232

Ala Ser Asp Tyr Gly Asp Tyr Phe Tyr Tyr Phe Asp Tyr
 1               5                  10

<210> SEQ ID NO 233
<211> LENGTH: 4
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Tyr or His
<220> FEATURE:
<221> NAME/KEY: VARIANT
<222> LOCATION: 4
<223> OTHER INFORMATION: Xaa = His or Gly

<400> SEQUENCE: 233

Xaa Ala Met Xaa
 1

<210> SEQ ID NO 234
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = any amino acid or absent
<220> FEATURE:
<221> NAME/KEY: VARIANT
<222> LOCATION: 7
<223> OTHER INFORMATION: Xaa = Gly or Ser
```

```
<400> SEQUENCE: 234

Tyr Ala Xaa Ser Val Lys Xaa
1               5

<210> SEQ ID NO 235
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 8
<223> OTHER INFORMATION: Xaa = Gly or Glu
<220> FEATURE:
<221> NAME/KEY: VARIANT
<222> LOCATION: 11, 13
<223> OTHER INFORMATION: Xaa = His or Tyr

<400> SEQUENCE: 235

Ser Gly Ser Ser Ser Asn Ile Xaa Ser Asn Xaa Val Xaa
1               5                   10

<210> SEQ ID NO 236
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 3
<223> OTHER INFORMATION: Xaa = Ser or Gly
<220> FEATURE:
<221> NAME/KEY: VARIANT
<222> LOCATION: 2
<223> OTHER INFORMATION: Xaa = Asp or Asn
<220> FEATURE:
<221> NAME/KEY: VARIANT
<222> LOCATION: 7
<223> OTHER INFORMATION: Xaa = Ser or Asn

<400> SEQUENCE: 236

Xaa Xaa Xaa Ala Ala Trp Xaa
1               5

<210> SEQ ID NO 237
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 237

Arg Ile Tyr Tyr Arg Ser Lys Trp Tyr Tyr Asp Tyr Ala Val Ser Val
1               5                   10                  15

Lys Ser

<210> SEQ ID NO 238
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 238

Gly Ala Gly Arg Ser Phe Asp Leu
1               5
```

```
<210> SEQ ID NO 239
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = Ile or Thr
<220> FEATURE:
<221> NAME/KEY: VARIANT
<222> LOCATION: 3, 4, 12
<223> OTHER INFORMATION: Xaa = Tyr or His
<220> FEATURE:
<221> NAME/KEY: VARIANT
<222> LOCATION: 5
<223> OTHER INFORMATION: Xaa = Gly or Arg
<220> FEATURE:
<221> NAME/KEY: VARIANT
<222> LOCATION: 6
<223> OTHER INFORMATION: Xaa = any amino acid or absent
<220> FEATURE:
<221> NAME/KEY: VARIANT
<222> LOCATION: 7
<223> OTHER INFORMATION: Xaa = Lys or Arg
<220> FEATURE:
<221> NAME/KEY: VARIANT
<222> LOCATION: (8)...(0)
<223> OTHER INFORMATION: Xaa = Trp or Arg
<220> FEATURE:
<221> NAME/KEY: VARIANT
<222> LOCATION: (9)...(0)
<223> OTHER INFORMATION: Xaa = Tyr or Arg
<220> FEATURE:
<221> NAME/KEY: VARIANT
<222> LOCATION: (11)...(0)
<223> OTHER INFORMATION: Xaa = Asp or Gly
<220> FEATURE:
<221> NAME/KEY: VARIANT
<222> LOCATION: (14)...(16)
<223> OTHER INFORMATION: Xaa = Val or Ala
<220> FEATURE:
<221> NAME/KEY: VARIANT
<222> LOCATION: (15)...(0)
<223> OTHER INFORMATION: Xaa = Pro or Ser

<400> SEQUENCE: 239

Arg Xaa Xaa Xaa Xaa Xaa Xaa Xaa Xaa Asn Xaa Xaa Ala Xaa Xaa Xaa
 1               5                  10                  15

Lys Ser

<210> SEQ ID NO 240
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3, 4
<223> OTHER INFORMATION: Xaa = any amino acid or absent

<400> SEQUENCE: 240

Asp Val Xaa Xaa Arg Pro Ser
 1               5

<210> SEQ ID NO 241
<211> LENGTH: 11
<212> TYPE: PRT
<213> ORGANISM: Artificial Sequence
<220> FEATURE:
<223> OTHER INFORMATION: Synthetically generated peptide
```

```
<220> FEATURE:
<221> NAME/KEY: VARIANT
<222> LOCATION: 2
<223> OTHER INFORMATION: Xaa = Phe or Leu
<220> FEATURE:
<221> NAME/KEY: VARIANT
<222> LOCATION: 3
<223> OTHER INFORMATION: Xaa = Ile or Val
<220> FEATURE:
<221> NAME/KEY: VARIANT
<222> LOCATION: 4
<223> OTHER INFORMATION: Xaa = His or Tyr
<220> FEATURE:
<221> NAME/KEY: VARIANT
<222> LOCATION: 5
<223> OTHER INFORMATION: Xaa = Lys or Arg
<220> FEATURE:
<221> NAME/KEY: VARIANT
<222> LOCATION: 6
<223> OTHER INFORMATION: Xaa = any amino acid or absent

<400> SEQUENCE: 241

Leu Xaa Xaa Xaa Xaa Xaa Asn Gln Arg Pro Ser
 1               5                  10

<210> SEQ ID NO 242
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 242

Gly Asn Ser Gly Val Trp Asn Trp
 1               5

<210> SEQ ID NO 243
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 243

Thr Tyr Tyr Tyr Thr Tyr Lys Trp Tyr Ile Asp Tyr Ala Val Ser Val
 1               5                  10                  15

Lys Ser

<210> SEQ ID NO 244
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 244

Val Asp Tyr Thr Gly Ser Pro Val
 1               5

<210> SEQ ID NO 245
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 245

Ala Trp Asp Asp Ser
 1               5
```

```
<210> SEQ ID NO 246
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 7
<223> OTHER INFORMATION: Xaa = any amino acid or absent
<220> FEATURE:
<221> NAME/KEY: VARIANT
<222> LOCATION: 9
<223> OTHER INFORMATION: Xaa = Asp or Gly

<400> SEQUENCE: 246

Ser Ser Ser Trp Val Val Xaa Phe Xaa
 1               5

<210> SEQ ID NO 247
<211> LENGTH: 29
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2-8, 10-13, 15-24, 26, 28
<223> OTHER INFORMATION: Xaa = any amino acid

<400> SEQUENCE: 247

Cys Xaa Xaa Xaa Xaa Xaa Xaa Xaa Cys Xaa Xaa Xaa Xaa Cys Xaa Xaa
 1               5                  10                  15

Xaa Xaa Xaa Xaa Xaa Xaa Xaa Xaa Cys Xaa Cys Xaa Cys
            20                  25

<210> SEQ ID NO 248
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 248

Arg Thr Tyr Tyr Arg Ser Lys Trp Tyr Asn Asp Tyr Ala Val Ser Val
 1               5                  10                  15

Lys Ser Arg

<210> SEQ ID NO 249
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 249

Ser Ser Asn Ser Ala Ala Trp Asn
 1               5

<210> SEQ ID NO 250
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 250
```

```
Gly Ser Ser Asn Ala Ala Trp Asn
 1               5
```

<210> SEQ ID NO 251
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 251

```
Arg Thr Tyr Tyr Arg Ser Lys Trp Tyr Asn Asp Tyr Ala Val Ser Val
 1               5                  10                  15

Lys Ser Arg
```

<210> SEQ ID NO 252
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 252

```
Ser Ser Asn Ser Ala Ala Trp Asn
 1               5
```

<210> SEQ ID NO 253
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 253

```
Ser Ser Asn Ser Ala Ala Trp Asn
 1               5
```

<210> SEQ ID NO 254
<211> LENGTH: 121
<212> TYPE: PRT
<213> ORGANISM: Artificial Sequence
<220> FEATURE:
<223> OTHER INFORMATION: Synthetically generated peptide

<400> SEQUENCE: 254

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Thr Lys Trp Tyr Asn Glu Tyr Ala
    50                  55                  60

Ala Ser Val Lys Gly Arg Ala Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Thr Asp Pro Lys Gly Val Thr Thr Gly Tyr Trp Gly
            100                 105                 110

Gln Gly Thr Leu Val Thr Val Ser Ser
        115                 120
```

<210> SEQ ID NO 255
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 255

```
Gln Pro Val Leu Thr Gln Ser Pro Ser Ala Ser Gly Thr Pro Gly Gln
  1               5                  10                  15

Arg Val Thr Ile Ser Cys Ser Gly Ser Thr Ser Asn Ile Gly Arg Asn
             20                  25                  30

Tyr Val Tyr Trp Tyr Gln Arg Leu Pro Gly Thr Ala Pro Lys Leu Leu
         35                  40                  45

Ile Tyr Arg Asn Asn Gln Arg Pro Ser Gly Ala Pro Ala Arg Phe Ser
 50                  55                  60

Gly Ser Lys Ser Gly Thr Ser Thr Ser Leu Ala Ile Ser Gly Leu Arg
 65                  70                  75                  80

Ser Glu Asp Glu Ala Glu Tyr Phe Cys Ala Ala Trp Asp Asp Ser Leu
                 85                  90                  95

Ser Gly Trp Val Phe Gly Gly Gly Thr Gln Leu Thr Val Leu
            100                 105                 110
```

<210> SEQ ID NO 256
<211> LENGTH: 124
<212> TYPE: PRT
<213> ORGANISM: Artificial Sequence
<220> FEATURE:
<223> OTHER INFORMATION: Synthetically generated peptide

<400> SEQUENCE: 256

```
Gln Val Gln Leu Gln Gln Ser Gly Pro Gly Leu Val Lys Pro Ser Gln
  1               5                  10                  15

Thr Leu Ser Leu Thr Cys Gly Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Arg Trp Tyr Asn Asp Tyr Ala
 50                  55                  60

Ala Ser Val Lys Ser Arg Ile Thr Val Asn Ala Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Ser Val Arg Tyr Ser Ser Gly Trp Gly Phe Asp
            100                 105                 110

Tyr Trp Gly Gln Gly Thr Leu Val Thr Val Ser Ser
            115                 120
```

<210> SEQ ID NO 257
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 257

```
Gln Pro Val Leu Thr Gln Ser Pro Ser Ala Ser Gly Thr Pro Gly Gln
  1               5                  10                  15

Arg Ile Thr Ile Ser Cys Ser Gly Ser Ser Ser Asn Ile Gly Asn Asn
```

```
                    20                  25                  30
Tyr Val Tyr Trp Tyr Gln Gln Phe Pro Gly Thr Ala Pro Lys Leu Leu
        35                  40                  45
Val Tyr Arg Asn Asn Gln Arg Pro Ser Gly Val Pro Asp Arg Phe Ser
 50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Ala Trp Asp Asp Ser Leu
                85                  90                  95
Ser Gly Arg Trp Val Phe Gly Gly Gly Thr Lys Leu Thr Val Leu
               100                 105                 110

<210> SEQ ID NO 258
<211> LENGTH: 124
<212> TYPE: PRT
<213> ORGANISM: Artificial Sequence
<220> FEATURE:
<223> OTHER INFORMATION: Synthetically generated peptide

<400> SEQUENCE: 258

Gln Val Gln Leu Gln Gln Ser Gly Pro Gly Leu Val Lys Pro Ser Gln
 1               5                  10                  15
Thr Leu Ser Leu Thr Cys Ala Ile Ser Gly Asp Ser Val Ser Arg Asn
                20                  25                  30
Ser Ala Ala Trp Asn Leu Ile Arg Gln Ser Pro Ser Arg Gly Leu Glu
            35                  40                  45
Trp Leu Gly Arg Thr Tyr Tyr Arg Ser Lys Trp Tyr Thr Asp Tyr Ala
         50                  55                  60
Val Ser Val Lys Ser Arg Ile Thr Ile Asn Pro Asp Thr Ser Lys Asn
 65                  70                  75                  80
Gln Phe Ser Leu Arg Leu Asn Ser Val Thr Pro Glu Asp Thr Ala Val
                85                  90                  95
Tyr Tyr Cys Ala Arg Ser Gly Gly His Ala Ala Gly Lys Phe Asp
               100                 105                 110
Ser Trp Gly Arg Gly Thr Leu Val Thr Val Ser Ser
           115                 120

<210> SEQ ID NO 259
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 259

Gln Pro Val Leu Thr Gln Ser Pro Ser Ala Ser Gly Thr Pro Gly Gln
 1               5                  10                  15
Arg Val Thr Ile Pro Cys Ser Gly Ser Ser Ser Asn Ile Gly Ser Lys
                20                  25                  30
Tyr Val Tyr Trp Tyr Gln His Leu Pro Gly Thr Ala Pro Lys Leu Leu
            35                  40                  45
Ile Tyr Arg Asn Asn Gln Arg Pro Ser Gly Val Pro Asp Arg Phe Ser
         50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Ala Trp Asp Asp Ser Leu
                85                  90                  95
```

-continued

Ser Ala Trp Val Phe Gly Gly Gly Thr Lys Leu Thr Val Leu
            100                 105                 110

<210> SEQ ID NO 260
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 260

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
 50                  55                  60

Val Ser Val Lys Ser Arg Met Thr Ile Asn Pro Asp Thr Ser Lys Asn
65                  70                  75                  80

Gln Phe Ser Leu Gln Leu Asn Ser Val Thr Pro Asp Asp Arg Ala Val
                85                  90                  95

Tyr Tyr Cys Arg Gly Arg Leu Gly Gly Met Asp Val Trp Gly Gln
            100                 105                 110

Gly Thr Thr Val Thr Val Ser Ser
            115                 120

<210> SEQ ID NO 261
<211> LENGTH: 108
<212> TYPE: PRT
<213> ORGANISM: Artificial Sequence
<220> FEATURE:
<223> OTHER INFORMATION: Synthetically generated peptide

<400> SEQUENCE: 261

Gln Pro Val Leu Thr Gln Ser Pro Ser Ala Ser Gly Thr Pro Gly Gln
 1               5                  10                  15

Arg Val Thr Ile Ser Cys Ser Gly Ser Ser Ser Asn Ile Asn Tyr Val
            20                  25                  30

Tyr Trp Tyr Gln His Leu Pro Gly Thr Ala Pro Lys Leu Leu Ile Tyr
        35                  40                  45

Thr Asn Asn Arg Arg Pro Ser Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Phe Cys Ala Ala Trp Asp Asp Ser Leu Ser Gly
                85                  90                  95

Trp Val Phe Gly Gly Gly Thr Lys Val Thr Val Leu
            100                 105

<210> SEQ ID NO 262
<211> LENGTH: 121
<212> TYPE: PRT
<213> ORGANISM: Artificial Sequence
<220> FEATURE:
<223> OTHER INFORMATION: Synthetically generated peptide

<400> SEQUENCE: 262

Gln Val Gln Leu Val Gln Ser Glu Gly Gly Val Val Gln Pro Gly Arg

-continued

```
                1               5                   10                  15
Ser Leu Arg Leu Ser Cys Gly Val Ser Gly Phe Thr Phe Ser Ser Tyr
                20                  25                  30

Ala Met His Trp Val Arg Gln Ala Pro Gly Lys Gly Leu Glu Trp Val
                35                  40                  45

Ala Val Ile Ser Tyr Asp Gly Ser Lys Lys Tyr Tyr Ala Asp Ser Val
                50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Arg Val Thr Thr Gly Ile Thr Arg Tyr Phe Asp Leu Trp Gly
                100                 105                 110

Arg Gly Thr Leu Val Thr Val Ser Ser
                115                 120
```

<210> SEQ ID NO 263
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 263

```
Gln Ser Val Leu Thr Gln Pro Ala Ser Val Ser Gly Ser Pro Gly Gln
 1               5                   10                  15

Ser Ile Thr Ile Ser Cys Thr Gly Thr Asn Ser Asp Ile Gly Gly Tyr
                20                  25                  30

Asn Tyr Val Ser Trp Tyr Gln Gln His Pro Gly Lys Ala Pro Lys Leu
                35                  40                  45

Met Ile Phe Glu Val Thr Asn Arg Pro Ser Gly Val Pro Asp Arg Phe
                50                  55                  60

Ser Ala Ser Lys Ser Gly Asn Thr Ala Ser Leu Thr Ile Ser Gly Leu
 65                 70                  75                  80

Gln Ala Asp Asp Glu Ala Asp Tyr Tyr Cys Ser Ser Tyr Ala Gly Ser
                85                  90                  95

Asn Thr Pro Ser Val Phe Gly Thr Gly Thr Lys Leu Thr Val Leu
                100                 105                 110
```

<210> SEQ ID NO 264
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 264

```
Gln Val Gln Leu Gln Gln Ser Gly Pro Gly Leu Val Lys Pro Ser Gln
 1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
                35                  40                  45

Trp Leu Gly Arg Thr Tyr Tyr Arg Ser Lys Trp Tyr Asn Asp Tyr Ala
                50                  55                  60

Val Ser Val Lys Gly Arg Ile Thr Ile Asn Pro Asp Thr Ser Lys Asn
 65                 70                  75                  80
```

```
Gln Phe Ser Leu Gln Leu Asn Ser Val Thr Pro Glu Asp Thr Ala Met
                85                  90                  95

Tyr Tyr Cys Val Arg Ser Gly Gly Arg Val Asp Pro Trp Gly Gln
            100                 105                 110

Gly Thr Leu Val Thr Val Ser Ser
        115                 120

<210> SEQ ID NO 265
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 265

Gln Pro Val Leu Thr Gln Ser Pro Ser Ala Ser Gly Thr Pro Gly Gln
 1               5                  10                  15

Arg Val Thr Ile Ser Cys Ser Gly Ser Arg Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn His Gln Arg Pro Ser Gly Val Pro Asp Arg Phe Ser
    50                  55                  60

Ala Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Leu Thr Val Leu
            100                 105                 110

<210> SEQ ID NO 266
<211> LENGTH: 119
<212> TYPE: PRT
<213> ORGANISM: Artificial Sequence
<220> FEATURE:
<223> OTHER INFORMATION: Synthetically generated peptide

<400> SEQUENCE: 266

Gln Val Gln Leu Val Gln Ser Glu Gly Gly Val Val Gln Pro Gly Arg
 1               5                  10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Pro Glu Asp Thr Ala Leu Tyr Tyr Cys
                85                  90                  95

Ala Arg Glu Ala Ser Ser Gly Trp Tyr Ile Asp Ser Trp Gly Gln Gly
            100                 105                 110

Thr Leu Val Thr Val Ser Ser
        115

<210> SEQ ID NO 267
<211> LENGTH: 109
<212> TYPE: PRT
<213> ORGANISM: Artificial Sequence
```

```
<220> FEATURE:
<223> OTHER INFORMATION: Synthetically generated peptide

<400> SEQUENCE: 267

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Gln
                85                  90                  95

Val Thr Phe Gly Gln Gly Thr Arg Leu Glu Val Lys Ser
            100                 105

<210> SEQ ID NO 268
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 268

Arg Val Gln Leu Gln Gln Leu Gly Pro Gly Leu Val Lys Pro Ser Gln
1               5                   10                  15

Thr Leu Ser Leu Thr Cys Ala Ile Phe Gly Asp Ser Val Ser Ser Asn
            20                  25                  30

Gly Ala Ala Trp Ser Trp Ile Arg Gln Ser Leu Ser Arg Gly Leu Glu
        35                  40                  45

Trp Leu Gly Arg Ala Tyr Tyr Arg Ser Lys Trp Tyr Asn Asp Tyr Ala
50                  55                  60

Val Ser Val Arg Gly Arg Ile Thr Ile Asn Ala Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Thr Gly Tyr Ser Ser Ser Arg Val Val Ser Ser
            100                 105                 110

Gly Tyr Trp Gly Gln Gly Thr Leu Val Ala Val Ser Ser
        115                 120                 125

<210> SEQ ID NO 269
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 269

Gln Pro Val Leu Thr Gln Ser Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45
```

```
Ile Tyr Lys Ser Asn Arg Arg Pro Ser Gly Val Pro Gly Arg Phe Ser
    50                  55                  60

Gly Ser Lys Ser Gly Thr Ala Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu
            100                 105                 110

<210> SEQ ID NO 270
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 270

Gln Val Gln Leu Gln Gln Ser Gly Pro Gly Leu Val Lys Pro Ser Pro
  1               5                  10                  15

Thr Leu Ser Leu Thr Cys Ala Ile Ser Gly Asp Ser Val Ser Ser Asn
             20                  25                  30

Ser Ala Ala Trp Asn Trp Val Arg Gln Ser Leu Ser Arg Gly Leu Glu
         35                  40                  45

Trp Leu Gly Arg Thr Tyr Tyr Arg Ser Lys Trp Tyr Asn Gly Tyr Ala
     50                  55                  60

Val Ser Val Arg Gly Arg Ile Thr Thr Asn Ala Asp Thr Ser Arg Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Thr Gly Tyr Ser Ser Ser Trp Val Val Asn Ser
            100                 105                 110

Asn Tyr Trp Gly Gln Gly Thr Leu Val Thr Val Ser Ser
        115                 120                 125

<210> SEQ ID NO 271
<211> LENGTH: 110
<212> TYPE: PRT
<213> ORGANISM: Artificial Sequence
<220> FEATURE:
<223> OTHER INFORMATION: Synthetically generated peptide

<400> SEQUENCE: 271

Gln Pro Ala Leu Thr Gln Ser Pro Ser Ala Ser Gly Thr Pro Gly Gln
  1               5                  10                  15

Arg Val Thr Ile Ser Cys Ser Gly Ser Ser Ser Asn Ile Gly Ser Asn
             20                  25                  30

Tyr Val Tyr Trp Tyr Gln Gln Leu Pro Gly Thr Ala Pro Lys Leu Leu
         35                  40                  45

Ile Tyr Lys Asn Asn Gln Arg Pro Ser Gly Val Pro Gly Arg Phe Ser
    50                  55                  60

Gly Ser Lys Ser Gly Thr Ala Ala Ser Leu Ala Ile Ser Gly Leu Arg
 65                  70                  75                  80

Ser Lys Asp Glu Ala Asp Tyr Tyr Cys Ala Ala Trp Asp Asp Ser Leu
                 85                  90                  95

Arg Gly Tyr Val Phe Gly Thr Gly Thr Lys Leu Thr Val Leu
            100                 105                 110

<210> SEQ ID NO 272
```

<211> LENGTH: 258
<212> TYPE: PRT
<213> ORGANISM: Artificial Sequence
<220> FEATURE:
<223> OTHER INFORMATION: Synthetically generated peptide

<400> SEQUENCE: 272

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Thr Lys Trp Tyr Asn Glu Tyr Ala
 50                  55                  60

Ala Ser Val Lys Gly Arg Ala Thr Ile Asn Pro Asp Thr Ser Lys Asn
 65                  70                  75                  80

Gln Phe Ser Leu Gln Leu Asn Ser Val Thr Pro Glu Asp Thr Ala Val
                85                  90                  95

Tyr Tyr Cys Ala Thr Asp Pro Lys Gly Val Thr Thr Gln Tyr Trp Gly
            100                 105                 110

Gln Gly Thr Leu Val Thr Val Ser Ser Gly Ser Ala Ser Ala Ser Thr
        115                 120                 125

Gly Ile Leu Gly Ser Gly Gly Gly Ser Gly Gly Gly Ser Gly
130                 135                 140

Gly Gly Gly Ser Gln Pro Val Leu Thr Gln Ser Pro Ser Ala Ser Gly
145                 150                 155                 160

Thr Pro Gly Gln Arg Val Thr Ile Ser Cys Ser Gly Ser Thr Ser Asn
                165                 170                 175

Ile Gly Arg Asn Tyr Val Tyr Trp Tyr Gln Arg Leu Pro Gly Thr Ala
            180                 185                 190

Pro Lys Leu Leu Ile Tyr Arg Asn Asn Gln Arg Pro Ser Gly Ala Pro
        195                 200                 205

Ala Arg Phe Ser Gly Ser Lys Ser Gly Thr Ser Thr Ser Leu Ala Ile
    210                 215                 220

Ser Gly Leu Arg Ser Glu Asp Glu Ala Glu Tyr Phe Cys Ala Ala Trp
225                 230                 235                 240

Asp Asp Ser Leu Ser Gly Trp Val Phe Gly Gly Thr Gln Leu Thr
                245                 250                 255

Val Leu
```

<210> SEQ ID NO 273
<211> LENGTH: 255
<212> TYPE: PRT
<213> ORGANISM: Artificial Sequence
<220> FEATURE:
<223> OTHER INFORMATION: Synthetically generated peptide

<400> SEQUENCE: 273

```
Gln Val Gln Leu Gln Gln Ser Gly Pro Gly Leu Val Lys Pro Ser Gln
 1               5                  10                  15

Thr Leu Ser Leu Thr Cys Gly Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Arg Trp Tyr Asn Asp Tyr Ala
 50                  55                  60
```

```
Ala Ser Val Lys Ser Arg Ile Thr Val Asn Ala Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Ser Val Arg Tyr Ser Ser Gly Trp Gly Phe Asp
            100                 105                 110

Tyr Trp Gly Gln Gly Thr Leu Val Thr Val Ser Ser Gly Ile Leu Gly
        115                 120                 125

Ser Gly Gly Gly Gly Ser Gly Gly Gly Gly Ser Gly Gly Gly Gly Ser
    130                 135                 140

Gln Pro Val Leu Thr Gln Ser Pro Ser Ala Ser Gly Thr Pro Gly Gln
145                 150                 155                 160

Arg Ile Thr Ile Ser Cys Ser Gly Ser Ser Ser Asn Ile Gly Asn Asn
                165                 170                 175

Tyr Val Tyr Trp Tyr Gln Gln Phe Pro Gly Thr Ala Pro Lys Leu Leu
            180                 185                 190

Val Tyr Arg Asn Asn Gln Arg Pro Ser Gly Val Pro Asp Arg Phe Ser
        195                 200                 205

Gly Ser Lys Ser Gly Thr Ser Ala Ser Leu Ala Ile Ser Gly Leu Arg
    210                 215                 220

Ser Glu Asp Glu Ala Asp Tyr Tyr Cys Ala Ala Trp Asp Asp Ser Leu
225                 230                 235                 240

Ser Gly Arg Trp Val Phe Gly Gly Gly Thr Lys Leu Thr Val Leu
                245                 250                 255

<210> SEQ ID NO 274
<211> LENGTH: 254
<212> TYPE: PRT
<213> ORGANISM: Artificial Sequence
<220> FEATURE:
<223> OTHER INFORMATION: Synthetically generated peptide

<400> SEQUENCE: 274

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Arg Asn
                 20                  25                  30

Ser Ala Ala Trp Asn Leu Ile Arg Gln Ser Pro Ser Arg Gly Leu Glu
            35                  40                  45

Trp Leu Gly Arg Thr Tyr Tyr Arg Ser Lys Trp Tyr Thr Asp Tyr Ala
        50                  55                  60

Val Ser Val Lys Ser Arg Ile Thr Ile Asn Pro Asp Thr Ser Lys Asn
 65                  70                  75                  80

Gln Phe Ser Leu Arg Leu Asn Ser Val Thr Pro Glu Asp Thr Ala Val
                 85                  90                  95

Tyr Tyr Cys Ala Arg Ser Gly Gly Gly His Ala Ala Gly Lys Phe Asp
            100                 105                 110

Ser Trp Gly Arg Gly Thr Leu Val Thr Val Ser Ser Gly Ile Leu Gly
        115                 120                 125

Ser Gly Gly Gly Gly Ser Gly Gly Gly Gly Ser Gly Gly Gly Gly Ser
    130                 135                 140

Gln Pro Val Leu Thr Gln Ser Pro Ser Ala Ser Gly Thr Pro Gly Gln
145                 150                 155                 160

Arg Val Thr Ile Pro Cys Ser Gly Ser Ser Ser Asn Ile Gly Ser Lys
                165                 170                 175
```

Tyr Val Tyr Trp Tyr Gln His Leu Pro Gly Thr Ala Pro Lys Leu Leu
            180                 185                 190

Ile Tyr Arg Asn Asn Gln Arg Pro Ser Gly Val Pro Asp Arg Phe Ser
            195                 200                 205

Gly Ser Lys Ser Gly Thr Ser Ala Ser Leu Ala Ile Ser Gly Leu Arg
            210                 215                 220

Ser Glu Asp Glu Ala Asp Tyr Tyr Cys Ala Ala Trp Asp Asp Ser Leu
225                 230                 235                 240

Ser Ala Trp Val Phe Gly Gly Gly Thr Lys Leu Thr Val Leu
                245                 250

<210> SEQ ID NO 275
<211> LENGTH: 248
<212> TYPE: PRT
<213> ORGANISM: Artificial Sequence
<220> FEATURE:
<223> OTHER INFORMATION: Synthetically generated peptide

<400> SEQUENCE: 275

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
50                  55                  60

Val Ser Val Lys Ser Arg Met Thr Ile Asn Pro Asp Thr Ser Lys Asn
65                  70                  75                  80

Gln Phe Ser Leu Gln Leu Asn Ser Val Thr Pro Asp Asp Arg Ala Val
                85                  90                  95

Tyr Tyr Cys Arg Gly Arg Leu Gly Gly Met Asp Val Trp Gly Gln
            100                 105                 110

Gly Thr Thr Val Thr Val Ser Ser Gly Ile Leu Gly Ser Gly Gly
            115                 120                 125

Gly Ser Gly Gly Gly Ser Gly Gly Gly Ser Gln Pro Val Leu
        130                 135                 140

Thr Gln Ser Pro Ser Ala Ser Gly Thr Pro Gly Gln Arg Val Thr Ile
145                 150                 155                 160

Ser Cys Ser Gly Ser Ser Asn Ile Asn Tyr Val Tyr Trp Tyr Gln
            165                 170                 175

His Leu Pro Gly Thr Ala Pro Lys Leu Leu Ile Tyr Thr Asn Asn Arg
            180                 185                 190

Arg Pro Ser Gly Val Pro Asp Arg Phe Ser Gly Ser Lys Ser Gly Thr
            195                 200                 205

Ser Ala Ser Leu Ala Ile Ser Gly Leu Arg Ser Glu Asp Glu Ala Asp
            210                 215                 220

Tyr Phe Cys Ala Ala Trp Asp Asp Ser Leu Ser Gly Trp Val Phe Gly
225                 230                 235                 240

Gly Gly Thr Lys Val Thr Val Leu
                245

<210> SEQ ID NO 276
<211> LENGTH: 252
<212> TYPE: PRT
<213> ORGANISM: Artificial Sequence

```
<220> FEATURE:
<223> OTHER INFORMATION: Synthetically generated peptide

<400> SEQUENCE: 276

Gln Val Gln Leu Val Gln Ser Glu Gly Gly Val Val Gln Pro Gly Arg
1               5                   10                  15

Ser Leu Arg Leu Ser Cys Gly Val Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Thr Thr Gly Ile Thr Arg Tyr Phe Asp Leu Trp Gly
            100                 105                 110

Arg Gly Thr Leu Val Thr Val Ser Ser Gly Ile Leu Gly Ser Gly Gly
        115                 120                 125

Gly Gly Ser Gly Gly Gly Ser Gly Gly Gly Ser Gln Ser Val
    130                 135                 140

Leu Thr Gln Pro Ala Ser Val Ser Gly Ser Pro Gly Gln Ser Ile Thr
145                 150                 155                 160

Ile Ser Cys Thr Gly Thr Asn Ser Asp Ile Gly Gly Tyr Asn Tyr Val
                165                 170                 175

Ser Trp Tyr Gln Gln His Pro Gly Lys Ala Pro Lys Leu Met Ile Phe
            180                 185                 190

Glu Val Thr Asn Arg Pro Ser Gly Val Pro Asp Arg Phe Ser Ala Ser
        195                 200                 205

Lys Ser Gly Asn Thr Ala Ser Leu Thr Ile Ser Gly Leu Gln Ala Asp
    210                 215                 220

Asp Glu Ala Asp Tyr Tyr Cys Ser Ser Tyr Ala Gly Ser Asn Thr Pro
225                 230                 235                 240

Ser Val Phe Gly Thr Gly Thr Lys Leu Thr Val Leu
                245                 250

<210> SEQ ID NO 277
<211> LENGTH: 250
<212> TYPE: PRT
<213> ORGANISM: Artificial Sequence
<220> FEATURE:
<223> OTHER INFORMATION: Synthetically generated peptide

<400> SEQUENCE: 277

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Gly Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Met
```

```
                    85                  90                  95
Tyr Tyr Cys Val Arg Ser Gly Gly Arg Val Asp Pro Trp Gly Gln
            100                 105                 110

Gly Thr Leu Val Thr Val Ser Ser Gly Ile Leu Gly Ser Gly Gly
            115                 120                 125

Gly Ser Gly Gly Gly Ser Gly Gly Gly Ser Gln Pro Val Leu
            130                 135                 140

Thr Gln Ser Pro Ser Ala Ser Gly Thr Pro Gly Gln Arg Val Thr Ile
145                 150                 155                 160

Ser Cys Ser Gly Ser Arg Ser Asn Ile Gly Ser Asn Tyr Val Tyr Trp
                165                 170                 175

Tyr Gln Gln Leu Pro Gly Thr Ala Pro Lys Leu Leu Ile Tyr Arg Asn
            180                 185                 190

His Gln Arg Pro Ser Gly Val Pro Asp Arg Phe Ser Ala Ser Lys Ser
            195                 200                 205

Gly Thr Ser Ala Ser Leu Ala Ile Ser Gly Leu Arg Ser Glu Asp Glu
            210                 215                 220

Ala Asp Tyr Tyr Cys Ala Ala Trp Asp Asp Ser Leu Ser Gly Tyr Val
225                 230                 235                 240

Phe Gly Thr Gly Thr Lys Leu Thr Val Leu
                245                 250

<210> SEQ ID NO 278
<211> LENGTH: 255
<212> TYPE: PRT
<213> ORGANISM: Artificial Sequence
<220> FEATURE:
<223> OTHER INFORMATION: Synthetically generated peptide

<400> SEQUENCE: 278

Gln Val Gln Leu Val Gln Ser Glu Gly Gly Val Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Pro Glu Asp Thr Ala Leu Tyr Tyr Cys
                85                  90                  95

Ala Arg Glu Ala Ser Ser Gly Trp Tyr Ile Asp Ser Trp Gly Gln Gly
            100                 105                 110

Thr Leu Val Thr Val Ser Ser Ala Ser Thr Lys Gly Pro Ser Gly Ile
            115                 120                 125

Leu Gly Ser Gly Gly Gly Gly Ser Gly Gly Gly Ser Gly Gly Gly
            130                 135                 140

Gly Ser Glu Ile Val Leu Thr Gln Ser Pro Gly Thr Leu Ser Leu Ser
145                 150                 155                 160

Pro Gly Glu Arg Ala Thr Leu Ser Cys Arg Ala Ser Gln Ser Val Ser
                165                 170                 175

Ser Ser Tyr Leu Ala Trp Tyr Gln Gln Lys Pro Gly Gln Ala Pro Arg
            180                 185                 190

Leu Leu Ile Tyr Gly Ala Ser Ser Arg Ala Thr Gly Ile Pro Asp Arg
```

```
                195                 200                 205
Phe Ser Gly Ser Gly Ser Gly Thr Asp Phe Thr Leu Thr Ile Ser Arg
    210                 215                 220

Leu Glu Pro Glu Asp Phe Ala Val Tyr Tyr Cys Gln Gln Tyr Gly Ser
225                 230                 235                 240

Ser Gln Val Thr Phe Gly Gln Gly Thr Arg Leu Glu Val Lys Ser
                245                 250                 255

<210> SEQ ID NO 279
<211> LENGTH: 262
<212> TYPE: PRT
<213> ORGANISM: Artificial Sequence
<220> FEATURE:
<223> OTHER INFORMATION: Synthetically generated peptide

<400> SEQUENCE: 279

Arg Val Gln Leu Gln Gln Leu Gly Pro Gly Leu Val Lys Pro Ser Gln
1               5                   10                  15

Thr Leu Ser Leu Thr Cys Ala Ile Phe Gly Asp Ser Val Ser Ser Asn
            20                  25                  30

Gly Ala Ala Trp Ser Trp Ile Arg Gln Ser Leu Ser Arg Gly Leu Glu
        35                  40                  45

Trp Leu Gly Arg Ala Tyr Tyr Arg Ser Lys Trp Tyr Asn Asp Tyr Ala
    50                  55                  60

Val Ser Val Arg Gly Arg Ile Thr Ile Asn Ala Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Thr Gly Tyr Ser Ser Arg Val Val Ser Ser
            100                 105                 110

Gly Tyr Trp Gly Gln Gly Thr Leu Val Ala Val Ser Ser Gly Ser Ala
        115                 120                 125

Ser Ala Pro Ile Gly Ile Leu Gly Ser Gly Gly Gly Ser Gly Gly
    130                 135                 140

Gly Gly Ser Gly Gly Gly Ser Gln Pro Val Leu Thr Gln Ser Pro
145                 150                 155                 160

Ser Ala Ser Gly Thr Pro Gly Gln Arg Val Thr Ile Ser Cys Ser Gly
                165                 170                 175

Ser Ser Ser Asn Ile Gly Ser Asn Tyr Val Tyr Trp Tyr Gln Gln Leu
            180                 185                 190

Pro Gly Thr Ala Pro Lys Leu Leu Ile Tyr Lys Ser Asn Arg Arg Pro
        195                 200                 205

Ser Gly Val Pro Gly Arg Phe Ser Gly Ser Lys Ser Gly Thr Ala Ala
    210                 215                 220

Ser Leu Ala Ile Ser Gly Leu Gln Ser Glu Asp Glu Ala Asp Tyr Tyr
225                 230                 235                 240

Cys Ala Ala Trp Asp Asp Ser Leu Arg Gly Tyr Val Phe Gly Thr Gly
                245                 250                 255

Thr Lys Leu Thr Val Leu
            260

<210> SEQ ID NO 280
<211> LENGTH: 262
<212> TYPE: PRT
<213> ORGANISM: Artificial Sequence
<220> FEATURE:
<223> OTHER INFORMATION: Synthetically generated peptide
```

<400> SEQUENCE: 280

Gln Val Gln Leu Gln Gln Ser Gly Pro Gly Leu Val Lys Pro Ser Pro
1               5                   10                  15

Thr Leu Ser Leu Thr Cys Ala Ile Ser Gly Asp Ser Val Ser Ser Asn
            20                  25                  30

Ser Ala Ala Trp Asn Trp Val Arg Gln Ser Leu Ser Arg Gly Leu Glu
        35                  40                  45

Trp Leu Gly Arg Thr Tyr Tyr Arg Ser Lys Trp Tyr Asn Gly Tyr Ala
    50                  55                  60

Val Ser Val Arg Gly Arg Ile Thr Thr Asn Ala Asp Thr Ser Arg Asn
65                  70                  75                  80

Gln Phe Ser Leu Gln Leu Asn Ser Val Thr Pro Glu Asp Thr Ala Val
                85                  90                  95

Tyr Tyr Cys Ala Arg Thr Gly Tyr Ser Ser Trp Val Val Asn Ser
            100                 105                 110

Asn Tyr Trp Gly Gln Gly Thr Leu Val Thr Val Ser Ser Gly Ser Ala
        115                 120                 125

Ser Ala Pro Thr Gly Ile Leu Gly Ser Gly Gly Gly Ser Gly Gly
    130                 135                 140

Gly Gly Ser Gly Gly Gly Ser Gln Pro Ala Leu Thr Gln Ser Pro
145                 150                 155                 160

Ser Ala Ser Gly Thr Pro Gly Gln Arg Val Thr Ile Ser Cys Ser Gly
                165                 170                 175

Ser Ser Ser Asn Ile Gly Ser Asn Tyr Val Tyr Trp Tyr Gln Gln Leu
            180                 185                 190

Pro Gly Thr Ala Pro Lys Leu Leu Ile Tyr Lys Asn Asn Gln Arg Pro
        195                 200                 205

Ser Gly Val Pro Gly Arg Phe Ser Gly Ser Lys Ser Gly Thr Ala Ala
    210                 215                 220

Ser Leu Ala Ile Ser Gly Leu Arg Ser Lys Asp Glu Ala Asp Tyr Tyr
225                 230                 235                 240

Cys Ala Ala Trp Asp Asp Ser Leu Arg Gly Tyr Val Phe Gly Thr Gly
                245                 250                 255

Thr Lys Leu Thr Val Leu
            260

<210> SEQ ID NO 281
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 281

Arg Thr Tyr Tyr Arg Thr Lys Trp Tyr Asn Glu Tyr Ala Ala Ser Val
1               5                   10                  15

Lys Gly

<210> SEQ ID NO 282
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 282

```
Asp Pro Lys Gly Val Thr Thr Gln Tyr
 1               5
```

<210> SEQ ID NO 283
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 283

```
Ser Gly Ser Thr Ser Asn Ile Gly Arg Asn Tyr Val Tyr
 1               5                  10
```

<210> SEQ ID NO 284
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 284

```
Lys Leu Leu Ile Tyr Arg Asn Asn Gln Arg Pro Ser
 1               5                  10
```

<210> SEQ ID NO 285
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 285

```
Ala Ala Trp Asp Asp Ser Leu Ser Gly Trp Val
 1               5                  10
```

<210> SEQ ID NO 286
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 286

```
Arg Thr Tyr Tyr Arg Ser Arg Trp Tyr Asn Asp Tyr Ala Ala Ser Val
 1               5                  10                  15

Lys Ser
```

<210> SEQ ID NO 287
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 287

```
Ser Val Arg Tyr Ser Ser Gly Trp Gly Phe Asp Tyr
 1               5                  10
```

<210> SEQ ID NO 288
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 288

```
Ser Gly Ser Ser Ser Asn Ile Gly Asn Asn Tyr Val Tyr
1               5                   10

<210> SEQ ID NO 289
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 289

Lys Leu Leu Val Tyr Arg Asn Asn Gln Arg Pro Ser
1               5                   10

<210> SEQ ID NO 290
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 290

Ala Ala Trp Asp Asp Ser Leu Ser Gly Arg Trp Val
1               5                   10

<210> SEQ ID NO 291
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 291

Arg Asn Ser Ala Ala Trp Asn
1               5

<210> SEQ ID NO 292
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 292

Arg Thr Tyr Tyr Arg Ser Lys Trp Tyr Thr Asp Tyr Ala Val Ser Val
1               5                   10                  15

Lys Ser

<210> SEQ ID NO 293
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 293

Ser Gly Gly Gly His Ala Ala Gly Lys Phe Asp Ser
1               5                   10

<210> SEQ ID NO 294
<211> LENGTH: 13
<212> TYPE: PRT
<213> ORGANISM: Artificial Sequence
<220> FEATURE:
<223> OTHER INFORMATION: Synthetically generated peptide
```

-continued

```
<400> SEQUENCE: 294

Ser Gly Ser Ser Ser Asn Ile Gly Ser Lys Tyr Val Tyr
1               5                   10

<210> SEQ ID NO 295
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 295

Ala Ala Trp Asp Asp Ser Leu Ser Ala Trp Val
1               5                   10

<210> SEQ ID NO 296
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 296

Ser Asn Ser Ala Thr Trp Asn
1               5

<210> SEQ ID NO 297
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 297

Gly Gly Arg Leu Gly Gly Gly Met Asp Val
1               5                   10

<210> SEQ ID NO 298
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 298

Ser Gly Ser Ser Ser Asn Ile Asn Tyr Val Tyr
1               5                   10

<210> SEQ ID NO 299
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 299

Lys Leu Leu Ile Tyr Thr Asn Asn Arg Arg Pro Ser
1               5                   10

<210> SEQ ID NO 300
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 300
```

```
Val Ile Ser Tyr Asp Gly Ser Lys Lys Tyr Tyr Ala Asp Ser Val Lys
1               5                   10                  15

Gly

<210> SEQ ID NO 301
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 301

Arg Val Thr Thr Gly Ile Thr Arg Tyr Phe Asp Leu
1               5                   10

<210> SEQ ID NO 302
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 302

Thr Gly Thr Asn Ser Asp Ile Gly Gly Tyr Asn Tyr Val Ser
1               5                   10

<210> SEQ ID NO 303
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 303

Lys Leu Met Ile Phe Glu Val Thr Asn Arg Pro Ser
1               5                   10

<210> SEQ ID NO 304
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 304

Ser Ser Tyr Ala Gly Ser Asn Thr Pro Ser Val
1               5                   10

<210> SEQ ID NO 305
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 305

Arg Thr Tyr Tyr Arg Ser Lys Trp Tyr Asn Asp Tyr Ala Val Ser Val
1               5                   10                  15

Lys Gly

<210> SEQ ID NO 306
<211> LENGTH: 8
<212> TYPE: PRT
<213> ORGANISM: Artificial Sequence
<220> FEATURE:
```

```
<223> OTHER INFORMATION: Synthetically generated peptide

<400> SEQUENCE: 306

Ser Gly Gly Gly Arg Val Asp Pro
1               5

<210> SEQ ID NO 307
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 307

Ser Gly Ser Arg Ser Asn Ile Gly Ser Asn Tyr Val Tyr
1               5                   10

<210> SEQ ID NO 308
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 308

Lys Leu Leu Ile Tyr Arg Asn His Gln Arg Pro Ser
1               5                   10

<210> SEQ ID NO 309
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 309

Ala Ala Trp Asp Asp Ser Leu Ser Gly Tyr Val
1               5                   10

<210> SEQ ID NO 310
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 310

Asp Tyr Ala Met His
1               5

<210> SEQ ID NO 311
<211> LENGTH: 17
<212> TYPE: PRT
<213> ORGANISM: Artificial Sequence
<220> FEATURE:
<223> OTHER INFORMATION: Synthetically generated peptide

<400> SEQUENCE: 311

Val Ile Ser Tyr Asp Gly Ser Asn Lys Tyr Tyr Thr Asp Ser Val Lys
1               5                   10                  15

Gly

<210> SEQ ID NO 312
<211> LENGTH: 10
<212> TYPE: PRT
<213> ORGANISM: Artificial Sequence
```

```
<220> FEATURE:
<223> OTHER INFORMATION: Synthetically generated peptide

<400> SEQUENCE: 312

Glu Ala Ser Ser Gly Trp Tyr Ile Asp Ser
 1               5                  10

<210> SEQ ID NO 313
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 313

Gln Gln Tyr Gly Ser Ser Gln Val Thr
 1               5

<210> SEQ ID NO 314
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 314

Ser Asn Gly Ala Ala Trp Ser
 1               5

<210> SEQ ID NO 315
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 315

Arg Ala Tyr Tyr Arg Ser Lys Trp Tyr Asn Asp Tyr Ala Val Ser Val
 1               5                  10                  15

Arg Gly

<210> SEQ ID NO 316
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 316

Thr Gly Tyr Ser Ser Ser Arg Val Val Ser Ser Gly Tyr
 1               5                  10

<210> SEQ ID NO 317
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 317

Lys Leu Leu Ile Tyr Lys Ser Asn Arg Arg Pro Ser
 1               5                  10

<210> SEQ ID NO 318
<211> LENGTH: 18
<212> TYPE: PRT
```

```
-continued

<213> ORGANISM: Artificial Sequence
<220> FEATURE:
<223> OTHER INFORMATION: Synthetically generated peptide

<400> SEQUENCE: 318

Arg Thr Tyr Tyr Arg Ser Lys Trp Tyr Asn Gly Tyr Ala Val Ser Val
1               5                   10                  15

Arg Gly

<210> SEQ ID NO 319
<211> LENGTH: 13
<212> TYPE: PRT
<213> ORGANISM: Artificial Sequence
<220> FEATURE:
<223> OTHER INFORMATION: Synthetically generated peptide

<400> SEQUENCE: 319

Thr Gly Tyr Ser Ser Ser Trp Val Val Asn Ser Asn Tyr
1               5                   10
```

ANTI-HYDROXYLASE ANTIBODIES AND USES THEREOF

This application claims the benefit of the filing date of U.S. Ser. No. 60/563,514, filed Apr. 19, 2004, and U.S. Ser. No. 60/520,114, filed Nov. 14, 2003. The contents of both prior applications are hereby incorporated by reference in their entirety.

STATEMENT REGARDING FEDERALLY FUNDED RESEARCH

The work described herein was funded, in part, through a grant from the National Science Foundation (Grant No. 9843342). The United States government may, therefore, have certain rights in the invention.

TECHNICAL FIELD

The present invention relates to antibodies that recognize aspartyl (asparaginyl) β-hydroxylase and to methods of using those antibodies to, for example, detect aspartyl (asparaginyl) β-hydroxylase and/or modulate its activity.

BACKGROUND

Aspartyl (asparaginyl) β-hydroxylase (AAH) catalyzes post-translational hydroxylation of β carbons of specific aspartate and asparagine residues in epidermal growth factor-like domains of numerous proteins, including extracellular matrix proteins, low-density lipoprotein (LDL) receptor, Notch homologs, and Notch ligand homologs (Jia et al., *Proc. Natl. Acad. Sci. USA* 91(15):7227-7231, 1994; Jia et al., *J. Biol. Chem.* 267(20):14322-14327, 1992; Gronke et al., *Proc Natl Acad Sci USA* 86(10):3609-13, 1989). This transmembrane enzyme is a member of the α-ketoglutarate-dependent dioxygenase family of prolyl and lysyl hydroxylases. Overexpression of human AAH (HAAH) has been detected in a number of human cancers, including hepatocellular carcinomas, cholangiocarcinomas, and, neuroectodermal tumors (Lavaissiere et al., *J. Clin. Investig.* 98:1313-1323, 1996; Sepe et al., *Lab. Investig.* 82(7):81-891, 2002). The finding that AAH is overexpressed in numerous tumors, and that forced expression increases cell motility and survival indicates that AAH may contribute to malignant transformation in vivo (Sepe et al., *Lab. Investig.* 82(7):881-891, 2002).

SUMMARY

This invention is based, in part, on our discovery of human single-chain antibodies that bind aspartyl (asparaginyl) β-hydroxylase (AAH). Accordingly, the invention features antibodies, including complete, multimeric antibodies (e.g., human tetrameric antibodies of the G class (an IgG)) and fragments or other variants thereof that specifically bind an AAH protein. These fragments and variants include single-chain anti-AAH antibodies, fragments or portions of multimeric (e.g., tetrameric) anti-AAH antibodies and other variants that specifically bind an AAH protein. Any of the anti-AAH antibodies or fragments or variants thereof may have been mutagenized by, for example, an affinity maturation process.

The compositions of the invention include anti-AAH antibodies (e.g., a human monoclonal antibody), fragments or other variants thereof, pharmaceutical compositions containing them, and kits containing them. The antibodies, fragments or other variants thereof may, but do not necessarily, inhibit one or more of AAH's biological activities (e.g., hydroxylation of suitable substrates, whether naturally occurring or non-naturally occurring, in vitro, in cell or tissue culture, or in vivo) and/or one or more of the cellular events mediated by AAH (e.g., cellular growth or proliferation, or cellular motility). As undesirable cellular proliferation and motility occur in connection with pathological conditions in which AAH is overactive or overexpressed (such as cancer), the compositions of the invention can be used to identify patients having such a condition, to assess their prognosis, and/or to treat a patient having, or at risk for developing, such a condition (e.g., cancers or other disorders associated with elevated AAH expression or activity).

More specifically, the invention features methods of identifying a patient amenable to treatment (e.g., a patient having a cell (or cells) in which AAH is overactive or overexpressed) and therapeutic or prophylactic methods of treating such a patient by administering an effective amount of an anti-AAH antibody (or a fragment or other variant thereof) to the patient (e.g., a human monoclonal antibody or a human single-chain antibody (scFv) that specifically binds HAAH). Also provided are nucleic acids that can be used to express the antibodies of the invention; vectors that include those nucleic acids; cells that contain those nucleic acids or vectors; methods of formulating pharmaceutically acceptable compositions that include an anti-AAH antibody and/or a fragment or other variant thereof; methods of identifying and/or assessing the properties of anti-AAH antibodies (e.g., anti-HAAH antibodies) and/or fragments or other variants thereof; and methods of affinity-maturing anti-AAH antibodies (e.g., human anti-HAAH antibodies) and/or fragments or other variants thereof.

For ease of reading, we do not repeat the phrase "and/or fragments or other variants thereof" following every occurrence of "antibody" or "antibodies." It is to be understood that wherever an anti-AAH antibody can be used, a fragment or other variant thereof that specifically binds an AAH protein to any useful degree can also be used. We may refer to AAH as "an AAH protein." Unless a contrary meaning is clear, we use the terms "protein," "peptide" and "polypeptide" interchangeably to refer to chains of two or more amino acid residues. Similarly, wherever a nucleic acid encoding an anti-AAH antibody can be used, a nucleic acid encoding a functional fragment or other variant of the anti-AAH antibody can be used; wherever a cell comprising an anti-AAH antibody can be used, one can use a cell comprising a fragment or other variant of an anti-AAH antibody; and so forth. A fragment of an anti-AAH antibody may also be referred to as an "antigen-binding portion" of an anti-AAH antibody, as the fragment may be a portion of an anti-AAH antibody that specifically binds an AAH antigen. While fragments and variants are described further below, we note here that they include Fab, Fab' and F(ab')2 fragments as well as scFvs (e.g., a human scFv that specifically binds HAAH).

The anti-AAH antibodies or fragments or other variants thereof can consist of, or can include, the amino acid sequences in the Tables of FIGS. 34-38. Alternatively, the anti-AAH antibodies can consist of, or can include, sequences that exhibit a certain degree of identity to the amino acid sequences in the Tables of FIGS. 34-38. For example, the antibodies can include a variable region of the heavy chain (VH) that is at least 80% identical (e.g., 85%, 90%, 95%, 98% or 100% identical) to one of the VH sequences shown in FIGS. 34 and 35. Alternatively, the antibodies can be scFv that are at least 80% identical (e.g., 85%, 90%, 95%, 98% or 100%) to one of the scFvs shown in FIG. 36. Alternatively, the antibodies or fragments or other variants thereof can include complementarity determining regions (CDRs) that are at least 40% identical (e.g., at least 40%, 50%, 60%, 70%, 80%, 85%, 90%, 95%, or 98%) identical to the CDRs shown The antibody can include a variable light chain (VL or VLC) including a first CDR including (or consisting of) the amino acid sequence Ser-Gln-Ser/Asn-Val-Ser-Ser/His-(Xaa)-Tyr/His-Leu-Ala (SEQ ID NO:229); a second CDR including (or consisting of) the amino acid sequence Asp-Val-Ala-Asn-Xaa-Ala-Ala (SEQ ID NO:230); and a third CDR including (or consisting of) the amino acid sequence Gln-Gln-Arg-Ser-Gln-Trp-Pro-Gln (SEQ ID NO:231). Unless indicated otherwise, in these sequences and those that follow, "Xaa" is any amino acid residue or no amino acid residue. Alternatively, or in addition, the antibody can include a VHC including a first CDR including (or consisting of) the amino acid sequence Tyr/His-Ala-Met-His/Gly (SEQ ID NO:233) and a second CDR including (or consisting of) the amino acid sequence Tyr-Ala-Xaa-Ser-Val-Lys-Gly/Ser (SEQ ID NO:234). In other embodiments, the antibody can include a VLC including a CDR (e.g., a first CDR) including (or consisting of) the amino acid sequence Ser-Gly-Ser-Ser-Ser-Asn-Ile-Gly/Glu-Ser-Asn-His/Tyr-Val-His/Tyr (SEQ ID NO:235). Alternatively, or in addition, the antibody can include a VHC including a CDR (e.g., a first CDR) including (or consisting of) the amino acid sequence Ser/Gly-Asp/Asn-Ser/Gly-Ala-Ala-Trp-Ser/Asn (SEQ ID NO:236) and a second CDR including (or consisting of) the amino acid sequence Arg-Ile/Thr-Tyr/His-Tyr/His-Gly/Arg-Xaa-Lys/Arg-Trp/Arg-Tyr/Arg-Asn-Asp/Gly-Tyr/His-Ala-Val/Ala-Pro/Ser-Val/Ala-Lys-Ser (SEQ ID NO:239). In other embodiments, the antibody can include a VLC including a CDR (e.g., a second CDR) including (or consisting of) the amino acid sequence Asp-Val-Xaa-Xaa-Arg-Pro-Ser (SEQ ID NO:240). Alternatively, the antibody can include a CDR (e.g., a second CDR) including (or consisting of) the amino acid sequence Leu-Phe/Leu-Ile/Val-His/Tyr-Lys/Arg-Xaa-Asn-Gln-Arg-Pro-Ser (SEQ ID NO:241) and, optionally, a CDR (e.g., a third CDR) including (or consisting of) the amino acid sequence Ala-Trp-Asp-Asp-Ser (SEQ ID NO:245). For example, the third CDR can consist of the sequence Ala-Ala-Trp-Asp-Asp-Ser-Leu-Arg-Gly-Tyr-Val (SEQ ID NO:51). The antibody can also include a VHC including a CDR (e.g., a third CDR) including (or consisting of) the amino acid sequence Ser-Ser-Ser-Trp-Val-Val-Xaa-Phe-Asp/Gly (SEQ ID NO:246) (e.g., Thr-Gly-Tyr-Ser-Ser-Ser-Trp-Val-Val-Asn-Phe-Asp-Tyr (SEQ ID NO:96).

Any of the antibodies of the invention, regardless of their sequence, can be monoclonal (e.g., monospecific) or polyclonal antibodies; any of the antibodies can be human or humanized; any of the antibodies can be affinity matured; and any of the antibodies can be isolated (e.g., purified to some degree from an animal or cells in which they are produced). Human antibodies include antibodies that have variable and constant regions from human germline immunoglobulin sequences. Such antibodies may have all, or a portion of, a human immunoglobulin heavy chain and all, or a portion of, a human immunoglobulin light chain. This is not to say that the antibodies of the invention (human or non-human) must contain naturally occurring sequences. The antibodies of the invention may include amino acid residues not encoded by human germline immunoglobulin nucleic acid sequences (e.g., mutations introduced by random or site-specific mutagenesis in vitro). Mutated or affinity matured antibodies are described further below.

While the antibodies are not limited to those that bind an AAH in a particular manner, the antibodies may bind the catalytic domain of an AAH (e.g., a catalytic domain of HAAH) or they may bind AAH in such a way as to alter the conformation of the catalytic domain or otherwise render it less active. The extent to which the activity of the bound AAH antigen is inhibited can vary. Useful antibodies (or fragments or other variants thereof) within the scope of the present invention include those that inhibit an activity of an AAH (e.g., the catalytic activity of HAAH) to a clinically beneficial degree upon administration to a patient or to an extent that they are useful in in vitro assays. For example, the antibodies can inhibit an enzymatic activity of AAH or HAAH by more than about 10%, 20%, 30%, 40%, 50%, 60%, 70%, 80%, or 90% (e.g., about 95%, 98%, or 99%). The inhibition can be assessed relative to a control or a reference sample or standard. Alternatively, an anti-AAH antibody can specifically bind an AAH protein without inhibiting the activity of the AAH protein. Such antibodies are useful in detecting AAH and can be used to identify a patient having cells in which AAH is overexpressed. The identification process can take place, for example, prior to administering an anti-AAH antibody to the patient that inhibits a biological activity of (e.g., the catalytic activity of) AAH.

The antibodies of the invention can be further characterized or assessed in terms of their ability to inhibit tumor cell growth or tumor cell motility in cell culture and/or to inhibit tumor cell growth or metastasis in vivo. Affinity can also be measured. For example, an antibody of the invention can have an affinity for an AAH protein (e.g., HAAH) that is equal to or less than about 1 µM. The antibodies of the invention can also be assessed for competition with other antibodies. For example, an antibody of the invention (e.g., a human or humanized antibody) may compete with an anti-AAH murine antibody (e.g., the monoclonal antibody FB50 or the monoclonal antibody 15C7) for binding to an epitope bound by the murine antibody. FB50 and 15C7 are explicitly excluded from the scope of the present invention. An antibody of the invention may also be assessed for its ability to compete with the clone 11 antibody (described herein (see FIG. 34)) for binding to an epitope bound by the clone 11 antibody. Antibodies that effectively compete with the clone 11 antibody are within the scope of the present invention.

In view of the foregoing, we may use the terms "specific binding" or "specifically binds to" refer to the ability of an antibody to: (1) bind to an AAH with a useful affinity (e.g., an affinity of at least $1 \times 10^6$ $M^{-1}$, or (2) bind to the AAH with an affinity that is greater than (e.g., at least two-fold greater than) its affinity for a nonspecific antigen, or (3) bind to the AAH with an affinity sufficient to produce a clinically desirable outcome (e.g., an improvement in a sign or symptom of a subject in need of treatment (e.g., a subject who has cancer or other unwanted cellular proliferation)).

The antibodies can include one or more Fc domains (e.g., an Fc domain of the gamma isotype (e.g., $IgG_1$)). We use the term "isotype" in its conventional sense to refer to the antibody class (e.g., IgM, IgA, IgE, IgD, or IgG1) that is encoded by heavy chain constant region genes. The antibodies of the invention can be of any isotype. Alternatively, or in addition, the antibodies can include a label (e.g., a polypeptide that serves as a marker or reporter sequence or that facilitates purification of the antibody sequence to which it is attached). Suitable labels include a FLAG tag, a histidine tag, or an enzymatically active or fluorescent protein. Alternatively, or in addition, the antibodies can include a toxin.

In other aspects, the invention features isolated nucleic acid molecules that include a sequence encoding an antibody of the invention (e.g., an anti-AAH scFv); expression vectors (e.g., plasmids) including a nucleic acid sequence encoding an antibody of the invention; and host cells including one or more types of those nucleic acid molecules or expression vectors (e.g., prokaryotic cells or eukaryotic cells such as a yeast or mammalian cells (e.g., Chinese hamster ovary (CHO) cells or tumor cells (e.g., myeloma cells))). Anti-AAH scFvs can be readily converted to multimeric anti-AAH antibodies (e.g., IgGs). More specifically, the invention features antibodies expressed on the surfaces of cells (e.g., displayed on yeast cells). We may use the term "recombinant" to refer to an antibody that is prepared by recombinant means (e.g., an antibody that is expressed using a recombinant expression vector transfected into a host cell, antibodies isolated from a recombinant, combinatorial antibody library, antibodies isolated from an animal (e.g., a mouse) that is transgenic for a human immunoglobulin gene (or genes), or antibodies prepared by any other means that involves splicing of human immunoglobulin gene sequences to other DNA sequences). Recombinant antibodies include humanized or CDR grafted antibodies; chimeric antibodies; and antibodies generated in vitro (e.g., by phage display). The antibodies may include constant regions derived from human germline immunoglobulin sequences.

The invention also features kits containing one or more of the compositions listed above and instructions (regardless of form; whether printed, audio- or visual) for use. For example, the kits of the invention can include an anti-AAH antibody (in a lyophilized or concentrated form or suspended in a physiologically acceptable diluent at a concentration suitable for use (e.g., at a concentration suitable for performing a diagnostic assay or administration to a patient)). The kits can also include nucleic acids, vectors, and/or host cells as described herein. Optionally, any of the kits of the invention can include paraphernalia for administering an anti-AAH antibody (e.g., needles, syringes, alcohol swabs, and bandages) or for using it in a diagnostic assay (e.g., reagents useful as controls).

The methods of the invention include methods of evaluating AAH expression in a cell. The cell can be a human or non-human cell and/or a cell in which AAH is overactive or overexpressed; the cell can be a cell in vivo or one maintained in tissue culture; the cell can be cancerous (e.g., a tumor cell); and the cell can be obtained from essentially any tissue type (e.g., a cell of the lung, liver, colon, pancreas, prostate, ovary, bile duct, brain, or breast). The cell may or may not be intact (e.g., a tissue homogenate can be used, as can proteins that have been purified from the cell). The methods can include providing an anti-AAH antibody (any of those described herein can be used); contacting the cell (or tissue homogenate or protein purified from the cell) with the antibody under conditions, and for a time, sufficient to allow the antibody to bind AAH expressed by the cell; and detecting the antibody or antigen-binding portion thereof (by, e.g., Western blot analysis, immunohistochemistry, or other antibody-based detection method). The detection step may provide a qualitative or quantitative assessment of AAH expression, and the result can be compared with that obtained from a control sample or with a reference sample or standard. Such methods can be carried out effectively with antibodies that specifically bind AAH, but have no impact on AAH's activity. The methods may be performed as part of an effort to diagnose patients amenable to treatment with the AAH-inhibitory antibodies of the invention.

The methods of the invention also include methods of modulating (e.g., inhibiting) the activity of an AAH protein in a cell. As with the evaluative methods described above, the cell can be a human or non-human cell and/or a cell in which AAH is overactive or overexpressed; the cell can be a cell in vivo or one maintained in tissue culture; the cell can be cancerous (e.g., a tumor cell); and the cell can be obtained from essentially any tissue type (e.g., a cell of the lung, liver, colon, pancreas, prostate, ovary, bile duct, brain, or breast). The methods can include providing a cell and exposing that cell to an antibody (or fragment or other variant) described herein, for a time, and under conditions sufficient to modulate (e.g., inhibit) AAH activity in the cell. When the cell is exposed to an anti-AAH antibody in vivo, the methods can be described as methods for treating a patient who has a disorder (e.g., a cancer or other disorder of unwanted cellular proliferation) or who is a risk for developing such a disorder (e.g., a patient in which AAH is overactive or overexpressed but who does not yet have a detectable tumor or other sign of cancer). The methods can include administering an antibody (or fragment or other variant thereof) described herein to the patient in an amount and for a time sufficient for the antibody to inhibit proliferation or metastasis of a cancerous cell in the patient. While methods of treatment are described further below, we note that a composition including an anti-AAH antibody can be administered locally (e.g., to the site of a tumor or to tissue remaining after a tumor has been surgically removed) or systemically (e.g., by intravenous injection). The patient can receive a single type of anti-AAH antibody or a combination of antibodies, and the antibody (or antibodies) can be administered in combination with a second agent (e.g., a second chemotherapeutic agent, an analgesic, or anti-emetic).

Terms relating to treatment refer to the application or administration of a composition of the invention to a patient or to a cell provided from a patient. The composition can be an anti-AAH antibody, a nucleic acid molecule or expression vector encoding same, or a host cell expressing same (any of which can be combined with a physiologically acceptable diluent). The composition can be administered ex vivo to cells isolated from (e.g., removed from) a subject, preferably from the patient in need of treatment. Upon conclusion of the treatment, the cells can be returned to the patient. Moreover, the treatment methods can be prophylactic. For example, they can be applied to a patient who is at risk for developing cancer (there are well established indicators of risk (e.g., levels of cancer-associated antigens, such as PSA and, as noted, AAH per se)). The treatment can be one that cures or heals the patient, but the invention is not so limited. The methods of the invention may also alleviate, relieve, alter, ameliorate, palliate, or improve a sign or symptom of the cancer or the patient's predisposition toward the cancer.

A "therapeutically effective amount" of an anti-AAH antibody is an amount of an anti-AAH antibody effective to treat a sign or symptom of a disorder (e.g., a cancer, e.g., a tumor or other neoplasm or dysplastic syndrome). A "prophylactically effective amount" of an anti-AAH antibody is an amount of an anti-AAH antibody effective in delaying the occurrence of the onset or recurrence of a disorder (e.g., a cancer), or reducing the severity of a sign or symptom thereof.

While patients amenable to treatment are described further below, we note here that the patient can have any proliferative disorder associated with overactive or overexpressed AAH. For example, the patient can have a tumor within the lung, liver, colon, pancreas, prostate, ovary, bile duct, brain, or breast containing AAH-positive cells.

In another aspect, the invention features methods of identifying an antibody that specifically binds to an AAH. The methods can include, for example: (a) providing a library of antibodies (e.g., human antibodies, which may be scFvs); (b) contacting members of the library with AAH proteins or fragments thereof, under conditions that allow the antibodies to bind the polypeptides; and (c) selecting an antibody that binds to the AAH protein (or AAH fragment). The method can further include affinity-maturing the selected antibody. Maturation can be achieved with, for example, methods such as error-prone PCR, or methods in which a nucleic acid encoding the antibody is subjected to recombination with nucleic acid(s) of a library, e.g., using CDR shuffling or chain shuffling techniques. The invention also features methods for making a human monoclonal antibody that specifically binds to an AAH. The methods can include the steps of: identifying an antibody that specifically binds to an AAH protein; expressing a nucleic acid sequence encoding the antibody in a cell; and isolating the expressed antibody from the cell. We may refer to these methods as production methods, and anti-AAH antibodies made by these methods are within the scope of the present invention.

The antibodies of the invention may be advantageous for various reasons. For example, when less than full-length antibodies are used, the antibody fragments or variants may penetrate tumors more readily. When human or humanized antibodies are administered to human patients, they are unlikely to stimulate an undesirable immune response as potent as that triggered by non-human proteins. The antibodies of the invention are also unlikely to generate other undesirable side effects because HAAH expression is very low or undetectable in non-cancerous tissues, and antibodies directed to HAAH may be less toxic to non-cancerous tissue than less specific treatments. To our knowledge, we have the first human antibodies that bind to HAAH.

All publications, patent applications, patents, and other references mentioned herein are incorporated by reference in their entirety. Other features and advantages of the invention will be apparent from the following detailed description, and from the claims.

BRIEF DESCRIPTION OF THE DRAWINGS

FIG. 6 is a bar graph depicting binding of soluble scFv fragments of 6 unique clones to the catalytic domain of HAAH.

FIG. 11 is a depiction of the amino acid sequence of an affinity-matured clone 11 scFv fragment (SEQ ID NO:59). Amino acid residues that are changed relative to clone 11 are bold and underlined.

FIG. 12 is a set of dot-plot graphs depicting two types of fluorescence detected by flow cytometry in experiments in which the original clone 11 scFv fragments, a first round of mutant clone 11 scFv fragments, and a clone derived from the first round of mutants were analyzed. Fluorescence intensity depicted on the X-axis corresponds to the level of scFv fragments displayed on yeast cells. Fluorescence intensity on the Y-axis corresponds to the level of binding to HAAH of the cells.

FIG. 13 is a set of dot-plot graphs depicting two types of fluorescence detected by flow cytometry in experiments in which the mutant clone 11 scFv fragments were analyzed. Fluorescence intensity depicted on the X-axis corresponds to the level of scFv fragments displayed on yeast cells. Fluorescence intensity on the Y-axis corresponds to the level of binding to HAAH of the cells.

FIG. 15 is a depiction of the amino acid sequence of an affinity-matured clone 13 scFv fragment (SEQ ID NO:61), 13m1. Amino acid residues that are changed relative to clone 13 are bold and underlined.

FIGS. 19A-K are dot-plot graphs depicting two types of fluorescence detected by flow cytometry in experiments in which the clones produced by chain shuffling were analyzed (FIG. 19A, clone LLm1; FIG. 19B, clone LLm3; FIG. 19C, clone LLm5; FIG. 19D, clone LLm6; FIG. 19E, clone LLm7; FIG. 19F, clone LLm8; FIG. 19G, clone LLm9; FIG. 19H, clone LLm11; FIG. 19I, clone LLm14; FIG. 19J, clone LLm15(3); FIG. 19K, clone LLm20(8)). Fluorescence intensity depicted on the X-axis corresponds to the level of scFv fragments displayed on yeast cells. Fluorescence intensity on the Y-axis corresponds to the level of binding to HAAH of the cells.

FIG. 20 is a depiction of the amino acid sequences of CDR1 SEQ ID NOs 94, 167, 171, 173, 179, 183, 187, 192, 195. 249, 204, and 250 respectively, CDR2 SEQ ID NOs 97, 168, 248, 174, 180, 185, 188, 193, 197, 199, 205, and 210 respectively, and CDR3 SEQ ID NOs 118, 169, 172, 175, 181, 186, 191, 194, 198, 203. and 211 respectively, regions of a wild-type scFv clone and eleven clones derived by chain shuffling.

FIGS. 22A-D are dot-plot graphs depicting two types of fluorescence detected by flow cytometry in experiments in which the clones produced by chain shuffling were analyzed (FIG. 22A, CM1; FIG. 22B, CM2; FIG. 22C, CM3; FIG. 22D, CM4). Fluorescence intensity depicted on the X-axis corresponds to the level of scFv fragments displayed on yeast cells. Fluorescence intensity on the Y-axis corresponds to the level of binding to HAAH of the cells.

FIG. 23 is a depiction of the amino acid sequences of CDR1 SEQ ID NOs 94, 94, 252, 221 and 253, CDR2 SEQ ID NOs 251, 251, 216, 222 and 227, and CDR3 regions of a wild-type scFv clone, and four clones derived by CDR shuffling SEQ ID NOs 212, 215, 217, 223 and 228, respectively.

FIG. 32A is a graph depicting the binding of HAAH to yeast expressing different scFv fragments in the presence or absence of competition by CDRm4 IgG antibody.

FIG. 32B is a graph depicting the binding of HAAH to yeast expressing different scFv fragments in the presence or absence of competition by LLm11 IgG antibody.

FIG. 33A is a graph depicting the binding of HAAH to yeast displaying scFv CDRm4 and the second generation mutant scFv C4m18. Dissociation constants are indicated on the graph.

FIG. 33B is a graph depicting the display level of first and second generation scFv mutants on yeast.

FIG. 34 is a Table containing amino acid sequences that can be used as, or that can be included in, anti-AAH antibodies or fragments or other variants thereof.

FIG. 35 is a Table containing amino acid sequences that can be used as, or that can be included in, anti-AAH antibodies or fragments or other variants thereof (e.g., anti-HAAH affinity-matured, mutagenized antibody regions).

FIG. 36 is a Table containing amino acid sequences that can be used as, or that can be included in, anti-AAH antibodies or fragments or other variants thereof (e.g., anti-HAAH scFv antibodies).

FIG. 37 is a Table containing amino acid sequences (anti-AAH antibody CDRs) that can be included in anti-AAH antibodies or fragments or other variants thereof.

FIG. 38 is a Table containing amino acid sequences (affinity-matured, mutagenized anti-HAAH antibody CDRs) that can be included in anti-AAH antibodies or fragments or other variants thereof.

DETAILED DESCRIPTION

Figure 1:
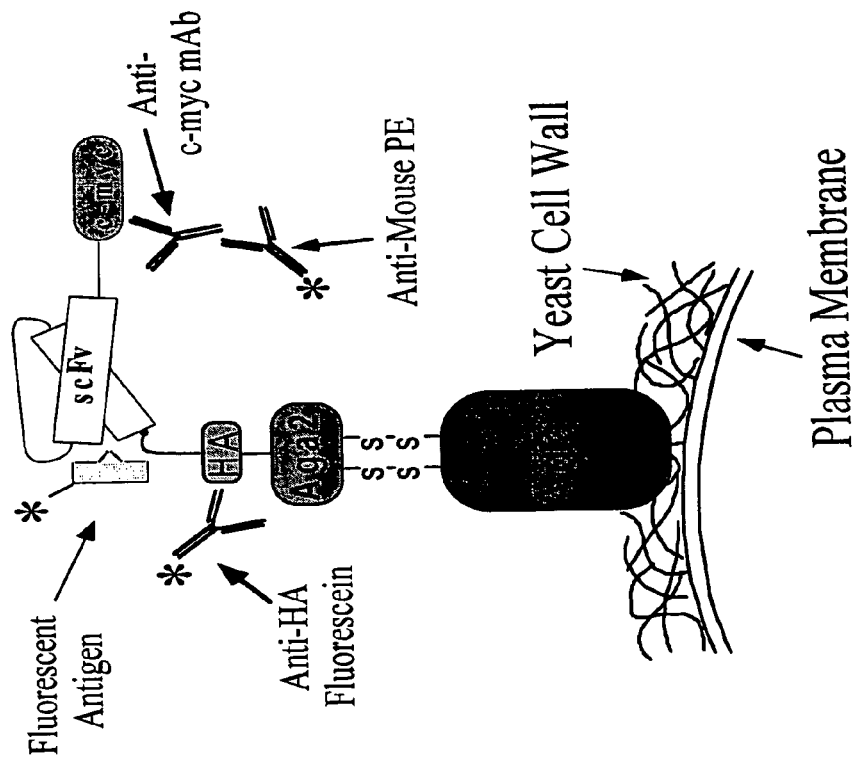
FIG. 1 is a schematic diagram depicting the fusion proteins displayed on yeast cells for performing screening and binding studies with the yeast surface display technique. Also depicted are various epitope tags and an antigen that can be employed for detection. The fluorescent antigen used in the experiments described herein was a recombinant HAAH protein corresponding to full-length or catalytic domain only, as indicated.

Aspartyl (asparaginyl) β-hydroxylase (AAH) is a highly conserved alpha-ketoglutarate-dependent dioxygenase that catalyzes post-translational hydroxylation of β carbons of specific aspartate and asparagine residues in epidermal growth factor-like domains of numerous proteins, including extracellular matrix proteins, low-density lipoprotein (LDL) receptor, Notch homologs, and Notch ligand homologs (Jia et al., *Proc. Natl. Acad. Sci. USA* 91(15):7227-7231, 1994; Jia et al., *J. Biol. Chem.* 267(20):14322-14327, 1992; Gronke et al., *Proc Natl Acad Sci USA* 86(10):3609-13, 1989). Overexpression of human AAH (HAAH) has been detected in a number of human cancers, including hepatocellular carcinomas, cholangiocarcinomas, and, neuroectodermal tumors (Lavaissiere et al., *J. Clin. Investig.* 98:1313-1323, 1996; Sepe et al., *Lab. Investig.* 82(7):81-891, 2002). The finding that AAH is overexpressed in numerous tumors, and that forced expression increases cell motility and survival indicates that AAH may contribute to malignant transformation in vivo (Sepe et al., *Lab. Investig.* 82(7):881-891, 2002). Inventions relating to the use of HAAH for diagnosis and treatment of cancer have been described (Radosevich, U.S. Pat. No. 6,166,176; Radosevich, U.S. Pat. No. 6,727,080; Wands et al., U.S. Pat. No. 6,783,758; Wands et al., U.S. Pat. No. 6,797,696; Wands et al., U.S. Pat. No. 6,812,206; Wands et al., U.S. Pat. No. 6,815,415).

The present invention relates to antibodies and antigen binding portions thereof having binding specificity for AAH or a portion of AAH. In particular, the invention relates to human monoclonal antibodies that specifically bind to AAH. In one embodiment, the antibodies or antigen binding portions thereof have specificity for human AAH (HAAH). Antibodies that inhibit one or more functions characteristic of a AAH are within the scope of the present invention, whether that function is an enzymatic activity (e.g., hydroxylase activity) or a function manifested on the cellular level (e.g., facilitating motility of a tumor cell). Thus, for example, an anti-AAH antibody can be one that inhibits motility of a tumor cell. Alternatively, or in addition, an antibody of the invention may inhibit (reduce or prevent) the interaction of AAH with a natural ligand, such as a protein containing an EGF-like domain (e.g., an extracellular matrix protein). Human monoclonal antibodies directed against (e.g., antibodies that specifically bind) AAH can inhibit functions mediated by AAH, including modulation of substrate activity by hydroxylation. Preferably, the antibodies and antigen binding portions thereof can bind AAH with an affinity of greater than $1 \times 10^6$ $M^{-1}$.

The HAAH amino acid sequence is found in GenBank® under accession number I38423 (GI:7433245). One of ordinary skill in the art can readily retrieve the sequence from GenBank® or another source. The transmembrane domain of HAAH is designated as being between amino acids 341-374 of the GenBank® sequence. The extracellular (or luminal) portion of the molecule corresponds to the C-terminal end. Anti-AAH antibodies, whether full-length or not, will interact with (e.g., bind to) AAH or a fragment of that protein (e.g., an anti-HAAH antibody will bind to HAAH). The antibody may bind to an epitope of AAH (e.g., a conformational or a linear epitope) or to a fragment of the full-length AAH protein. Conformational epitopes are typically lost when exposed to a denaturing solvent.

Antibodies: Antibodies of the invention can assume various configurations. For example, the antibody can be a tetramer (e.g., an antibody having two heavy chains and two light chains) or a single-chain antibody. Accordingly, the antibodies of the invention include proteins that may have one or two heavy (H) chain variable regions, and one or two light chain variable regions. The VHC and VLC regions can be further subdivided into regions of hypervariability, termed "complementarity determining regions" (CDRs), interspersed with regions that are more conserved, termed "framework regions" (FRs). The extent of the FRs and CDRs has been defined (see, Kabat, E. A., et al. *Sequences of Proteins of Immunological Interest*, Fifth Edition, U.S. Department of Health and Human Services, NIH Publication No. 91-3242, 1991, and Chothia, et al., *J. Mol. Biol.* 196:901-917, 1987, which are incorporated herein by reference). Where an antibody of the invention includes one or more VHCs and/or one or more VLCs, each VHC and VLC can be composed of three CDRs and four FRs, arranged from amino-terminus to carboxy-terminus in the following order: FR1, CDR1, FR2, CDR2, FR3, CDR3, FR4.

The VHC or VLC chain of an antibody of the invention can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains: CH1, CH2 and CH3. The light chain constant region is comprised of one domain: CL. The variable regions of the heavy and light chains contain a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof (e.g., $IgG_1$, $IgG_2$, $IgG_3$, and $IgG_4$)), wherein the light chains of the immunoglobulin may be of types kappa or lambda.

Antibodies may also be referred to as "immunoglobulins" (proteins consisting of one or more polypeptides substantially encoded by immunoglobulin genes, the anti-AAH antibodies of the invention may also be referred to as anti-AAH immunoglobulins, and may contain sequences encoded by one or more of the human immunoglobulin genes). The recognized human immunoglobulin genes include the kappa, lambda, alpha ($IgA_1$ and $IgA_2$), gamma ($IgG_1$, $IgG_2$, $IgG_3$, $IgG_4$), delta, epsilon, and mu constant region genes, as well as the myriad immunoglobulin variable region genes. Full-length immunoglobulin "light chains" (about 25 kDa and 214 amino acids) are encoded by a variable region gene at the $NH_2$-terminus (about 110 amino acids) and a kappa or lambda constant region gene at the COOH-terminus. Full-length immunoglobulin heavy chains (about 50 kDa and 446 amino acids), are similarly encoded by a variable region gene (about 116 amino acids) and one of the other aforementioned constant region genes, e.g., gamma (encoding about 330 amino acids). The antibodies or immunoglobulins of the present invention may include CDRs (which are described further herein) from a human or non-human source. The framework of the immunoglobulin can be human, humanized, or non-human, e.g., a murine framework modified to decrease antigenicity in humans, or a synthetic framework, e.g., a consensus sequence.

The term "antigen-binding portion" of an antibody (or simply "antibody portion," or "portion"), as used herein, refers to a portion of an antibody that specifically binds to an AAH (e.g., HAAH), e.g., a molecule in which one or more immunoglobulin chains is not full length, but which specifically binds to an AAH. Examples of binding portions encompassed within the term "fragment (or antigen-binding portion) or other variant thereof" of an antibody include (i) an Fab fragment, a monovalent fragment consisting of the VLC, VHC, CL and CH1 domains; (ii) a $F(ab')_2$ fragment, a bivalent fragment comprising two Fab fragments linked by a disulfide bridge at the hinge region; (iii) a Fd fragment consisting of the VHC and CH1 domains; (iv) a Fv fragment consisting of the VLC and VHC domains of a single arm of an antibody, (v) a dAb fragment (Ward et al., *Nature* 341:544-546, 1989), which consists of a VHC domain; and (vi) an isolated complementarity determining region (CDR) having sufficient framework to specifically bind, e.g., an antigen binding portion of a variable region. An antigen-binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. *Science* 242:423-426, 1988; and Huston et al. *Proc. Natl. Acad. Sci. USA* 85:5879-5883, 1988). Such single chain antibodies are also intended to be encompassed within the term "antigen-binding portion" of an antibody. These antibody portions are obtained using conventional techniques known to those with skill in the art, and the portions are screened for utility in the same manner as are intact antibodies. An Fab fragment can result from cleavage of a tetrameric antibody with papain; Fab' and F(ab')2 fragments can be generated by cleavage with pepsin.

As used herein, the term "human antibody" includes any antibody in which the framework residues correspond to human germline sequences and the CDRs result from V(D)J recombination and somatic mutations. However, human antibodies may also comprise amino acid residues not encoded in human germline immunoglobulin nucleic acid sequences (e.g., mutations introduced by random or site-specific mutagenesis in vitro). It has been demonstrated that in vivo somatic mutation of human variable genes results in mutation of framework residues (see *Nat. Immunol.* 2:537, 2001). Such an antibody would be termed "human" given its source, despite the framework mutations. Mouse antibody variable domains also contain somatic mutations in framework residues (See *Sem. Immunol* 8:159, 1996). Consequently, transgenic mice containing the human Ig locus produce antibodies that are commonly referred to as "fully human," even though they possess an average of 4.5 framework mutations (a range of 1-8 in this work: Nat Genet. 1997 February; 15(2):146-56). Accepted usage therefore indicates that an antibody variable domain gene based on germline sequence but possessing framework mutations introduced by, for example, an in vivo somatic mutational process is termed "human." Thus, the invention encompasses human antibodies that specifically bind AAH (e.g., HAAH, even where those antibodies include mutations (e.g., mutations within the FR) and fragments or other variants thereof (e.g., single chain antibodies that include the VLC and VHC of a multimeric human antibody). For example, the human antibodies of the invention can have 1-8 framework mutation (e.g., about 2, 4, 6, or 8 substitutions, additions, or deletions). Preferably, the sequence of the original human antibody is a human germline sequence.

Human single-chain antibodies specific for HAAH were produced as described herein. In a particular embodiment, the invention provides antibodies that have specificity for HAAH, and bind to an epitope bound by an antibody described herein (e.g., the antibody encoded by clone 11 or an affinity-matured derivative of clone 11). Antibodies that bind an epitope that overlaps with an epitope bound be an antibody described herein can be identified by their ability to compete with an EGF-like domain for binding to HAAH (e.g., to cells bearing HAAH, such as HAAH transfectants, or H460 tumor cells). The binding site of an anti-AAH antibody can be within the catalytic domain of HAAH.

The anti-AAH antibodies can be polyclonal or monoclonal. The antibodies and antigen binding portions thereof described herein are useful in therapeutic compositions and regimens, diagnostic compositions and regimens, and in assays requiring an agent that can identify or inhibit an AAH protein. The present invention encompasses an antibody or antigen binding portion thereof for use in therapy (including prophylaxis) or diagnosis (e.g., of particular diseases or conditions such as cancers), and use of such antibodies or antigen binding portions thereof for the manufacture of a medicament for use in treatment of diseases or conditions as described herein.

Single chain antibodies, and chimeric, humanized or CDR-grafted antibodies, as well as chimeric or CDR-grafted single chain antibodies, comprising portions derived from different species, are also encompassed by the present invention and the term "antibody." The various portions of these antibodies can be joined together chemically by conventional techniques, or can be prepared as contiguous polypeptides using genetic engineering techniques. For example, nucleic acids encoding a chimeric or humanized chain can be expressed to produce a contiguous polypeptide. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman et al., *BioTechnology* 10:1455-1460, 1992, regarding CDR-graft antibody, and Ladner et al., U.S. Pat. No. 4,946,778 and Bird, R. E. et al., *Science* 242: 423-426, 1988 regarding single chain antibodies.

In addition, antigen binding portions of antibodies, including fragments of chimeric, humanized, CDR-grafted or single chain antibodies, can also be produced and are within the scope of the present invention. Antigen binding portions of the antibodies retain at least one binding function of the full-length antibody from which they are derived. Preferred antigen binding portions retain an antigen binding function of a corresponding full-length antibody (e.g., specificity for an AAH). Functional fragments can retain the ability of the full-length antibody to inhibit one or more functions characteristic of a AAH, such as AAH's hydroxylase activity. For example, a functional fragment can inhibit hydroxylation of an EGF-like domain. These EGF-like domains contain conserved motifs that form repetitive sequences in diverse proteins, such as clotting factors, extracellular matrix proteins, low-density lipoprotein receptor, Notch homologues or Notch ligand homologues. Any AAH substrate, including those just described, can be used in assays to assess an anti-AAH antibody. Exemplary AAH assay substrates include EGF-IX$_H$ (Gronke et al., *Proc Natl Acad Sci USA* 86(10): 3609-13, 1989), EGF-X$_{1H}$ (Gronke et al., *J. Biol. Chem.* 265: 8558-8565, 1990), and EGF-Asn (Gronke et al., *J. Biol. Chem.* 265:8558-8565, 1990; Wang et al., *J. Biol. Chem.* 266:14004-14010, 1991).

For example, antibody portions capable of binding to a AAH or a fragment thereof include Fv, Fab, Fab' and F(ab')$_2$ fragments. Such portions can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

The invention provides chimeric antibodies that can be prepared as a contiguous polypeptide using genetic engineering techniques (e.g., DNA encoding the protein portions of the chimeric antibody can be expressed to produce a contiguous polypeptide chain). One example of a chimeric antibody of the present invention is an antibody containing one or more antibody chains comprising a CDR (e.g., one or more CDRs of an antibody described herein) and a framework region derived from a light and/or heavy chain of a second antibody (e.g., of human origin; e.g., CDR-grafted antibodies with or without framework changes). In one embodiment, the chimeric antibody can compete with the murine 15C7 or FB50 monoclonal antibody for binding to HAAH. The antigen binding region of the chimeric antibody can be derived from an antibody clone described herein (e.g., clone 11, or a mutant of clone 11; e.g., as in a chimeric antibody comprising CDR1, CDR2 and CDR3 of the clone 11 light chain and CDR1, CDR2 and CDR3 of the clone 11 heavy chain). Chimeric or CDR-grafted single chain antibodies also include humanized immunoglobulin. See, e.g., Cabilly et al., U.S. Pat. No. 4,816, 567; Cabilly et al., European Patent No. 0,125,023 B1; Queen et al., European Patent No. 0,451,216 B1; Boss et al., U.S. Pat. No. 4,816,397; Boss et al., European Patent No. 0,120, 694 B1; Neuberger et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird et al., *Science* 242: 423-426, 1988), regarding single chain antibodies.

Chimeric antibodies can be produced using synthetic and/or recombinant nucleic acids to prepare genes (e.g., cDNA) encoding the desired chimeric chain. For example, nucleic acid (e.g., DNA) sequences coding for variable regions can be constructed using PCR mutagenesis methods to alter DNA sequences encoding an antibody chain, e.g., using methods employed to generate humanized antibodies (see e.g., Kanunan, et al., *Nucl. Acids Res.* 17: 5404, 1989; Sato, et al., *Cancer Research* 53: 851-856, 1993; Daugherty, et al., *Nucleic Acids Res. L*9(9): 2471-2476, 1991; and Lewis and Crowe, *Gene* 101: 297-302, 1991). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

Other suitable methods of producing or isolating anti-AAH antibodies include, for example, methods that rely upon immunization of transgenic animals (e.g., mice) capable of producing a full repertoire of human antibodies (see e.g., Jakobovits et al., *Proc. Natl. Acad. Sci. USA* 90: 2551-2555, 1993; Jakobovits et al., *Nature* 362: 255-258, 1993; Lonberg et al., U.S. Pat. No. 5,545,806; Surani et al., U.S. Pat. No. 5,545,807).

Antibodies that specifically bind to AAH can be identified by expressing recombinant antibodies in a library and selecting members of the library that bind AAH. The affinity of the selected antibodies for AAH can be further enhanced by affinity-maturing these antibodies, e.g., using PCR mutagenesis, chain shuffling, or CDR shuffling techniques in conjunction with one or more cycles of screening, as described herein. Other methods can also be used to generate anti-AAH antibodies. For example, anti-AAH antibodies can be produced by immunizing animals. A variety of methods have been described for preparing antigen for immunization and for generating monoclonal antibodies from immunized animals (see e.g., Kohler et al., *Nature* 256:495-497, 1975; Kohler and Milstein, *Eur. J. Immunol.* 6:511-519, 1976; Milstein et al., *Nature* 266:550-552, 1977; Koprowski et al., U.S. Pat. No. 4,172,124; Harlow, E. and D. Lane, 1988, Antibodies: A Laboratory Manual, (Cold Spring Harbor Laboratory Press: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line) with antibody producing cells. The antibody producing cell, preferably those of the spleen or lymph nodes, are obtained from immunized animals. The fused cells (hybridomas) can be isolated using selective culture conditions and cloned by limiting dilution. Cells that produce antibodies with the desired specificity can be selected by a suitable assay (e.g., ELISA).

The antibody or an antigen-binding portion thereof can include, for example, a variable heavy chain region at least 80% identical (e.g., 85%, 90%, 95%, 98% or 100%) to one of the following sequences: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:119, SEQ ID NO:121; SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:254, SEQ ID NO:256, SEQ ID NO:258, SEQ ID NO:260; SEQ ID NO:262, SEQ ID NO:264, SEQ ID NO:266, SEQ ID NO:268, and SEQ ID NO:270.

The antibody or an antigen-binding portion thereof can include, for example, a variable light chain region at least 80% identical (e.g., 85%, 90%, 95%, 98% or 100%) to one of the following sequences: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:255, SEQ ID NO:257, SEQ ID NO:259, SEQ ID NO:261; SEQ ID NO:263, SEQ ID NO:265, SEQ ID NO:267, SEQ ID NO:269, and SEQ ID NO:271.

The antibody or an antigen-binding portion thereof can include, for example, a variable heavy chain region at least 80% identical (e.g., 85%, 90%, 95%, 98% or 100%) to SEQ BD NO:1 and a variable light chain region at least 80% identical to (e.g., 85%, 90%, 95%, 98% or 100%) SEQ ID NO:2; a variable heavy chain region at least 80% identical (e.g., 85%, 90%, 95%, 98% or 100%) to SEQ ID NO:3 and a variable light chain region at least 80% identical (e.g., 85%, 90%, 95%, 98% or 100%) to SEQ ID NO:4; a variable heavy chain region at least 80% identical (e.g., 85%, 90%, 95%, 98% or 100%) to SEQ ID NO:5 and a variable light chain region at least 80% identical (e.g., 85%, 90%, 95%, 98% or 100%) to SEQ ID NO:6; a variable heavy chain region at least 80% identical to (e.g., 85%, 90%, 95%, 98% or 100%) SEQ ID NO:7 and a variable light chain region at least 80% identical (e.g., 85%, 90%, 95%, 98% or 100%) to SEQ ID NO:8; a variable heavy chain region at least 80% identical (e.g., 85%, 90%, 95%, 98% or 100%) to SEQ ID NO:9 and a variable light chain region at least 80% identical (e.g., 85%, 90%, 95%, 98% or 100%) to SEQ ID NO:10; a variable heavy chain region at least 80% identical (e.g., 85%, 90%, 95%, 98% or 100%) to SEQ ID NO:11 and a variable light chain region at least 80% identical (e.g., 85%, 90%, 95%, 98% or 100%) to SEQ ID NO:12; a variable heavy chain region at least 80% identical (e.g., 85%, 90%, 95%, 98% or 100%) to SEQ ID NO:13 and a variable light chain region at least 80% identical (e.g., 85%, 90%, 95%, 98% or 100%) to SEQ ID NO:14; a variable heavy chain region at least 80% identical (e.g., 85%, 90%, 95%, 98% or 100%) to SEQ ID NO:15 and a variable light chain region at least 80% identical (e.g., 85%, 90%, 95%, 98% or 100%) to SEQ ID NO:16; a variable heavy chain region at least 80% identical (e.g., 85%, 90%, 95%, 98% or 100%) to SEQ ID NO:17 and a variable light chain region at least 80% identical (e.g., 85%, 90%, 95%, 98% or 100%) to SEQ ID NO:18; a variable heavy chain region at least 80% identical (e.g., 85%, 90%, 95%, 98% or 100%) to SEQ ID NO:19 and a variable light chain region at least 80% identical (e.g., 85%, 90%, 95%, 98% or 100%) to SEQ ID NO:20; a variable heavy chain region at least 80% identical (e.g., 85%, 90%, 95%, 98% or 100%) to SEQ ID NO:21 and a variable light chain region at least 80% identical (e.g., 85%, 90%, 95%, 98% or 100%) to SEQ ID NO:22; a variable heavy chain region at least 80% identical (e.g., 85%, 90%, 95%, 98% or 100%) to SEQ ID NO:23 and a variable light chain region at least 80% identical (e.g., 85%, 90%, 95%, 98% or 100%) to SEQ ID NO:24; a variable heavy chain region at least 80% identical (e.g., 85%, 90%, 95%, 98% or 100%) to SEQ ID NO:25 and a variable light chain region at least 80% identical (e.g., 85%, 90%, 95%, 98% or 100%) to SEQ ID NO:26; a variable heavy chain region at least 80% identical (e.g., 85%, 90%, 95%, 98% or 100%) to SEQ ID NO:27 and a variable light chain region at least 80% identical (e.g., 85%, 90%, 95%, 98% or 100%) to SEQ ID NO:28; a variable heavy chain region at least 80% identical (e.g., 85%, 90%, 95%, 98% or 100%) to SEQ ID NO:29 and a variable light chain region at least 80% identical (e.g., 85%, 90%, 95%, 98% or 100%) to SEQ ID NO:30; a variable heavy chain region at least 80% identical (e.g., 85%, 90%, 95%, 98% or 100%) to SEQ ID NO:119 and a variable light chain region at least 80% identical (e.g., 85%, 90%, 95%, 98% or 100%) to SEQ ID NO:120; a variable heavy chain region at least 80% identical (e.g., 85%, 90%, 95%, 98% or 100%) to SEQ ID NO:121 and a variable light chain region at least 80% identical (e.g., 85%, 90%, 95%, 98% or 100%) to SEQ ID NO:122; a variable heavy chain region at least 80% identical (e.g., 85%, 90%, 95%, 98% or 100%) to SEQ ID NO:123 and a variable light chain region at least 80% identical (e.g., 85%, 90%, 95%, 98% or 100%) to SEQ ID NO:124; a variable heavy chain region at least 80% identical (e.g., 85%, 90%, 95%, 98% or 100%) to SEQ ID NO:125 and a variable light chain region at least 80% identical (e.g., 85%, 90%, 95%, 98% or 100%) to SEQ ID NO:126; a variable heavy chain region at least 80% identical (e.g., 85%, 90%, 95%, 98% or 100%) to SEQ ID NO:127 and a variable light chain region at least 80% identical (e.g., 85%, 90%, 95%, 98% or 100%) to SEQ ID NO:128; a variable heavy chain region at least 80% identical (e.g., 85%, 90%, 95%, 98% or 100%) to SEQ ID NO:129 and a variable light chain region at least 80% identical (e.g., 85%, 90%, 95%, 98% or 100%) to SEQ ID NO:130; a variable heavy chain region at least 80% identical (e.g., 85%, 90%, 95%, 98% or 100%) to SEQ ID NO:131 and a variable light chain region at least 80% identical (e.g., 85%, 90%, 95%, 98% or 100%) to SEQ ID NO:132; a variable heavy chain region at least 80% identical (e.g., 85%, 90%, 95%, 98% or 100%) to SEQ ID NO:133 and a variable light chain region at least 80% identical (e.g., 85%, 90%, 95%, 98% or 100%) to SEQ ID NO:134; a variable heavy chain region at least 80% identical (e.g., 85%, 90%, 95%, 98% or 100%) to SEQ ID NO:135 and a variable light chain region at least 80% identical (e.g., 85%, 90%, 95%, 98% or 100%) to SEQ ID NO:136; a variable heavy chain region at least 80% identical (e.g., 85%, 90%, 95%, 98% or 100%) to SEQ ID NO:137 and a variable light chain region at least 80% identical (e.g., 85%, 90%, 95%, 98% or 100%) to SEQ ID NO:138; a variable heavy chain region at least 80% identical (e.g., 85%, 90%, 95%, 98% or 100%) to SEQ ID NO:139 and a variable light chain region at least 80% identical (e.g., 85%, 90%, 95%, 98% or 100%) to SEQ ID NO:140; a variable heavy chain region at least 80% identical (e.g., 85%, 90%, 95%, 98% or 100%) to SEQ ID NO:141 and a variable light chain region at least 80% identical (e.g., 85%, 90%, 95%, 98% or 100%) to SEQ ID NO:142; a variable heavy chain region at least 80% identical (e.g., 85%, 90%, 95%, 98% or 100%) to SEQ ID NO:143 and a variable light chain region at least 80% identical (e.g., 85%, 90%, 95%, 98% or 100%) to SEQ ID NO:144; a variable heavy chain region at least 80% identical (e.g., 85%, 90%, 95%, 98% or 100%) to SEQ ID NO:145 and a variable light chain region at least 80% identical (e.g., 85%, 90%, 95%, 98% or 100%) to SEQ ID NO:146; a variable heavy chain region at least 80% identical (e.g., 85%, 90%, 95%, 98% or 100%) to SEQ ID NO:147 and a variable light chain region at least 80% identical (e.g., 85%, 90%, 95%, 98% or 100%) to SEQ ID NO:148; a variable heavy chain region at least 80% identical (e.g., 85%, 90%, 95%, 98% or 100%) to SEQ ID NO:254 and a variable light chain region at least 80% identical (e.g., 85%, 90%, 95%, 98% or 100%) to SEQ ID NO:255; a variable heavy chain region at least 80% identical (e.g., 85%, 90%, 95%, 98% or 100%) to SEQ ID NO:256 and a variable light chain region at least 80% identical (e.g., 85%, 90%, 95%, 98% or 100%) to SEQ ID NO:257; a variable heavy chain region at least 80% identical (e.g., 85%, 90%, 95%, 98% or 100%) to SEQ ID NO:258 and a variable light chain region at least 80% identical (e.g., 85%, 90%, 95%, 98% or 100%) to SEQ ID NO:259; a variable heavy chain region at least 80% identical (e.g., 85%, 90%, 95%, 98% or 100%) to SEQ ID NO:260 and a variable light chain region at least 80% identical (e.g., 85%, 90%, 95%, 98% or 100%) to SEQ ID NO:261; a variable heavy chain region at least 80% identical (e.g., 85%, 90%, 95%, 98% or 100%) to SEQ ID NO:262 and a variable light chain region at least 80% identical (e.g., 85%, 90%, 95%, 98% or 100%) to SEQ ID NO:263; a variable heavy chain region at least 80% identical (e.g., 85%, 90%, 95%, 98% or 100%) to SEQ ID NO:264 and a variable light chain region at least 80% identical (e.g., 85%, 90%, 95%, 98% or 100%) to SEQ ID NO:265; a variable heavy chain region at least 80% identical (e.g., 85%, 90%, 95%, 98% or 100%) to SEQ ID NO:266 and a variable light chain region at least 80% identical (e.g., 85%, 90%, 95%, 98% or 100%) to SEQ ID NO:267; a variable heavy chain region at least 80% identical (e.g., 85%, 90%, 95%, 98% or 100%) to SEQ ID NO:268 and a variable light chain region at least 80% identical (e.g., 85%, 90%, 95%, 98% or 100%) to SEQ ID NO:269; or a variable heavy chain region at least 80% identical (e.g., 85%, 90%, 95%, 98% or 100%) to SEQ ID NO:270 and a variable light chain region at least 80% identical (e.g., 85%, 90%, 95%, 98% or 100%) to SEQ ID NO:271.

In various embodiments, the antibody or antigen-binding portion thereof includes a complementarity determining region (CDR) that is at least 40% identical (e.g., 40%, 60%, 80%, 85%, 90%, 95%, 98% or 100%) to any one of SEQ ID NOs. 46-81 or 281-313.

In various embodiments, the antibody or fragment or other variant thereof includes a complementarity determining region (CDR) that is at least 40% identical (e.g., 40%, 60%, 80%, 85%, 90%, 95%, 98% or 100%) to any one of SEQ ID NOs. 46-51, 54, 56, 82-117, 164-250, or 314-319. The antibody or fragment or other variant thereof can also be, or can include: a variable heavy chain region at least 80% identical to SEQ ID NO:1 and a variable light chain region at least 80% identical to SEQ ID NO:2; a variable heavy chain region at least 80% identical to SEQ ID NO:3 and a variable light chain region at least 80% identical to SEQ ID NO:4; a variable heavy chain region at least 80% identical to SEQ ID NO:5 and a variable light chain region at least 80% identical to SEQ ID NO:6; a variable heavy chain region at least 80% identical to SEQ ID NO:7 and a variable light chain region at least 80% identical to SEQ ID NO:8; a variable heavy chain region at least 80% identical to SEQ ID NO:9 and a variable light chain region at least 80% identical to SEQ ID NO:10; a variable heavy chain region at least 80% identical to SEQ ID NO:11 and a variable light chain region at least 80% identical to SEQ ID NO:12; a variable heavy chain region at least 80% identical to SEQ ID NO:13 and a variable light chain region at least 80% identical to SEQ ID NO:14; a variable heavy chain region at least 80% identical to SEQ ID NO:15 and a variable light chain region at least 80% identical to SEQ ID NO:16; a variable heavy chain region at least 80% identical to SEQ ID NO:17 and a variable light chain region at least 80% identical to SEQ ID NO:18; a variable heavy chain region at least 80% identical to SEQ ID NO:19 and a variable light chain region at least 80% identical to SEQ ID NO:20; a variable heavy chain region at least 80% identical to SEQ ID NO:21 and a variable light chain region at least 80% identical to SEQ ID NO:22; a variable heavy chain region at least 80% identical to SEQ ID NO:23 and a variable light chain region at least 80% identical to SEQ ID NO:24; a variable heavy chain region at least 80% identical to SEQ ID NO:25 and a variable light chain region at least 80% identical to SEQ ID NO:26; a variable heavy chain region at least 80% identical to SEQ ID NO:27 and a variable light chain region at least 80% identical to SEQ ID NO:28; a variable heavy chain region at least 80% identical to SEQ ID NO:29 and a variable light chain region at least 80% identical to SEQ ID NO:30; a variable heavy chain region at least 80% identical to SEQ ID NO:119 and a variable light chain region at least 80% identical to SEQ ID NO:120; a variable heavy chain region at least 80% identical to SEQ ID NO:121 and a variable light chain region at least 80% identical to SEQ ID NO:122; a variable heavy chain region at least 80% identical to SEQ ID NO:123 and a variable light chain region at least 80% identical to SEQ ID NO:124; a variable heavy chain region at least 80% identical to SEQ ID NO:125 and a variable light chain region at least 80% identical to SEQ ID NO:126; a variable heavy chain region at least 80% identical to SEQ ID NO:127 and a variable light chain region at least 80% identical to SEQ ID NO:128; a variable heavy chain region at least 80% identical to SEQ ID NO:129 and a variable light chain region at least 80% identical to SEQ ID NO:130; a variable heavy chain region at least 80% identical to SEQ ID NO:131 and a variable light chain region at least 80% identical to SEQ ID NO:132; a variable heavy chain region at least 80% identical to SEQ ID NO:133 and a variable light chain region at least 80% identical to SEQ ID NO:134; a variable heavy chain region at least 80% identical to SEQ ID NO:135 and a variable light chain region at least 80% identical to SEQ ID NO:136; a variable heavy chain region at least 80% identical to SEQ ID NO:137 and a variable light chain region at least 80% identical to SEQ ID NO:138; a variable heavy chain region at least 80% identical to SEQ ID NO:139 and a variable light chain region at least 80% identical to SEQ ID NO:140; a variable heavy chain region at least 80% identical to SEQ ID NO:141 and a variable light chain region at least 80% identical to SEQ ID NO:142; a variable heavy chain region at least 80% identical to SEQ ID NO:143 and a variable light chain region at least 80% identical to SEQ ID NO:144; a variable heavy chain region at least 80% identical to SEQ ID NO:145 and a variable light chain region at least 80% identical to SEQ ID NO:146; a variable heavy chain region at least 80% identical to SEQ ID NO:147 and a variable light chain region at least 80% identical to SEQ ID NO:148; a variable heavy chain region at least 80% identical to SEQ ID NO:254 and a variable light chain region at least 80% identical to SEQ ID NO:255; a variable heavy chain region at least 80% identical to SEQ ID NO:256 and a variable light chain region at least 80% identical to SEQ ID NO:257; a variable heavy chain region at least 80% identical to SEQ ID NO:258 and a variable light chain region at least 80% identical to SEQ ID NO:259; a variable heavy chain region at least 80% identical to SEQ ID NO:260 and a variable light chain region at least 80% identical to SEQ ID NO:261; a variable heavy chain region at least 80% identical to SEQ ID NO:262 and a variable light chain region at least 80% identical to SEQ ID NO:263; a variable heavy chain region at least 80% identical to SEQ ID NO:264 and a variable light chain region at least 80% identical to SEQ ID NO:265; a variable heavy chain region at least 80% identical to SEQ ID NO:266 and a variable light chain region at least 80% identical to SEQ ID NO:267; a variable heavy chain region at least 80% identical to SEQ ID NO:268 and a variable light chain region at least 80% identical to SEQ ID NO:269; or a variable heavy chain region at least 80% identical to SEQ ID NO:270 and a variable light chain region at least 80% identical to SEQ ID NO:271.

As used herein, the term "substantially identical" (or "substantially homologous") refers to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the first antibody.

Calculations of "homology" or "identity" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In different embodiments, the length of a reference sequence aligned for comparison purposes is at least 50% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. The percent homology between two amino acid sequences is determined using the Needleman and Wunsch, *J. Mol. Biol.* 48:444-453, 1970, algorithm which has been incorporated into the GAP program in the GCG software package, using a BLOSUM 62 scoring matrix with a gap penalty of 12, a gap extend penalty of 4, and a frameshift gap penalty of 5.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. 6.3.1-6.3.6, 1989, which is incorporated herein by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5 M sodium phosphate, 7% SDS at 65° C., followed by one or more washes at 0.2×SSC, 1% SDS at 65° C.

It is understood that the antibodies and antigen binding portions thereof of the invention may have additional conservative or non-essential amino acid substitutions (a "non-essential" amino acid residue is a residue that can be altered from the wild-type sequence of a polypeptide, such as a binding agent, e.g., an antibody, without substantially altering a biological activity, whereas an "essential" amino acid residue results in such a change).

Whether or not a particular substitution will be tolerated, i.e., will not adversely affect desired biological properties, such as binding activity, can be determined as described in Bowie et al., *Science,* 247:1306-1310, 1990. A "conservative amino acid substitution" is one in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As described herein, antibodies of the present invention can inhibit hydroxylase activity of AAH and/or inhibit a function associated with hydroxylase activity, such as cell motility. As discussed below, various methods can be used to assess inhibition of AAH activity and/or function associated with the activity.

Binding Assays

As used herein "mammalian AAH protein" refers to naturally occurring or endogenous mammalian AAH proteins and to proteins having an amino acid sequence which is the same as that of a naturally occurring or endogenous corresponding mammalian AAH protein (e.g., recombinant proteins). Accordingly, as defined herein, the term includes polymorphic or allelic variants, and other isoforms of a mammalian AAH (e.g., produced by alternative splicing or other cellular processes), and modified or unmodified forms of the foregoing (e.g., glycosylated, unglycosylated). AAH proteins can be isolated and/or recombinant proteins (including synthetically produced proteins). Naturally occurring or endogenous mammalian AAH can be recovered or isolated from a source which naturally produces AAH, for example, a tumor cell.

"Functional variants" of AAH proteins include functional fragments, functional mutant proteins, and/or functional fusion proteins (e.g., produced via mutagenesis and/or recombinant techniques). Generally, fragments or portions of AAH proteins include those having a deletion (i.e., one or more deletions) of an amino acid (i.e., one or more amino acids) relative to the mature mammalian AAH (such as N-terminal, C-terminal or internal deletions).

Generally, mutants of AAH proteins include natural or artificial variants of an AAH protein differing by the addition, deletion and/or substitution of one or more contiguous or non-contiguous amino acid residues. Such mutations can be in a conserved region or nonconserved region, extracellular, cytoplasmic, or transmembrane region, for example.

A "functional fragment or portion", "functional mutant" and/or "functional fusion protein" of an AAH protein refers to an isolated and/or recombinant protein or polypeptide which has at least one function characteristic of a AAH protein as described herein, such as a hydroxylase activity.

A composition comprising an isolated and/or recombinant mammalian AAH or portion thereof can be maintained under conditions suitable for binding, the receptor is contacted with an antibody to be tested, and binding is detected or measured. In one embodiment, a receptor protein can be expressed in cells which express AAH or in cells stably or transiently transfected with a construct comprising a nucleic acid sequence which encodes an AAH or portion thereof. The cells are maintained under conditions appropriate for expression of receptor. The cells are contacted with an antibody under conditions suitable for binding (e.g., in a suitable binding buffer), and binding is detected by standard techniques. To measure binding, the extent of binding can be determined relative to a suitable control (e.g., compared with background determined in the absence of antibody, compared with binding of a second antibody (i.e., a standard), compared with binding of antibody to untransfected cells). A cellular fraction, such as a membrane fraction, containing AAH can be used in lieu of whole cells.

In one embodiment, the antibody is labeled with a suitable label (e.g., fluorescent label, isotope label, enzyme label), and binding is determined by detection of the label. In another embodiment, bound antibody can be detected by labeled second antibody. Specificity of binding can be assessed by competition or displacement, for example, using unlabeled antibody or a ligand as competitor.

Binding inhibition assays can also be used to identify antibodies that bind AAH and inhibit binding of another compound such as an EGF-like domain. For example, a binding assay can be conducted in which a reduction in the binding of an EGF-like domain (in the absence of an antibody), as compared to binding of the ligand in the presence of the antibody, is detected or measured. AAH can be contacted with a protein containing an EGF-like domain and antibody simultaneously, or one after the other, in either order. A reduction in the extent of binding of the protein in the presence of the antibody, is indicative of inhibition of binding by the antibody. For example, binding of the EGF-like domain could be decreased or abolished.

Other methods of identifying the presence of an antibody which binds AAH are available, such as other suitable binding assays, or methods which monitor events which are triggered by AAH activity, e.g., cellular transformation, or cell motility.

It will be understood that the inhibitory effect of antibodies of the present invention can be assessed in a binding inhibition assay. Competition between antibodies for binding can also be assessed in the method. Antibodies which are identified in this manner can be further assessed to determine whether, subsequent to binding, they act to inhibit other functions of AAH and/or to assess their therapeutic utility.

Assays to Determine Antibody Activity

AAH hydroxylates the β carbon of aspartic acid or asparagines residues in epidermal growth factor (EGF)-like domains of proteins in the presence of ferrous iron. EGF-like domains, which contain a conserved $CX_7CX_4CX_{10}CXCX_8C$ sequence (SEQ ID NO:247), are present in many diverse proteins, such as clotting factors, extracellular matrix proteins, low density lipoprotein receptor, Notch homologs, and Notch ligand homologs. Hydroxylation of AAH substrates can involve direct detection of hydroxylase activity, or can be measured by indirectly, e.g., using assays that detect a biological activity downstream of hydroxylation.

An assay to determine whether a human anti-AAH antibody inhibits AAH activity can be performed by comparing the level of hydroxylation in an enzymatic reaction in which the test antibody is present compared to a parallel reaction in the absence of a compound, or compared to a predetermined control value. Standard hydroxylase assays are known. See, e.g., Lavaissiere et al., *J. Clin. Invest.* 98:1313-1323, 1996; Jia et al., *J. Biol. Chem.* 267:14322-14327, 1992; Wang et al., *J. Biol. Chem.* 266:14004-14010, 1991; or Gronke et al., *J. Biol. Chem.* 265:8558-8565, 1990. Hydroxylase activity can be measured using carbon dioxide ($^{14}CO_2$ capture assay) in a microtiter plate (Zhang et al., *Anal. Biochem.* 271:137-142, 1999).

Modulation of AAH activity can be determined by examining biochemical effects downstream of hydroxylation, including effects on specific substrates, and effects on cellular processes. AAH activity increases cell motility, proliferation, survival, and cell cycle progression. Inhibition of AAH activity by an antibody can be determined by detecting a reduction in one of these processes in the presence of the antibody.

Modulation of cell motility can be assayed, e.g., using a motility assay. Generally, motility assays monitor the directional movement or migration of a suitable cell (such as a tumor cell) into or through a barrier (e.g., a filter), toward increased levels of a compound (e.g., a growth factor or other polypeptide), from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. One can detect or measure inhibition of the migration of cells in a suitable container from a first chamber into or through a microporous membrane into a second chamber which contains an antibody to be tested, and which is divided from the first chamber by the membrane. A suitable membrane, having a suitable pore size for monitoring specific migration in response to compound, including, for example, nitrocellulose, polycarbonate, is selected. For example, pore sizes of about 3-8 microns can be used.

To assess migration and inhibition of migration, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed in the presence and absence of the antibody by determining the presence of the label adherent to the membrane and/or present in the second chamber using an appropriate method (e.g., by detecting radioactivity, fluorescence, immunoassay). The extent of migration induced by an antibody agonist can be determined relative to a suitable control (e.g., compared to background migration determined in the absence of the antibody, compared to the extent of migration induced by a second compound (i.e., a standard), compared with migration of untransfected cells induced by the antibody). A reduction in the extent of migration induced by the compound (e.g., calf serum) in the presence of the antibody is indicative of inhibitory activity.

In one embodiment, cells are placed in the upper chamber of a Boyden chamber-type culture insert in serum-free medium. Medium supplemented with 1%-2% fetal calf serum is placed in the lower chamber to provide a stimulus for migration. Cells are incubated for approximately 4 hours to allow migration to occur. Cell numbers in the upper and lower chambers are quantified. Viable cells in each chamber can be quantified using an ATP monitoring system such as ATPLite™ (Perkin Elmer®; see, e.g., Sepe, et al. *Lab. Invest.* 82:881-891, 2002 for a description of a motility assay).

AAH overexpression is linked to cellular proliferation and malignant transformation. Inhibition of AAH activity can be assayed by measuring cellular characteristics of malignant phenotypes, such as transformation, anchorage-independent cell growth, and tumorigenicity in nude mice. Transformation can be assessed by transfecting NIH 3T3 cells with AAH and observing the number of transformed foci (Copeland and Cooper, *Cell* 16(2):347-56, 1979). Anchorage-independent cell growth can be assayed by transfecting cells with AAH, isolating transfectants, and suspending transfectants in complete medium containing 0.4% low-melting agarose laid over a bottom layer of medium containing 0.53% low-melting agarose.

To assay tumorigenicity in vivo, AAH-transfected clones (or AAH-expressing tumor cells) are injected into nude mice. In a typical assay, approximately 1-10 million cells are injected subcutaneously. After growth for 1 week-1 month, animals are sacrificed, and tumors are removed and weighed. Antibodies can be tested by injection into animals implanted with AAH-transfectants or tumor cells and comparing growth of the implanted cells to growth of cells in animals receiving a control injection (e.g., saline, or a non-specific antibody).

Antibodies with inhibitory activity may reduce efficiency of cell growth, transformation, and tumorigenicity in these assays.

Diagnostic and Therapeutic Applications

The antibodies of the present invention are useful in a variety of applications, including research, diagnostic and therapeutic applications. In one embodiment, the antibodies are labeled with a suitable label (e.g., fluorescent label, chemiluminescent label, isotope label, epitope or enzyme label).

Overexpression of HAAH is associated with malignant transformation. Antibodies or antigen binding portions thereof that block and/or inhibit the activity of HAAH can be used to inhibit cell transformation and/or to diagnose transformed cells. Accordingly, the present invention provides a method of inhibiting AAH activity of a cell which expresses an AAH or portion thereof, comprising contacting the cell with an effective amount of an antibody or antigen binding portion thereof which binds to the AAH or a portion of the AAH. The cell can be a cell of a subject (e.g., a tumor cell), and the antibody or antigen binding portion thereof can be administered to the subject in vivo. Therapeutic use of an antibody or antigen binding portion thereof includes prophylactic use (e.g., for treatment of a patient who may be at risk for developing a cancer).

The anti-AAH antibody or antigen binding portion thereof can be administered in combination with one or more other therapeutic agents such as an anti-cancer agent. Nonlimiting examples of anti-cancer agents include, e.g., antimicrotubule agents, topoisomerase inhibitors, antimetabolites, mitotic inhibitors, alkylating agents, intercalating agents, agents capable of interfering with a signal transduction pathway, agents that promote apoptosis (including cell death genes), radioactive compounds, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5-fluorouracil (5-FU), methotrexate, 6-mercaptopurine, 6-thioguanine, fludarabine phosphate, cytarabine/Ara-C, trimetrexate, gemcitabine, acivicin, alanosine, pyrazofurin, N-Phosphoracetyl-L-Asparate (PALA), pentostatin, 5-azacitidine, 5-Aza 2'-deoxycytidine, ara-A, cladribine, 5-fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenylsulphonyl)-2-hydroxy-2-methyl-3'-(trifluoromethyl) propionanilide.

The anti-AAH antibodies of the present invention also have value in diagnostic applications. An anti-AAH antibody can be used to monitor growth and/or metastasis of a tumor in vivo, and may be used as a diagnostic indicator of disease stage. Human antibodies are not immunogenic in humans, and therefore human antibodies may be more appropriate for in vivo diagnostic applications than mouse antibodies.

For diagnostic purposes, the antibodies or antigen binding portions can be labeled or unlabeled. Typically, diagnostic assays entail detecting the formation of a complex resulting from the binding of an antibody or portion to AAH. The antibodies or portions can be directly labeled. A variety of labels can be employed, including, but not limited to, radionuclides, fluorescers, enzymes, enzyme substrates, enzyme cofactors, enzyme inhibitors and ligands (e.g., biotin, haptens, and the like). Numerous appropriate immunoassays are known to the skilled artisan (see, for example, U.S. Pat. Nos. 3,817,827; 3,850,752; 3,901,654 and 4,098,876). Unlabeled antibodies or fragments can also be used in combination with another (i.e., one or more) suitable reagent that can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

Kits for use in detecting the presence of AAH in a biological sample can also be prepared. Such kits will include an antibody or antigen binding portion thereof which binds to an AAH protein or portion of said receptor, as well as one or more ancillary reagents suitable for detecting the presence of a complex between the antibody or portion and AAH or portion thereof. The antibody compositions of the present invention can be provided in lyophilized form, either alone or in combination with additional antibodies specific for other epitopes. The antibodies, whether labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the antibodies can be provided as a lyophilized mixture with the adjunct ingredients, or the adjunct ingredients can be separately provided for combination by the user. Where a second antibody capable of binding to the monoclonal antibody is employed, such antibody can be provided in the kit, for instance in a separate vial or container. The second antibody, if present, is typically labeled, and can be formulated in an analogous manner with the antibody formulations described above.

Similarly, the present invention also relates to a method of detecting and/or quantifying expression of AAH or portion of the enzyme by a cell, in which a composition comprising a cell or fraction thereof (e.g., membrane fraction) is contacted with an antibody or functional portion thereof which binds to AAH or portion of AAH (e.g., the catalytic domain) under conditions appropriate for binding of the antibody, and antibody binding is monitored. Detection of the antibody, indicative of the formation of a complex between antibody and AAH or a portion thereof, indicates the presence of AAH. Binding of antibody to the cell can be determined as described above under the heading "Binding Assays", for example. The method can be used to detect expression of AAH in cells from an individual (e.g., in a tumor biopsy sample). A quantitative expression of AAH on the surface of tumor cells can be evaluated, for instance, by flow cytometry, and the staining intensity can be correlated with disease progression or risk.

AAH has a role in cell motility, and so anti-AAH antibodies can be used to inhibit (reduce or prevent) tumor growth or metastasis. Accordingly, the antibodies of the present invention can also be used to modulate AAH function in research and therapeutic applications. For instance, the antibodies described herein can act as inhibitors to inhibit (reduce or prevent) (a) binding (e.g., of an EGF-like domain of a protein) to AAH, (b) a receptor signaling function mediated by AAH, and/or (c) a stimulatory function (e.g., of a substrate of AAH or an AAH-pathway). Antibodies which act as inhibitors of receptor function can block AAH binding directly or indirectly (e.g., by causing a conformational change). Thus, the present invention provides a method of inhibiting cell motility in a mammal (e.g., a human patient), comprising administering to the mammal an effective amount of an antibody or antigen binding portion thereof which binds to a AAH or portion of AAH. Diseases which can be treated according to the method include cancers and can result in amelioration of the disease state. The cancers which can be treated include, but are not limited to solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), liver, pharynx, prostate, ovary, cholangiocarcinomas, as well as adenocarcinomas which include malignancies such as most colon cancers, rectal cancer, renal-cell carcinoma, liver cancer, non-small cell carcinoma of the lung, cancer of the small intestine, neuroectodermal tumors, and so forth. Metastatic lesions of the aforementioned cancers can also be treated or prevented using the methods and compositions of the invention.

The subject method can be useful in treating malignancies of the various organ systems, such as those affecting lung, breast, lymphoid, gastrointestinal (e.g., colon), and genitourinary tract, prostate, ovary, pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. Exemplary solid tumors that can be treated include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Patients amenable to treatment with the anti-AAH antibodies described herein may be described as having cancer or a "carcinoma." Carcinomas are recognized by those of ordinary skill in the art as malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is recognized by those skilled in the art and refers to malignant tumors of mesenchymal derivation.

The methods of the invention can also be used to inhibit the proliferation of hyperplastic/neoplastic cells of hematopoietic origin, e.g., arising from myeloid, lymphoid or erythroid lineages, or precursor cells thereof. For instance, the present invention contemplates the treatment of various myeloid disorders including, but not limited to, acute promyeloid leukemia (APML), acute myelogenous leukemia (AML) and chronic myelogenous leukemia (CML) (reviewed in Vaickus, Crit Rev. in Oncol./Hemotol. 11:267-97, 1991). Lymphoid malignancies which may be treated by the subject method include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated by the treatment method of the present invention include, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

Modes of Administration

According to the method, one or more antibodies or antigen binding portions thereof can be administered to the host by an appropriate route, either alone or in combination with (before, simultaneous with, or after) another drug. For example, the antibodies of the present invention can also be used in combination with other monoclonal or polyclonal antibodies or with chemotherapeutic treatments.

An effective amount of an antibody (i.e., one or more antibodies or fragments) is administered. An effective amount is an amount sufficient to achieve the desired therapeutic effect, under the conditions of administration, such as an amount sufficient for inhibition of an AAH function, and thereby, inhibition of a tumor cell.

A variety of routes of administration are possible including, but not necessarily limited to, parenteral (e.g., intravenous, intraarterial, intramuscular, subcutaneous injection), oral, dietary, topical, inhalation (e.g., intrabronchial, intranasal or oral inhalation, intranasal drops), depending on the disease or condition to be treated. Other suitable methods of administration can also include rechargeable or biodegradable devices and slow release polymeric devices. The pharmaceutical compositions described herein can also be administered as part of a combinatorial therapy with other agents.

Formulation of an antibody or portion thereof to be administered will vary according to the route of administration selected (e.g., solution, emulsion, capsule). An appropriate pharmaceutical composition comprising an antibody or antigen binding portion thereof to be administered can be prepared in a physiologically acceptable vehicle or carrier. A mixture of antibodies and/or portions can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the compound can be solubilized and loaded into a suitable dispenser for administration (e.g., an atomizer, nebulizer or pressurized aerosol dispenser).

EXAMPLES

The invention is further described in the following examples, which do not limit the scope of the invention described in the claims.

Example 1

Library Screen for Anti-HAAH Antibodies

A yeast surface display technique (Boder and Wittrup, Nat Biotechnol. 15(6):553-7, 1997) was used to screen a naïve human single-chain Fv library for anti-HAAH Fv fragments. This library was prepared as described in Feldhaus et al. (Nature Biotech. 21:163-170, 2003). Briefly, human antibody variable genes were cloned by PCR from commercially available spleen and lymph node poly(A) mRNA pooled from 58 adults. Primers to IgG, IgM, κ and λ were used for first-strand cDNA synthesis. Separate VH and VL libraries were constructed, then assembled together in single-chain Fv (scFv) format by overlap extension PCR. The scFv library was then subcloned for expression as an Aga2p fusion on the yeast surface. The Aga2p-scFv fusion protein is depicted schematically in FIG. 1. A library of approximately $10^9$ scFv fragments was expressed in yeast.

Figure 2:
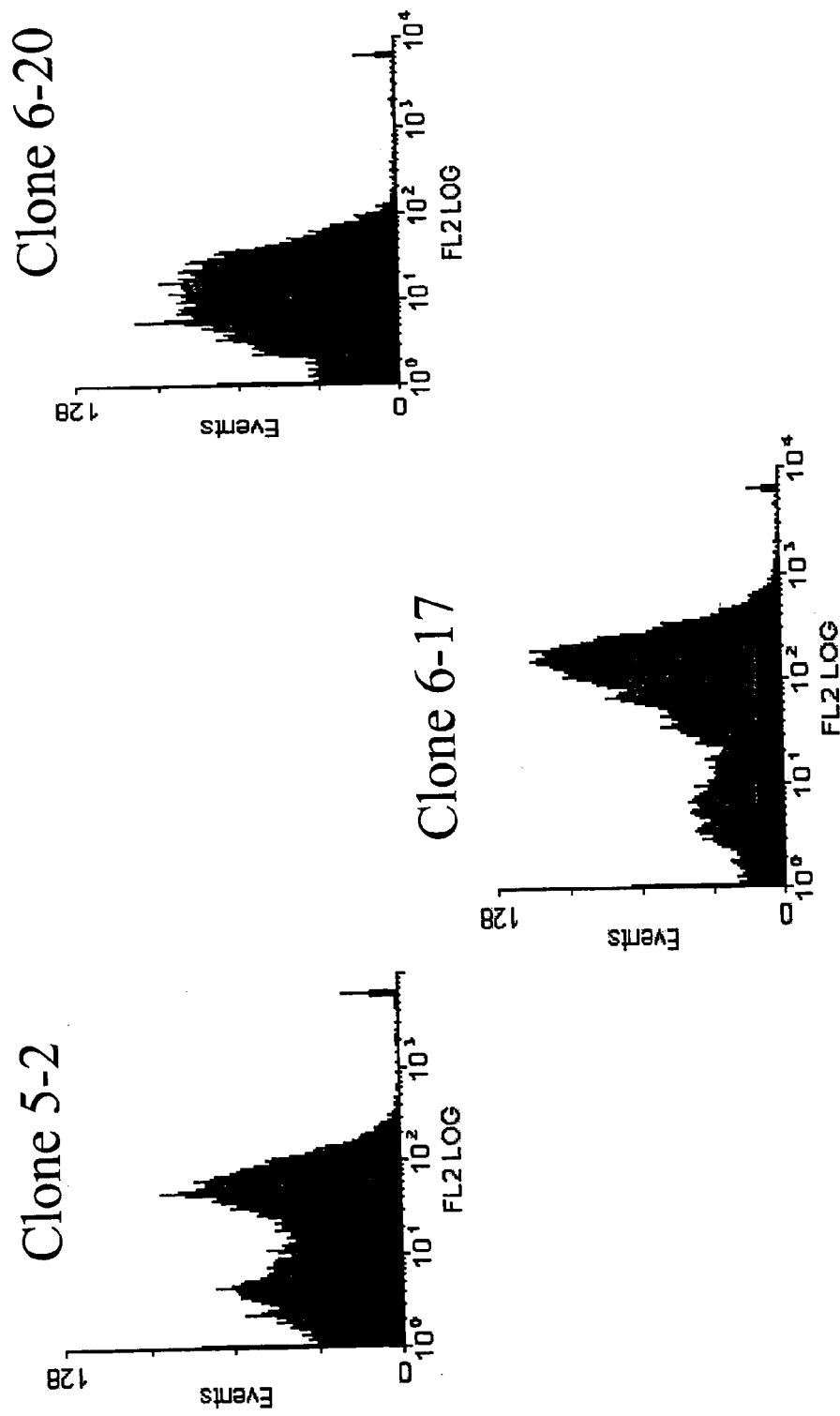
FIG. 2 is a set of graphs depicting the fluorescence detected by flow cytometry in experiments in which three unique scFv clones expressed on yeast cells were incubated with fluorescent HAAH.
Figure 3:
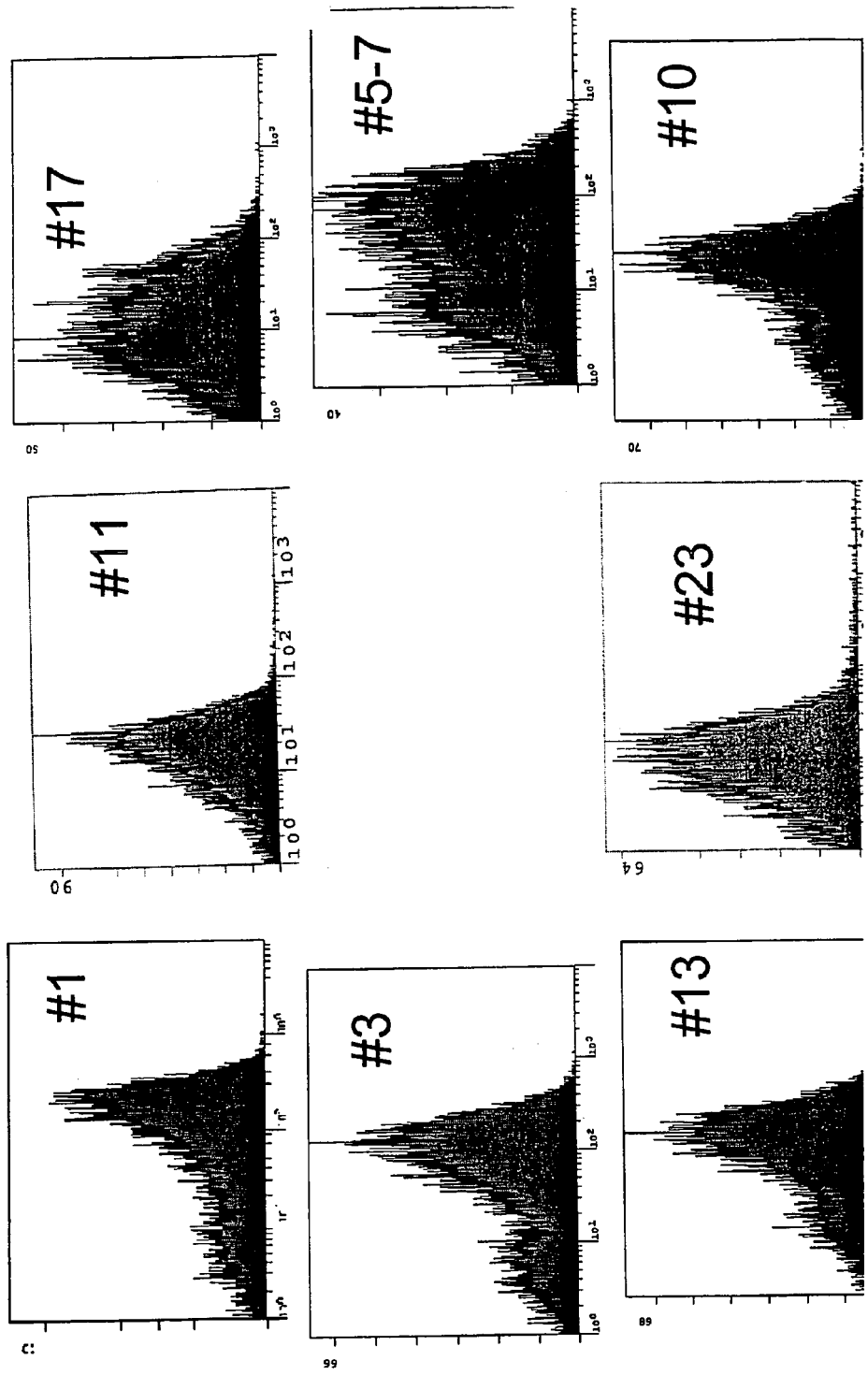
FIG. 3 is a set of graphs depicting the fluorescence detected by flow cytometry in experiments in which eight unique scFv clones expressed on yeast cells were incubated with a fluorescently labeled fragment of HAAH containing the catalytic domain.

The library was screened for binding to a recombinant form of HAAH comprising the extracellular domain as described in Boder and Wittrup (Biotechnol Prog. 14(1):55-62, 1998). Briefly, yeast cells expressing Aga2p-scFv fusions are assayed for binding to fluorescent HAAH by flow cytometry (FACS). Binders are selected by sorting and re-analyzed. Six rounds of screening for binding in 300 nM HAAH allowed the identification of 16 unique clones. FACS analysis of binding of three unique clones to HAAH is depicted in FIG. 2. FACS analysis of binding of 8 unique clones to the catalytic domain of HAAH is depicted in FIG. 3. Of these clones, eight bound to the catalytic domain of HAAH.

Example 2

Binding Activity of Anti-HAAH Antibodies

Figure 4:
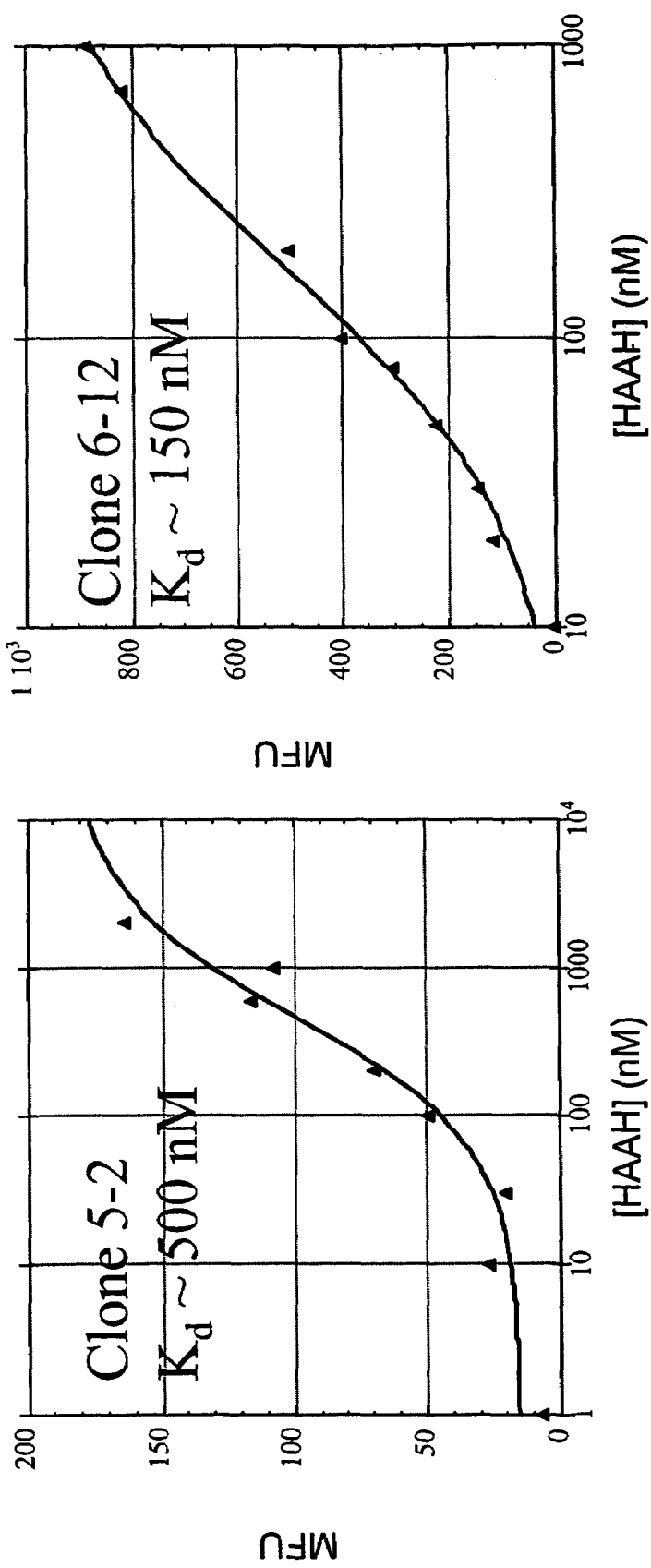
FIG. 4 is a set of graphs depicting affinity measurements for two anti-HAAH scFv antibody clones.

The affinity of various scFv clones for HAAH was determined by performing a titration in which cells displaying a given scFv are labeled with varying concentrations of unlabeled HAAH, then varying concentrations of labeled HAAH, and detecting the labeling intensity by FACS. The affinities for two representative anti-HAAH scFv clones are depicted in FIG. 4. Clone 5-2 displayed an affinity for HAAH of approximately 500 nm. Clone 6-12 displayed an affinity for HAAH of approximately 150 nM.

Figure 5:
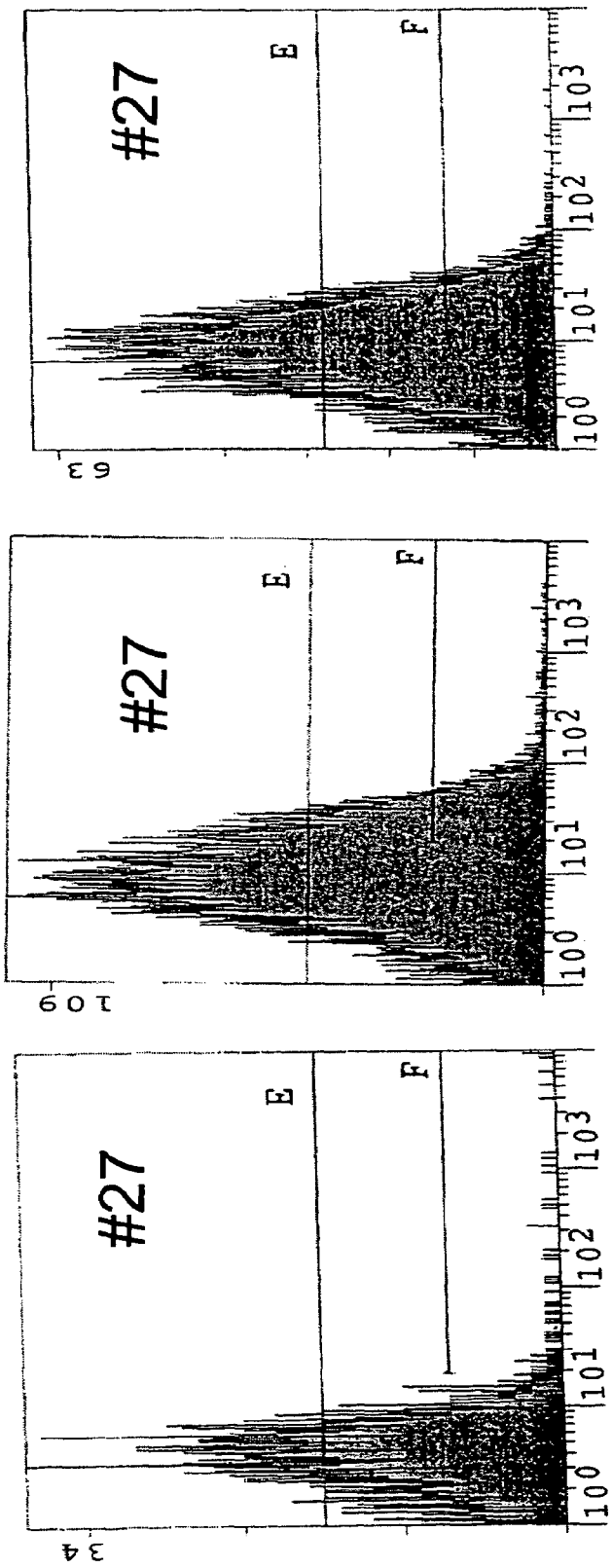
FIG. 5 is a set of graphs depicting the fluorescence detected by flow cytometry in experiments in which one scFv clone expressed on yeast cells was incubated with a fluorescently labeled catalytic domain of HAAH or conjugated full-length HAAH. The conjugated full length HAAH proteins were detected using FB50 IgG or 15C7 IgG, as indicated.

One antibody clone, clone 27, was isolated which bound to full-length HAAH, but not to the catalytic domain of HAAH. FACS analysis of binding of this scFv clone to the catalytic domain of HAAH and full-length HAAH is depicted in FIG. 5.

Example 3

Binding by Soluble Anti-HAAH scFv Fragments

Figure 6:
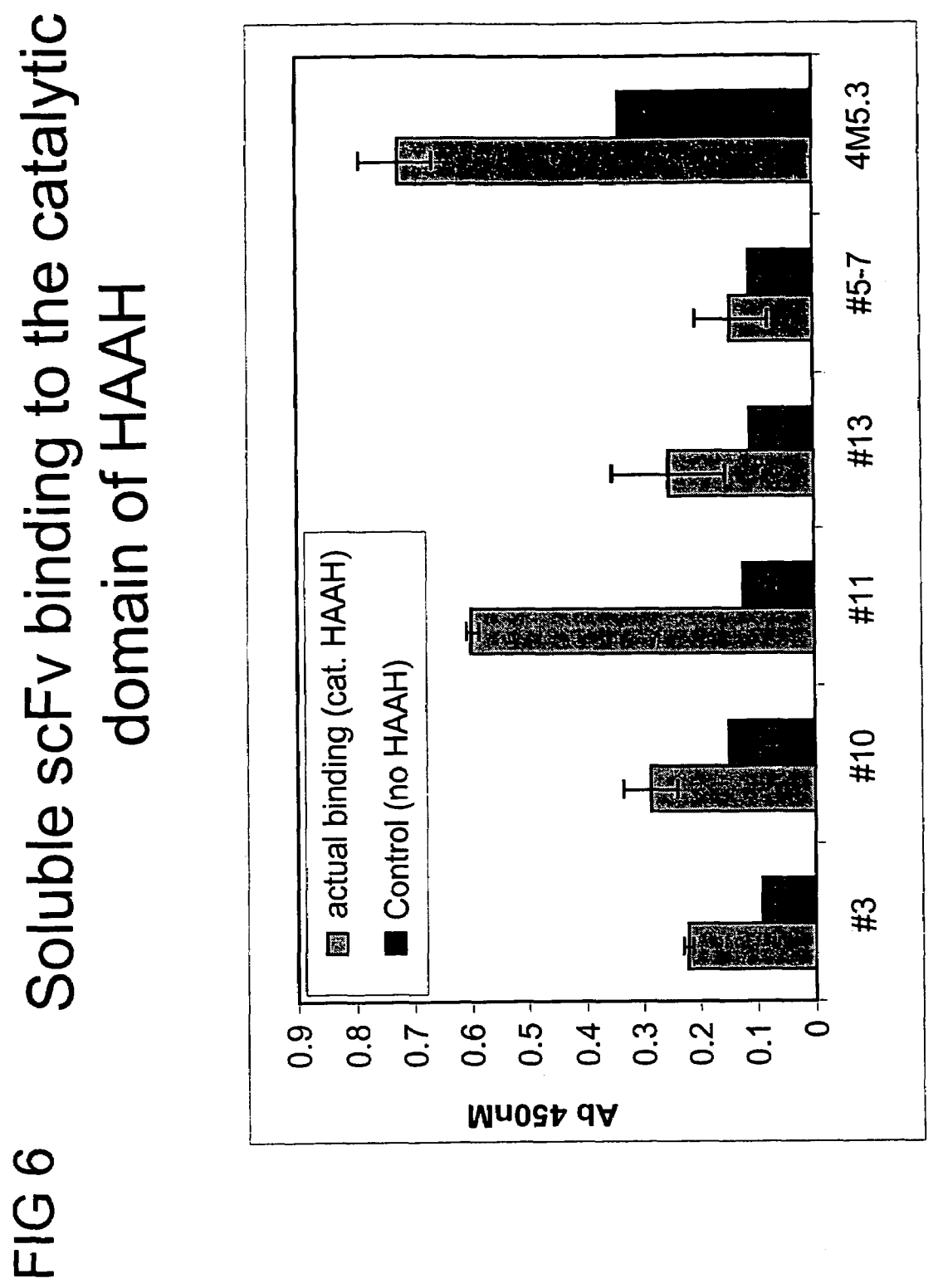
Figure 7:
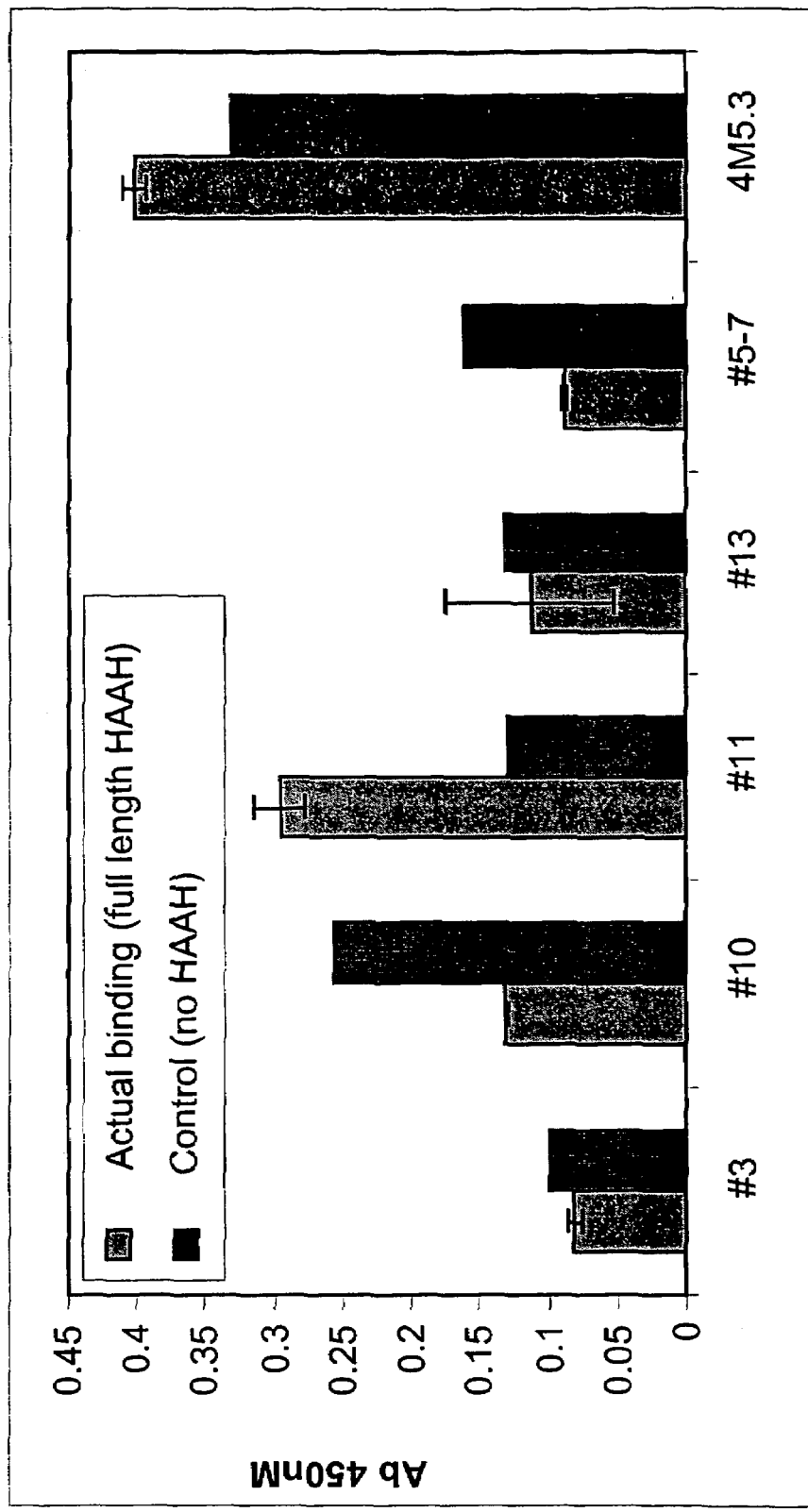
FIG. 7 is a bar graph depicting binding of soluble scFv fragments of 6 unique clones to full length HAAH.

The clones that bound to the catalytic domain were expressed in soluble form and analyzed for binding and other biological activities. Soluble scFv fragments of six unique clones were analyzed for binding to the catalytic domain of HAAH (FIG. 6), and full-length HAAH (FIG. 7). ScFv fragments were present at 1-2 μM. Clone 11 showed the highest level of non-specific binding in these assays.

Figure 8:
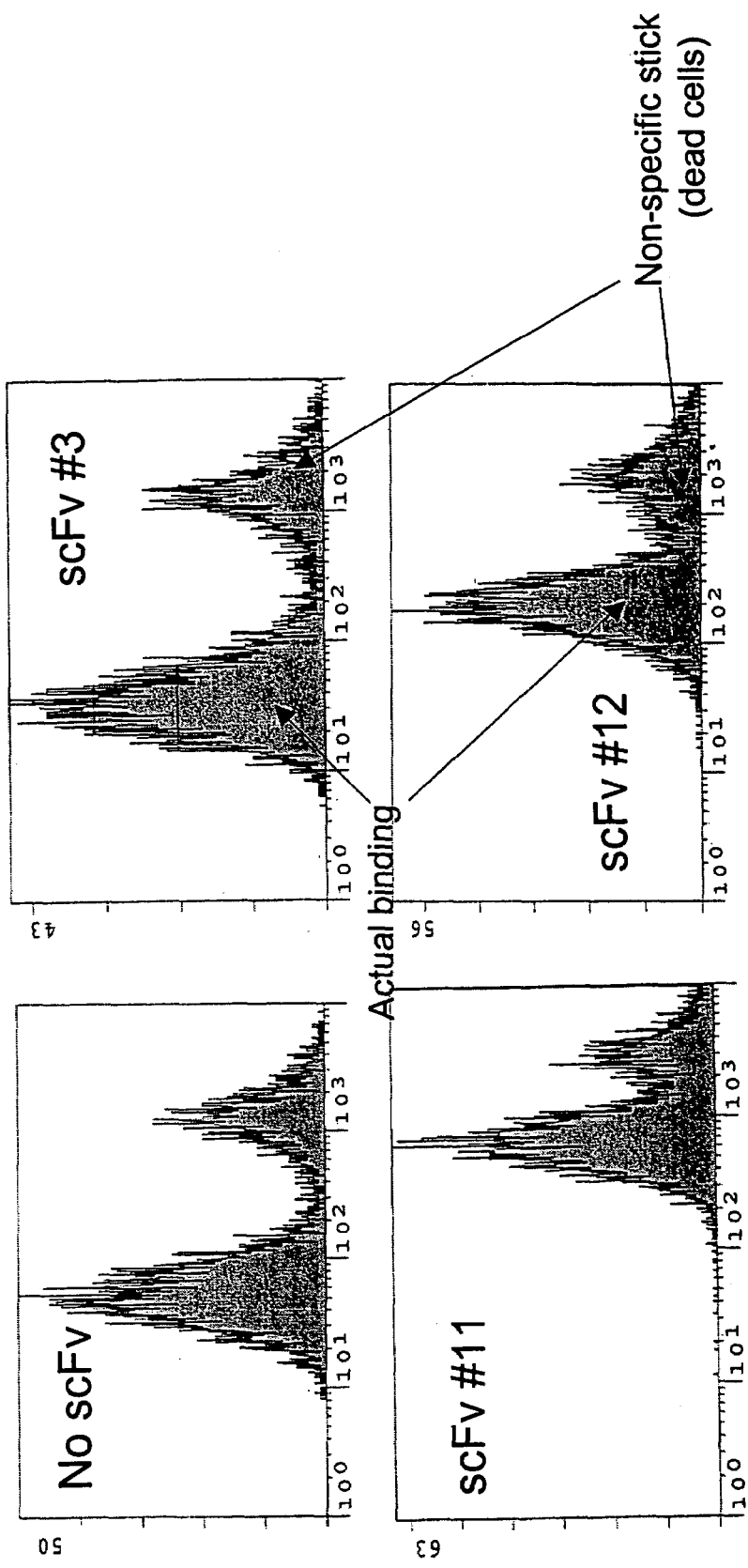
FIG. 8 is a set of graphs depicting the fluorescence detected by flow cytometry in experiments in which scFv fragments of three unique clones bound to H640 tumor cells.

Next, binding by 3 unique scFv clones to H460 human lung carcinoma cells, which express HAAH, was assessed. ScFv fragments were tested at approximately 1 μM. The results of these experiments are depicted in FIG. 8. Clone 11 scFv also showed the highest level of binding in these assays. Clone 12 also bound H460 cells.

Example 4

Inhibition of Cell Motility by Soluble Anti-HAAH scFv Fragments

Figure 9:
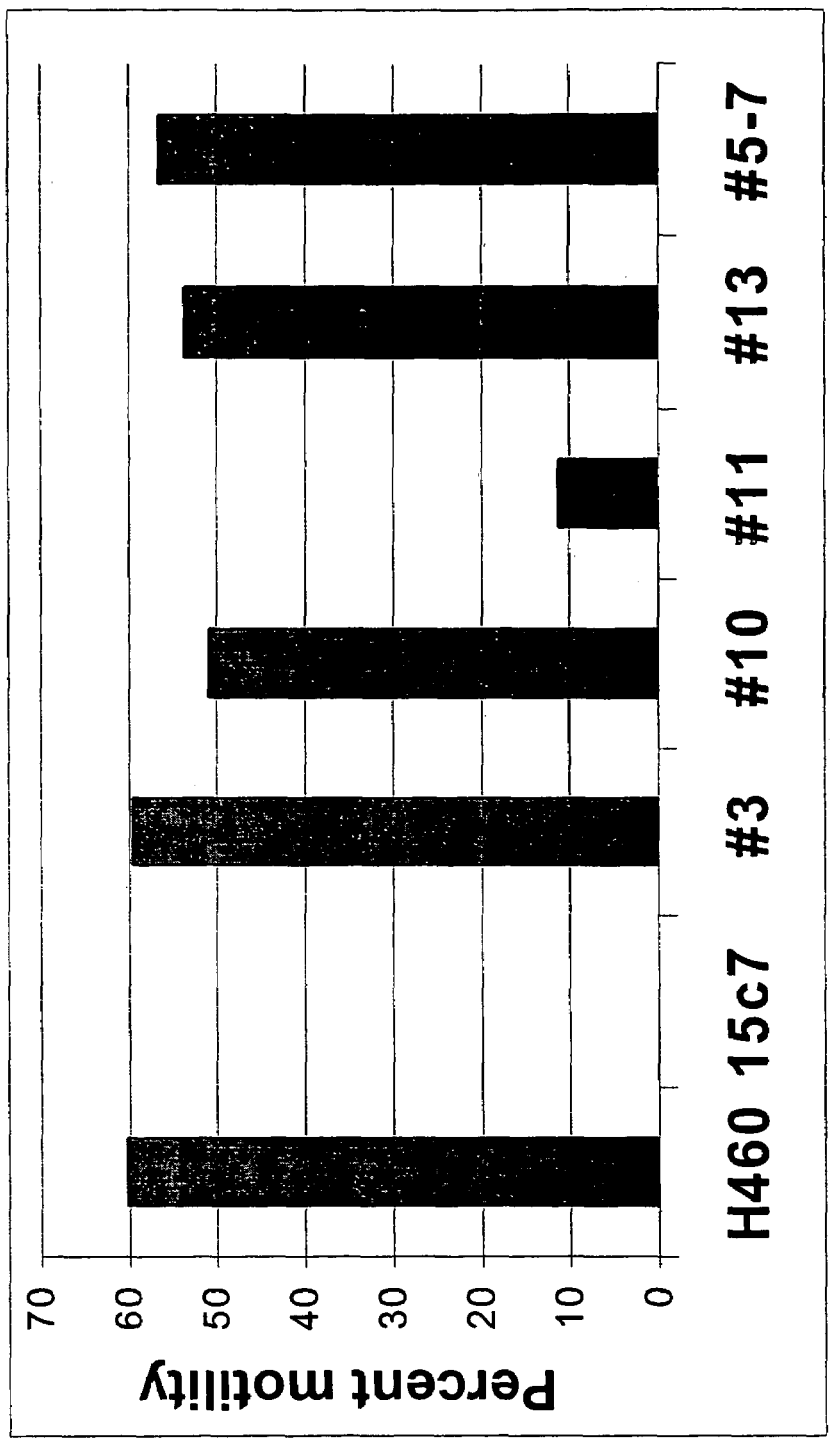
FIG. 9 is a bar graph depicting the percentage of motile H460 tumor cells in the presence of scFv fragments of 5 unique clones, 15C7 (mouse IgG), and in the absence of antibody (first bar).

Five unique soluble scFv clones and one mouse IgG, 15C7, were tested for inhibition of H460 cell motility (FIG. 9). Cells were placed in serum-free medium in a filter cup with a pore size of approximately 8 microns. The filter cup was placed into medium containing serum, and cells were incubated to allow migration through the filter. After the incubation, cell number on each side of the filter was determined by staining with crystal violet and counting using a microscope and a hemocytometer. Sixty percent of H460 cells were motile in the absence of antibody. Antibodies were present at 2 μM in the motility assays. 15C7 blocked motility by 100%. Only about 10% of cells were motile in the presence of clone 11 scFv. Clones 10 and 13 also showed modest inhibition of cell motility. Inhibition of cell growth by clone 11 was also assayed. Clone 11 did not demonstrate inhibition of H460 growth at 2 μM (data not shown).

Example 5

Error Prone PCR for Affinity Maturation of Anti-HAAH scFv Fragments

Next, nucleic acids encoding HAAH-binding scFv were mutagenized and reselected for binding in order to produce "affinity-matured" antibodies in vitro. Mutagenesis was performed by subjecting the scFv-encoding DNA to error prone PCR using nucleotide analogs as described in Zaccolo et al. (*J. Mol. Biol.*, 255:589-603, 1996) and Zaccolo et al. (*J. Mol. Biol.* 285:775-783, 1999). The initial post-mutagenesis (pre-affinity selection) library had approximately $3 \times 10^6$ members. Selected clones isolated from the library after mutagenesis and which contained full-length open reading frames were sequenced. The mean number of amino acid sequence changes in clones derived from clone 11, relative to the input sequences, was 7±8 (out of 266 amino acids total).

The mutagenized nucleic acids were re-expressed with yeast surface display and screened for binding using FACS as described above. DNA encoding binders was isolated, re-mutagenized, re-expressed and screened, and so forth for six rounds. Five of the six rounds were performed with sequentially decreasing concentrations of HAAH, starting at 1 μM and ending with 200 mM. One round was performed with detection antibodies in the absence of HAAH to deplete clones that bound to the detection antibody. The mean number of amino acid sequence changes in seven clones derived from clone 11 after this sorting step was 23±16, relative to the input sequences. The number of mutations in germline-encoded framework regions ranged from 8 to 35, as compared to 4 mutations in the original clone (relative to the germline sequence).

Figure 10:
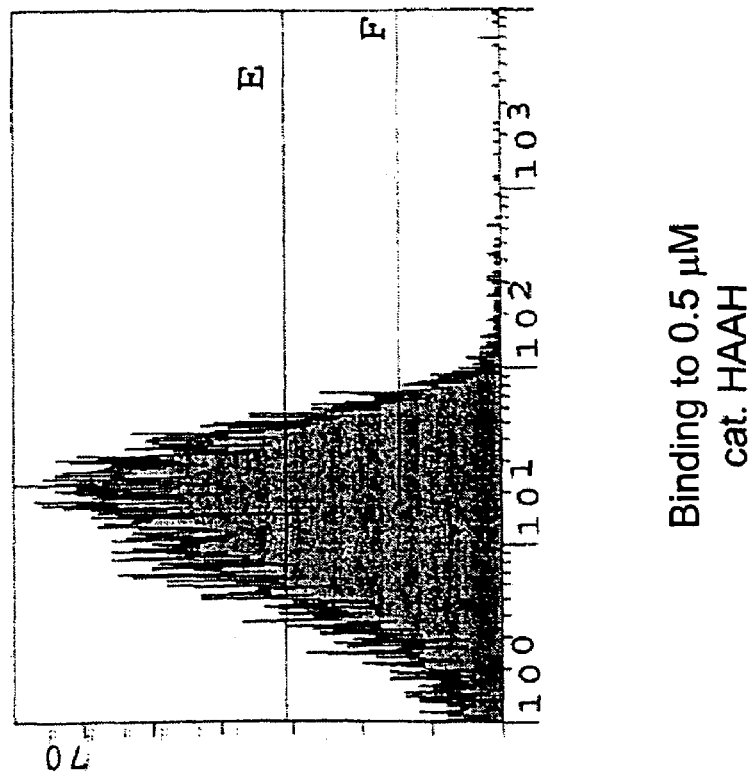
FIG. 10 is a graph depicting the fluorescence detected by flow cytometry in an experiment in which affinity matured scFv fragments derived from clone 11 bound to the catalytic domain of HAAH.

The binding of an improved clone 11 scFv mutant was assayed for binding to the catalytic domain of HAAH (0.5 μM) (FIG. 10). The amino acid sequence of this improved clone is depicted in FIG. 11. Amino acid changes relative to the original clone 11 are shown in bold-faced type and underlined.

HAAH binding of clone 11 mutants from successive rounds of mutagenesis was assayed by FACS as described above. The level of expression of scFv on yeast cells was analyzed in parallel. The results of these experiments are depicted in FIG. 12. As shown in FIG. 12, the mutants produced after four rounds of screening ("1$^{st}$ round mutants") displayed a higher level of binding to HAAH as compared to original clone 11. One clone, 11m1-2, also displayed a uniformly higher level of binding as compared to original clone 11. Binding of other affinity matured clone 11 mutants is shown in FIG. 13. The dissociation rate constant of the best-improved clones (e.g., 11m1-2) was determined to be 220±60 nM, an improvement of two orders of magnitude over the initial, non-mutagenized scFv from which it was derived.

Five out of seven affinity matured clones derived from clone 11 had a mutation of cysteine to arginine or tyrosine at position H22 (according to Kabat numbering) in the heavy chain. This cysteine forms an intra-domain disulfide bond. Of the five clones with this mutation, three of them have an addition of a cysteine, with the occurrence of the cysteine residue in either the heavy chain framework region 3 (FW3) or in the light chain CDR3. Of the two clones that did not have a cysteine H22 mutation, one lacked additional cysteines. The other had a replacement of a tyrosine with a cysteine in the heavy chain CDR3 loop, four residues away from cysteine H22. The frequent cysteine mutations may indicate that relaxation of the heavy chain structure can lead to improved binding.

Figure 14:
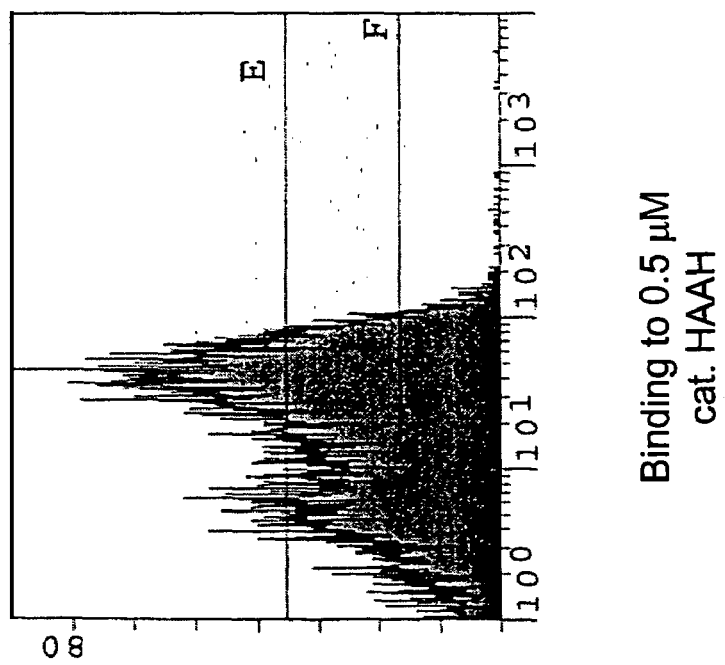
FIG. 14 is a graph depicting the fluorescence detected by flow cytometry in an experiment in which affinity matured scFv fragments derived from clone 13 bound to the catalytic domain of HAAH.
Figure 16:
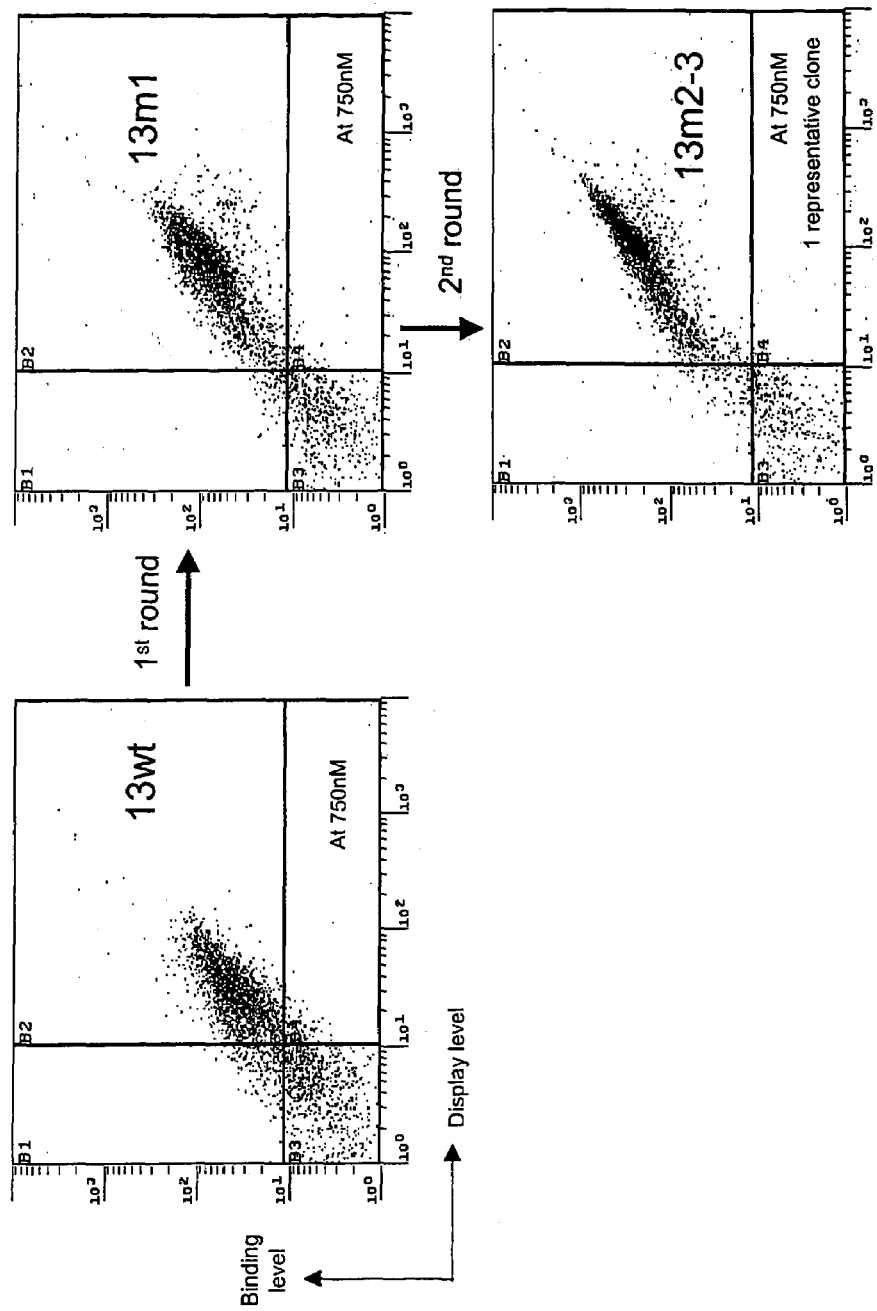
FIG. 16 is a set of dot-plot graphs depicting two types of fluorescence detected by flow cytometry in experiments in which the original clone 13 scFv fragments, a first round mutant clone 13 scFv, and a second round mutant clone 13 scFv, were analyzed. Fluorescence intensity depicted on the X-axis corresponds to the level of scFv displayed on yeast cells. Fluorescence intensity on the Y-axis corresponds to the level of binding to HAAH of the cells.

Affinity maturation was also performed with clone 13. Binding of a clone 13 mutant, 13m1, to the catalytic domain of HAAH is shown in FIG. 14. 13m1 was generated after five cycles of mutagenesis/screening. The amino acid sequence of this mutant is depicted in FIG. 15. Amino acid changes relative to the original clone 13 are bold and underlined. Binding of successive mutants of clone 13 was assayed as described for the clone 11 mutants. As shown in FIG. 16, clone 13m1, and a clone generated from 13 ml, 12 m2-3, both displayed an enhanced level of binding relative to original clone 13.

Example 6

Chain Shuffling for Affinity Maturation of Anti-HAAH scFv Fragments

Figure 17:
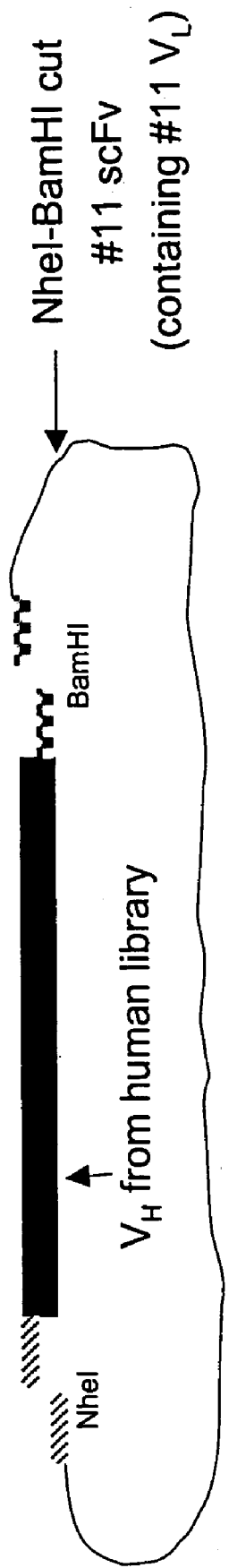
FIG. 17 is a schematic depiction of a DNA plasmid with restriction enzyme sites for chain shuffling.
Figures 18A, 18B:
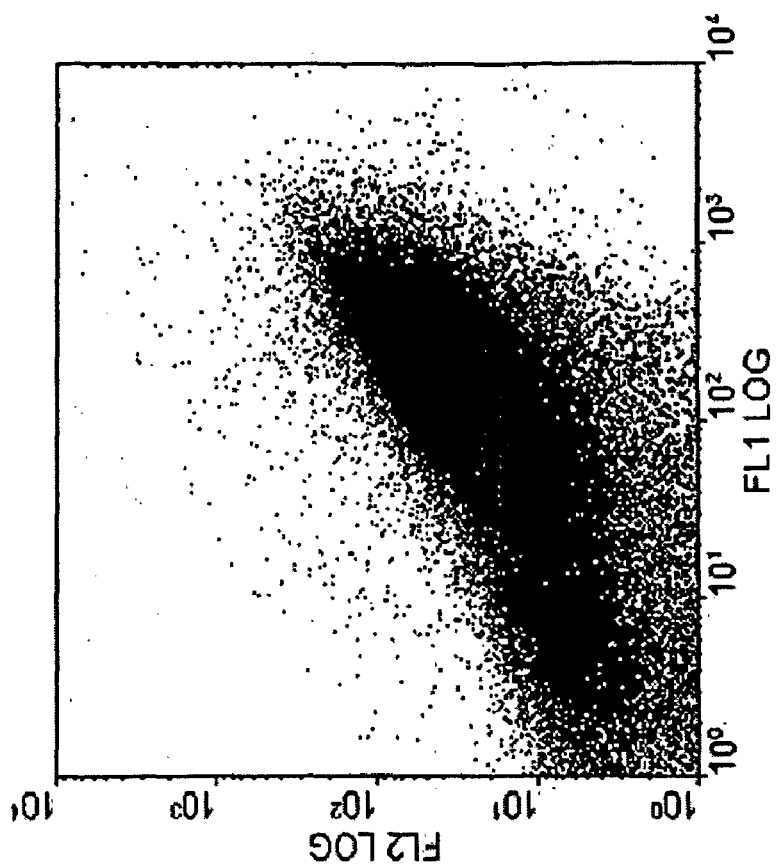
FIG. 18A is a chart listing the VH and VL regions in a wild type clone and five clones generated by chain shuffling from the wild type clone.
FIG. 18B is a dot-plot graph depicting two types of fluorescence detected by flow cytometry in experiments in which the pool of mutant clones derived from wild type clone 11 by chain shuffling were analyzed. Fluorescence intensity depicted on the X-axis corresponds to the level of scFv fragments displayed on yeast cells. Fluorescence intensity on the Y-axis corresponds to the level of binding to HAAH of the cells.

Chain shuffling is a mutagenesis technique whereby an entire antibody chain or portion of a chain is recombined with other chains. In order to generate anti-HAAH scFv fragments with increased affinity for HAAH, a library was constructed by shuffling heavy chains from the naïve library against the wild type anti-HAAH light chain (to preserve the light chain sequence and link it with different heavy chain sequences). Specifically, heavy chain fragments from the human naïve library were extracted by restriction digestion with NheI and BamHI and ligated into a NheI-BamHI-digested yeast display plasmid containing the light chain of the wild type scFv as depicted in FIG. 17. The initial library generated by this process had approximately $1.2 \times 10^5$ members. Five clones from the initial library were sequenced, and all had heavy chains which were different from the initial heavy chain. FIG. 18A contains a chart listing the heavy chains and light chains in each clone.

Next, six rounds of FACS screening were performed in the presence of decreasing concentrations of antigen (from 800 nM to 500 nM of HAAH) to screen for improved binders. An additional step of screening in the absence HAAH was performed to eliminate clones binding to the detection antibodies. The scFv display level (X-axis) and HAAH binding (Y-axis) of yeast cells from the pool of mutagenized cells was analyzed by FACS. FIG. 18B shows that clones with high levels of high-affinity scFv fragments were present in the pool.

Twenty clones were sequenced after the sixth round of screening. Eleven of the clones that were sequenced were unique and each contained a different heavy chain from the wild type scFv. The scFv display level (X-axis) and HAAH binding (Y-axis) of these clones is shown in FIGS. 19A-19K. The dissociation constants for two selected clones, LLm11 and LLm13, were determined to be 240±70 nM and 160±50 nM respectively, which is an improvement of over two orders of magnitude with respect to wild type.

The framework sequences of the clones generated by this technique had minimal deviation from the germline framework sequences (on average 4±2 mutations from heavy chain germline framework), rendering them less likely to be immunogenic than clones with a greater number of framework mutations. Because all these clones have different heavy chain CDR3, they may have slightly different binding specificities. Multiple binders having different specificities against the same target can be readily screened for secondary desired properties such as minimal binding towards particular human tissues.

Example 7

Affinity Maturation of Anti-HAAH scFv Fragments Using CDR Shuffling

A third technique, CDR shuffling (also referred to as domain shuffling) was used to generate scFv clones with enhanced affinity for HAAH. To perform CDR shuffling, yeast cells are co-transformed with an acceptor vector and multiple linear insert sequences. The acceptor vector and the insert sequences are designed to have homologous sequences at one or both of their 5' and 3' ends. Homologous recombination between these sites, and at random sites within the gene of interest (e.g., antibody chain) generates "shuffled" products. Further details for performing CDR shuffling are described in Swers et al. (*Nucl. Acids Res.* 2(3):e36, 2004).

Figure 21:
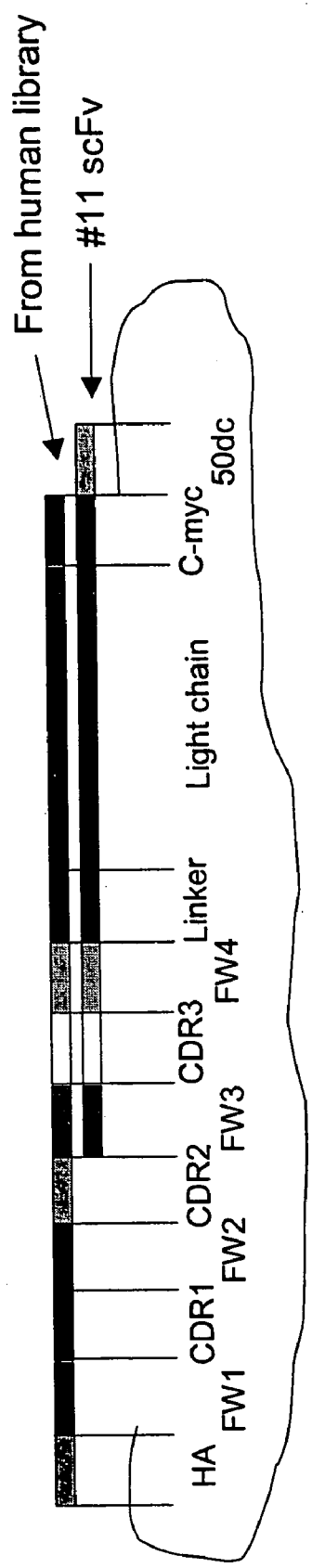
FIG. 21 is a schematic depiction of an acceptor DNA plasmid encoding a wild type clone 11 scFv and a human library insert sequence to be recombined with the plasmid for CDR shuffling.

CDR shuffling was performed with DNA encoding the wild type clone 11 scFv fragment as the acceptor vector, and sequences from a human scFv library as the insert sequences (FIG. 21). The insert sequences had a light chain identical to the clone 11 light chain and the insert sequences of each of three libraries contained regions corresponding to HC FW1 to CDR1, HC FW1 to CDR2, or HC FW1 to CDR3, replaced with naïve heavy chain gene sequences from the same VH family as the original clone. The libraries containing replacements of HC FW1 to CDR1 and HC FW1 to CDR2 regions result in a mutagenesis event similar to receptor editing, which naturally occurs in B cells in vivo.

The libraries with HC FW1 to CDR1, HC FW1 to CDR2, or HC FW1 to CDR3 inserts contained $1.1 \times 10^4$, $1.2 \times 10^4$, and $1.1 \times 10^4$ members, respectively. The libraries were pooled for screening. Six rounds of screening by FACS were performed with decreasing concentrations of antigen, ranging from 500 nM to 160 nM of HAAH. An additional step of screening in the absence HAAH was performed to eliminate clones binding to the detection antibodies.

Ten clones were isolated and sequenced, and four of the clones were unique. The scFv display level (X-axis) and HAAH binding of these clones (Y-axis) is shown in FIGS. 22A-22D. The amino acid sequences of the CDRs of the wild type clone and the four mutagenized clones are shown in FIG. 23. Of the four unique sequences, three had a replacement in the region from FW1 to CDR3 with naïve library sequences. The fourth clone had a replacement of the FW1 to CDR2 sequence with a naïve library sequence. The dissociation constant of this mutant was 1 µM-2 µM, an order of magnitude improvement over the original wild type clone. Only two amino acid positions in the framework regions of this mutant differed from the germline framework regions.

Figure 24:
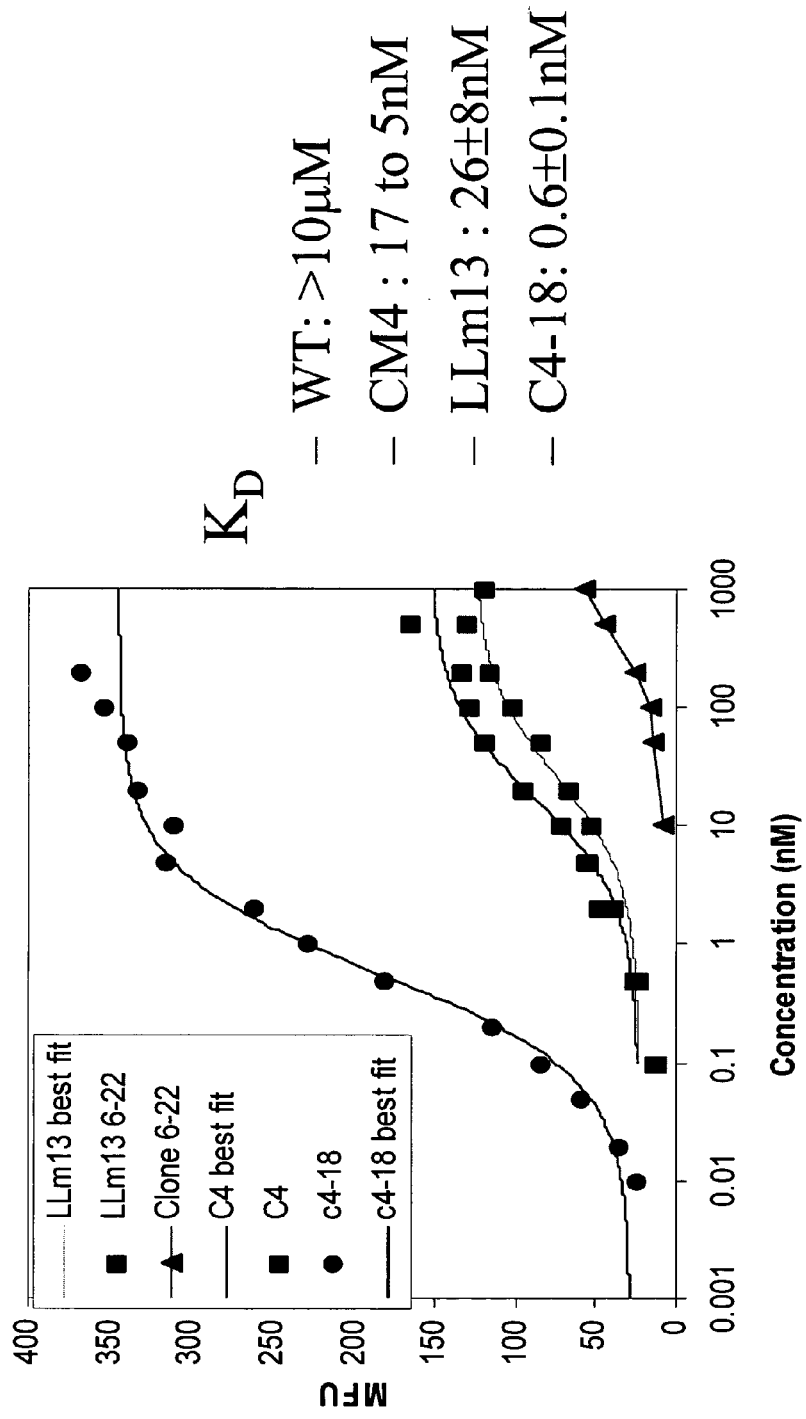
FIG. 24 is a graph depicting the concentration of selected anti-HAAH scFv fragments vs. anti-HAAH binding activity (as measured by fluorescence).

The dissociation constants of various clones were determined. Binding vs. concentration of each clone is shown in FIG. 24. The $K_D$ measurements for each clone compared in the graph are as follows:

| Wild type clone 6-22: | >10 µM |
| Clone LLm13: | 26 ± 8 nM |
| Clone CM4: | 17 to 5 nM |
| Clone C4m18: | 0.6 ± 0.1 nM |

Example 8

Expression of Selected scFv Fragments as IgG Antibodies

Figure 25:
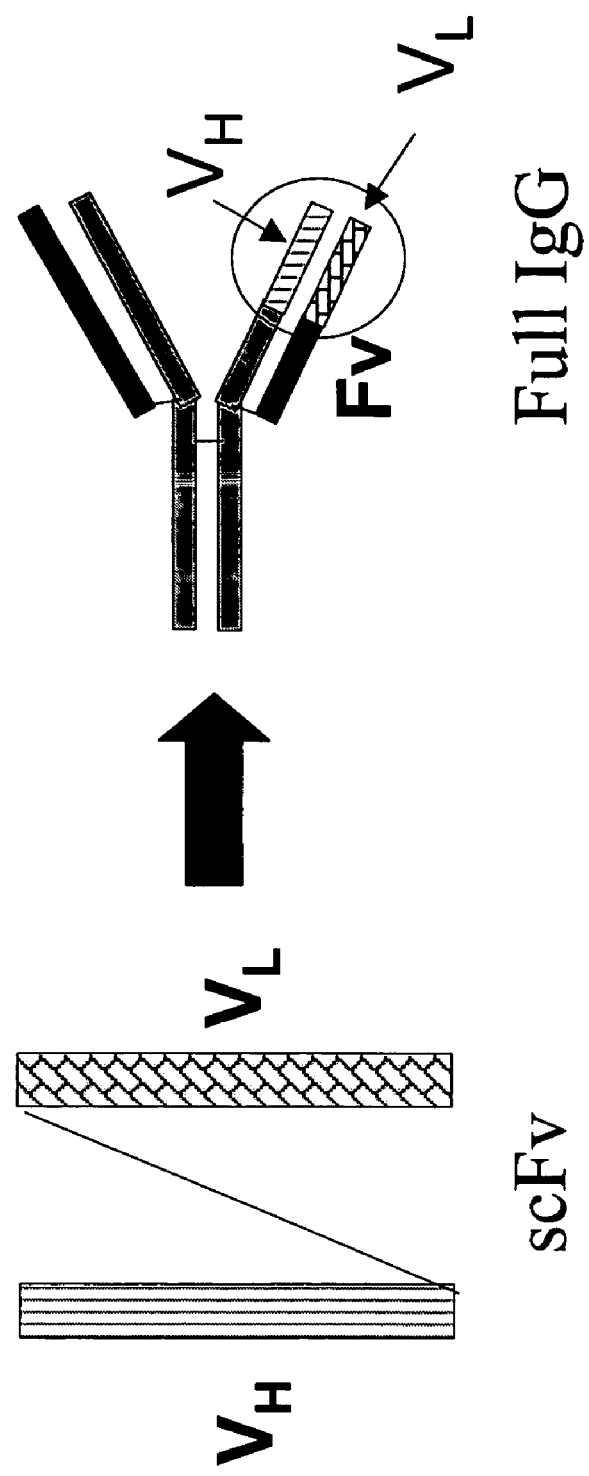
FIG. 25 is a schematic diagram depicting the conversion of an scFv fragment to a full length IgG antibody.

Full length IgG antibodies were created from scFv fragments by inserting the isolated variable heavy and variable light chain sequences into an expression vector containing a sequence encoding the constant regions of the heavy and light IgG chains, the resulting vector expressing a full length IgG antibody (FIG. 25). In brief, the heavy and light chain sequences of the selected scFv fragments were separately amplified by PCR. The resulting fragments were then ligated into the expression vector pPNL501 at the appropriate locations (Pacific Northwest National Laboratory). The resulting vectors were cloned, isolated, and sequenced to confirm the correct sequences were inserted. The vectors were then transfected into COS-7L cells (Invitrogen) by standard methods. These resulting COS-7L cells express and secrete IgG into the culture medium. The medium was then isolated, and the IgG was purified using a Protein A resin by standard methods.

Figure 26:
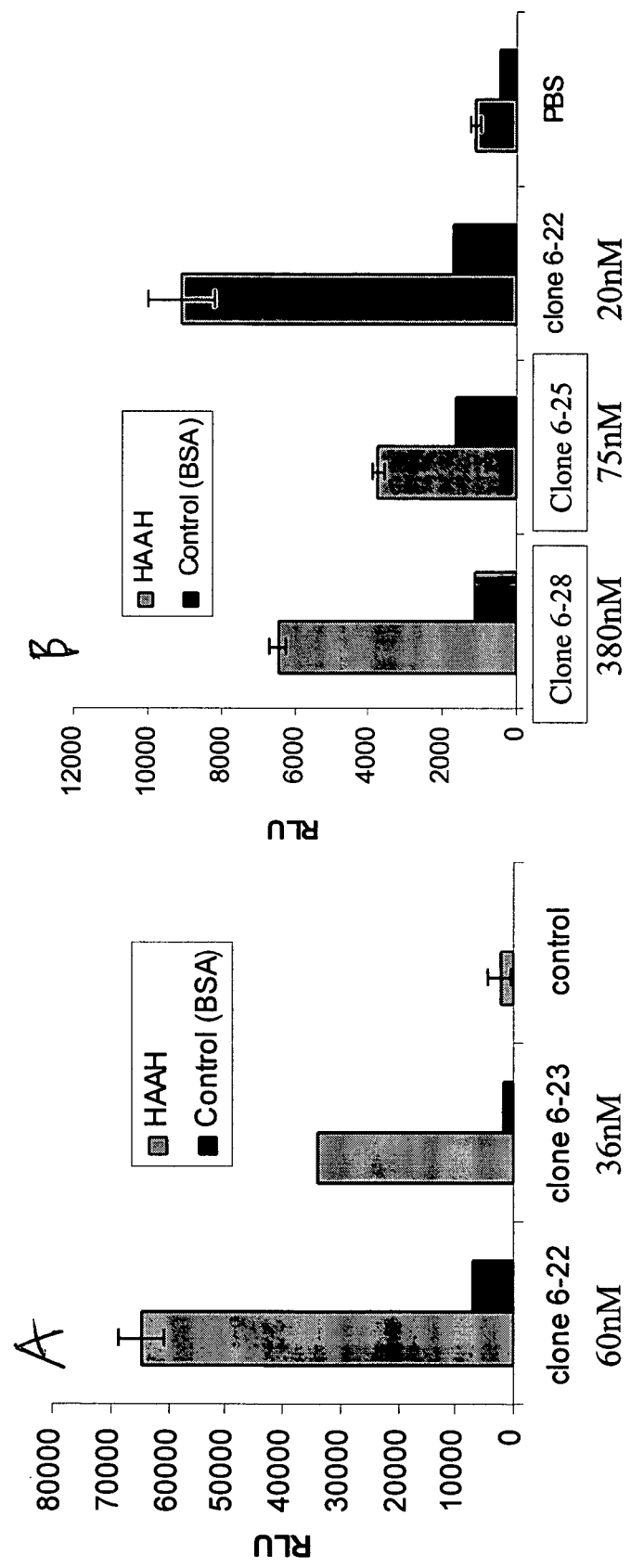
FIGS. 26A-B are graphs depicting the binding of wild-type anti-HAAH IgG antibodies to HAAH as determined by ELISA. The concentration used for each antibody is indicated below the graphs.
Figure 27:
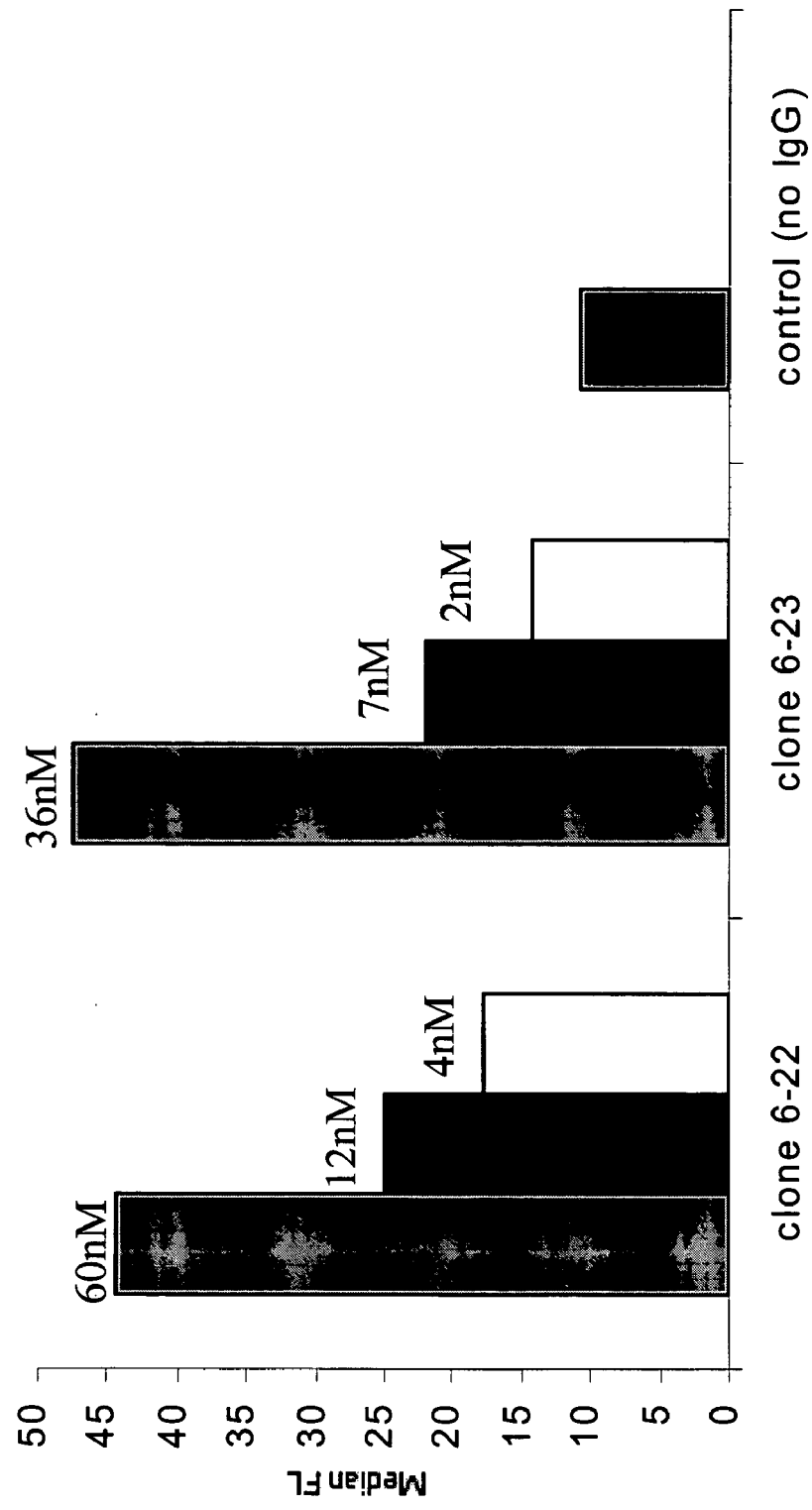
FIG. 27 is a graph depicting the binding of wild-type anti-HAAH IgG antibodies to H460 tumor cells as determined by FACS. The concentrations of antibody used are indicated on the graph.
Figure 28:
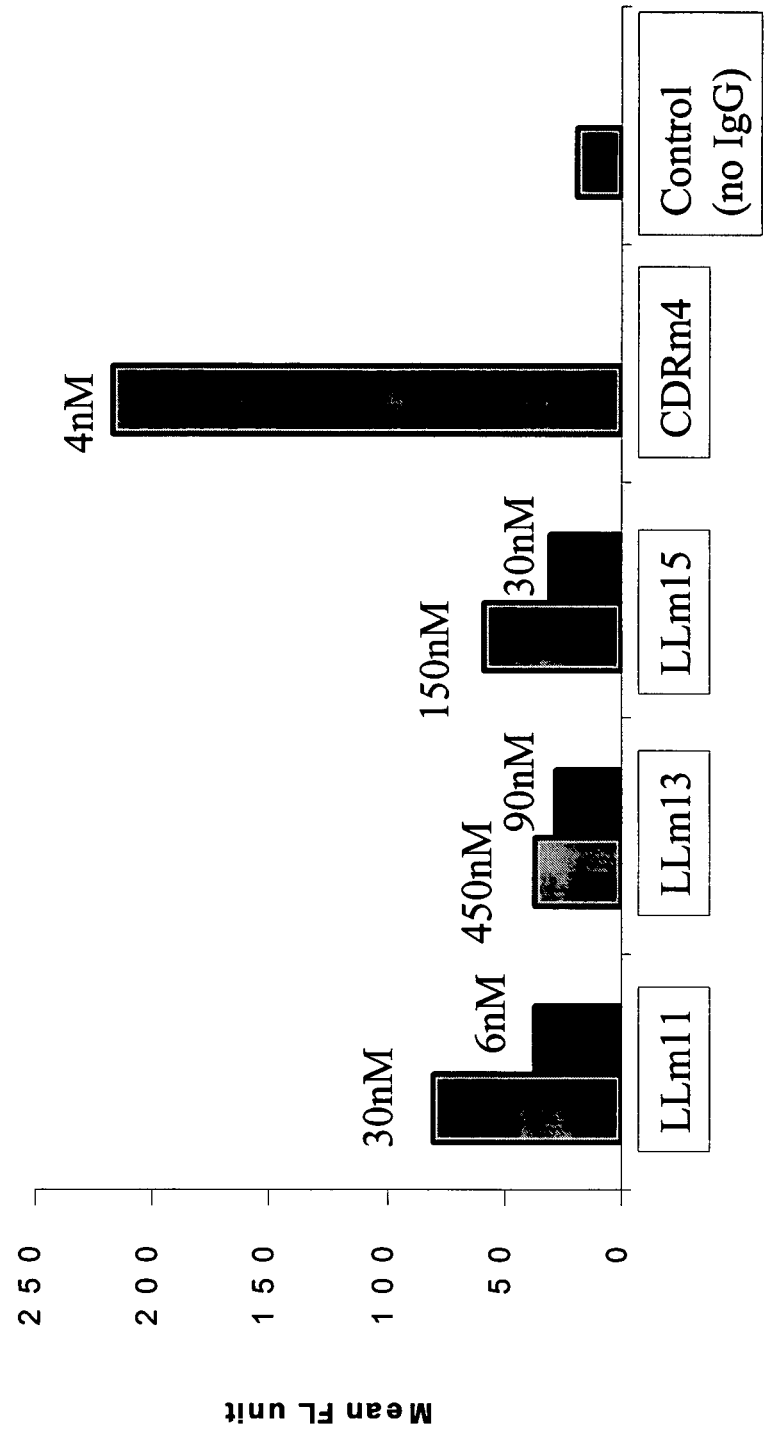
FIG. 28 is a graph depicting the binding of selected anti-HAAH IgG mutant antibodies to H460 tumor cells as determined by FACS. The concentrations of antibody used are indicated on the graph.

Binding specificity of the full length IgG antibodies was determined by ELISA and by binding to tumor cells expressing HAAH. For determination of binding specificity by ELISA, either HAAH or bovine serum albumin (BSA) was coated on an ELISA well, and different amounts of IgG were allowed to bind in each well. Detection was performed with a goat anti-human IgG-peroxidase conjugate and a chemoluminescent substrate. The results of this experiment for IgG 6-22, 6-23, 6-25, and 6-28 are shown in FIG. 26. For determination of binding specificity to HAAH-expressing tumor cells, different amounts of IgG antibodies were allowed to bind to H460 tumor cells, which express high levels of HAAH. Binding of IgG antibodies to the cells was detected using a goat anit-human IgG-FITC conjugate with detection by FACS. Results for IgG 6-22 and 6-23 are shown in FIG. 27; results for IgG LLm11, LLm13, LLm15, and CDRm4 are shown in FIG. 28.

Figure 29:
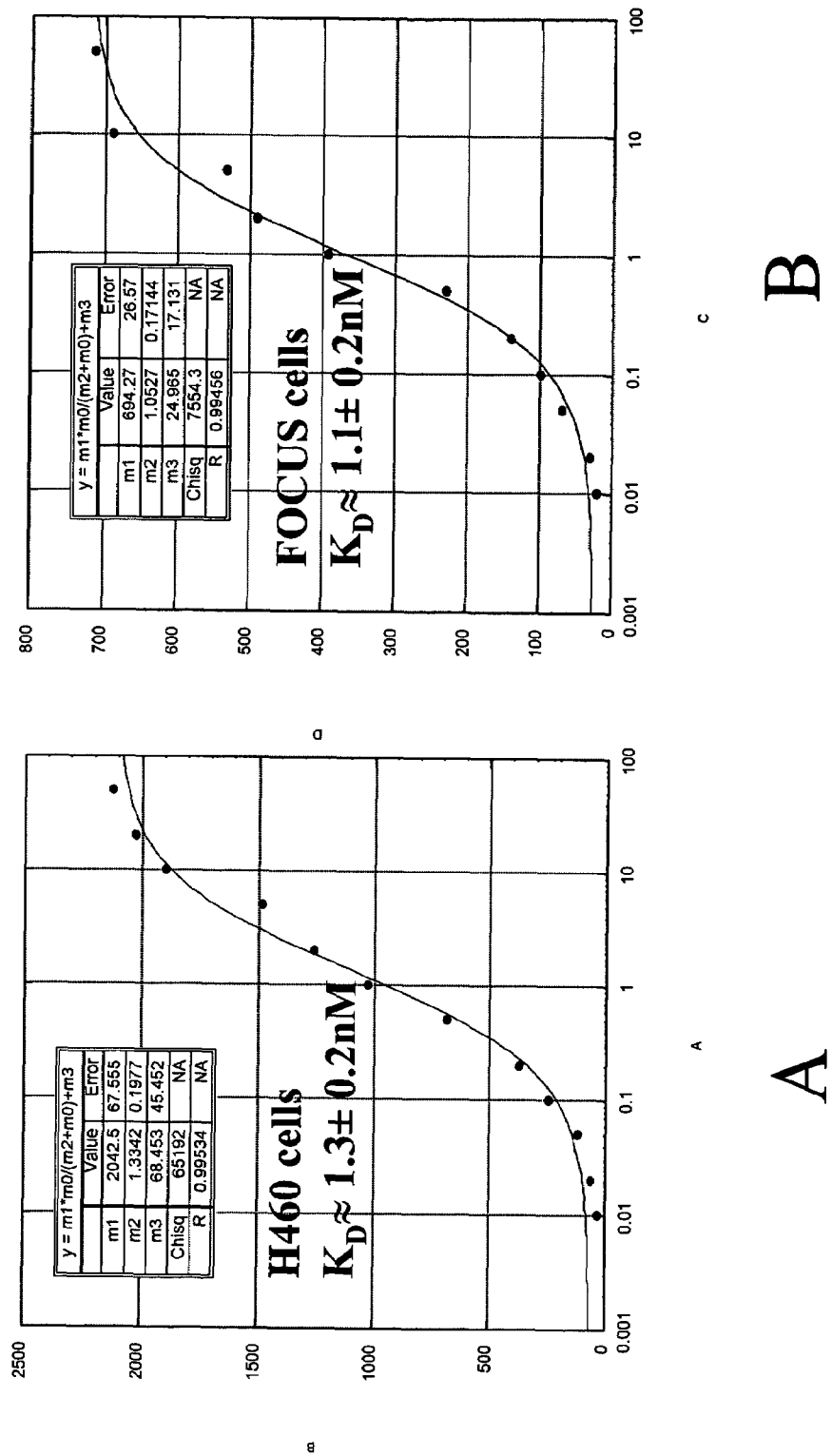
FIG. 29A is a graph depicting the concentration of 6-22 IgG antibody vs. binding to H460 cells (as measured by fluorescence).
FIG. 29B is a graph depicting the concentration of 6-22 IgG antibody vs. binding to FOCUS cells (as measured by fluorescence).
Figure 30:
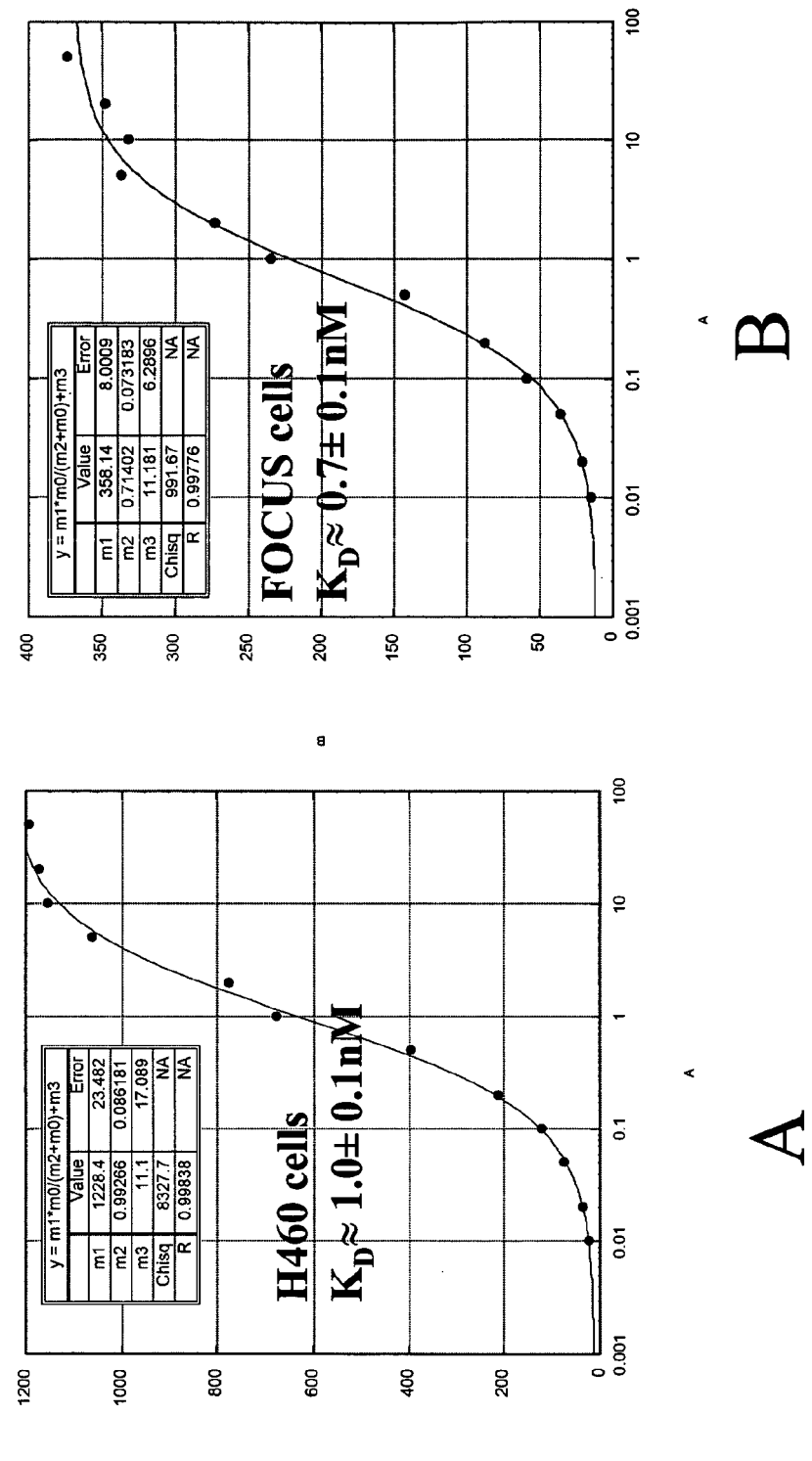
FIG. 30A is a graph depicting the concentration of CDRm4 IgG antibody vs. binding to H460 cells (as measured by fluorescence).
FIG. 30B is a graph depicting the concentration of CDRm4 IgG antibody vs. binding to FOCUS cells (as measured by fluorescence).

The dissociation constants of IgG 6-22 and CDRm4 were determined. Different concentrations of IgG were allowed to bind either H460 or FOCUS cells at 4° C. FOCUS cells are a hepatocellular carcinoma line which also expresses HAAH. After allowing IgG to bind, the cells were labeled with goat anti-human IgG-phycoerythrin conjugates and fluorescence was detected by FACS. Binding vs. concentration for 6-22 IgG is shown in FIG. 29; binding vs. concentration for CDRm4 IgG is shown in FIG. 30. The $K_D$ measurements determined are as follows:

|  | H460 | FOCUS |
|---|---|---|
| 6-22 IgG | 1.3 ± 0.2 nM | 1.1 ± 0.2 nM |
| CDRm4 IgG | 1.0 ± 0.1 nM | 0.7 ± 0.1 nM |

Figure 31:
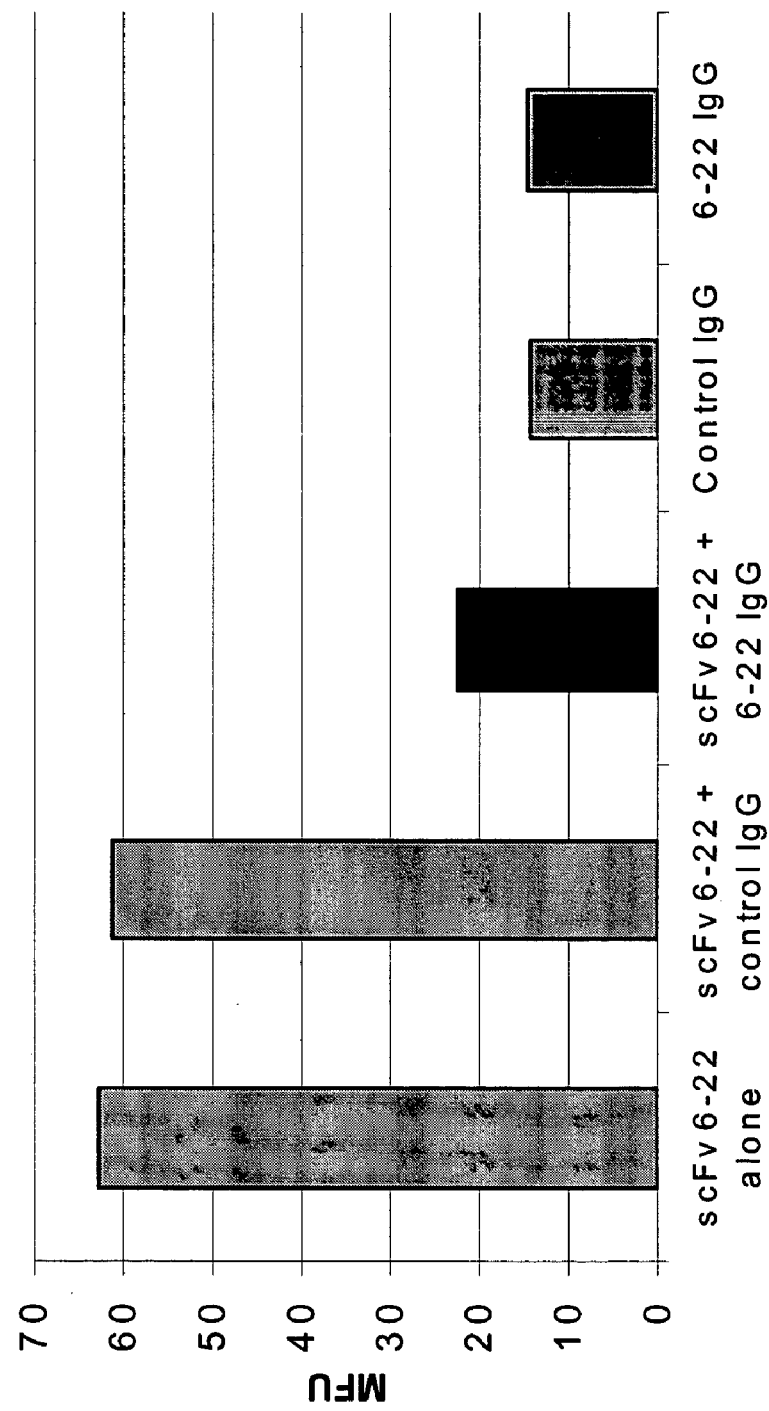
FIG. 31 is a graph depicting the binding of scFv 6-22 to H460 cells in the presence or absence of competition from 6-22 IgG antibody.

Experiments were performed to determine if the anit-HAAH scFv fragments and derived IgG antibodies bind to similar epitopes on HAAH. FLAG-tagged scFv fragment 6-22 was allowed to bind H460 cells in the presence of 6-22 IgG or a control IgG Binding of the tagged scFv 6-22 was determined by labeling the FLAG tag, present only on the scFv 6-22, with a biotinylated mouse anti-FLAG antibody followed by binding to a streptavidin-phycoerythrin conjugate. IgG 6-22, but not control IgQ competed off the binding of scFv 6-22, indicating that the IgG form of 6-22 binds a similar epitope on HAAH as the scFv 6-22 (FIG. 31).

To further demonstrate that the scFv fragments and IgG antibodies bind to similar HAAH epitopes, yeast cells displaying different scFv fragments were allowed to bind 15 nM of HAAH in the presence of competing CDRm4 IgG, competing LLm11 IgG, or buffer alone. Binding of HAAH to cells displaying scFv fragments was detected by FACS as described above. The results, shown in FIG. 32, indicate that the IgG antibodies are capable of competing for binding to HAAH, further indicating that the IgG antibodies and scFv fragments bind similar epitopes.

Example 9

Second Generation Affinity Maturation of an Anti-HAAH scFv Fragment by Error-Prone PCR Affinity maturation was performed on the CDRm4 mutant scFv to generate the second generation mutants C4m8 and C4m18. As described above, mutagenesis was performed by subjecting the CDRm4 scFv-encoding DNA to error prone PCR using nucleotide analogs. The mutagenized nucleic acids were re-expressed with yeast surface display and screened for binding using FACS as described above. DNA encoding binders was isolated, re-mutagenized, re-expressed and screened, and so forth for four rounds as described above. From this process, the improved second generation scFv clones were isolated.

The binding of improved clone C4m18 scFv mutant displayed on yeast was assayed for binding to HAAH as described above. This improved mutant was improved approximately 2-fold in both binding and display over CDRm4 (FIG. 33).

A number of embodiments of the invention have been described. Nevertheless, it will be understood that various modifications may be made without departing from the spirit and scope of the invention. Accordingly, other embodiments are within the scope of the following claims.

We claim:

1. An isolated human antibody or a fragment thereof, which comprises at least three complementarity determining regions (CDRs), wherein one of the at least three CDRs has the sequence of SEQ ID NO:51 and which antibody or fragment thereof specifically binds to an aspartyl (asparaginyl) β-hydroxylase (AAH).

2. The antibody of claim 1, which is a single chain antibody (scFv).

3. The antibody or fragment of claim 1, which specifically binds to a catalytic domain of the AAH.

4. The antibody or fragment of claim 1, which has an affinity for AAH equal to or less than about 1 μM.

5. The antibody or fragment of claim 1, which comprises a light chain variable region selected from any of SEQ ID NOs. 2, 20, 24, 26, 30, 120, 122, 124, 126, 128, 130, 132, 134, 136, 138, 140, 142, 144, 146, 148, 269, or 271.

6. The antibody or fragment of claim 1, which effectively competes with clone 11 for binding to an epitope bound by clone 11.

7. The antibody of claim 2, wherein the scFv comprises an amino acid sequence selected from any of SEQ ID NOs. 2, 20, 24, 26, 30, 120, 122, 124, 126, 128, 130, 132, 134, 136, 138, 140, 142, 144, 146, 148, 269, 271, 31, 40, 42, 43, 45, 149, 150, 151, 152, 153, 154, 155, 156, 157, 158, 159, 160, 161, 162, 163, 279, or 280.

8. The antibody or fragment of claim 1, which is in a composition comprising a physiologically acceptable diluent.

9. The antibody or fragment of claim 1, which further comprises a label or a toxin.

10. The antibody or fragment of claim 1, wherein the CDR having SEQ ID NO:51 is within a variable light chain region (VL).

11. The antibody or fragment of claim 1, wherein the other two CDRs of the at least three CDRs have the sequences of SEQ ID NO:49 and SEQ ID NO:50.

12. The antibody or fragment of claim 1, which further comprises a CDR having the sequence of SEQ ID NO:46.

13. The antibody or fragment of claim 1, which further comprises a CDR having the sequence of SEQ ID NO:47 or SEQ ID NO:48.

14. The antibody of claim 2, which has the amino acid sequence of SEQ ID NO:31.

15. The antibody of claim 2, which has the amino acid sequence of SEQ ID NO: 20.

16. An isolated human antibody, which comprises at least three complementarity determining regions (CDRs), one of which has the sequence of SEQ ID NO:51, and which antibody specifically binds to human aspartyl (asparaginyl) β-hydroxylase (HAAH).

* * * * *

UNITED STATES PATENT AND TRADEMARK OFFICE
CERTIFICATE OF CORRECTION

PATENT NO. : 7,413,737 B2  Page 1 of 1
APPLICATION NO. : 10/989462
DATED : August 19, 2008
INVENTOR(S) : K. Dane Wittrup It is certified that error appears in the above-identified patent and that said Letters Patent is hereby corrected as shown below:

Please delete the paragraph titled 'FEDERALLY SPONSORED RESEARCH OR DEVELOPMENT' encompassing column 1, lines 13-16:

"The work described herein was funded, in part, through a grant from the National Science Foundation (Grant No. 9843342). The United States government may, therefore, have certain rights in the invention."

and replace with:

--This invention was made with government support under Grant No. EEC9843342 awarded by the National Science Foundation. The government has certain rights in this invention.--

Signed and Sealed this
Ninth Day of October, 2012

David J. Kappos
*Director of the United States Patent and Trademark Office*